(12) United States Patent
Zhang et al.

(10) Patent No.: US 11,958,891 B2
(45) Date of Patent: Apr. 16, 2024

(54) TISSUE-SPECIFIC WNT SIGNAL ENHANCING MOLECULES AND USES THEREOF

(71) Applicant: Surrozen Operating, Inc., South San Francisco, CA (US)

(72) Inventors: Zhengjian Zhang, Albany, CA (US); Jennifer Jean Brady, Mountain View, CA (US); Aaron Ken Sato, Burlingame, CA (US); Wen-Chen Yeh, Belmont, CA (US); Yang Li, Mountain View, CA (US); Teppei Yamaguchi, El Cerrito, CA (US)

(73) Assignee: Surrozen Operating, Inc., South San Francisco, CA (US)

( * ) Notice: Subject to any disclaimer, the term of this patent is extended or adjusted under 35 U.S.C. 154(b) by 389 days.

(21) Appl. No.: 16/481,001

(22) PCT Filed: Jan. 26, 2018

(86) PCT No.: PCT/US2018/015595
§ 371 (c)(1),
(2) Date: Jul. 25, 2019

(87) PCT Pub. No.: WO2018/140821
PCT Pub. Date: Aug. 2, 2018

(65) Prior Publication Data
US 2020/0048324 A1 Feb. 13, 2020

Related U.S. Application Data

(60) Provisional application No. 62/487,135, filed on Apr. 19, 2017, provisional application No. 62/450,804, filed on Jan. 26, 2017.

(51) Int. Cl.
| | |
|---|---|
| *C07K 14/705* | (2006.01) |
| *A61K 47/65* | (2017.01) |
| *C07K 14/47* | (2006.01) |
| *C07K 16/28* | (2006.01) |
| *C07K 16/40* | (2006.01) |
| *C07K 19/00* | (2006.01) |
| *C12N 15/62* | (2006.01) |

(52) U.S. Cl.
CPC ............ *C07K 14/705* (2013.01); *A61K 47/65* (2017.08); *C07K 14/47* (2013.01); *C07K 16/2851* (2013.01); *C07K 16/2881* (2013.01); *C07K 16/40* (2013.01); *C12N 15/62* (2013.01); *C07K 2317/622* (2013.01); *C07K 2317/71* (2013.01); *C07K 2317/75* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 8,278,036 B2 | 10/2012 | Kariko et al. |
| 8,507,442 B2 | 8/2013 | Gurney et al. |
| 8,691,966 B2 | 4/2014 | Kariko et al. |
| 8,748,089 B2 | 6/2014 | Kariko et al. |
| 8,835,108 B2 | 9/2014 | Kariko et al. |
| 8,969,526 B2 | 3/2015 | Baehner et al. |
| 9,296,826 B2 | 3/2016 | Cong et al. |
| 9,771,427 B2 | 9/2017 | Hofer et al. |
| 2003/0044409 A1 | 3/2003 | Carson et al. |
| 2007/0244061 A1 | 10/2007 | Niehrs et al. |
| 2008/0038272 A1 | 2/2008 | Buehring et al. |
| 2008/0267955 A1 | 10/2008 | Schluesener et al. |
| 2010/0092457 A1 | 4/2010 | Aburatani et al. |
| 2010/0172895 A1 | 7/2010 | Boone et al. |
| 2013/0230521 A1 | 9/2013 | Nakamura et al. |
| 2014/0044713 A1 | 2/2014 | De Lau et al. |
| 2014/0105917 A1 | 4/2014 | Gurney |
| 2014/0328859 A1 | 11/2014 | Cong et al. |
| 2015/0299324 A1 | 10/2015 | Hofer et al. |
| 2017/0158775 A1 | 6/2017 | Linden et al. |
| 2017/0240633 A1 | 8/2017 | Wang et al. |
| 2017/0306029 A1 | 10/2017 | Garcia et al. |
| 2017/0349659 A1 | 12/2017 | Garcia et al. |
| 2018/0066067 A1 | 3/2018 | Cong et al. |
| 2020/0024338 A1 | 1/2020 | Luca et al. |
| 2020/0199237 A1 | 6/2020 | Garcia et al. |
| 2020/0199238 A1 | 6/2020 | Garcia et al. |
| 2020/0308287 A1 | 10/2020 | Li et al. |
| 2021/0079089 A1 | 3/2021 | Li et al. |
| 2021/0087280 A1 | 3/2021 | Li et al. |
| 2021/0292422 A1 | 9/2021 | Li |
| 2021/0380678 A1 | 12/2021 | Zhang et al. |

(Continued)

FOREIGN PATENT DOCUMENTS

| | | | |
|---|---|---|---|
| EP | 2305274 A1 | 4/2011 |
| EP | 2331136 B1 | 1/2018 |

(Continued)

OTHER PUBLICATIONS

Skolnik et al. (2000). Trends in Biotech. 18(1):34-39.*
Arumugam, T. et al. (Apr. 2015) "New Blocking Antibodies against Novel AGR2-C4.4A Pathway Reduce Growth and Metastasis of Pancreatic Tumors and Increase Survival in Mice" Molecular Cancer Therapeutics, 14(4):941-951.
Bhanot, P. et al. (Jul. 18, 1996) "A new member of the frizzled family from *Drosophila* functions as a Wingless receptor" Nature, 382:225-230.
Brott, B.K. and S.Y. Sokol (Sep. 2002) "Regulation of Wnt/LRP Signaling by Distinct Domains of Dickkopf Proteins" Mol Cell Biol, 22(17):6100-6110.
Clevers, H. et al. (Oct. 3, 2014) "An integral program for tissue renewal and regeneration: Wnt signaling and stem cell control" Science, 346(6205):1248012-1-1248012-7.

(Continued)

*Primary Examiner* — Christine J Saoud
*Assistant Examiner* — Jon M Lockard
(74) *Attorney, Agent, or Firm* — Cooley LLP

(57) ABSTRACT

The present disclosure provides tissue-specific Wnt signal enhancing molecules, and related methods of using these molecules to increase Wnt signaling in targeted tissues.

14 Claims, 20 Drawing Sheets

Specification includes a Sequence Listing.

(56) References Cited

U.S. PATENT DOCUMENTS

| | | |
|---|---|---|
| 2021/0403578 A1 | 12/2021 | Garcia et al. |
| 2022/0064337 A1 | 3/2022 | Li et al. |
| 2022/0112278 A1 | 4/2022 | Li et al. |
| 2022/0175884 A1 | 6/2022 | Lee et al. |
| 2022/0195053 A1 | 6/2022 | Li et al. |

FOREIGN PATENT DOCUMENTS

| | | |
|---|---|---|
| WO | WO 2008/093646 A1 | 8/2008 |
| WO | WO 2010/090513 A2 | 8/2010 |
| WO | WO 2010/092457 A1 | 8/2010 |
| WO | WO 2011/130624 A2 | 10/2011 |
| WO | WO 2012/014076 A2 | 2/2012 |
| WO | WO 2012/045075 A1 | 4/2012 |
| WO | WO 2012/138453 A1 | 10/2012 |
| WO | WO 2012/140274 A2 | 10/2012 |
| WO | WO 2013/052523 A1 | 4/2013 |
| WO | WO 2013/054307 A2 | 4/2013 |
| WO | WO 2013/071047 A1 | 5/2013 |
| WO | WO 2013/078199 A2 | 5/2013 |
| WO | WO 2013/130364 A1 | 9/2013 |
| WO | WO 2013/151666 A2 | 10/2013 |
| WO | WO 2014/023709 A1 | 2/2014 |
| WO | WO 2014/081507 A1 | 5/2014 |
| WO | WO 2014/093924 A1 | 6/2014 |
| WO | WO 2014/164253 A1 | 10/2014 |
| WO | WO 2015/164392 A2 | 10/2015 |
| WO | WO 2016/040895 A1 | 3/2016 |
| WO | WO 2016/073906 A2 | 5/2016 |
| WO | WO 2016/081640 A1 | 5/2016 |
| WO | WO 2017/069628 A2 | 4/2017 |
| WO | WO 2017/100467 A2 | 6/2017 |
| WO | WO-2018107116 A1 | 6/2018 |
| WO | WO 2018/132572 A1 | 7/2018 |
| WO | WO-2018140821 A1 | 8/2018 |
| WO | WO 2018/203567 A1 | 11/2018 |
| WO | WO 2018/215614 A1 | 11/2018 |
| WO | WO 2019/126398 A1 | 6/2019 |
| WO | WO-2019126399 A1 | 6/2019 |
| WO | WO-2019126401 A1 | 6/2019 |
| WO | WO 2020/014271 A1 | 1/2020 |
| WO | WO-2020010308 A1 | 1/2020 |
| WO | WO-2020132356 A1 | 6/2020 |
| WO | WO-2020167848 A1 | 8/2020 |
| WO | WO-2020185960 A1 | 9/2020 |
| WO | WO-2020206005 A1 | 10/2020 |
| WO | WO 2020/250156 A1 | 12/2020 |
| WO | WO-2021003054 A1 | 1/2021 |
| WO | WO-2021173726 A1 | 9/2021 |
| WO | WO-2022104280 A1 | 5/2022 |
| WO | WO-2022192445 A1 | 9/2022 |

OTHER PUBLICATIONS

Colman, P.M. (1994) "Effects of amino acid sequence changes on antibody-antigen interactions" Research in Immunology, 145(1):33-36.

D'Souza, A.A. et al. (2015) "Asialoglycoprotein receptor mediated hepatocyte targeting—Strategies and applications", Journal of Controlled Release, 203:126-139.

Eppink, B. et al. (Dec. 1, 2015) "Abstract C21: Generation of Wnt- and mitogenic receptor binding bispecific antibodies to target cancer stem cells" AACR-NCI-EORTC International Conference: Molecular Targets and Cancer Therapeutics; Nov. 5-9, 2015; Boston, MA. Molecular Cancer Therapeutics, 14(12 Suppl 2):Abstract C21, DOI: 10.1158/1535-7163.TARG-15-C21; 1 page.

Ettenberg S.A. et al. (Aug. 31, 2010) "Inhibition of tumorigenesis driven by different Wnt proteins requires blockade of distinct ligand-binding regions by LRP6 antibodies" Proc Natl Acad Sci USA, 107(35):15473-15478.

Gong, Y. et al. (2010) "Wnt Isoform-Specific Interactions with Coreceptor Specify Inhibition or Potentiation of Signaling by LRP6 Antibodies" PLoS One, 5(9):e12682, doi:10.1371/journal.pone.0012682; 17 pages.

Hao, H-X. et al. (May 10, 2012) "ZNRF3 promotes Wnt receptor turnover in an R-spondin-sensitive manner" Nature, 485(7397):195-200.

Heupel, W-M. et al. (Aug. 1, 2008) "Pemphigus Vulgaris IgG Directly Inhibit Desmoglein 3-Mediated Transinteraction" Journal of Immunology, 181(3):1825-1834.

Hombach, A.A. et al. (Jan. 1, 2012) "Antibody-IL 2 fusion proteins for tumor targeting" Antibody Engineering: Methods and Protocols, 2nd Ed. Methods in Molecular Biology, vol. 907, p. 611-626.

Ingham, P. W. (Oct. 1996) "Has the quest for a Wnt receptor finally frizzled out?" Trends Genet, 12(10):382-384.

Jacobsen, F.W. et al. (Feb. 3, 2017) "Engineering an IgG Scaffold Lacking Effector Function with Optimized Developability" J Biol Chem, 292:1865-1875.

Jacobsen, B. et al. (Oct. 10, 2014) "C4.4A as a biomarker in pulmonary adenocarcinoma and squamous cell carcinoma" World Journal of Clinical Oncology, 5(4):621-632.

Janda, C.Y. et al. (May 11, 2017) "Surrogate Wnt agonists that phenocopy canonical Wnt and β-catenin signaling" Nature, 545(7653):234-237. HHS Public Access Author Manuscript, 35 pages.

Jin, Y-R. and J.K. Yoon (Dec. 2012) "The R-spondin family of proteins: Emerging regulators of WNT signaling" Int J Biochem Cell Biol, 44(12):2278-2287, doi: 10.1016/j.biocel.2012.09.006.

Keerthivasan, S. et al. (Feb. 2014) "Wnt/Beta-catenin signaling in T-cells drives epigenetic imprinting of pro-inflammatory properties and promotes colitis and colon cancer" Sci Transl Med, 6(225):225ra28, doi:10.1126/scitranslmed.3007607. NIH Public Access Author Manuscript, 28 pages.

Kim, K.-A. et al. (Jun. 2008) "R-Spondin Family Members Regulate the Wnt Pathway by a Common Mechanism" Mol Biol Cell, 19(6):2588-2596.

Knight, M.N. and K. Hankenson (2014) "R-spondins: Novel matricellular regulators of the skeleton" Matrix Biology, 37:157-161.

Krupnik, V.E. et al. (1999) "Functional and structural diversity of the human Dickkopf gene family" Gene, 238(2):301-313.

Li, L. et al. (Feb. 22, 2002) "Second Cysteine-rich Domain of Dickkopf-2 Activates Canonical Wnt Signaling Pathway via LRP-6 Independently of Dishevelled" J Biol Chem, 277(8):5977-5981.

Lo, M. et al. (Mar. 3, 2017) "Effector-attenuating Substitutions That Maintain Antibody Stability and Reduce Toxicity in Mice" J Biol Chem, 292:3900-3908.

Mannstadt, M. et al. (1999) "Receptors for PTH and PTHrP: their biological importance and functional properties" American Journal of Physiology, 277:F665-F675.

McMahon, A.P. (Jul. 1992) "The Wnt family of developmental regulators" Trends Genet, 8:236-242.

Miller, J.R. (Dec. 28, 2001) "The Wnts" Genome Biol, 3(1):3001.1-3001.15.

Moon, B-I. et al. (2015) "Functional Modulation of Regulatory T Cells by IL-2" PLoS One, 10(11):e0141864, doi:10.1371/journal.pone.0141864; 13 pages.

Ngora, H. et al. (Feb. 2012) "Membrane-Bound and Exosomal Metastasis-Associated C4.4A Promotes Migration by Associating with the α6β4 Integrin and MT1-MMP[1,2]" Neoplasia, 14(2):95-107.

Pace, L. et al. (2005) "IL-4 Modulation of CD4+ CD25+ T Regulatory Cell-Mediated Suppression" J Immunol, 174(12):7645-7653.

Papkoff, J. et al. (May 1996) "Wnt-1 Regulates Free Pools of Catenins and Stabilizes APC-Catenin Complexes" Mol Cell Biol, 16:2128-2134.

Paret, B. et al. (Jul. 10, 2005) "Ly6 family member C4.4A binds laminins 1 and 5, associates with Galectin-3 and supports cell migration" International Journal of Cancer, 115(5):724-733.

Paul, W.E. (1993) "Fv Structure and Diversity in Three Dimensions" in Fundamental Immunology, 3rd ed. Raven Press, NY; Chap. 9, pp. 292-295.

Rudikoff, S. et al. (1982) "Single amino acid substitution altering antigen-binding specificity" Proc Natl Acad Sci USA, 79:1979-1983.

(56) References Cited

OTHER PUBLICATIONS

Sanhueza, C.A. et al. (2017) "Efficient Liver Targeting by Polyvalent Display of a Compact Ligand for the Asialoglycoprotein Receptor" J Am Chem Soc, 139:3528-3536.
Sato, T. et al. (May 14, 2009) "Single Lgr5 stem cells build crypt-villus structures in vitro without a mesenchymal niche" Nature, 459:262-265, www.nature.com/doifinder/10.1038/nature07935; with "Methods", 1 page.
Sato, T. et al. (2011) "Long-term Expansion of Epithelial Organoids From Human Colon, Adenoma, Adenocarcinoma, and Barrett's Epithelium" Gastroenterology, 141:1762-1772.
Stockert, R.J. et al. (1991) "Structural Characteristics and Regulation of the Asialoglycoprotein Receptor" Targeted Diagnostics and Therapy 4:41-64.
Thomason, H.A. et al. (2010) "Desmosomes: adhesive strength and signalling in health and disease" Biochemical Journal, 429(3):419-433.
UniProtKB, Membrane protein. UniProtKB Accession No. A0A0M8ZAH5. Last Modified: Dec. 9, 2015. [online]. [Retrieved on Mar. 8, 2018]. Retrieved from the Internet: <URL: http://www.uniprot.org/uniproUAOA0M8ZAH5> Protein, and Sequence (370 a.a.); 3 printed pages.
Worthen, C.A. and C.A. ENNS (Mar. 6, 2014) "The role of hepatic transferring receptor 2 in the regulation of iron homeostasis in the body" Frontiers in Pharmacology, 5:34, 8 pages.
Xie, Y. et al. (Oct. 2013) "Interaction with both ZNRF3 and LGR4 is required for the signalling activity of R-spondin" EMBO Reports, 14(12):1120-1126.
Yan, H. et al. (Nov. 13, 2012) "Sodium taurocholate cotransporting polypeptide is a functional receptor for human hepatitis B and D virus" eLife, 1:e00049, http://dx.doi.org/10.7554/eLife.00049; 28 pages.
Yan, J-J. et al. (2015) "Active radar guides missile to its target: receptor-based targeted treatment of hepatocellular carcinoma by nanoparticulate systems" Tumor Biology, 36:55-67.
Yang-Snyder, J. et al. (1996) "A *frizzled* homolog functions in a vertebrate Wnt signaling pathway" Curr Biol, 6:1302-1306.
You, J. et al. (2008) "Wnt pathway-related gene expression in inflammatory bowel disease" Dig Dis Sci, 53(4):1013-1019.
GenBank Accession No. AF177394.2 "*Homo sapiens* dickkopf-1 (DKK-1) mRNA, complete cds" Dec. 20, 2016, 2 pages.
GenBank Accession No. AF177395.1 "*Homo sapiens* dickkopf-2 (DKK-2) mRNA, complete cds" Dec. 20, 2016, 2 pages.
GenBank Accession No. NM_001466.4 "*Homo sapiens* frizzled class receptor 2 (FZD2), mRNA" Feb. 17, 2021, 5 pages.
GenBank Accession No. NM_002335.2 "*Homo sapiens* low density lipoprotein receptor-related protein 5 (LRP5), mRNA" May 3, 2014, 5 pages.
GenBank Accession No. NM_002336.2 "*Homo sapiens* LDL receptor related protein 6 (LRP6), mRNA" Oct. 20, 2018, 8 pages.
GenBank Accession No. NM_003391.3 "*Homo sapiens* Wnt family member 2 (WNT2), transcript variant 1, mRNA" Feb. 17, 2021, 4 pages.
GenBank Accession No. NM_003392.7 "*Homo sapiens* Wnt family member 5A (WNT5A), transcript variant 1, mRNA" Feb. 21, 2021, 5 pages.
GenBank Accession No. NM_003393.4 "*Homo sapiens* Wnt family member 8B (WNT8B), mRNA" Mar. 7, 2021, 4 pages.
GenBank Accession No. NM_003394.4 "*Homo sapiens* Wnt family member 10B (WNT10B), mRNA" Feb. 16, 2021, 4 pages.
GenBank Accession No. NM_003395.4 "*Homo sapiens* Wnt family member 9A (WNT9A), mRNA" Feb. 16, 2021, 4 pages.
GenBank Accession No. NM_003396.3 "*Homo sapiens* Wnt family member 9B (WNT9B), transcript variant 1, mRNA" Feb. 16, 2021, 4 pages.
GenBank Accession No. NM_003468.4 "*Homo sapiens* frizzled class receptor 5 (FZD5), mRNA" Feb. 18, 2021, 6 pages.
GenBank Accession No. NM_003505.2 "*Homo sapiens* frizzled class receptor 1 (FZD1), mRNA" Nov. 22, 2020, 4 pages.
GenBank Accession No. NM_003506.4 "*Homo sapiens* frizzled class receptor 6 (FZD6), transcript variant 1, mRNA" Feb. 16, 2021, 5 pages.
GenBank Accession No. NM_003507.2 "*Homo sapiens* frizzled class receptor 7 (FZD7), mRNA" Feb. 21, 2021, 5 pages.
GenBank Accession No. NM_003508.3 "*Homo sapiens* frizzled class receptor 9 (FZD9), mRNA" Feb. 17, 2021, 5 pages.
GenBank Accession No. NM_004185.4 "*Homo sapiens* Wnt family member 2B (WNT2B), transcript variant WNT-2B1, mRNA" Feb. 13, 2021, 4 pages.
GenBank Accession No. NM_004625.4 "*Homo sapiens* Wnt family member 7A (WNT7A), mRNA" Feb. 17, 2021, 5 pages.
GenBank Accession No. NM_004626.3 "*Homo sapiens* Wnt family member 11 (WNT11), mRNA" Feb. 17, 2021, 4 pages.
GenBank Accession No. NM_005430.4 "*Homo sapiens* Wnt family member 1 (WNT1), mRNA" Feb. 21, 2021, 4 pages.
GenBank Accession No. NM_006522.4 "*Homo sapiens* Wnt family member 6 (WNT6), mRNA" Feb. 16, 2021, 4 pages.
GenBank Accession No. NM_007197.4 "*Homo sapiens* frizzled class receptor 10 (FZD10), mRNA" Mar. 2, 2021, 5 pages.
GenBank Accession No. NM_012193.4 "*Homo sapiens* frizzled class receptor 4 (FZD4), mRNA" Mar. 16, 2021, 6 pages.
GenBank Accession No. NM_014419.4 "*Homo sapiens* dickkopf like acrosomal protein 1 (DKKL1), transcript variant 1, mRNA" Feb. 18, 2021, 4 pages.
GenBank Accession No. NM_014420.3 "*Homo sapiens* dickkopf WNT signaling pathway inhibitor 4 (DKK4), mRNA" Feb. 15, 2021, 4 pages.
GenBank Accession No. NM_014421.3 "*Homo sapiens* dickkopf WNT signaling pathway inhibitor 2 (DKK2), mRNA" Feb. 13, 2021, 4 pages.
GenBank Accession No. NM_015881.6 "*Homo sapiens* dickkopf WNT signaling pathway inhibitor 3 (DKK3), transcript variant 1, mRNA" Feb. 23, 2021, 5 pages.
GenBank Accession No. NM_016087.2 "*Homo sapiens* Wnt family member 16 (WNT16), transcript variant 2, mRNA" Jan. 18, 2021, 4 pages.
GenBank Accession No. NM_024494.2 "*Homo sapiens* Wnt family member 2B (WNT2B), transcript variant WNT-2B2, mRNA*Homo sapiens* Wnt family member 2B (WNT2B), transcript variant WNT-2B2, mRNA" Nov. 12, 2018, 4 pages.
GenBank Accession No. NM_025216.3 "*Homo sapiens* Wnt family member 10A (WNT10A), mRNA" Feb. 17, 2021, 4 pages.
GenBank Accession No. NM_030753.5 "*Homo sapiens* Wnt family member 3 (WNT3), mRNA" Mar. 2, 2021, 4 page.
GenBank Accession No. NM_030761.5 "*Homo sapiens* Wnt family member 4 (WNT4), mRNA" Feb. 15, 2021, 4 pages.
GenBank Accession No. NM_031866.3 "*Homo sapiens* frizzled class receptor 8 (FZD8), mRNA" Mar. 16, 2021, 5 pages.
GenBank Accession No. NM_032642.3 "*Homo sapiens* Wnt family member 5B (WNT5B), transcript variant 1, mRNA" Mar. 22, 2021, 4 pages.
GenBank Accession No. NM_033131.4 "*Homo sapiens* Wnt family member 3A (WNT3A), mRNA" Mar. 2, 2021, 4 pages.
GenBank Accession No. NM_058238.3 "*Homo sapiens* Wnt family member 7B (WNT7B), mRNA" Feb. 16, 2021, 4 pages.
GenBank Accession No. NM_058244.4 "*Homo sapiens* Wnt family member 8A (WNT8A), transcript variant 3, mRNA" Feb. 23, 2021, 4 pages.
GenBank Accession No. NM_145866.2 "*Homo sapiens* frizzled class receptor 3 (FZD3), transcript variant 2, mRNA" Feb. 21, 2021, 7 pages.
GenBank Accession No. NP_001017403.1 "Leucine-rich repeat-containing G-protein coupled receptor 6 isoform 1 precursor [*Homo sapiens*]" Mar. 2, 2021, 6 pages.
GenBank Accession No. NP_001017404.1 "Leucine-rich repeat-containing G-protein coupled receptor 6 isoform 3 [*Homo sapiens*]" Mar. 3, 2021, 4 pages.
GenBank Accession No. NP_001025042.2 "R-spondin-4 isoform 1 precursor [*Homo sapiens*]" Dec. 12, 2020, 3 pages.
GenBank Accession No. NP_001033722.1 "R-spondin-1 isoform 1 precursor [*Homo sapiens*]" Feb. 20, 2021, 3 pages.

(56) References Cited

OTHER PUBLICATIONS

GenBank Accession No. NP_001035096.1 "R-spondin-4 isoform 2 precursor [*Homo sapiens*]" Dec. 12, 2020, 3 pages.
GenBank Accession No. NP_001193927.1 "E3 ubiquitin-protein ligase ZNRF3 isoform 1 precursor [*Homo sapiens*]" Feb. 17, 2021, 3 pages.
GenBank Accession No. NP_001229838.1 "R-spondin-1 isoform 2 [*Homo sapiens*]" Feb. 19, 2021, 3 pages.
GenBank Accession No. NP_001229839.1 "R-spondin-1 isoform 3 precursor [*Homo sapiens*]" Feb. 20, 2021, 3 pages.
GenBank Accession No. NP_001264155.1 "Leucine-rich repeat-containing G-protein coupled receptor 5 isoform 2 precursor [*Homo sapiens*]" Mar. 22, 2021, 4 pages.
GenBank Accession No. NP_001264156.1 "Leucine-rich repeat-containing G-protein coupled receptor 5 isoform 3 precursor [*Homo sapiens*]" Mar. 22, 2021, 4 pages.
GenBank Accession No. NP_001269792.1 "R-spondin-2 isoform 2 precursor [*Homo sapiens*]" Feb. 22, 2021, 3 pages.
GenBank Accession No. NP_001292473.1 "E3 ubiquitin-protein ligase RNF43 isoform 1 precursor [*Homo sapiens*]" Dec. 30, 2020, 4 pages.
GenBank Accession No. NP_001292474.1 "E3 ubiquitin-protein ligase RNF43 isoform 2 [*Homo sapiens*]" Feb. 14, 2021, 3 pages.
GenBank Accession No. NP_001304871.1 "R-spondin-2 isoform 3 [*Homo sapiens*]" Feb. 23, 2021, 3 pages.
GenBank Accession No. NP_001333361.1 "Leucine-rich repeat-containing G-protein coupled receptor 4 isoform 2 precursor [*Homo sapiens*]" Mar. 16, 2021, 3 pages.
GenBank Accession No. NP_001662.1 "Asialoglycoprotein receptor 1 isoform a [*Homo sapiens*]" Feb. 16, 2021, 3 pages.
GenBank Accession No. NP_003658.1 "Leucine-rich repeat-containing G-protein coupled receptor 5 isoform 1 precursor [*Homo sapiens*]" Mar. 22, 2021, 4 pages.
GenBank Accession No. NP_036374.1 "Dickkopf-related protein 1 precursor [*Homo sapiens*]" Mar. 3, 2021, 3 pages.
GenBank Accession No. NP_055236.1 "Dickkopf-related protein 2 precursor [*Homo sapiens*]" Feb. 13, 2021, 3 pages.
GenBank Accession No. NP_060233.3 "E3 ubiquitin-protein ligase RNF43 isoform 1 precursor [*Homo sapiens*]" Dec. 15, 2020, 4 pages.
GenBank Accession No. NP_060960.2 "Leucine-rich repeat-containing G-protein coupled receptor 4 isoform 1 precursor [*Homo sapiens*]" Mar. 16, 2021, 5 pages.
GenBank Accession No. NP_067649.2 "Leucine-rich repeat-containing G-protein coupled receptor 6 isoform 2 [*Homo sapiens*]" Mar. 2, 2021, 4 pages.
GenBank Accession No. NP_115549.2 "E3 ubiquitin-protein ligase ZNRF3 isoform 2 [*Homo sapiens*]" Feb. 21, 2021, 3 pages.
GenBank Accession No. NP_116173.2 "R-spondin-3 precursor [*Homo sapiens*]" Mar. 16, 2021, 4 pages.
GenBank Accession No. NP_550436.1 "Asialoglycoprotein receptor 2 isoform c [*Homo sapiens*]" Feb. 13, 2021, 3 pages.
GenBank Accession No. NP_848660.3 "R-spondin-2 isoform 1 precursor [*Homo sapiens*]" Feb. 16, 2021, 3 pages.
GenBank Accession No. XP_005582755.1 "Predicted: asialoglycoprotein receptor 1 isoform X1 [Macaca fascicularis]" Jan. 25, 2016, 2 pages.
GenBank Accession No. XP_006710646.1 "R-spondin-1 isoform X1 [*Homo sapiens*]" Feb. 28, 2021, 1 page.
GenBank Accession No. XP_011515320.1 "R-spondin-2 isoform X1 [*Homo sapiens*]" Feb. 28, 2021, 2 pages.
GenBank Accession No. XP_011515321.1 "R-spondin-2 isoform X2 [*Homo sapiens*]" Feb. 28, 2021, 2 pages.
GenBank Accession No. XP_011523257.1 "E3 ubiquitin-protein ligase RNF43 isoform X1 [*Homo sapiens*]" Feb. 28, 2021, 2 pages.
GenBank Accession No. XP_011523258.1 "E3 ubiquitin-protein ligase RNF43 isoform X2 [*Homo sapiens*]" Feb. 28, 2021, 2 pages.
GenBank Accession No. XP_016868884.1 "R-spondin-2 isoform X3 [*Homo sapiens*]" Feb. 28, 2021, 1 page.
GenBank Accession No. XP_016880289.1 "E3 ubiquitin-protein ligase RNF43 isoform X1 [*Homo sapiens*]" Feb. 28, 2021, 2 pages.
Apte, U. et al. (Sep. 2009) Beta-catenin activation promotes liver regeneration after acetaminophen-induced injury. The American Journal of Pathology. 175(3):1056-1065. DOI: 10.2353/ajpath.2009. 080976.
Bhushan, B. et al. (Nov. 2014) Pro-regenerative signaling after acetaminophen-induced acute liver injury in mice identified using a novel incremental dose model. The American Journal of Pathology. 184(11):3013-3025. DOI: 10.1016/j.ajpath.2014.07.019.
Meier, M. et al. (2000) Crystal Structure of the Carbohydrate Recognition Domain of the H1 Subunit of the Asialoglycoprotein Receptor. J Mol Biol. 300:857-865.
Scatchard, G. (1949) The attractions of proteins for small molecules and ions. Ann. NY Acad Sci USA. 51:660-672.
UniProtKB, (ASGR1_HUMAN) Asialoglycoprotein receptor 1. UniProtKB Accession No. P07306. Last Modified: Feb. 23, 2022. [online]. Retrieved Mar. 24, 2022 from: https://www.dot.uniprot.org/uniprot/P07306; 16 printed pages.
Witzigmann, D. et al. (2016) Variable asialoglycoprotein receptor 1 expression in liver disease: Implications fo therapeutic intervention. Hepatology Research. 46(7):686-696.
Yang, W.H. et al. (2018) Accelerated Aging and Clearance of Host Anti-inflammatory Enzymes by Discrete Pathogens Fuels Sepsis. Cell Host Microbe. 24(4):500-513.
Zapata, G. et al. (1995) Engineering linear F(ab')$_2$ fragments for efficient production in *Escherichia coli* and enhanced antiproferative activity. Protein Eng. 8(10):1057-1062.
International Search Report and Written Opinion for Application No. PCTUS201815595, dated May 29, 2018, 12 pages.
Perez De La Lastra, J.M. et al. (Apr. 1999) Epitope mapping of 10 monoclonal antibodies against the pig analogue of human membrane cofactor protein (MCP). Immunology, vol. 96, No. 4, pp. 663-670. DOI: 10.1046/j.1365-2567.1999.00732.x.
Russell, J.O. and S. P. Monga. (2018) Wnt/beta-Catenin Signaling in Liver Development, Homeostasis, and Pathobiology. Annu. Rev. Pathol. Mech. Dis, 13:351-378, DOI: 10.1146/annurev-pathol-020117-044010.
Shilpi, S. et al. (Jul. 2018) Drug targeting strategies for liver cancer and other liver diseases. Moj Drug Design Development & Therapy, vol. 2, No. 4, pp. 171-177.
Tao, Guo-Zhong et al. (Jun. 2013) Wnt/[beta]-Catenin Signaling Protects Mouse Liver against Oxidative Stress-induced Apoptosis through the Inhibition of Forkhead Transcription Factor FoxO3 J Biol Chem, 288(24):17214-17224.
Zhang, Z. et al. (Aug. 2020) Tissue-targeted Rspondin mimetics for liver regeneration. Scientific Reports, vol. 10, No. 1, Article 13951; DOI: 10.1038/s41598-020-70912-3, 14 pages.
International Preliminary Report on Patentability for Application No. PCT/US2018/15595, dated Jul. 30, 2019, 8 pages.

\* cited by examiner

FIG. 4

```
Rspo1  MRLGLC-VVALVLSWTHLTISSRGIKGKRQRRISAEGSQACAKGCELCSEVNGCLKCSPK  59
Rspo2  MQFRLFSPALIILNCMDYSHCQGNR-WRRSKR-ASYVSNPICKGCLSCSKDNGCSRCQQK  58
Rspo3  MHLRLISWLFIILNFMEYIGSQNASRGRRQRRMHPNVSQGCQGGCATCSDYNGCLSCKPR  60
Rspo4  MRAPLCLLLL-VAHAVDMLA------LNRRKKQVGTGLGGNCTGCIICSEENGCSTCQQR  53
       *:  *     :      .*  ::              **  **. ***   *  :  :

Rspo1  LFILLERNDIRQVGVCLPSCPPGYFDARNPDMNKCIK                        119
Rspo2  LFFFLRREGMRQYGECLHSCPSGYYGHRAPDMNRCAR                        118
Rspo3  LFFALERIGMRQIGVCLSSCPSGYYGTRYPDINKCTK                        119
Rspo4  LFLFIRREGIRQYGKCLHDCPPGYFGIRGQEVNRCKK                        112
       **.:  *  : * :*  **  **  ** :  *   :*:*

Rspo1                                       SPAQCEMSEWSPWGPCSKKQQLCGFRRGSEERTRRV  179
Rspo2                                       --GCEVGHWSEWGTCSRNNRTCGFKWGLETRTRQI  176
Rspo3                                       IVHCEVSEWNPWSPCTKKGKTCGFKRGTETRVREI  179
Rspo4                                       --ECELGPWGGWSPCTHNGKTCGSAWGLESRVREA  170
                                             **:. *. *. *::: :  **    *  *  *.*.

Rspo1  LHAPVGDHAACSDTKETRRCTVRRVPCPEGQKR--RKGGQGRRENANRNLARKESKE---  234
Rspo2  VKKPVKDTILCPTIAESRRCKMTMRHCPGGKRT--PKAKEKRNKKKKRKLIERAQEQHSV  234
Rspo3  IQHPSAKGNLCPPTNETRKCTVQRKKCQKGERG--KKGRERKRKKPNKGESKEAIPDSKS  237
Rspo4  GRAGHEEAATCQVLSESRKCPIQR-PCPGERSPGQKKGRKDRRPRKDRKLDRRLDVR---  226
          :       *     *:*:*  :    *        *.  :  :. . .:  ..

Rspo1  --AGAGS-RRRKGQQQQQ------QQGTVGPLTSAGPA   263  (SEQ ID NO:1)
Rspo2  FLA-----TDRANQ------------------------  243  (SEQ ID NO:2)
Rspo3  LESSKEIPEQRENKQQQKKRKVQDKQKSVSVSTVH---  272  (SEQ ID NO:3)
Rspo4  --------PRQPGLQP----------------------  234  (SEQ ID NO:4)
             :  .
```

░░ Fu1
▓▓ Fu2

FIG. 5
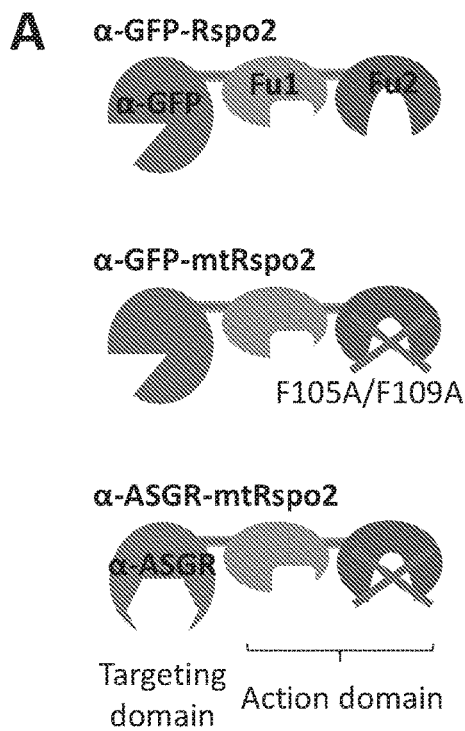
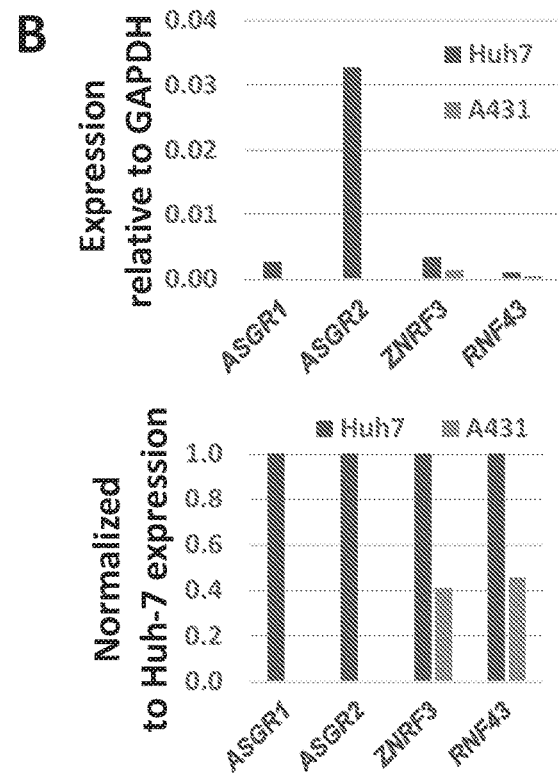
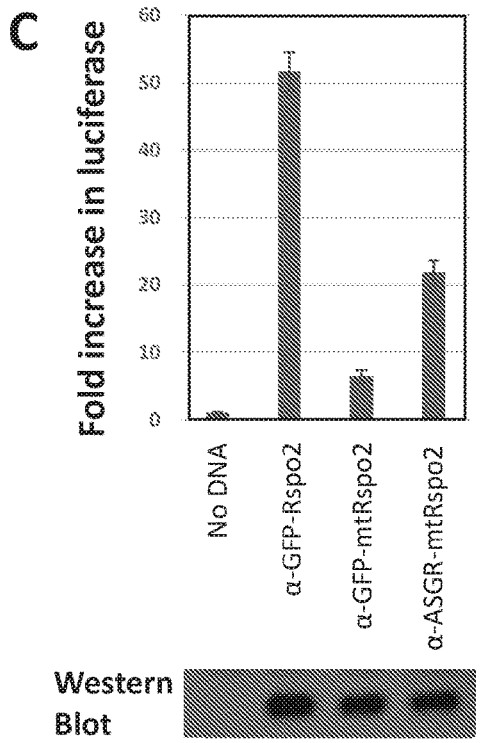
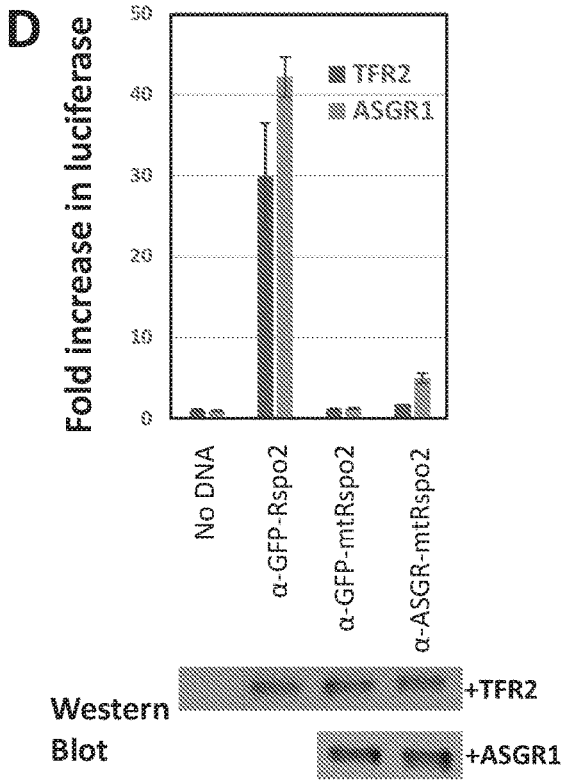

FIG. 6
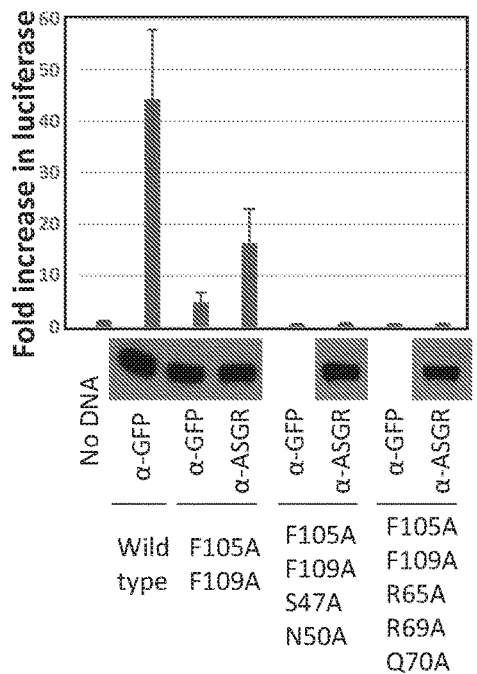
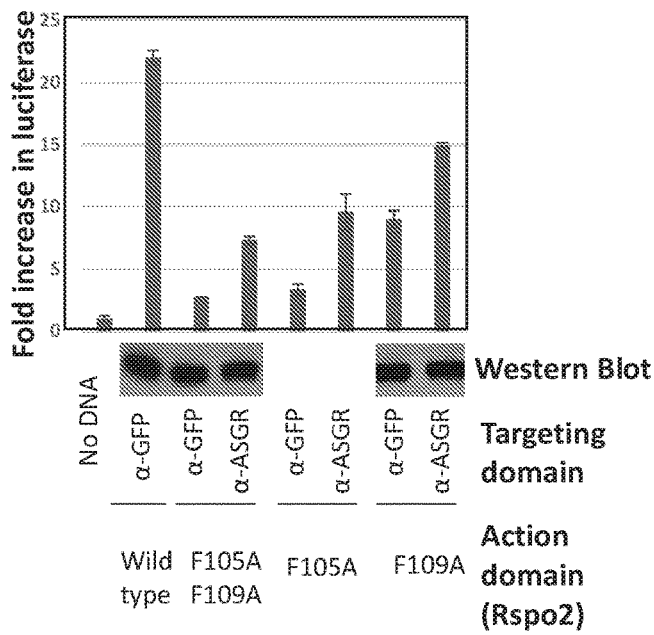
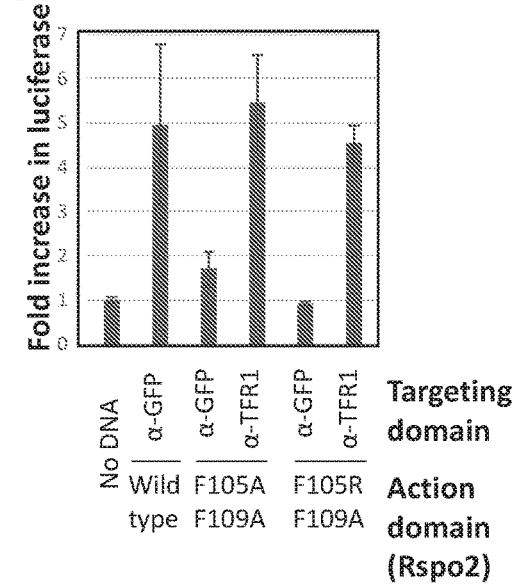

FIG. 7
A
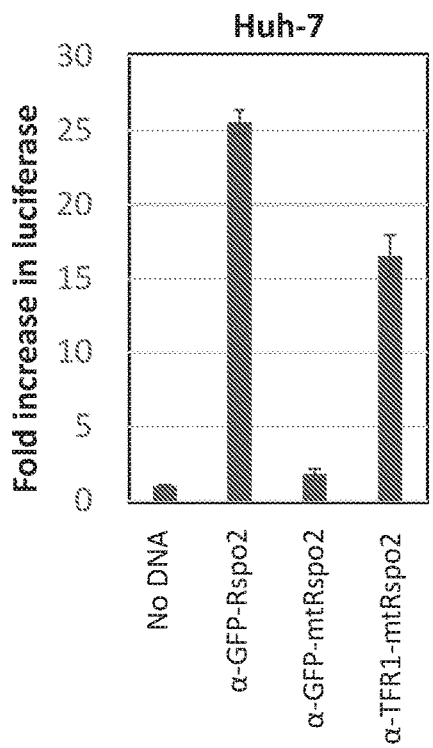
Western Blot
B
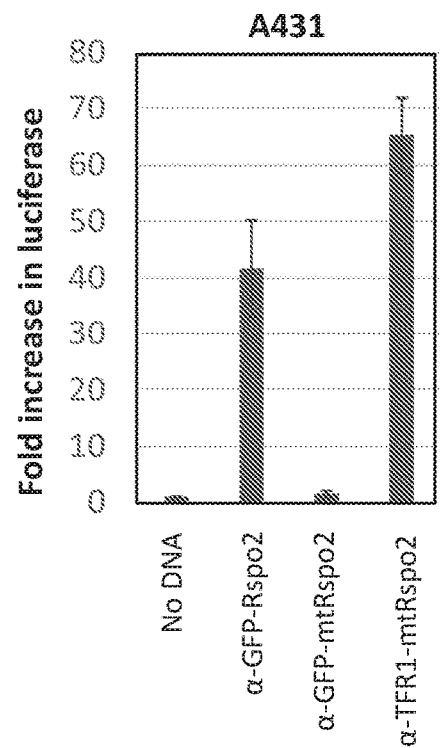
Western Blot FIG. 14
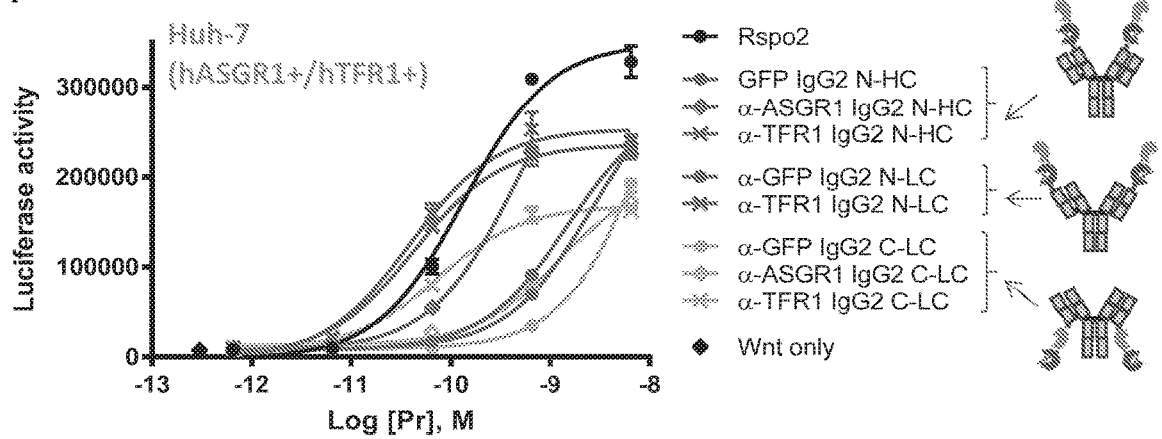
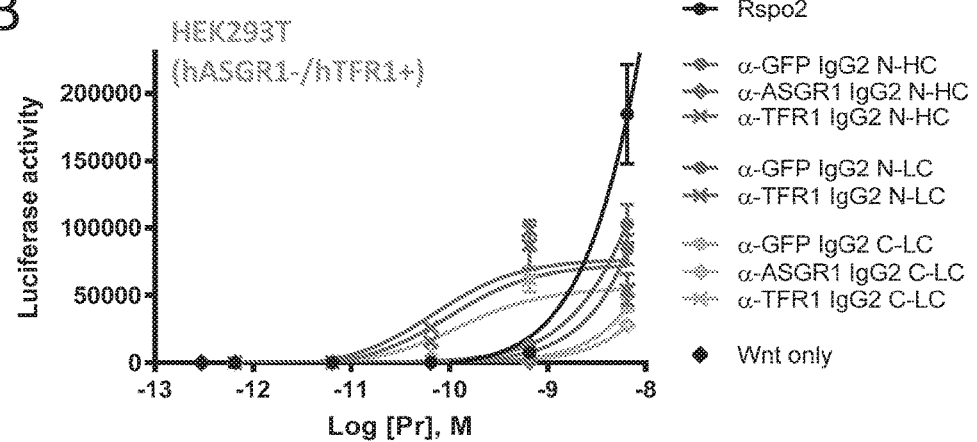
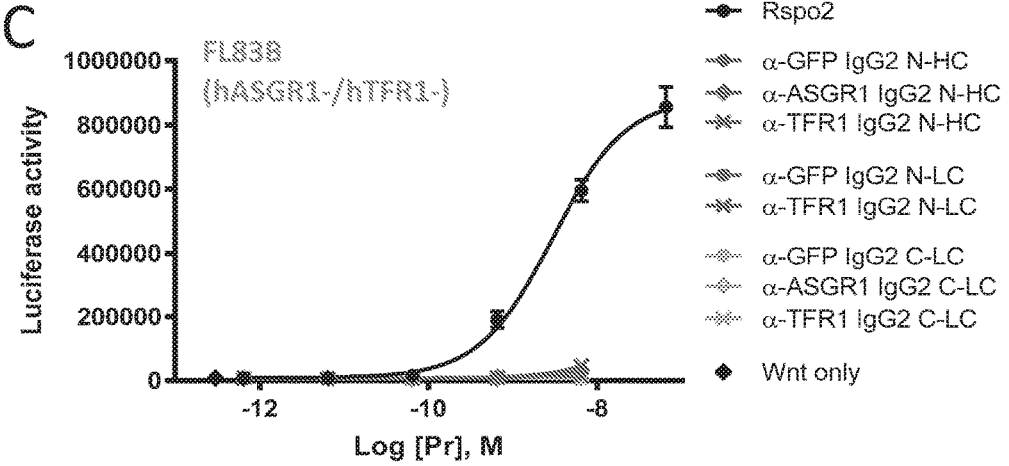

FIG. 14 (cont.)
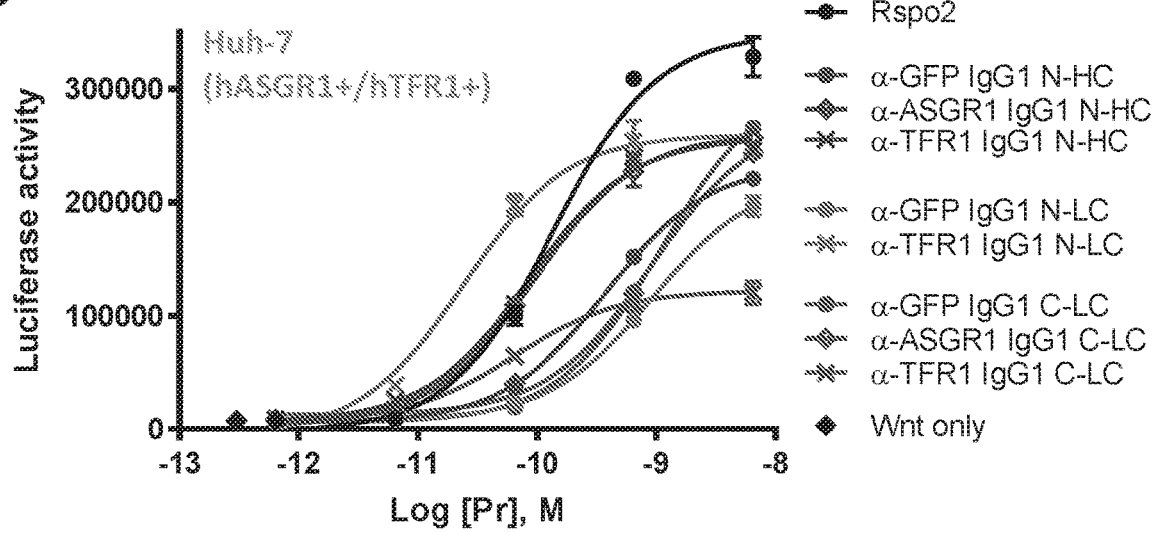
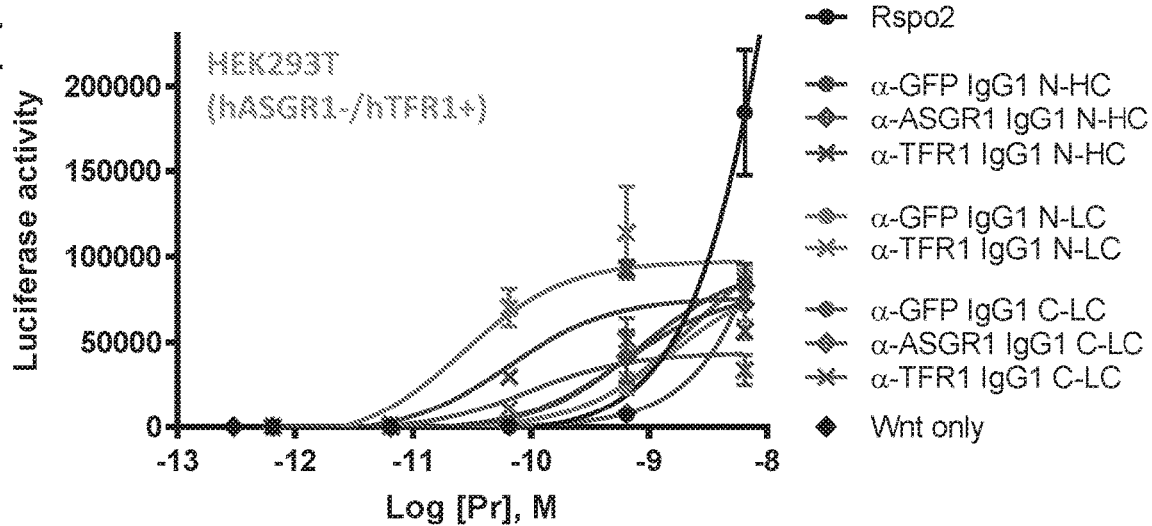

FIG. 15
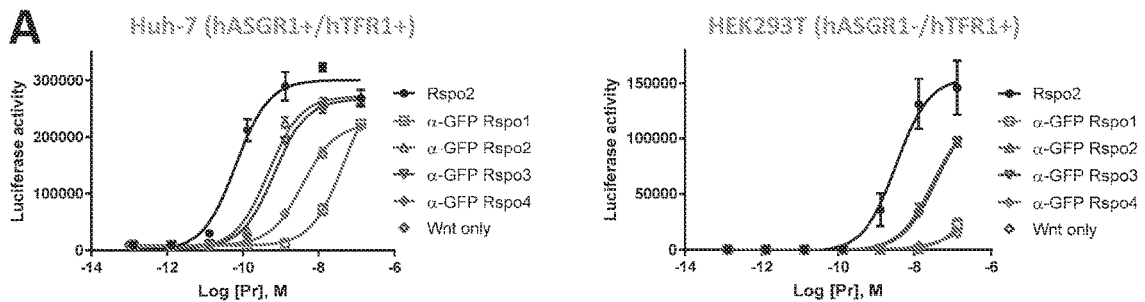
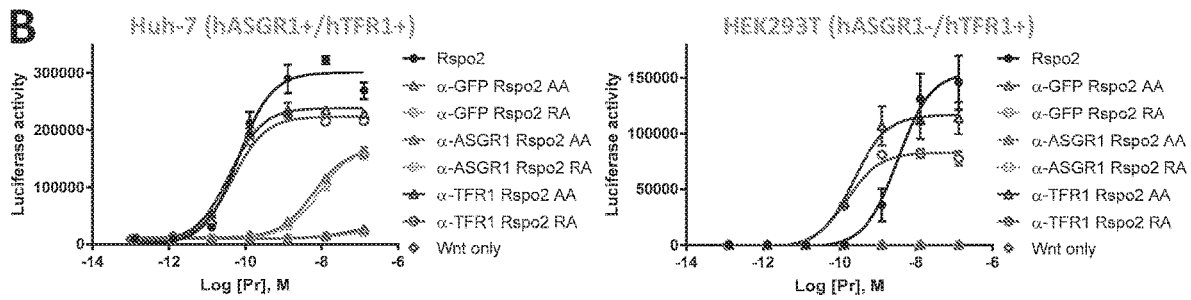
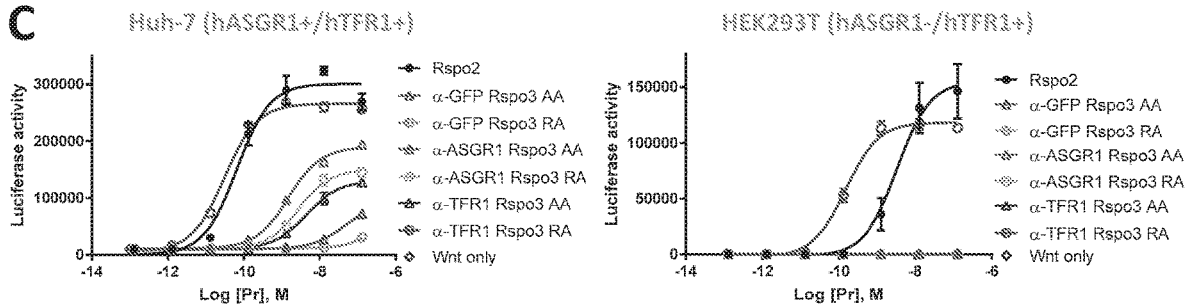

Fig. 16
A
Rspo3 mutations tested:
Rspo3 RA:       F106R/F110A
Rspo3 RR:       F106R/F110R
Rspo3 EE:       F106E/F110E
Rspo3 RE:       F106R/F110E
Rspo3 EA:       F106E/F110A
Rspo3 EEARA:    R60E/R88E/N93A/F106R/F110A
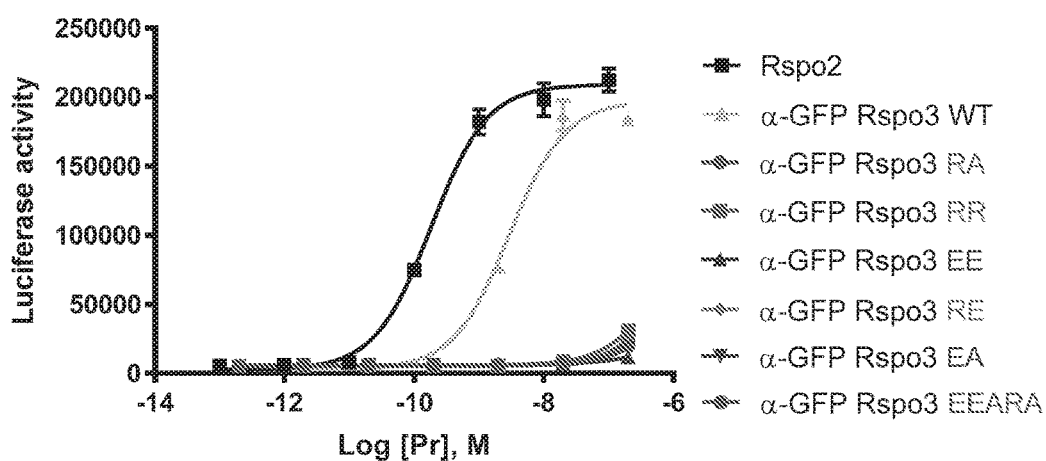
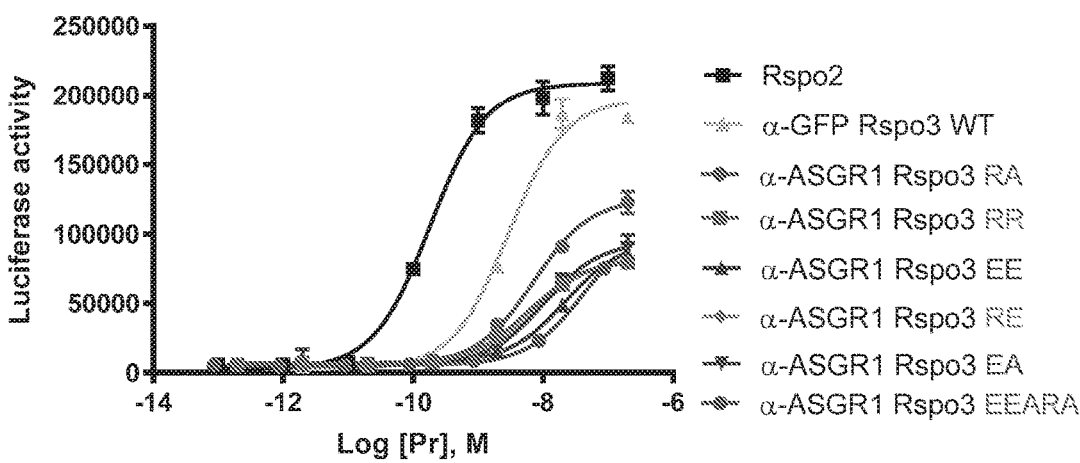

FIG. 17
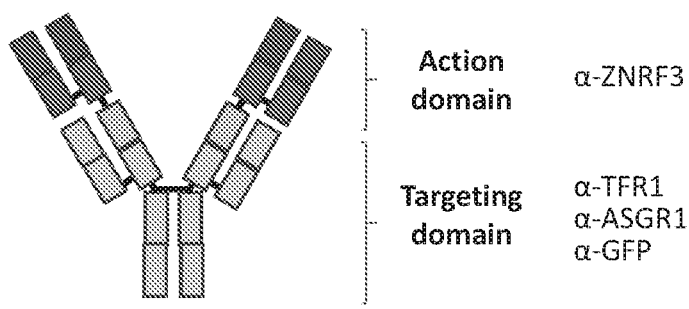
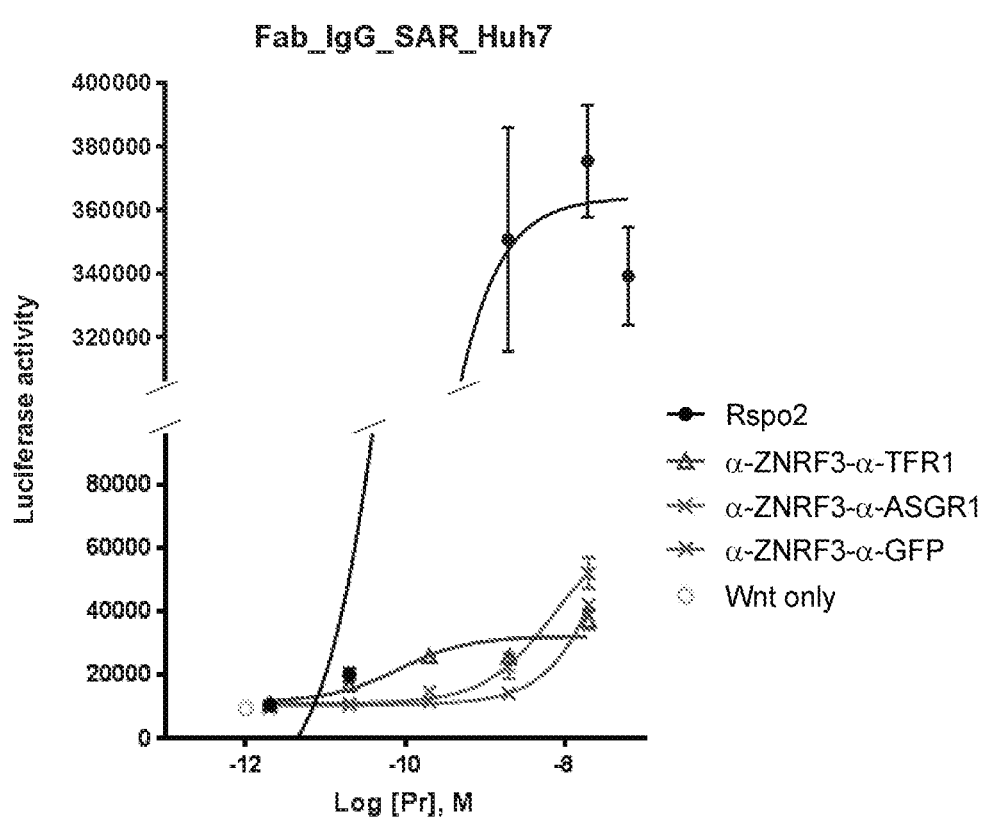

```
                              SEQUENCE LISTING

<160> NUMBER OF SEQ ID NOS: 186

<210> SEQ ID NO 1
<211> LENGTH: 263
<212> TYPE: PRT
<213> ORGANISM: Homo sapiens

<400> SEQUENCE: 1

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Arg Ile
            20                  25                  30

Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Arg Thr
            165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
        195                 200                 205

Gly Gln Lys Arg Arg Lys Gly Gly Gln Gly Arg Arg Glu Asn Ala Asn
    210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
            245                 250                 255

Leu Thr Ser Ala Gly Pro Ala
            260

<210> SEQ ID NO 2
<211> LENGTH: 243
<212> TYPE: PRT
<213> ORGANISM: Homo sapiens

<400> SEQUENCE: 2

Met Gln Phe Arg Leu Phe Ser Phe Ala Leu Ile Ile Leu Asn Cys Met
1               5                   10                  15

Asp Tyr Ser His Cys Gln Gly Asn Arg Trp Arg Arg Ser Lys Arg Ala
```

```
            20                  25                  30
Ser Tyr Val Ser Asn Pro Ile Cys Lys Gly Cys Leu Ser Cys Ser Lys
         35                  40                  45

Asp Asn Gly Cys Ser Arg Cys Gln Gln Lys Leu Phe Phe Phe Leu Arg
 50                  55                  60

Arg Glu Gly Met Arg Gln Tyr Gly Glu Cys Leu His Ser Cys Pro Ser
 65                  70                  75                  80

Gly Tyr Tyr Gly His Arg Ala Pro Asp Met Asn Arg Cys Ala Arg Cys
                 85                  90                  95

Arg Ile Glu Asn Cys Asp Ser Cys Phe Ser Lys Asp Phe Cys Thr Lys
                100                 105                 110

Cys Lys Val Gly Phe Tyr Leu His Arg Gly Arg Cys Phe Asp Glu Cys
                115                 120                 125

Pro Asp Gly Phe Ala Pro Leu Glu Glu Thr Met Glu Cys Val Glu Gly
                130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Leu Cys Pro Thr Ile Ala Glu
                180                 185                 190

Ser Arg Arg Cys Lys Met Thr Met Arg His Cys Pro Gly Gly Lys Arg
                195                 200                 205

Thr Pro Lys Ala Lys Glu Lys Arg Asn Lys Lys Lys Arg Lys Leu
                210                 215                 220

Ile Glu Arg Ala Gln Glu Gln His Ser Val Phe Leu Ala Thr Asp Arg
225                 230                 235                 240

Ala Asn Gln

<210> SEQ ID NO 3
<211> LENGTH: 272
<212> TYPE: PRT
<213> ORGANISM: Homo sapiens

<400> SEQUENCE: 3

Met His Leu Arg Leu Ile Ser Trp Leu Phe Ile Ile Leu Asn Phe Met
 1               5                  10                  15

Glu Tyr Ile Gly Ser Gln Asn Ala Ser Arg Gly Arg Gln Arg Arg
                 20                  25                  30

Met His Pro Asn Val Ser Gln Gly Cys Gln Gly Gly Cys Ala Thr Cys
                 35                  40                  45

Ser Asp Tyr Asn Gly Cys Leu Ser Cys Lys Pro Arg Leu Phe Phe Ala
 50                  55                  60

Leu Glu Arg Ile Gly Met Lys Gln Ile Gly Val Cys Leu Ser Ser Cys
 65                  70                  75                  80

Pro Ser Gly Tyr Tyr Gly Thr Arg Tyr Pro Asp Ile Asn Lys Cys Thr
                 85                  90                  95

Lys Cys Lys Ala Asp Cys Asp Thr Cys Phe Asn Lys Asn Phe Cys Thr
                100                 105                 110

Lys Cys Lys Ser Gly Phe Tyr Leu His Leu Gly Lys Cys Leu Asp Asn
                115                 120                 125

Cys Pro Glu Gly Leu Glu Ala Asn Asn His Thr Met Glu Cys Val Ser
                130                 135                 140

Ile Val His Cys Glu Val Ser Glu Trp Asn Pro Trp Ser Pro Cys Thr
```

```
            145                 150                 155                 160
Lys Lys Gly Lys Thr Cys Gly Phe Lys Arg Gly Thr Glu Thr Arg Val
                    165                 170                 175
Arg Glu Ile Ile Gln His Pro Ser Ala Lys Gly Asn Leu Cys Pro Pro
                    180                 185                 190
Thr Asn Glu Thr Arg Lys Cys Thr Val Gln Arg Lys Lys Cys Gln Lys
                    195                 200                 205
Gly Glu Arg Gly Lys Lys Gly Arg Glu Arg Lys Arg Lys Lys Pro Asn
        210                 215                 220
Lys Gly Glu Ser Lys Glu Ala Ile Pro Asp Ser Lys Ser Leu Glu Ser
225                 230                 235                 240
Ser Lys Glu Ile Pro Glu Gln Arg Glu Asn Lys Gln Gln Lys Lys
                    245                 250                 255
Arg Lys Val Gln Asp Lys Gln Lys Ser Val Ser Val Ser Thr Val His
                    260                 265                 270

<210> SEQ ID NO 4
<211> LENGTH: 234
<212> TYPE: PRT
<213> ORGANISM: Homo sapiens

<400> SEQUENCE: 4

Met Arg Ala Pro Leu Cys Leu Leu Leu Val Ala His Ala Val Asp
1               5                   10                  15
Met Leu Ala Leu Asn Arg Arg Lys Lys Gln Val Gly Thr Gly Leu Gly
                    20                  25                  30
Gly Asn Cys Thr Gly Cys Ile Ile Cys Ser Glu Glu Asn Gly Cys Ser
                    35                  40                  45
Thr Cys Gln Gln Arg Leu Phe Leu Phe Ile Arg Arg Glu Gly Ile Arg
        50                  55                  60
Gln Tyr Gly Lys Cys Leu His Asp Cys Pro Pro Gly Tyr Phe Gly Ile
65                  70                  75                  80
Arg Gly Gln Glu Val Asn Arg Cys Lys Lys Cys Gly Ala Thr Cys Glu
                    85                  90                  95
Ser Cys Phe Ser Gln Asp Phe Cys Ile Arg Cys Lys Arg Gln Phe Tyr
                    100                 105                 110
Leu Tyr Lys Gly Lys Cys Leu Pro Thr Cys Pro Pro Gly Thr Leu Ala
                    115                 120                 125
His Gln Asn Thr Arg Glu Cys Gln Gly Glu Cys Glu Leu Gly Pro Trp
        130                 135                 140
Gly Gly Trp Ser Pro Cys Thr His Asn Gly Lys Thr Cys Gly Ser Ala
145                 150                 155                 160
Trp Gly Leu Glu Ser Arg Val Arg Glu Ala Gly Arg Ala Gly His Glu
                    165                 170                 175
Glu Ala Ala Thr Cys Gln Val Leu Ser Glu Ser Arg Lys Cys Pro Ile
                    180                 185                 190
Gln Arg Pro Cys Pro Gly Glu Arg Ser Pro Gly Gln Lys Lys Gly Arg
                    195                 200                 205
Lys Asp Arg Arg Pro Arg Lys Asp Arg Lys Leu Asp Arg Arg Leu Asp
        210                 215                 220
Val Arg Pro Arg Gln Pro Gly Leu Gln Pro
225                 230

<210> SEQ ID NO 5
<211> LENGTH: 1119
```

<212> TYPE: DNA
<213> ORGANISM: Artificial Sequence
<220> FEATURE:
<223> OTHER INFORMATION: Made in Lab - Wnt signal enhancing fusion protein

<400> SEQUENCE: 5

```
caggtccagt tggtggaatc cggagggggt tggtccagc ctggtggaag cctgcgcctc      60
tcatgcgccg ctagcggatt caccttctcc cgatacggca tgcattgggt cagacaggca    120
cccggaaaag gactcgaatg ggtgtcgggc atttcctcga tcgggtcaaa cacctattac    180
gccgactccg tgaagggacg gttcaccatt agccgggata cagcaagaa cactctgtac     240
ttgcaaatga actccctgcg ggctgaggac accgccgtgt actactgtgc gcggtggtac    300
aagacctata ttgacgtctg gggacagggt accctcgtga ccgtgtcatc cggtggtgga    360
ggatccggag gcggaggaag cggaggaggg ggttcagaca tcgaactcac ccagcccccg    420
tcagtgtccg tggcccctgg acagactgcg cgcatctcct gctccggcga caacctgggg    480
aagaaatacg tgtactggta ccagcagaag ccaggtcaag cccctgtgct ggtcatctac    540
ggcgacgacg aaaggccgtc aggcatccca gagcgcttct ccggctccaa ctccgggaat    600
actgccaccc ttaccatttc cggaacccag gccgaggatg aagcggatta ctattgcgcg    660
agctacgata gcagccacat cctgatcgtg tttggaggcg gtactaagct gaccgtgctg    720
ggaagcggtg gatcaaaccc aatttgcaag ggatgcctga gctgtagcaa ggacaacgga    780
tgttcacggt gccagcaaaa gctgtttttc ttcctccggc gggaaggaat gcggcagtac    840
ggcgaatgtc tccactcctg cccctcgggg tattacggac accgcgcgcc tgacatgaac    900
cgatgcgcca gatgccggat cgagaactgc gatagctgct tcagcaagga cttctgcact    960
aagtgcaaag tcggcttcta ccttcaccgg ggcagatgtt ttgacgaatg cccggatggc   1020
ttcgcccgc tggaggagac tatggaatgc gtggagggcg agactacaa ggacgacgat     1080
gacaagggct cccaccatca ccaccatcat caccactag                          1119
```

<210> SEQ ID NO 6
<211> LENGTH: 372
<212> TYPE: PRT
<213> ORGANISM: Artificial Sequence
<220> FEATURE:
<223> OTHER INFORMATION: Made in Lab - Wnt signal enhancing fusion protein

<400> SEQUENCE: 6

```
Gln Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Arg Tyr
            20                  25                  30
Gly Met His Trp Val Arg Gln Ala Pro Gly Lys Gly Leu Glu Trp Val
        35                  40                  45
Ser Gly Ile Ser Ser Ile Gly Ser Asn Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Trp Tyr Lys Thr Tyr Ile Asp Val Trp Gly Gln Gly Thr Leu
            100                 105                 110
Val Thr Val Ser Ser Gly Gly Gly Gly Ser Gly Gly Gly Gly Ser Gly
```

```
                115                 120                 125
Gly Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240

Gly Ser Gly Gly Ser Asn Pro Ile Cys Lys Gly Cys Leu Ser Cys Ser
                245                 250                 255

Lys Asp Asn Gly Cys Ser Arg Cys Gln Gln Lys Leu Phe Phe Phe Leu
            260                 265                 270

Arg Arg Glu Gly Met Arg Gln Tyr Gly Glu Cys Leu His Ser Cys Pro
        275                 280                 285

Ser Gly Tyr Tyr Gly His Arg Ala Pro Asp Met Asn Arg Cys Ala Arg
    290                 295                 300

Cys Arg Ile Glu Asn Cys Asp Ser Cys Phe Ser Lys Asp Phe Cys Thr
305                 310                 315                 320

Lys Cys Lys Val Gly Phe Tyr Leu His Arg Gly Arg Cys Phe Asp Glu
                325                 330                 335

Cys Pro Asp Gly Phe Ala Pro Leu Glu Glu Thr Met Glu Cys Val Glu
            340                 345                 350

Gly Gly Asp Tyr Lys Asp Asp Asp Lys Gly Ser His His His His
        355                 360                 365

His His His His
    370

<210> SEQ ID NO 7
<211> LENGTH: 1119
<212> TYPE: DNA
<213> ORGANISM: Artificial Sequence
<220> FEATURE:
<223> OTHER INFORMATION: Made in Lab - Wnt signal enhancing fusion
      protein

<400> SEQUENCE: 7
caggtccagt tggtggaatc cggagggggt tggtccagc ctggtggaag cctgcgcctc      60
tcatgcgccg ctagcggatt caccttctcc cgatacggca tgcattgggt cagacaggca    120
cccggaaaag gactcgaatg ggtgtcgggc atttcctcga tcgggtcaaa cacctattac    180
gccgactccg tgaagggacg gttcaccatt agccgggata cagcaagaa cactctgtac     240 ttgcaaatga actccctgcg ggctgaggac accgccgtgt actactgtgc gcggtggtac    300
aagacctata ttgacgtctg gggacagggt accctcgtga ccgtgtcatc cggtggtgga    360
ggatccggag gcggaggaag cggaggaggg ggttcagaca tcgaactcac ccagccccg    420 tcagtgtccg tggcccctgg acagactgcg cgcatctcct gctccggcga caacctgggg    480
aagaaatacg tgtactggta ccagcagaag ccaggtcaag cccctgtgct ggtcatctac    540
```

| | |
|---|---|
| ggcgacgacg aaaggccgtc aggcatccca gagcgcttct ccggctccaa ctccgggaat | 600 |
| actgccaccc ttaccatttc cggaacccag gccgaggatg aagcggatta ctattgcgcg | 660 |
| agctacgata gcagccacat cctgatcgtg tttggaggcg gtactaagct gaccgtgctg | 720 |
| ggaagcggtg gatcaaaccc aatttgcaag ggatgcctga gctgtagcaa ggacaacgga | 780 |
| tgttcacggt gccagcaaaa gctgtttttc ttcctccggc gggaaggaat gcggcagtac | 840 |
| ggcgaatgtc tccactcctg cccctcgggg tattacggac accgcgcgcc tgacatgaac | 900 |
| cgatgcgcca gatgccggat cgagaactgc gatagctgcg ccagcaagga cgcctgcact | 960 |
| aagtgcaaag tcggcttcta ccttcaccgg ggcagatgtt ttgacgaatg cccggatggc | 1020 |
| ttcgccccgc tggaggagac tatggaatgc gtggagggcg agactacaa ggacgacgat | 1080 |
| gacaagggct cccaccatca ccaccatcat caccactag | 1119 |

<210> SEQ ID NO 8
<211> LENGTH: 372
<212> TYPE: PRT
<213> ORGANISM: Artificial Sequence
<220> FEATURE:
<223> OTHER INFORMATION: Made in Lab - Wnt signal enhancing fusion
      protein

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240

Gly Ser Gly Gly Ser Asn Pro Ile Cys Lys Gly Cys Leu Ser Cys Ser
                245                 250                 255

```
Lys Asp Asn Gly Cys Ser Arg Cys Gln Gln Lys Leu Phe Phe Leu
            260                 265                 270
Arg Arg Glu Gly Met Arg Gln Tyr Gly Glu Cys Leu His Ser Cys Pro
        275                 280                 285
Ser Gly Tyr Tyr Gly His Arg Ala Pro Asp Met Asn Arg Cys Ala Arg
        290                 295                 300
Cys Arg Ile Glu Asn Cys Asp Ser Cys Ala Ser Lys Asp Ala Cys Thr
305                 310                 315                 320
Lys Cys Lys Val Gly Phe Tyr Leu His Arg Gly Arg Cys Phe Asp Glu
            325                 330                 335
Cys Pro Asp Gly Phe Ala Pro Leu Glu Glu Thr Met Glu Cys Val Glu
        340                 345                 350
Gly Gly Asp Tyr Lys Asp Asp Asp Asp Lys Gly Ser His His His His
        355                 360                 365
His His His His
        370

<210> SEQ ID NO 9
<211> LENGTH: 1125
<212> TYPE: DNA
<213> ORGANISM: Artificial Sequence
<220> FEATURE:
<223> OTHER INFORMATION: Made in Lab - Wnt signal enhancing fusion
      protein

<400> SEQUENCE: 9
gaagtgcagc tgctggaatc cggggggcgga ctggtgcaac ccggggggatc cctcagactg        60 tcctgtgccg catcgggttt cactttctcc tcctacgcga tgtcatgggt cagacaggcc       120
cctggaaaag gcctcgaatg ggtgtcggct atctccggat cggggggatc tacttactac       180
gccgactccg tgaagggccg gttcactatc tcgagggaca actccaagaa taccctgtac       240
ttgcaaatga actccctgcg cgccgaggat accgcggtgt attactgcgc caaggacttc       300
agctcacgcc ggtggtacct tgagtactgg ggacaggga cccttgtcac cgtgtccagc       360
ggtggcggcg gaagcggcgg gggcggatcc ggtggcgggg gctcagagct cacccaggac       420
cccgctgtgt ccgtggcctt gggacagacc gtgcgcatca catgccaggg cgatagcctg       480
cggagctatt acgcctcgtg gtaccagcag aagcctggtc aagcgccggt cctggtcatc       540 tacgaaaga caaccgccc gtccggaatt ccagacaggt tcagcggatc cagctcgggg       600
aacaccgcct cactgactat caccggagca caggccgaag atgaagccga ctactactgc       660
aactccctgg agcggattgg atacctgagc tacgtgtttg gtggcggcac gaagctcacc       720
gtgctgggaa gcgtggatc aaacccaatt gcaagggat gcctgagctg tagcaaggac       780 aacgatgtt cacggtgcca gcaaaagctg ttttcttcc tccggcggga aggaatgcgg       840
cagtacggcg aatgtctcca ctcctgcccc tcggggtatt acggacaccg cgcgcctgac       900
atgaaccgat cgccagatg ccggatcgag aactgcgata gctgcgccag caaggacgcc       960
tgcactaagt gcaaagtcgg cttctaccct taccggggca gatgttttga cgaatgcccg      1020
gatggcttcg cccccgctgg aggagactat gaatgcgtgg agggcggaga ctacaaggac      1080
gacgatgaca agggctccca ccatcaccac catcatcacc actag                     1125

<210> SEQ ID NO 10
<211> LENGTH: 374
<212> TYPE: PRT
<213> ORGANISM: Artificial Sequence
<220> FEATURE:
```

<223> OTHER INFORMATION: Made in Lab - Wnt signal enhancing fusion
protein

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Ser Gly Gly Gly Gly
        115                 120                 125

Gly Ser Gly Gly Gly Ser Glu Leu Thr Gln Asp Pro Ala Val Ser
130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
            165                 170                 175

Val Leu Val Ile Tyr Gly Lys Asn Asn Arg Pro Ser Gly Ile Pro Asp
        180                 185                 190

Arg Phe Ser Gly Ser Ser Ser Gly Asn Thr Ala Ser Leu Thr Ile Thr
    195                 200                 205

Gly Ala Gln Ala Glu Asp Glu Ala Asp Tyr Tyr Cys Asn Ser Leu Glu
210                 215                 220

Arg Ile Gly Tyr Leu Ser Tyr Val Phe Gly Gly Gly Thr Lys Leu Thr
225                 230                 235                 240

Val Leu Gly Ser Gly Gly Ser Asn Pro Ile Cys Lys Gly Cys Leu Ser
            245                 250                 255

Cys Ser Lys Asp Asn Gly Cys Ser Arg Cys Gln Gln Lys Leu Phe Phe
        260                 265                 270

Phe Leu Arg Arg Glu Gly Met Arg Gln Tyr Gly Glu Cys Leu His Ser
    275                 280                 285

Cys Pro Ser Gly Tyr Tyr Gly His Arg Ala Pro Asp Met Asn Arg Cys
290                 295                 300

Ala Arg Cys Arg Ile Glu Asn Cys Asp Ser Cys Ala Ser Lys Asp Ala
305                 310                 315                 320

Cys Thr Lys Cys Lys Val Gly Phe Tyr Leu His Arg Gly Arg Cys Phe
            325                 330                 335

Asp Glu Cys Pro Asp Gly Phe Ala Pro Leu Glu Glu Thr Met Glu Cys
        340                 345                 350

Val Glu Gly Gly Asp Tyr Lys Asp Asp Asp Asp Lys Gly Ser His His
    355                 360                 365

His His His His His
    370
```

<210> SEQ ID NO 11

<211> LENGTH: 1119
<212> TYPE: DNA
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 11

```
caggtccagt tggtggaatc cggagggggt ttggtccagc ctggtggaag cctgcgcctc     60
tcatgcgccg ctagcggatt caccttctcc cgatacggca tgcattgggt cagacaggca    120
cccggaaaag gactcgaatg ggtgtcgggc atttcctcga tcgggtcaaa cacctattac    180
gccgactccg tgaagggacg gttcaccatt agccgggata cagcaagaa cactctgtac     240
ttgcaaatga actccctgcg ggctgaggac accgccgtgt actactgtgc gcggtggtac    300
aagacctata ttgacgtctg gggacagggt accctcgtga ccgtgtcatc cggtggtgga    360
ggatccggag gcggaggaag cggaggaggg ggttcagaca tcgaactcac ccagcccccg    420
tcagtgtccg tggcccctgg acagactgcg cgcatctcct gctccggcga caacctgggg    480
aagaaatacg tgtactggta ccagcagaag ccaggtcaag cccctgtgct ggtcatctac    540
ggcgacgacg aaaggccgtc aggcatccca gagcgcttct ccggctccaa ctccgggaat    600
actgccaccc ttaccatttc cggaacccag gccgaggatg aagcggatta ctattgcgcg    660
agctacgata gcagccacat cctgatcgtg tttggaggcg gtactaagct gaccgtgctg    720
ggaagcggtg gatcaaaccc aatttgcaag ggatgcctga gctgtgccaa ggacgcagga    780
tgttcacggt gccagcaaaa gctgtttttc ttcctccggc gggaaggaat gcggcagtac    840
ggcgaatgtc tccactcctg cccctcgggg tattacggac accgcgcgcc tgacatgaac    900
cgatgcgcca gatgccggat cgagaactgc gatagctgcg ccagcaagga cgcctgcact    960
aagtgcaaag tcggcttcta ccttcaccgg ggcagatgtt ttgacgaatg cccggatggc   1020
ttcgccccgc tggaggagac tatggaatgc gtggagggcg agactacaa ggacgacgat   1080
gacaagggct cccaccatca ccaccatcat caccactag                         1119
```

<210> SEQ ID NO 12
<211> LENGTH: 372
<212> TYPE: PRT
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 12

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110
```

```
Val Thr Val Ser Ser Gly Gly Gly Ser Gly Gly Gly Ser Gly
            115                 120                 125

Gly Gly Gly Ser Asp Ile Glu Leu Thr Gln Pro Pro Ser Val Ser Val
            130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
            195                 200                 205

Thr Gln Ala Glu Asp Glu Ala Asp Tyr Tyr Cys Ala Ser Tyr Asp Ser
            210                 215                 220

Ser His Ile Leu Ile Val Phe Gly Gly Gly Thr Lys Leu Thr Val Leu
225                 230                 235                 240

Gly Ser Gly Gly Ser Asn Pro Ile Cys Lys Gly Cys Leu Ser Cys Ala
                245                 250                 255

Lys Asp Ala Gly Cys Ser Arg Cys Gln Gln Lys Leu Phe Phe Phe Leu
            260                 265                 270

Arg Arg Glu Gly Met Arg Gln Tyr Gly Glu Cys Leu His Ser Cys Pro
            275                 280                 285

Ser Gly Tyr Tyr Gly His Arg Ala Pro Asp Met Asn Arg Cys Ala Arg
            290                 295                 300

Cys Arg Ile Glu Asn Cys Asp Ser Cys Ala Ser Lys Asp Ala Cys Thr
305                 310                 315                 320

Lys Cys Lys Val Gly Phe Tyr Leu His Arg Gly Arg Cys Phe Asp Glu
                325                 330                 335

Cys Pro Asp Gly Phe Ala Pro Leu Glu Glu Thr Met Glu Cys Val Glu
            340                 345                 350

Gly Gly Asp Tyr Lys Asp Asp Asp Lys Gly Ser His His His His
            355                 360                 365

His His His His
    370

<210> SEQ ID NO 13
<211> LENGTH: 1125
<212> TYPE: DNA
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 13
gaagtgcagc tgctggaatc cggggggcgga ctggtgcaac ccggggggatc cctcagactg      60 tcctgtgccg catcgggttt cactttctcc tcctacgcga tgtcatgggt cagacaggcc     120
cctggaaaag gcctcgaatg ggtgtcggct atctccggat cgggggggatc tacttactac     180 gccgactccg tgaagggccg gttcactatc tcgagggaca actccaagaa taccctgtac     240
ttgcaaatga actccctgcg cgccgaggat accgcggtgt attactgcgc aaggacttc      300 agctcacgcc ggtggtacct tgagtactgg ggacagggaa ccctttgtcac cgtgtccagc     360 ggtggcggcg gaagcggcgg gggcggatcc ggtggcgggg gctcagagct cacccaggac     420
cccgctgtgt ccgtggcctt gggacagacc gtgcgcatca catgccaggg cgatagcctg     480
cggagctatt acgcctcgtg gtaccagcag aagcctggtc aagcgccggt cctggtcatc     540
```

```
tacggaaaga acaaccgccc gtccggaatt ccagacaggt tcagcggatc cagctcgggg    600
aacaccgcct cactgactat caccggagca caggccgaag atgaagccga ctactactgc    660
aactccctgg agcggattgg atacctgagc tacgtgtttg gtggcggcac gaagctcacc    720
gtgctgggaa gcgtggatc aaacccaatt tgcaagggat gcctgagctg tgccaaggac    780
gcaggatgtt cacggtgcca gcaaaagctg ttttcttcc tccggcggga aggaatgcgg    840
cagtacggcg aatgtctcca ctcctgcccc tcggggtatt acgacaccg cgcgcctgac    900 atgaaccgat gcgccagatg ccggatcgag aactgcgata gctgcgccag caaggacgcc    960
tgcactaagt gcaaagtcgg cttctacctt caccgggca gatgttttga cgaatgcccg    1020
gatggcttcg ccccgctgga ggagactatg gaatgcgtgg agggcggaga ctacaaggac    1080
gacgatgaca agggctccca ccatcaccac catcatcacc actag                    1125
```

<210> SEQ ID NO 14
<211> LENGTH: 374
<212> TYPE: PRT
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
        195                 200                 205

Gly Ala Gln Ala Glu Asp Glu Ala Asp Tyr Tyr Cys Asn Ser Leu Glu
    210                 215                 220

Arg Ile Gly Tyr Leu Ser Tyr Val Phe Gly Gly Thr Lys Leu Thr
225                 230                 235                 240

Val Leu Gly Ser Gly Gly Ser Asn Pro Ile Cys Lys Gly Cys Leu Ser
                245                 250                 255
```

```
Cys Ala Lys Asp Ala Gly Cys Ser Arg Cys Gln Gln Lys Leu Phe Phe
            260                 265                 270

Phe Leu Arg Arg Glu Gly Met Arg Gln Tyr Gly Glu Cys Leu His Ser
        275                 280                 285

Cys Pro Ser Gly Tyr Tyr Gly His Arg Ala Pro Asp Met Asn Arg Cys
    290                 295                 300

Ala Arg Cys Arg Ile Glu Asn Cys Asp Ser Cys Ala Ser Lys Asp Ala
305                 310                 315                 320

Cys Thr Lys Cys Lys Val Gly Phe Tyr Leu His Arg Gly Arg Cys Phe
                325                 330                 335

Asp Glu Cys Pro Asp Gly Phe Ala Pro Leu Glu Glu Thr Met Glu Cys
            340                 345                 350

Val Glu Gly Gly Asp Tyr Lys Asp Asp Asp Asp Lys Gly Ser His His
        355                 360                 365

His His His His His His
    370

<210> SEQ ID NO 15
<211> LENGTH: 1119
<212> TYPE: DNA
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 15
caggtccagt tggtggaatc cggagggggt ttggtccagc ctggtggaag cctgcgcctc      60
tcatgcgccg ctagcggatt caccttctcc cgatacggca tgcattgggt cagacaggca     120
cccggaaaag gactcgaatg ggtgtcgggc atttcctcga tcgggtcaaa cacctattac     180
gccgactccg tgaagggacg gttcaccatt agccgggata cagcaagaa cactctgtac      240
ttgcaaatga actccctgcg ggctgaggac accgccgtgt actactgtgc gcggtggtac     300
aagacctata ttgacgtctg gggacagggt accctcgtga ccgtgtcatc cggtggtgga     360
ggatccggag gcggaggaag cggaggaggg ggttcagaca tcgaactcac ccagcccccg     420
tcagtgtccg tggcccctgg acagactgcg cgcatctcct gctccggcga caacctgggg     480
aagaaatacg tgtactggta ccagcagaag ccaggtcaag cccctgtgct ggtcatctac     540
ggcgacgacg aaaggccgtc aggcatccca gagcgcttct ccggctccaa ctccgggaat     600
actgccaccc ttaccatttc cggaacccag gccgaggatg aagcggatta ctattgcgcg     660
agctacgata gcagccacat cctgatcgtg tttggaggcg gtactaagct gaccgtgctg     720
ggaagcggtg gatcaaaccc aatttgcaag ggatgcctga ctgtagcaa ggacaacgga     780
tgttcacggt gccagcaaaa gctgtttttc ttcctccggg ccgaaggaat ggccgcatac     840
ggcgaatgtc tccactcctg cccctcgggg tattacggac accgcgcgcc tgacatgaac     900
cgatgcgcca gatgccggat cgagaactgc gatagctgcg ccagcaagga cgcctgcact     960
aagtgcaaag tcggcttcta ccttcaccgg ggcagatgtt ttgacgaatg cccggatggc    1020
ttcgccccgc tggaggagac tatggaatgc gtggagggcg agactacaa ggacgacgat    1080
gacaagggct cccaccatca ccaccatcat caccactag                          1119

<210> SEQ ID NO 16
<211> LENGTH: 372
<212> TYPE: PRT
<213> ORGANISM: Artificial Sequence
```

<220> FEATURE:
<223> OTHER INFORMATION: Made in Lab - fusion construct design of
tissue-specific Wnt signal enhancing molecules

<400> SEQUENCE: 16

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240

Gly Ser Gly Gly Ser Asn Pro Ile Cys Lys Gly Cys Leu Ser Cys Ser
                245                 250                 255

Lys Asp Asn Gly Cys Ser Arg Cys Gln Gln Lys Leu Phe Phe Phe Leu
            260                 265                 270

Arg Ala Glu Gly Met Ala Ala Tyr Gly Glu Cys Leu His Ser Cys Pro
        275                 280                 285

Ser Gly Tyr Tyr Gly His Arg Ala Pro Asp Met Asn Arg Cys Ala Arg
    290                 295                 300

Cys Arg Ile Glu Asn Cys Asp Ser Cys Ala Ser Lys Asp Ala Cys Thr
305                 310                 315                 320

Lys Cys Lys Val Gly Phe Tyr Leu His Arg Gly Arg Cys Phe Asp Glu
                325                 330                 335

Cys Pro Asp Gly Phe Ala Pro Leu Glu Glu Thr Met Glu Cys Val Glu
            340                 345                 350

Gly Gly Asp Tyr Lys Asp Asp Asp Lys Gly Ser His His His His His
        355                 360                 365

His His His His
    370
```

<210> SEQ ID NO 17
<211> LENGTH: 1125
<212> TYPE: DNA
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 17

| | |
|---|---|
| gaagtgcagc tgctggaatc cggggcgga ctggtgcaac ccgggggatc cctcagactg | 60 |
| tcctgtgccg catcgggttt cactttctcc tcctacgcga tgtcatgggt cagacaggcc | 120 |
| cctggaaaag gcctcgaatg ggtgtcggct atctccggat cggggggatc tacttactac | 180 |
| gccgactccg tgaagggccg gttcactatc tcgaggggaca actccaagaa tacccctgtac | 240 |
| ttgcaaatga actccctgcg cgccgaggat accgcggtgt attactgcgc caaggacttc | 300 |
| agctcacgcc ggtggtacct tgagtactgg ggacaggga cccttgtcac cgtgtccagc | 360 |
| ggtggcggcg aagcggcgg gggcggatcc ggtggcgggg gctcagagct cacccaggac | 420 |
| cccgctgtgt ccgtggcctt gggacagacc gtgcgcatca catgccaggg cgatagcctg | 480 |
| cggagctatt acgcctcgtg gtaccagcag aagcctggtc aagcgccggt cctggtcatc | 540 |
| tacggaaaga caaccgccc gtccggaatt ccagacaggt tcagcggatc cagctcgggg | 600 |
| aacaccgcct cactgactat caccggagca caggccgaag atgaagccga ctactactgc | 660 |
| aactccctgg agcggattgg atacctgagc tacgtgtttg gtggcggcac gaagctcacc | 720 |
| gtgctgggaa gcggtggatc aaacccaatt gcaagggat gcctgagctg tagcaaggac | 780 |
| aacgatgtt cacggtgcca gcaaaagctg ttttttcttcc tccgggccga aggaatggcc | 840 |
| gcatacggcg aatgtctcca ctcctgcccc tcggggtatt acggacaccg cgcgcctgac | 900 |
| atgaaccgat gcgccagatg ccggatcgag aactgcgata gctgcgccag caaggacgcc | 960 |
| tgcactaagt gcaaagtcgg cttctacctt caccggggca gatgttttga cgaatgcccg | 1020 |
| gatggcttcg ccccgctgga ggagactatg gaatgcgtgg agggcggaga ctacaaggac | 1080 |
| gacgatgaca agggctccca ccatcaccac catcatcacc actag | 1125 |

<210> SEQ ID NO 18
<211> LENGTH: 374
<212> TYPE: PRT
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

```
Gly Thr Leu Val Thr Val Ser Ser Gly Gly Gly Ser Gly Gly Gly
            115                 120                 125
Gly Ser Gly Gly Gly Ser Glu Leu Thr Gln Asp Pro Ala Val Ser
    130                 135                 140
Val Ala Leu Gly Gln Thr Val Arg Ile Thr Cys Gln Gly Asp Ser Leu
145                 150                 155                 160
Arg Ser Tyr Tyr Ala Ser Trp Tyr Gln Gln Lys Pro Gly Gln Ala Pro
                165                 170                 175
Val Leu Val Ile Tyr Gly Lys Asn Asn Arg Pro Ser Gly Ile Pro Asp
            180                 185                 190
Arg Phe Ser Gly Ser Ser Ser Gly Asn Thr Ala Ser Leu Thr Ile Thr
        195                 200                 205
Gly Ala Gln Ala Glu Asp Glu Ala Asp Tyr Tyr Cys Asn Ser Leu Glu
    210                 215                 220
Arg Ile Gly Tyr Leu Ser Tyr Val Phe Gly Gly Gly Thr Lys Leu Thr
225                 230                 235                 240
Val Leu Gly Ser Gly Gly Ser Asn Pro Ile Cys Lys Gly Cys Leu Ser
                245                 250                 255
Cys Ser Lys Asp Asn Gly Cys Ser Arg Cys Gln Gln Lys Leu Phe Phe
            260                 265                 270
Phe Leu Arg Ala Glu Gly Met Ala Ala Tyr Gly Glu Cys Leu His Ser
        275                 280                 285
Cys Pro Ser Gly Tyr Tyr Gly His Arg Ala Pro Asp Met Asn Arg Cys
    290                 295                 300
Ala Arg Cys Arg Ile Glu Asn Cys Asp Ser Cys Ala Ser Lys Asp Ala
305                 310                 315                 320
Cys Thr Lys Cys Lys Val Gly Phe Tyr Leu His Arg Gly Arg Cys Phe
                325                 330                 335
Asp Glu Cys Pro Asp Gly Phe Ala Pro Leu Glu Glu Thr Met Glu Cys
            340                 345                 350
Val Glu Gly Gly Asp Tyr Lys Asp Asp Asp Lys Gly Ser His His
        355                 360                 365
His His His His His His
    370

<210> SEQ ID NO 19
<211> LENGTH: 1119
<212> TYPE: DNA
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 19
caggtccagt tggtggaatc cggaggggt ttggtccagc ctggtggaag cctgcgcctc      60
tcatgcgccg ctagcggatt caccttctcc cgatacggca tgcattgggt cagacaggca    120
cccggaaaag gactcgaatg ggtgtcgggc atttcctcga tcgggtcaaa cacctattac    180
gccgactccg tgaagggacg gttcaccatt agccgggata acagcaagaa cactctgtac    240
ttgcaaatga actccctgcg ggctgaggac accgccgtgt actactgtgc gcggtggtac    300
aagacctata ttgacgtctg gggacagggt accctcgtga ccgtgtcatc cggtggtgga    360
ggatccggag gcgaggaag cggaggaggg ggttcagaca tcgaactcac ccagccccg     420
tcagtgtccg tggcccctgg acagactgcg cgcatctcct gctccggcga caacctgggg    480
```

```
aagaaatacg tgtactggta ccagcagaag ccaggtcaag cccctgtgct ggtcatctac    540
ggcgacgacg aaaggccgtc aggcatccca gagcgcttct ccggctccaa ctccgggaat    600
actgccaccc ttaccatttc cggaacccag gccgaggatg aagcggatta ctattgcgcg    660
agctacgata gcagccacat cctgatcgtg tttggaggcg gtactaagct gaccgtgctg    720
ggaagcggtg gatcaaaccc aatttgcaag ggatgcctga gctgtagcaa ggacaacgga    780
tgttcacggt gccagcaaaa gctgtttttc ttcctccggc gggaaggaat gcggcagtac    840
ggcgaatgtc tccactcctg cccctcgggg tattacggac accgcgcgcc tgacatgaac    900
cgatgcgcca gatgccggat cgagaactgc gatagctgcg ccagcaagga cttctgcact    960
aagtgcaaag tcggcttcta ccttcaccgg ggcagatgtt ttgacgaatg cccggatggc   1020
ttcgccccgc tggaggagac tatggaatgc gtggagggcg agactacaa ggacgacgat    1080 gacaagggct cccaccatca ccaccatcat caccactag                          1119
```

<210> SEQ ID NO 20
<211> LENGTH: 372
<212> TYPE: PRT
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 20

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240

Gly Ser Gly Gly Ser Asn Pro Ile Cys Lys Gly Cys Leu Ser Cys Ser
```

```
                245                 250                 255
Lys Asp Asn Gly Cys Ser Arg Cys Gln Gln Lys Leu Phe Phe Phe Leu
            260                 265                 270

Arg Arg Glu Gly Met Arg Gln Tyr Gly Glu Cys Leu His Ser Cys Pro
        275                 280                 285

Ser Gly Tyr Tyr Gly His Arg Ala Pro Asp Met Asn Arg Cys Ala Arg
    290                 295                 300

Cys Arg Ile Glu Asn Cys Asp Ser Cys Ala Ser Lys Asp Phe Cys Thr
305                 310                 315                 320

Lys Cys Lys Val Gly Phe Tyr Leu His Arg Gly Arg Cys Phe Asp Glu
            325                 330                 335

Cys Pro Asp Gly Phe Ala Pro Leu Glu Glu Thr Met Glu Cys Val Glu
        340                 345                 350

Gly Gly Asp Tyr Lys Asp Asp Asp Lys Gly Ser His His His His His
    355                 360                 365

His His His His
    370

<210> SEQ ID NO 21
<211> LENGTH: 1125
<212> TYPE: DNA
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 21
gaagtgcagc tgctggaatc cggggggcgga ctggtgcaac cgggggatc cctcagactg      60 tcctgtgccg catcgggttt cactttctcc tcctacgcga tgtcatgggt cagacaggcc    120
cctggaaaag gcctcgaatg ggtgtcggct atctccggat cggggggatc tacttactac    180
gccgactccg tgaagggccg gttcactatc tcgaggaca actccaagaa tacccctgtac    240 ttgcaaatga actccctgcg cgccgaggat accgcggtgt attactgcgc caaggacttc    300
agctcacgcc ggtggtacct tgagtactgg ggacagggaa cccttgtcac cgtgtccagc    360
ggtggcggcg gaagcggcgg gggcggatcc ggtggcgggg gctcagagct cacccaggac    420
cccgctgtgt ccgtggcctt gggacagacc gtgcgcatca catgccaggg cgatagcctg    480
cggagctatt acgcctcgtg gtaccagcag aagcctggtc aagcgccggt cctggtcatc    540
tacggaaaga caaccgccc gtccggaatt ccagacaggt tcagcggatc cagctcgggg    600
aacaccgcct cactgactat caccggagca caggccgaag atgaagccga ctactactgc    660
aactccctgg agcggattgg atacctgagc tacgtgtttg gtggcggcac gaagctcacc    720
gtgctgggaa gcgtggatc aaacccaatt tgcaagggat gcctgagctg tagcaaggac    780
aacggatgtt cacggtgcca gcaaaagctg tttttcttcc tccggcggga aggaatgcgg    840
cagtacggcg aatgtctcca ctcctgcccc tcggggtatt acggacaccg cgcgcctgac    900
atgaaccgat gcgccagatg ccggatcgag aactgcgata gctgcgccag caaggacttc    960
tgcactaagt gcaaagtcgg cttctaccct caccggggca gatgttttga cgaatgcccg   1020
gatggcttcg ccccgctgga ggagactatg gaatgcgtgg agggcggaga ctacaaggac   1080
gacgatgaca agggctccca ccatcaccac catcatcacc actag                   1125

<210> SEQ ID NO 22
<211> LENGTH: 374
<212> TYPE: PRT
```

<213> ORGANISM: Artificial Sequence
<220> FEATURE:
<223> OTHER INFORMATION: Made in Lab - fusion construct design of tissue-specific Wnt signal enhancing molecules

<400> SEQUENCE: 22

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Glu Leu Thr Gln Asp Pro Ala Val Ser
130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
            165                 170                 175

Val Leu Val Ile Tyr Gly Lys Asn Asn Arg Pro Ser Gly Ile Pro Asp
        180                 185                 190

Arg Phe Ser Gly Ser Ser Ser Gly Asn Thr Ala Ser Leu Thr Ile Thr
    195                 200                 205

Gly Ala Gln Ala Glu Asp Glu Ala Asp Tyr Tyr Cys Asn Ser Leu Glu
210                 215                 220

Arg Ile Gly Tyr Leu Ser Tyr Val Phe Gly Gly Gly Thr Lys Leu Thr
225                 230                 235                 240

Val Leu Gly Ser Gly Gly Ser Asn Pro Ile Cys Lys Gly Cys Leu Ser
                245                 250                 255

Cys Ser Lys Asp Asn Gly Cys Ser Arg Cys Gln Gln Lys Leu Phe Phe
            260                 265                 270

Phe Leu Arg Arg Glu Gly Met Arg Gln Tyr Gly Glu Cys Leu His Ser
        275                 280                 285

Cys Pro Ser Gly Tyr Tyr Gly His Arg Ala Pro Asp Met Asn Arg Cys
    290                 295                 300

Ala Arg Cys Arg Ile Glu Asn Cys Asp Ser Cys Ala Ser Lys Asp Phe
305                 310                 315                 320

Cys Thr Lys Cys Lys Val Gly Phe Tyr Leu His Arg Gly Arg Cys Phe
                325                 330                 335

Asp Glu Cys Pro Asp Gly Phe Ala Pro Leu Glu Glu Thr Met Glu Cys
            340                 345                 350

Val Glu Gly Gly Asp Tyr Lys Asp Asp Asp Lys Gly Ser His His
        355                 360                 365

His His His His His
    370
```

<210> SEQ ID NO 23
<211> LENGTH: 1119
<212> TYPE: DNA
<213> ORGANISM: Artificial Sequence
<220> FEATURE:
<223> OTHER INFORMATION: Made in Lab - fusion construct design of tissue-specific Wnt signal enhancing molecules

<400> SEQUENCE: 23

| | | | | |
|---|---|---|---|---|
| caggtccagt tggtggaatc cggagggggt ttggtccagc ctggtggaag cctgcgcctc | 60 |
| tcatgcgccg ctagcggatt caccttctcc cgatacggca tgcattgggt cagacaggca | 120 |
| cccggaaaag gactcgaatg ggtgtcgggc atttcctcga tcgggtcaaa cacctattac | 180 |
| gccgactccg tgaagggacg gttcaccatt agccgggata cagcaagaa cactctgtac | 240 |
| ttgcaaatga actccctgcg ggctgaggac accgccgtgt actactgtgc gcggtggtac | 300 |
| aagacctata ttgacgtctg gggacagggt accctcgtga ccgtgtcatc cggtggtgga | 360 |
| ggatccggag gcggaggaag cggagggaggg ggttcagaca tcgaactcac ccagcccccg | 420 |
| tcagtgtccg tggcccctgg acagactgcg cgcatctcct gctccggcga acctggggg | 480 |
| aagaaatacg tgtactggta ccagcagaag ccaggtcaag cccctgtgct ggtcatctac | 540 |
| ggcgacgacg aaaggccgtc aggcatccca gagcgcttct ccggctccaa ctccgggaat | 600 |
| actgccaccc ttaccatttc cggaacccag gccgaggatg aagcggatta ctattgcgcg | 660 |
| agctacgata gcagccacat cctgatcgtg tttggaggcg gtactaagct gaccgtgctg | 720 |
| ggaagcggtg gatcaaaccc aatttgcaag ggatgcctga ctgtagcaa ggacaacgga | 780 |
| tgttcacggt gccagcaaaa gctgttttc ttcctccggc gggaaggaat gcggcagtac | 840 |
| ggcgaatgtc tccactcctg cccctcgggg tattacggac accgcgcgcc tgacatgaac | 900 |
| cgatgcgcca gatgccggat cgagaactgc gatagctgct cagcaagga cgcctgcact | 960 |
| aagtgcaaag tcggcttcta ccttcaccgg ggcagatgtt ttgacgaatg cccggatggc | 1020 |
| ttcgccccgc tggaggagac tatggaatgc gtggagggcg agactacaa ggacgacgat | 1080 |
| gacaagggct cccaccatca ccaccatcat caccactag | 1119 |

<210> SEQ ID NO 24
<211> LENGTH: 372
<212> TYPE: PRT
<213> ORGANISM: Artificial Sequence
<220> FEATURE:
<223> OTHER INFORMATION: Made in Lab - fusion construct design of tissue-specific Wnt signal enhancing molecules

<400> SEQUENCE: 24

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu

|   |   | 100 |   |   | 105 |   |   | 110 |   |   |
|---|---|---|---|---|---|---|---|---|---|---|

Val Thr Val Ser Ser Gly Gly Gly Ser Gly Gly Gly Ser Gly
            115                      120                      125

Gly Gly Gly Ser Asp Ile Glu Leu Thr Gln Pro Pro Ser Val Ser Val
     130                  135                  140

Ala Pro Gly Gln Thr Ala Arg Ile Ser Cys Ser Gly Asp Asn Leu Gly
145               150                  155                  160

Lys Lys Tyr Val Tyr Trp Tyr Gln Gln Lys Pro Gly Gln Ala Pro Val
                  165                  170              175

Leu Val Ile Tyr Gly Asp Asp Glu Arg Pro Ser Gly Ile Pro Glu Arg
            180                  185              190

Phe Ser Gly Ser Asn Ser Gly Asn Thr Ala Thr Leu Thr Ile Ser Gly
     195                  200              205

Thr Gln Ala Glu Asp Glu Ala Asp Tyr Tyr Cys Ala Ser Tyr Asp Ser
210               215                  220

Ser His Ile Leu Ile Val Phe Gly Gly Thr Lys Leu Thr Val Leu
225               230                  235                  240

Gly Ser Gly Gly Ser Asn Pro Ile Cys Lys Gly Cys Leu Ser Cys Ser
                  245                  250              255

Lys Asp Asn Gly Cys Ser Arg Cys Gln Gln Lys Leu Phe Phe Phe Leu
            260                  265              270

Arg Arg Glu Gly Met Arg Gln Tyr Gly Glu Cys Leu His Ser Cys Pro
            275                  280              285

Ser Gly Tyr Tyr Gly His Arg Ala Pro Asp Met Asn Arg Cys Ala Arg
     290                  295                  300

Cys Arg Ile Glu Asn Cys Asp Ser Cys Phe Ser Lys Asp Ala Cys Thr
305               310                  315                  320

Lys Cys Lys Val Gly Phe Tyr Leu His Arg Gly Arg Cys Phe Asp Glu
                  325                  330              335

Cys Pro Asp Gly Phe Ala Pro Leu Glu Glu Thr Met Glu Cys Val Glu
            340                  345              350

Gly Gly Asp Tyr Lys Asp Asp Asp Lys Gly Ser His His His His
            355                  360              365

His His His His
     370

```
<210> SEQ ID NO 25
<211> LENGTH: 1125
<212> TYPE: DNA
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 25
gaagtgcagc tgctggaatc cggggcgga ctggtgcaac ccggggatc cctcagactg        60 tcctgtgccg catcgggttt cactttctcc tcctacgcga tgtcatgggt cagacaggcc    120
cctggaaaag gcctcgaatg ggtgtcggct atctccggat cgggggatc tacttactac    180 gccgactccg tgaagggccg gttcactatc tcgaggaca actccaagaa tacccctgtac   240 ttgcaaatga actccctgcg cgccgaggat accgcggtgt attactgcgc caaggacttc   300
agctcacgcc ggtggtacct tgagtactgg ggacagggaa cccttgtcac cgtgtccagc   360
ggtggcggcg gaagcggcgg gggcggatcc ggtggcgggg gctcagagct cacccaggac   420
cccgctgtgt ccgtggcctt gggacagacc gtgcgcatca catgccaggg cgatagcctg   480
```

```
cggagctatt acgcctcgtg gtaccagcag aagcctggtc aagcgccggt cctggtcatc    540 tacgaaaga acaaccgccc gtccggaatt ccagacaggt tcagcggatc cagctcgggg    600
aacaccgcct cactgactat caccggagca caggccgaag atgaagccga ctactactgc    660
aactccctgg agcggattgg atacctgagc tacgtgtttg gtggcggcac gaagctcacc    720
gtgctgggaa gcggtggatc aaacccaatt tgcaagggat gcctgagctg tagcaaggac    780 aacgatgtt cacggtgcca gcaaaagctg ttttcttcc tccggcggga aggaatgcgg    840
cagtacggcg aatgtctcca ctcctgcccc tcggggtatt acggacaccg cgcgcctgac    900
atgaaccgat gcgccagatg ccggatcgag aactgcgata gctgcttcag caaggacgcc    960
tgcactaagt gcaaagtcgg cttctacctt caccggggca gatgttttga cgaatgcccg   1020
gatggcttcg ccccgctgga ggagactatg gaatgcgtgg agggcggaga ctacaaggac   1080
gacgatgaca agggctccca ccatcaccac catcatcacc actag                    1125
```

<210> SEQ ID NO 26
<211> LENGTH: 374
<212> TYPE: PRT
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 26

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Gly Asn Thr Ala Ser Leu Thr Ile Thr
        195                 200                 205

Gly Ala Gln Ala Glu Asp Glu Ala Asp Tyr Tyr Cys Asn Ser Leu Glu
    210                 215                 220

Arg Ile Gly Tyr Leu Ser Tyr Val Phe Gly Gly Gly Thr Lys Leu Thr
225                 230                 235                 240
```

```
Val Leu Gly Ser Gly Gly Ser Asn Pro Ile Cys Lys Gly Cys Leu Ser
                245                 250                 255

Cys Ser Lys Asp Asn Gly Cys Ser Arg Cys Gln Gln Lys Leu Phe Phe
            260                 265                 270

Phe Leu Arg Arg Glu Gly Met Arg Gln Tyr Gly Glu Cys Leu His Ser
        275                 280                 285

Cys Pro Ser Gly Tyr Tyr Gly His Arg Ala Pro Asp Met Asn Arg Cys
    290                 295                 300

Ala Arg Cys Arg Ile Glu Asn Cys Asp Ser Cys Phe Ser Lys Asp Ala
305                 310                 315                 320

Cys Thr Lys Cys Lys Val Gly Phe Tyr Leu His Arg Gly Arg Cys Phe
                325                 330                 335

Asp Glu Cys Pro Asp Gly Phe Ala Pro Leu Glu Glu Thr Met Glu Cys
            340                 345                 350

Val Glu Gly Gly Asp Tyr Lys Asp Asp Asp Lys Gly Ser His His
        355                 360                 365

His His His His His His
        370

<210> SEQ ID NO 27
<211> LENGTH: 1131
<212> TYPE: DNA
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 27
caagtgcaac tccaacaaag cggtcccgag ttggtccgac ccggcgtcag tgtgaaaatc      60
tcatgcaagg ggtccgggta taccttcact gactatgcaa tgcactgggt aaagcagagc    120
cacgccaagt ccttggagtg gatcggaggc attagtacct acttcggacg caccaactac    180
aatcaaaaat ttaagggtcg cgcaaccatg actgtagata atcatcaag taccgcgtac     240 atggaattgg ctagactgac ttctgaagat tccgcgctgt attactgtgc tcgcggtttg    300
tctggcaact atgttatgga ttactggggg caagggacca gcgtcacggt gtcctctggc    360
ggaggcgggt ccgggggggg tggttctggc ggaggcggat ccgatatagt tctgtttcaa    420
tcccctgcga gcctggcggt aagtttggga cagagagcca cgatttcctg ccgagcgagt    480
gaaagcgtag acgactacgg caattctttc atgcactggt atcaacagaa gccaggccaa    540
ccgccgaagc tgcttatcta tcgcgcgtcc aatttggagt cagggatccc tgcacgattt    600
tcaggttctg gaagtaggac agactttaca cttacgataa ccccgtggaa agcggatgac    660
gtcgcaacct actattgtca acaaagcaat gaagcaccac ctaccttcgg aggtggcact    720
aaattggaaa ttaggggaag cggtggatca aacccaattt gcaagggatg cctgagctgt    780
agcaaggaca cggatgttc acggtgccag caaaagctgt tttcttcct ccggcgggaa     840 ggaatgcggc agtacggcga atgtctccac tcctgccct cggggtatta cggacaccgc    900
gcgcctgaca tgaaccgatg cgccagatgc cggatcgaga actgcgatag ctgcgccagc    960
aaggacgcct gcactaagtg caaagtcggc ttctaccttc accggggcag atgttttgac   1020
gaatgcccgg atggcttcgc cccgctggag gagactatgg aatgcgtgga gggcggagac   1080
tacaaggacg acgatgacaa gggctcccac catcaccacc atcatcacca c           1131

<210> SEQ ID NO 28
<211> LENGTH: 377
```

```
<212> TYPE: PRT
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 28

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Gly Ile Ser Thr Tyr Phe Gly Arg Thr Asn Tyr Asn Gln Lys Phe
    50                  55                  60

Lys Gly Arg Ala Thr Met Thr Val Asp Lys Ser Ser Thr Ala Tyr
65                  70                  75                  80

Met Glu Leu Ala Arg Leu Thr Ser Glu Asp Ser Ala Leu Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser Gly Gly Gly Ser Gly Gly Gly
        115                 120                 125

Ser Gly Gly Gly Ser Asp Ile Val Leu Phe Gln Ser Pro Ala Ser
130                 135                 140

Leu Ala Val Ser Leu Gly Gln Arg Ala Thr Ile Ser Cys Arg Ala Ser
145                 150                 155                 160

Glu Ser Val Asp Asp Tyr Gly Asn Ser Phe Met His Trp Tyr Gln Gln
                165                 170                 175

Lys Pro Gly Gln Pro Pro Lys Leu Leu Ile Tyr Arg Ala Ser Asn Leu
            180                 185                 190

Glu Ser Gly Ile Pro Ala Arg Phe Ser Gly Ser Gly Ser Arg Thr Asp
        195                 200                 205

Phe Thr Leu Thr Ile Asn Pro Val Glu Ala Asp Asp Val Ala Thr Tyr
    210                 215                 220

Tyr Cys Gln Gln Ser Asn Glu Ala Pro Pro Thr Phe Gly Gly Gly Thr
225                 230                 235                 240

Lys Leu Glu Ile Arg Gly Ser Gly Gly Ser Asn Pro Ile Cys Lys Gly
                245                 250                 255

Cys Leu Ser Cys Ser Lys Asp Asn Gly Cys Ser Arg Cys Gln Gln Lys
            260                 265                 270

Leu Phe Phe Phe Leu Arg Arg Glu Gly Met Arg Gln Tyr Gly Glu Cys
        275                 280                 285

Leu His Ser Cys Pro Ser Gly Tyr Tyr Gly His Arg Ala Pro Asp Met
    290                 295                 300

Asn Arg Cys Ala Arg Cys Arg Ile Glu Asn Cys Asp Ser Cys Ala Ser
305                 310                 315                 320

Lys Asp Ala Cys Thr Lys Cys Lys Val Gly Phe Tyr Leu His Arg Gly
                325                 330                 335

Arg Cys Phe Asp Glu Cys Pro Asp Gly Phe Ala Pro Leu Glu Glu Thr
            340                 345                 350

Met Glu Cys Val Glu Gly Gly Asp Tyr Lys Asp Asp Asp Lys Gly
        355                 360                 365

Ser His His His His His His His
    370                 375
```

<210> SEQ ID NO 29
<211> LENGTH: 1116
<212> TYPE: DNA
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 29

```
caggtccagt tggtggaatc cggaggggt  ttggtccagc tggtggaag  cctgcgcctc      60
tcatgcgccg ctagcggatt caccttctcc cgatacggca tgcattgggt cagacaggca     120
cccggaaaag gactcgaatg ggtgtcgggc atttcctcga tcgggtcaaa cacctattac     180
gccgactccg tgaagggacg gttcaccatt agccgggata cagcaagaa  cactctgtac     240
ttgcaaatga actccctgcg ggctgaggac accgccgtgt actactgtgc gcggtggtac     300
aagacctata ttgacgtctg gggacagggt accctcgtga ccgtgtcatc cggtggtgga     360
ggatccggag gcggaggaag cggaggaggg ggttcagaca tcgaactcac ccagcccccg     420
tcagtgtccg tggcccctgg acagactgcg cgcatctcct gctccggcga caacctgggg     480
aagaaatacg tgtactggta ccagcagaag ccaggtcaag cccctgtgct ggtcatctac     540
ggcgacgacg aaaggccgtc aggcatccca gagcgcttct ccggctccaa ctccgggaat     600
actgccaccc ttaccatttc cggaacccag gccgaggatg aagcggatta ctattgcgcg     660
agctacgata gcagccacat cctgatcgtg tttggaggcg gtactaagct gaccgtgctg     720
ggaagcggtg gatcaaaccc aatttgcaag ggatgcctga ctgtagcaa  ggacaacgga     780
tgttcacggt gccagcaaaa gctgtttttc ttcctccggc gggaaggaat gcggcagtac     840
ggcgaatgtc tccactcctg cccctcgggg tattacggac accgcgcgcc tgacatgaac     900
cgatgcgcca gatgccggat cgagaactgc gatagctgcc gcagcaagga cgcctgcact     960
aagtgcaaag tcggcttcta ccttcaccgg ggcagatgtt ttgacgaatg cccggatggc    1020
ttcgccccgc tggaggagac tatggaatgc gtggagggcg agactacaa  ggacgacgat    1080
gacaagggct cccaccatca ccaccatcat caccac                              1116
```

<210> SEQ ID NO 30
<211> LENGTH: 372
<212> TYPE: PRT
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 30

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Trp Tyr Lys Thr Tyr Ile Asp Val Trp Gly Gln Gly Thr Leu
            100                 105                 110

Val Thr Val Ser Ser Gly Gly Gly Ser Gly Gly Gly Gly Ser Gly
        115                 120                 125

Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240

Gly Ser Gly Gly Ser Asn Pro Ile Cys Lys Gly Cys Leu Ser Cys Ser
                245                 250                 255

Lys Asp Asn Gly Cys Ser Arg Cys Gln Gln Lys Leu Phe Phe Phe Leu
            260                 265                 270

Arg Arg Glu Gly Met Arg Gln Tyr Gly Glu Cys Leu His Ser Cys Pro
        275                 280                 285

Ser Gly Tyr Tyr Gly His Arg Ala Pro Asp Met Asn Arg Cys Ala Arg
    290                 295                 300

Cys Arg Ile Glu Asn Cys Asp Ser Cys Arg Ser Lys Asp Ala Cys Thr
305                 310                 315                 320

Lys Cys Lys Val Gly Phe Tyr Leu His Arg Gly Arg Cys Phe Asp Glu
                325                 330                 335

Cys Pro Asp Gly Phe Ala Pro Leu Glu Glu Thr Met Glu Cys Val Glu
            340                 345                 350

Gly Gly Asp Tyr Lys Asp Asp Asp Lys Gly Ser His His His His
        355                 360                 365

His His His His
    370

<210> SEQ ID NO 31
<211> LENGTH: 1131
<212> TYPE: DNA
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 31
caagtgcaac tccaacaaag cggtcccgag ttggtccgac ccggcgtcag tgtgaaaatc      60
tcatgcaagg ggtccgggta taccttcact gactatgcaa tgcactgggt aaagcagagc    120
cacgccaagt ccttggagtg gatcggaggc attagtacct acttcggacg caccaactac    180
aatcaaaaat ttaagggtcg cgcaaccatg actgtagata atcatcaag taccgcgtac     240 atggaattgg ctagactgac ttctgaagat tccgcgctgt attactgtgc tcgcggtttg    300
tctggcaact atgttatgga ttactggggg caagggacca gcgtcacggt gtcctctggc    360
ggaggcgggt ccggggggggg tggttctggc ggaggcggat ccgatatagt tctgtttcaa    420

```
tcccctgcga gcctggcggt aagtttggga cagagagcca cgatttcctg ccgagcgagt    480
gaaagcgtag acgactacgg caattctttc atgcactggt atcaacagaa gccaggccaa    540
ccgccgaagc tgcttatcta tcgcgcgtcc aatttggagt cagggatccc tgcacgattt    600
tcaggttctg gaagtaggac agactttaca cttacgataa accccgtgga agcggatgac    660
gtcgcaacct actattgtca acaaagcaat gaagcaccac ctaccttcgg aggtggcact    720
aaattggaaa ttaggggaag cggtggatca aacccaattt gcaagggatg cctgagctgt    780
agcaaggaca acggatgttc acggtgccag caaaagctgt ttttcttcct ccggcgggaa    840
ggaatgcggc agtacggcga atgtctccac tcctgcccct cggggtatta cggacaccgc    900
gcgcctgaca tgaaccgatg cgccagatgc cggatcgaga actgcgatag ctgccgcagc    960
aaggacgcct gcactaagtg caaagtcggc ttctaccttc accggggcag atgttttgac   1020
gaatgcccgg atggcttcgc cccgctggag gagactatgg aatgcgtgga gggcggagac   1080
tacaaggacg acgatgacaa gggctcccac catcaccacc atcatcacca c            1131
```

<210> SEQ ID NO 32
<211> LENGTH: 377
<212> TYPE: PRT
<213> ORGANISM: Artificial Sequence
<220> FEATURE:
<223> OTHER INFORMATION: Made in Lab - fusion construct design of
      tissue-specific Wnt signal enhancing molecules

<400> SEQUENCE: 32

```
Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Gly Ile Ser Thr Tyr Phe Gly Arg Thr Asn Tyr Asn Gln Lys Phe
    50                  55                  60

Lys Gly Arg Ala Thr Met Thr Val Asp Lys Ser Ser Ser Thr Ala Tyr
65                  70                  75                  80

Met Glu Leu Ala Arg Leu Thr Ser Glu Asp Ser Ala Leu Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser Gly Gly Gly Ser Gly Gly Gly Gly
        115                 120                 125

Ser Gly Gly Gly Gly Ser Asp Ile Val Leu Phe Gln Ser Pro Ala Ser
    130                 135                 140

Leu Ala Val Ser Leu Gly Gln Arg Ala Thr Ile Ser Cys Arg Ala Ser
145                 150                 155                 160

Glu Ser Val Asp Asp Tyr Gly Asn Ser Phe Met His Trp Tyr Gln Gln
                165                 170                 175

Lys Pro Gly Gln Pro Pro Lys Leu Leu Ile Tyr Arg Ala Ser Asn Leu
            180                 185                 190

Glu Ser Gly Ile Pro Ala Arg Phe Ser Gly Ser Gly Ser Arg Thr Asp
        195                 200                 205

Phe Thr Leu Thr Ile Asn Pro Val Glu Ala Asp Asp Val Ala Thr Tyr
    210                 215                 220

Tyr Cys Gln Gln Ser Asn Glu Ala Pro Pro Thr Phe Gly Gly Gly Thr
225                 230                 235                 240
```

Lys Leu Glu Ile Arg Gly Ser Gly Gly Ser Asn Pro Ile Cys Lys Gly
            245                 250                 255

Cys Leu Ser Cys Ser Lys Asp Asn Gly Cys Ser Arg Cys Gln Gln Lys
        260                 265                 270

Leu Phe Phe Phe Leu Arg Arg Glu Gly Met Arg Gln Tyr Gly Glu Cys
    275                 280                 285

Leu His Ser Cys Pro Ser Gly Tyr Tyr Gly His Arg Ala Pro Asp Met
290                 295                 300

Asn Arg Cys Ala Arg Cys Arg Ile Glu Asn Cys Asp Ser Cys Arg Ser
305                 310                 315                 320

Lys Asp Ala Cys Thr Lys Cys Lys Val Gly Phe Tyr Leu His Arg Gly
                325                 330                 335

Arg Cys Phe Asp Glu Cys Pro Asp Gly Phe Ala Pro Leu Glu Glu Thr
            340                 345                 350

Met Glu Cys Val Glu Gly Gly Asp Tyr Lys Asp Asp Asp Lys Gly
        355                 360                 365

Ser His His His His His His
    370                 375

<210> SEQ ID NO 33
<211> LENGTH: 324
<212> TYPE: DNA
<213> ORGANISM: Homo sapiens

<400> SEQUENCE: 33
tcaaacccaa tttgcaaggg atgcctgagc tgtagcaagg acaacggatg ttcacggtgc      60
cagcaaaagc tgttttttct tcctccggcgg gaaggaatgc ggcagtacgg cgaatgtctc    120
cactcctgcc cctcggggta ttacggacac cgcgcgcctg acatgaaccg atgcgccaga    180
tgccggatcg agaactgcga tagctgcttc agcaaggact tctgcactaa gtgcaaagtc    240
ggcttctacc tcaccgggg cagatgtttt gacgaatgcc cggatggctt cgccccgctg     300
gaggagacta tggaatgcgt ggag                                           324

<210> SEQ ID NO 34
<211> LENGTH: 108
<212> TYPE: PRT
<213> ORGANISM: Homo sapiens

<400> SEQUENCE: 34

Ser Asn Pro Ile Cys Lys Gly Cys Leu Ser Cys Ser Lys Asp Asn Gly
1               5                   10                  15

Cys Ser Arg Cys Gln Gln Lys Leu Phe Phe Phe Leu Arg Arg Glu Gly
            20                  25                  30

Met Arg Gln Tyr Gly Glu Cys Leu His Ser Cys Pro Ser Gly Tyr Tyr
        35                  40                  45

Gly His Arg Ala Pro Asp Met Asn Arg Cys Ala Arg Cys Arg Ile Glu
    50                  55                  60

Asn Cys Asp Ser Cys Phe Ser Lys Asp Phe Cys Thr Lys Cys Lys Val
65                  70                  75                  80

Gly Phe Tyr Leu His Arg Gly Cys Phe Asp Glu Cys Pro Asp Gly
                85                  90                  95

Phe Ala Pro Leu Glu Glu Thr Met Glu Cys Val Glu
            100                 105

<210> SEQ ID NO 35

<211> LENGTH: 642
<212> TYPE: DNA
<213> ORGANISM: Artificial Sequence
<220> FEATURE:
<223> OTHER INFORMATION: Made in Lab

<400> SEQUENCE: 35

```
gacatcgaac tcacccagcc cccgtcagtg tccgtggccc ctggacagac tgcgcgcatc      60
tcctgctccg gcgacaacct ggggaagaaa tacgtgtact ggtaccagca gaagccaggt    120
caagcccctg tgctggtcat ctacggcgac gacgaaaggc cgtcaggcat cccagagcgc    180
ttctccggct ccaactccgg gaatactgcc acccttacca tttccggaac ccaggccgag    240
gatgaagcgg attactattg cgcgagctac gatagcagcc acatcctgat cgtgtttgga    300
ggcggtacca agcttaccgt cctaggtcag cccaaggctg cccccctcggt cactctgttc    360
ccgccctcct ctgaggagct tcaagccaac aaggccacac tggtgtgtct cataagtgac    420
ttctacccgg gagccgtgac agtggcctgg aaggcagata gcagccccgt caaggcggga    480
gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                       642
```

<210> SEQ ID NO 36
<211> LENGTH: 214
<212> TYPE: PRT
<213> ORGANISM: Artificial Sequence
<220> FEATURE:
<223> OTHER INFORMATION: Made in Lab

<400> SEQUENCE: 36

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Gly Lys Lys Tyr Val
            20                  25                  30

Tyr Trp Tyr Gln Gln Lys Pro Gly Gln Ala Pro Val Leu Val Ile Tyr
        35                  40                  45

Gly Asp Asp Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ser Tyr Asp Ser Ser His Ile Leu
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205
```

Ala Pro Thr Glu Cys Ser
    210

<210> SEQ ID NO 37
<211> LENGTH: 1695
<212> TYPE: DNA
<213> ORGANISM: Artificial Sequence
<220> FEATURE:
<223> OTHER INFORMATION: Made in Lab

<400> SEQUENCE: 37

| | | | | | |
|---|---|---|---|---|---|
| aacccaattt | gcaagggatg | cctgagctgt | agcaaggaca | acggatgttc | acggtgccag | 60 |
| caaaagctgt | ttttcttcct | ccggcgggaa | ggaatgcggc | agtacggcga | atgtctccac | 120 |
| tcctgcccct | cggggtatta | cggacaccgc | gcgcctgaca | tgaaccgatg | cgccagatgc | 180 |
| cggatcgaga | actgcgatag | ctgccgcagc | aaggacgcct | gcactaagtg | caaagtcggc | 240 |
| ttctaccttc | accggggcag | atgttttgac | gaatgcccgg | atggcttcgc | ccgctggag | 300 |
| gagactatgg | aatgcgtgga | gggtggtggt | ggctcgggag | gaggaggctc | cggtggcggt | 360 |
| ggcagccagg | tccagttggt | ggaatccgga | gggggtttgg | tccagcctgg | tggaagcctg | 420 |
| cgcctctcat | gcgccgctag | cggattcacc | ttctcccgat | acggcatgca | ttgggtcaga | 480 |
| caggcacccg | gaaaaggact | cgaatgggtg | tcggcatttt | cctcgatcgg | gtcaaacacc | 540 |
| tattacgccg | actccgtgaa | gggacggttc | accattagcc | gggataacag | caagaacact | 600 |
| ctgtacttgc | aaatgaactc | cctgcgggct | gaggacaccg | ccgtgtacta | ctgtgcgcgg | 660 |
| tggtacaaga | cctatattga | cgtctgggga | cagggtaccc | tcgtgaccgt | gtcgagtgct | 720 |
| agcaccaagg | gcccatcggt | cttccccctg | gcgccctgct | ccaggagcac | ctccgagagc | 780 |
| acagcggccc | tgggctgcct | ggtcaaggac | tacttccccg | aaccggtgac | ggtgtcgtgg | 840 |
| aactcaggcg | ctctgaccag | cggcgtgcac | accttcccag | ctgtcctaca | gtcctcagga | 900 |
| ctctactccc | tcagcagcgt | ggtgaccgtg | ccctccagca | acttcggcac | ccagacctac | 960 |
| acctgcaacg | tagatcacaa | gcccagcaac | accaaggtgg | acaagacagt | tgagcgcaaa | 1020 |
| tgttgtgtcg | agtgcccacc | gtgcccagca | ccacctgtgg | caggaccgtc | agtcttcctc | 1080 |
| ttccccccaa | aacccaagga | caccctcatg | atctcccgga | cccctgaggt | cacgtgcgtg | 1140 |
| gtggtggacg | tgagccacga | agaccccgag | gtccagttca | actggtacgt | ggacggcgtg | 1200 |
| gaggtgcata | atgccaagac | aaagccacgg | gaggagcagt | tcaacagcac | gttccgtgtg | 1260 |
| gtcagcgtcc | tcaccgttgt | gcaccaggac | tggctgaacg | gcaaggagta | caagtgcaag | 1320 |
| gtctccaaca | aaggcctccc | agcccccatc | gagaaaacca | tctccaaaac | caaagggcag | 1380 |
| ccccgagaac | cacaggtgta | caccctgccc | ccatcccggg | aggagatgac | caagaaccag | 1440 |
| gtcagcctga | cctgcctggt | caaaggcttc | taccccagcg | acatcgccgt | ggagtgggag | 1500 |
| agcaatgggc | agccggagaa | caactacaag | accacgcctc | ccatgctgga | ctccgacggc | 1560 |
| tccttcttcc | tctacagcaa | gctcaccgtg | gacaagagca | ggtggcagca | ggggaacgtc | 1620 |
| ttctcatgct | ccgtgatgca | tgaggctctg | cacaaccact | acacgcagaa | gagcctctcc | 1680 |
| ctgtctccgg | gtaaa | | | | | 1695 |

<210> SEQ ID NO 38
<211> LENGTH: 565
<212> TYPE: PRT
<213> ORGANISM: Artificial Sequence
<220> FEATURE:
<223> OTHER INFORMATION: Made in Lab

```
<400> SEQUENCE: 38

Asn Pro Ile Cys Lys Gly Cys Leu Ser Cys Ser Lys Asp Asn Gly Cys
1               5                   10                  15

Ser Arg Cys Gln Gln Lys Leu Phe Phe Phe Leu Arg Arg Glu Gly Met
            20                  25                  30

Arg Gln Tyr Gly Glu Cys Leu His Ser Cys Pro Ser Gly Tyr Tyr Gly
        35                  40                  45

His Arg Ala Pro Asp Met Asn Arg Cys Ala Arg Cys Arg Ile Glu Asn
    50                  55                  60

Cys Asp Ser Cys Arg Ser Lys Asp Ala Cys Thr Lys Cys Lys Val Gly
65                  70                  75                  80

Phe Tyr Leu His Arg Gly Arg Cys Phe Asp Glu Cys Pro Asp Gly Phe
                85                  90                  95

Ala Pro Leu Glu Glu Thr Met Glu Cys Val Gly Gly Gly Gly Gly Ser
            100                 105                 110

Gly Gly Gly Gly Ser Gly Gly Gly Ser Gln Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Phe Thr Phe Ser Arg Tyr Gly Met His Trp Val Arg
145                 150                 155                 160

Gln Ala Pro Gly Lys Gly Leu Glu Trp Val Ser Gly Ile Ser Ser Ile
            165                 170                 175

Gly Ser Asn Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
            195                 200                 205

Arg Ala Glu Asp Thr Ala Val Tyr Tyr Cys Ala Arg Trp Tyr Lys Thr
210                 215                 220

Tyr Ile Asp Val Trp Gly Gln Gly Thr Leu Val Thr Val Ser Ser Ala
225                 230                 235                 240

Ser Thr Lys Gly Pro Ser Val Phe Pro Leu Ala Pro Cys Ser Arg Ser
            245                 250                 255

Thr Ser Glu Ser Thr Ala Ala Leu Gly Cys Leu Val Lys Asp Tyr Phe
            260                 265                 270

Pro Glu Pro Val Thr Val Ser Trp Asn Ser Gly Ala Leu Thr Ser Gly
            275                 280                 285

Val His Thr Phe Pro Ala Val Leu Gln Ser Ser Gly Leu Tyr Ser Leu
290                 295                 300

Ser Ser Val Val Thr Val Pro Ser Ser Asn Phe Gly Thr Gln Thr Tyr
305                 310                 315                 320

Thr Cys Asn Val Asp His Lys Pro Ser Asn Thr Lys Val Asp Lys Thr
            325                 330                 335

Val Glu Arg Lys Cys Cys Val Glu Cys Pro Pro Cys Pro Ala Pro Pro
            340                 345                 350

Val Ala Gly Pro Ser Val Phe Leu Phe Pro Pro Lys Pro Lys Asp Thr
            355                 360                 365

Leu Met Ile Ser Arg Thr Pro Glu Val Thr Cys Val Val Val Asp Val
370                 375                 380

Ser His Glu Asp Pro Glu Val Gln Phe Asn Trp Tyr Val Asp Gly Val
385                 390                 395                 400

Glu Val His Asn Ala Lys Thr Lys Pro Arg Glu Glu Gln Phe Asn Ser
            405                 410                 415
```

```
Thr Phe Arg Val Val Ser Val Leu Thr Val Val His Gln Asp Trp Leu
                420                 425                 430

Asn Gly Lys Glu Tyr Lys Cys Lys Val Ser Asn Lys Gly Leu Pro Ala
            435                 440                 445

Pro Ile Glu Lys Thr Ile Ser Lys Thr Lys Gly Gln Pro Arg Glu Pro
        450                 455                 460

Gln Val Tyr Thr Leu Pro Pro Ser Arg Glu Glu Met Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Met Leu Asp Ser Asp Gly Ser Phe Phe Leu Tyr Ser Lys Leu
        515                 520                 525

Thr Val Asp Lys Ser Arg Trp Gln Gln Gly Asn Val Phe Ser Cys Ser
530                 535                 540

Val Met His Glu Ala Leu His Asn His Tyr Thr Gln Lys Ser Leu Ser
545                 550                 555                 560

Leu Ser Pro Gly Lys
            565

<210> SEQ ID NO 39
<211> LENGTH: 654
<212> TYPE: DNA
<213> ORGANISM: Artificial Sequence
<220> FEATURE:
<223> OTHER INFORMATION: Made in Lab

<400> SEQUENCE: 39
gatatagttc tgtttcaatc ccctgcgagc ctggcggtaa gtttgggaca gagagccacg     60
atttcctgcc gagcgagtga aagcgtagac gactacggca attctttcat gcactggtat    120
caacagaagc caggccaacc gccgaagctg cttatctatc gcgcgtccaa tttggagtca    180
gggatccctg cacgattttc aggttctgga agtaggacag actttacact tacgataaac    240
cccgtggaag cggatgacgt cgcaacctac tattgtcaac aaagcaatga agcaccacct    300
accttcggag gtggcactaa attggaaatt aaacgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc     600 acccatcagg gcctgagctc gcccgtcaca aagagcttca cagggagagtgt             654

<210> SEQ ID NO 40
<211> LENGTH: 218
<212> TYPE: PRT
<213> ORGANISM: Artificial Sequence
<220> FEATURE:
<223> OTHER INFORMATION: Made in Lab

<400> SEQUENCE: 40

Asp Ile Val Leu Phe Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30
```

Gly Asn Ser Phe Met His Trp Tyr Gln Gln Lys Pro Gly Gln Pro
                35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Ala Pro Pro Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
                210                 215

<210> SEQ ID NO 41
<211> LENGTH: 1701
<212> TYPE: DNA
<213> ORGANISM: Artificial Sequence
<220> FEATURE:
<223> OTHER INFORMATION: Made in Lab

<400> SEQUENCE: 41

```
aacccaattt gcaagggatg cctgagctgt agcaaggaca acggatgttc acggtgccag      60
caaaagctgt ttttcttcct ccggcgggaa ggaatgcggc agtacggcga atgtctccac     120
tcctgcccct cggggtatta cggacaccgc gcgcctgaca tgaaccgatg cgccagatgc     180
cggatcgaga actgcgatag ctgccgcagc aaggacgcct gcactaagtg caaagtcggc     240
ttctaccttc accggggcag atgttttgac gaatgcccgg atggcttcgc cccgctggag     300
gagactatgg aatgcgtgga gggtggtggt ggctcgggag gaggaggctc cggtggcggt     360
ggcagccaag tgcaactcca acaaagcggt cccgagttgg tccgacccgg cgtcagtgtg     420
aaaatctcat gcaagggtc cgggtatacc ttcactgact atgcaatgca ctgggtaaag     480
cagagccacg ccaagtcctt ggagtggatc ggaggcatta gtacctactt cggacgcacc     540
aactacaatc aaaaatttaa gggtcgcgca accatgactg tagataaatc atcaagtacc     600
gcgtacatgg aattggctag actgacttct gaagattccg cgctgtatta ctgtgctcgc     660
ggtttgtctg gcaactatgt tatggattac tgggggcaag ggaccagcgt cacggtgtcg     720
agtgctagca ccaagggccc atcggtcttc cccctggcgc cctgctccag gagcacctcc     780
gagagcacag cggccctggg ctgcctggtc aaggactact ccccgaacc ggtgacggtg     840 tcgtggaact caggcgctct gaccagcggc gtgcacacct tcccagctgt cctacagtcc     900
tcaggactct actccctcag cagcgtggtg accgtgccct ccagcaactt cggcacccag     960
acctacacct gcaacgtaga tcacaagccc agcaacacca aggtggacaa gacagttgag    1020
```

```
cgcaaatgtt gtgtcgagtg cccaccgtgc ccagcaccac ctgtggcagg accgtcagtc    1080
ttcctcttcc ccccaaaacc caaggacacc ctcatgatct cccggacccc tgaggtcacg    1140
tgcgtggtgg tggacgtgag ccacgaagac cccgaggtcc agttcaactg gtacgtggac    1200
ggcgtggagg tgcataatgc caagacaaag ccacgggagg agcagttcaa cagcacgttc    1260
cgtgtggtca gcgtcctcac cgttgtgcac caggactggc tgaacggcaa ggagtacaag    1320
tgcaaggtct ccaacaaagg cctcccagcc cccatcgaga aaccatctc caaaaccaaa     1380 gggcagcccc gagaaccaca ggtgtacacc ctgcccccat cccgggagga tgaccaag      1440 aaccaggtca gcctgacctg cctggtcaaa ggcttctacc ccagcgacat cgccgtggag    1500
tgggagagca atgggcagcc ggagaacaac tacaagacca cgcctcccat gctggactcc    1560
gacggctcct tcttcctcta cagcaagctc accgtggaca gagcaggtg gcagcagggg    1620 aacgtcttct catgctccgt gatgcatgag gctctgcaca accactacac gcagaagagc    1680
ctctccctgt ctccgggtaa a                                              1701
```

<210> SEQ ID NO 42
<211> LENGTH: 567
<212> TYPE: PRT
<213> ORGANISM: Artificial Sequence
<220> FEATURE:
<223> OTHER INFORMATION: Made in Lab

<400> SEQUENCE: 42

```
Asn Pro Ile Cys Lys Gly Cys Leu Ser Cys Ser Lys Asp Asn Gly Cys
1               5                   10                  15

Ser Arg Cys Gln Gln Lys Leu Phe Phe Phe Leu Arg Arg Glu Gly Met
            20                  25                  30

Arg Gln Tyr Gly Glu Cys Leu His Ser Cys Pro Ser Gly Tyr Tyr Gly
        35                  40                  45

His Arg Ala Pro Asp Met Asn Arg Cys Ala Arg Cys Arg Ile Glu Asn
    50                  55                  60

Cys Asp Ser Cys Arg Ser Lys Asp Ala Cys Thr Lys Cys Lys Val Gly
65                  70                  75                  80

Phe Tyr Leu His Arg Gly Arg Cys Phe Asp Glu Cys Pro Asp Gly Phe
                85                  90                  95

Ala Pro Leu Glu Glu Thr Met Glu Cys Val Glu Gly Gly Gly Ser
            100                 105                 110

Gly Gly Gly Gly Ser Gly Gly Gly Ser Gln Val Gln Leu Gln Gln
        115                 120                 125

Ser Gly Pro Glu Leu Val Arg Pro Gly Val Ser Val Lys Ile Ser Cys
    130                 135                 140

Lys Gly Ser Gly Tyr Thr Phe Thr Asp Tyr Ala Met His Trp Val Lys
145                 150                 155                 160

Gln Ser His Ala Lys Ser Leu Glu Trp Ile Gly Gly Ile Ser Thr Tyr
                165                 170                 175

Phe Gly Arg Thr Asn Tyr Asn Gln Lys Phe Lys Gly Arg Ala Thr Met
            180                 185                 190

Thr Val Asp Lys Ser Ser Thr Ala Tyr Met Glu Leu Ala Arg Leu
        195                 200                 205

Thr Ser Glu Asp Ser Ala Leu Tyr Tyr Cys Ala Arg Gly Leu Ser Gly
    210                 215                 220

Asn Tyr Val Met Asp Tyr Trp Gly Gln Gly Thr Ser Val Thr Val Ser
225                 230                 235                 240
```

```
Ser Ala Ser Thr Lys Gly Pro Ser Val Phe Pro Leu Ala Pro Cys Ser
            245                 250                 255
Arg Ser Thr Ser Glu Ser Thr Ala Ala Leu Gly Cys Leu Val Lys Asp
            260                 265                 270
Tyr Phe Pro Glu Pro Val Thr Val Ser Trp Asn Ser Gly Ala Leu Thr
            275                 280                 285
Ser Gly Val His Thr Phe Pro Ala Val Leu Gln Ser Ser Gly Leu Tyr
            290                 295                 300
Ser Leu Ser Ser Val Val Thr Val Pro Ser Ser Asn Phe Gly Thr Gln
305                 310                 315                 320
Thr Tyr Thr Cys Asn Val Asp His Lys Pro Ser Asn Thr Lys Val Asp
            325                 330                 335
Lys Thr Val Glu Arg Lys Cys Cys Val Glu Cys Pro Pro Cys Pro Ala
            340                 345                 350
Pro Pro Val Ala Gly Pro Ser Val Phe Leu Phe Pro Pro Lys Pro Lys
            355                 360                 365
Asp Thr Leu Met Ile Ser Arg Thr Pro Glu Val Thr Cys Val Val Val
            370                 375                 380
Asp Val Ser His Glu Asp Pro Glu Val Gln Phe Asn Trp Tyr Val Asp
385                 390                 395                 400
Gly Val Glu Val His Asn Ala Lys Thr Lys Pro Arg Glu Glu Gln Phe
            405                 410                 415
Asn Ser Thr Phe Arg Val Val Ser Val Leu Thr Val Val His Gln Asp
            420                 425                 430
Trp Leu Asn Gly Lys Glu Tyr Lys Cys Lys Val Ser Asn Lys Gly Leu
            435                 440                 445
Pro Ala Pro Ile Glu Lys Thr Ile Ser Lys Thr Lys Gly Gln Pro Arg
            450                 455                 460
Glu Pro Gln Val Tyr Thr Leu Pro Pro Ser Arg Glu Glu Met Thr Lys
465                 470                 475                 480
Asn Gln Val Ser Leu Thr Cys Leu Val Lys Gly Phe Tyr Pro Ser Asp
            485                 490                 495
Ile Ala Val Glu Trp Glu Ser Asn Gly Gln Pro Glu Asn Asn Tyr Lys
            500                 505                 510
Thr Thr Pro Pro Met Leu Asp Ser Asp Gly Ser Phe Phe Leu Tyr Ser
            515                 520                 525
Lys Leu Thr Val Asp Lys Ser Arg Trp Gln Gln Gly Asn Val Phe Ser
            530                 535                 540
Cys Ser Val Met His Glu Ala Leu His Asn His Tyr Thr Gln Lys Ser
545                 550                 555                 560
Leu Ser Leu Ser Pro Gly Lys
            565
```

<210> SEQ ID NO 43
<211> LENGTH: 1008
<212> TYPE: DNA
<213> ORGANISM: Artificial Sequence
<220> FEATURE:
<223> OTHER INFORMATION: Made in Lab - fusion construct

<400> SEQUENCE: 43

```
aacccaattt gcaagggatg cctgagctgt agcaaggaca acggatgttc acggtgccag      60
caaaagctgt ttttcttcct ccggcgggaa ggaatgcggc agtacggcga atgtctccac     120
tcctgcccct cggggtatta cggacaccgc gcgcctgaca tgaaccgatg cgccagatgc     180
```

-continued

```
cggatcgaga actgcgatag ctgccgcagc aaggacgcct gcactaagtg caaagtcggc      240
ttctaccttc accggggcag atgttttgac gaatgcccgg atggcttcgc cccgctggag      300
gagactatgg aatgcgtgga gggtggtggt ggctcgggag aggaggctc cggtggcggt       360 ggcagcgaca tcgaactcac ccagcccccg tcagtgtccg tggcccctgg acagactgcg      420
cgcatctcct gctccggcga caacctgggg aagaaatacg tgtactggta ccagcagaag      480
ccaggtcaag cccctgtgct ggtcatctac ggcgacgacg aaaggccgtc aggcatccca      540
gagcgcttct ccggctccaa ctccgggaat actgccaccc ttaccatttc cggaacccag      600
gccgaggatg aagcggatta ctattgcgcg agctacgata gcagccacat cctgatcgtg      660
tttggaggcg gtaccaagct taccgtccta ggtcagccca aggctgcccc ctcggtcact      720
ctgttcccgc cctcctctga ggagcttcaa gccaacaagg ccacactggt gtgtctcata      780
agtgacttct acccgggagc cgtgacagtg gcctggaagg cagatagcag ccccgtcaag      840
gcgggagtgg agaccaccac accctccaaa caaagcaaca caagtacgc ggccagcagc       900 tatctgagcc tgacgcctga gcagtggaag tcccacagaa gctacagctg ccaggtcacg      960
catgaaggga gcaccgtgga gaagacagtg gcccctacag aatgttca                  1008
```

<210> SEQ ID NO 44
<211> LENGTH: 336
<212> TYPE: PRT
<213> ORGANISM: Artificial Sequence
<220> FEATURE:
<223> OTHER INFORMATION: Made in Lab - fusion construct

<400> SEQUENCE: 44

```
Asn Pro Ile Cys Lys Gly Cys Leu Ser Cys Ser Lys Asp Asn Gly Cys
1               5                   10                  15

Ser Arg Cys Gln Gln Lys Leu Phe Phe Phe Leu Arg Arg Glu Gly Met
            20                  25                  30

Arg Gln Tyr Gly Glu Cys Leu His Ser Cys Pro Ser Gly Tyr Tyr Gly
        35                  40                  45

His Arg Ala Pro Asp Met Asn Arg Cys Ala Arg Cys Arg Ile Glu Asn
    50                  55                  60

Cys Asp Ser Cys Arg Ser Lys Asp Ala Cys Thr Lys Cys Lys Val Gly
65                  70                  75                  80

Phe Tyr Leu His Arg Gly Arg Cys Phe Asp Glu Cys Pro Asp Gly Phe
                85                  90                  95

Ala Pro Leu Glu Glu Thr Met Glu Cys Val Glu Gly Gly Gly Gly Ser
            100                 105                 110

Gly Gly Gly Gly Ser Gly Gly Gly Ser Asp Ile Glu Leu Thr Gln
            115                 120                 125

Pro Pro Ser Val Ser Val Ala Pro Gly Gln Thr Ala Arg Ile Ser Cys
130                 135                 140

Ser Gly Asp Asn Leu Gly Lys Lys Tyr Val Tyr Trp Tyr Gln Gln Lys
145                 150                 155                 160

Pro Gly Gln Ala Pro Val Leu Val Ile Tyr Gly Asp Asp Glu Arg Pro
                165                 170                 175

Ser Gly Ile Pro Glu Arg Phe Ser Gly Ser Asn Ser Gly Asn Thr Ala
            180                 185                 190

Thr Leu Thr Ile Ser Gly Thr Gln Ala Glu Asp Glu Ala Asp Tyr Tyr
        195                 200                 205

Cys Ala Ser Tyr Asp Ser Ser His Ile Leu Ile Val Phe Gly Gly Gly
```

```
            210                 215                 220
Thr Lys Leu Thr Val Leu Gly Gln Pro Lys Ala Ala Pro Ser Val Thr
225                 230                 235                 240

Leu Phe Pro Pro Ser Ser Glu Glu Leu Gln Ala Asn Lys Ala Thr Leu
                245                 250                 255

Val Cys Leu Ile Ser Asp Phe Tyr Pro Gly Ala Val Thr Val Ala Trp
            260                 265                 270

Lys Ala Asp Ser Ser Pro Val Lys Ala Gly Val Glu Thr Thr Thr Pro
        275                 280                 285

Ser Lys Gln Ser Asn Asn Lys Tyr Ala Ala Ser Ser Tyr Leu Ser Leu
    290                 295                 300

Thr Pro Glu Gln Trp Lys Ser His Arg Ser Tyr Ser Cys Gln Val Thr
305                 310                 315                 320

His Glu Gly Ser Thr Val Glu Lys Thr Val Ala Pro Thr Glu Cys Ser
                325                 330                 335
```

<210> SEQ ID NO 45
<211> LENGTH: 1329
<212> TYPE: DNA
<213> ORGANISM: Artificial Sequence
<220> FEATURE:
<223> OTHER INFORMATION: Made in Lab - fusion construct

<400> SEQUENCE: 45

```
caggtccagt tggtggaatc cggagggggt tggtccagc ctggtggaag cctgcgcctc      60
tcatgcgccg ctagcggatt caccttctcc cgatacggca tgcattgggt cagacaggca    120
cccggaaaag gactcgaatg ggtgtcgggc atttcctcga tcgggtcaaa cacctattac    180
gccgactccg tgaagggacg gttcaccatt agccgggata cagcaagaa cactctgtac     240 ttgcaaatga actccctgcg gctgaggac accgccgtgt actactgtgc gcggtggtac     300
aagacctata ttgacgtctg gggacagggt accctcgtga ccgtgtcgag tgctagcacc    360
aagggcccat cggtcttccc cctggcgccc tgctccagga gcacctccga gagcacagcg    420
gccctgggct gcctggtcaa ggactacttc cccgaaccgg tgacggtgtc gtggaactca    480
ggcgctctga ccagcggcgt gcacaccttc ccagctgtcc tacagtcctc aggactctac    540
tccctcagca gcgtggtgac cgtgccctcc agcaacttcg gcacccagac ctacacctgc    600
aacgtagatc acaagcccag caacaccaag gtggacaaga cagttgagcg caaatgttgt    660
gtcgagtgcc caccgtgccc agcaccacct gtggcaggac cgtcagtctt cctcttcccc    720
ccaaaaccca aggacaccct catgatctcc cggaccctg aggtcacgtg cgtggtggtg     780
gacgtgagcc acgaagaccc cgaggtccag ttcaactggt acgtggacgg cgtggaggtg    840
cataatgcca agacaaagcc acgggaggag cagttcaaca gcacgttccg tgtggtcagc    900
gtcctcaccg ttgtgcacca ggactggctg aacggcaagg agtacaagtg caaggtctcc    960
aacaaaggcc tcccagcccc catcgagaaa accatctcca aaaccaaagg gcagccccga   1020
gaaccacagg tgtacaccct gcccccatcc cgggaggaga tgaccaagaa ccaggtcagc   1080
ctgacctgcc tggtcaaagg cttctacccc agcgacatcg ccgtggagtg ggagagcaat   1140
gggcagccgg agaacaacta caagaccacg cctcccatgc tggactccga cggctccttc   1200
ttcctctaca gcaagctcac cgtggacaag agcaggtggc agcaggggaa cgtcttctca   1260
tgctccgtga tgcatgaggc tctgcacaac cactacacgc agaagagcct ctccctgtct   1320
ccgggtaaa                                                           1329
```

```
<210> SEQ ID NO 46
<211> LENGTH: 443
<212> TYPE: PRT
<213> ORGANISM: Artificial Sequence
<220> FEATURE:
<223> OTHER INFORMATION: Made in Lab - fusion construct

<400> SEQUENCE: 46

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365
```

```
Tyr Pro Ser Asp Ile Ala Val Glu Trp Glu Ser Asn Gly Gln Pro Glu
    370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
        435                 440

<210> SEQ ID NO 47
<211> LENGTH: 1020
<212> TYPE: DNA
<213> ORGANISM: Artificial Sequence
<220> FEATURE:
<223> OTHER INFORMATION: Made in Lab - Fusion construct

<400> SEQUENCE: 47
aacccaattt gcaagggatg cctgagctgt agcaaggaca acggatgttc acggtgccag      60
caaaagctgt ttttcttcct ccggcgggaa ggaatgcggc agtacggcga atgtctccac     120
tcctgcccct cggggtatta cggacaccgc gcgcctgaca tgaaccgatg cgccagatgc     180
cggatcgaga actgcgatag ctgccgcagc aaggacgcct gcactaagtg caaagtcggc     240
ttctaccttc accggggcag atgttttgac gaatgcccgg atggcttcgc cccgctggag     300
gagactatgg aatgcgtgga gggtggtggt ggctcgggag gaggaggctc cggtggcggt     360
ggcagcgata tagttctgtt tcaatcccct gcgagcctgg cggtaagttt gggacagaga     420
gccacgattt cctgccgagc gagtgaaagc gtagacgact acggcaattc tttcatgcac     480
tggtatcaac agaagccagg ccaaccgccg aagctgctta tctatcgcgc gtccaatttg     540
gagtcaggga tccctgcacg atttcaggt tctggaagta ggacagactt atacttacg     600
ataaaccccg tggaagcgga tgacgtcgca acctactatt gtcaacaaag caatgaagca     660
ccacctacct tcggaggtgg cactaaattg gaaattaaac gtacggtggc tgcaccatct     720
gtcttcatct tcccgccatc tgatgagcag ttgaaatctg gaactgcctc tgttgtgtgc     780
ctgctgaata acttctatcc cagagaggcc aaagtacagt ggaaggtgga taacgccctc     840
caatcgggta actcccagga gagtgtcaca gagcaggaca gcaaggacag cacctacagc     900
ctcagcagca ccctgacgct gagcaaagca gactacgaga acacaaaagt ctacgcctgc     960
gaagtcaccc atcagggcct gagctcgccc gtcacaaaga gcttcaacag gggagagtgt    1020
```

<210> SEQ ID NO 48
<211> LENGTH: 340
<212> TYPE: PRT
<213> ORGANISM: Artificial Sequence
<220> FEATURE:
<223> OTHER INFORMATION: Made in Lab - fusion construct

<400> SEQUENCE: 48

Asn Pro Ile Cys Lys Gly Cys Leu Ser Cys Ser Lys Asp Asn Gly Cys
1               5                   10                  15
Ser Arg Cys Gln Gln Lys Leu Phe Phe Phe Leu Arg Arg Glu Gly Met
            20                  25                  30
Arg Gln Tyr Gly Glu Cys Leu His Ser Cys Pro Ser Gly Tyr Tyr Gly
        35                  40                  45
His Arg Ala Pro Asp Met Asn Arg Cys Ala Arg Cys Arg Ile Glu Asn

```
            50                  55                  60
Cys Asp Ser Cys Arg Ser Lys Asp Ala Cys Thr Lys Cys Lys Val Gly
65                  70                  75                  80

Phe Tyr Leu His Arg Gly Arg Cys Phe Asp Glu Cys Pro Asp Gly Phe
                85                  90                  95

Ala Pro Leu Glu Glu Thr Met Glu Cys Val Glu Gly Gly Gly Gly Ser
            100                 105                 110

Gly Gly Gly Gly Ser Gly Gly Gly Ser Asp Ile Val Leu Phe Gln
            115                 120                 125

Ser Pro Ala Ser Leu Ala Val Ser Leu Gly Gln Arg Ala Thr Ile Ser
130                 135                 140

Cys Arg Ala Ser Glu Ser Val Asp Asp Tyr Gly Asn Ser Phe Met His
145                 150                 155                 160

Trp Tyr Gln Gln Lys Pro Gly Gln Pro Pro Lys Leu Leu Ile Tyr Arg
                165                 170                 175

Ala Ser Asn Leu Glu Ser Gly Ile Pro Ala Arg Phe Ser Gly Ser Gly
            180                 185                 190

Ser Arg Thr Asp Phe Thr Leu Thr Ile Asn Pro Val Glu Ala Asp Asp
            195                 200                 205

Val Ala Thr Tyr Tyr Cys Gln Gln Ser Asn Glu Ala Pro Pro Thr Phe
            210                 215                 220

Gly Gly Gly Thr Lys Leu Glu Ile Lys Arg Thr Val Ala Ala Pro Ser
225                 230                 235                 240

Val Phe Ile Phe Pro Pro Ser Asp Glu Gln Leu Lys Ser Gly Thr Ala
                245                 250                 255

Ser Val Val Cys Leu Leu Asn Asn Phe Tyr Pro Arg Glu Ala Lys Val
            260                 265                 270

Gln Trp Lys Val Asp Asn Ala Leu Gln Ser Gly Asn Ser Gln Glu Ser
            275                 280                 285

Val Thr Glu Gln Asp Ser Lys Asp Ser Thr Tyr Ser Leu Ser Ser Thr
            290                 295                 300

Leu Thr Leu Ser Lys Ala Asp Tyr Glu Lys His Lys Val Tyr Ala Cys
305                 310                 315                 320

Glu Val Thr His Gln Gly Leu Ser Ser Pro Val Thr Lys Ser Phe Asn
                325                 330                 335

Arg Gly Glu Cys
            340

<210> SEQ ID NO 49
<211> LENGTH: 1335
<212> TYPE: DNA
<213> ORGANISM: Artificial Sequence
<220> FEATURE:
<223> OTHER INFORMATION: Made in Lab - fusion construct

<400> SEQUENCE: 49
caagtgcaac tccaacaaag cggtcccgag ttggtccgac ccggcgtcag tgtgaaaatc      60
tcatgcaagg ggtccgggta taccttcact gactatgcaa tgcactgggt aaagcagagc     120
cacgccaagt ccttggagtg gatcggaggc attagtacct acttcggacg caccaactac     180
aatcaaaaat ttaagggtcg cgcaaccatg actgtagata atcatcaag taccgcgtac     240 atggaattgg ctagactgac ttctgaagat tccgcgctgt attactgtgc tcgcggtttg     300
tctggcaact atgttatgga ttactggggg caagggacca gcgtcacggt gtcgagtgct     360
agcaccaagg gcccatcggt cttccccctg gcgccctgct ccaggagcac ctccgagagc     420
```

-continued

```
acagcggccc tgggctgcct ggtcaaggac tacttcccg  aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca acttcggcac ccagacctac    600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa aacccaagga caccctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900
gtcagcgtcc tcaccgttgt gcaccaggac tggctgaacg gcaaggagta caagtgcaag    960
gtctccaaca aaggcctccc agcccccatc gagaaaacca tctccaaaac caaagggcag   1020
ccccgagaac cacaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacgcctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaa                                                     1335
```

<210> SEQ ID NO 50
<211> LENGTH: 445
<212> TYPE: PRT
<213> ORGANISM: Artificial Sequence
<220> FEATURE:
<223> OTHER INFORMATION: Made in Lab - fusion construct

<400> SEQUENCE: 50

```
Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Gly Ile Ser Thr Tyr Phe Gly Arg Thr Asn Tyr Asn Gln Lys Phe
    50                  55                  60

Lys Gly Arg Ala Thr Met Thr Val Asp Lys Ser Ser Thr Ala Tyr
65                  70                  75                  80

Met Glu Leu Ala Arg Leu Thr Ser Glu Asp Ser Ala Leu Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 51
<211> LENGTH: 1122
<212> TYPE: DNA
<213> ORGANISM: Artificial Sequence
<220> FEATURE:
<223> OTHER INFORMATION: Made in Lab - fusion construct

<400> SEQUENCE: 51
gaagtgcagc tgctggaatc cggggggcgga ctggtgcaac ccggggggatc cctcagactg      60 tcctgtgccg catcgggttt cactttctcc tcctacgcga tgtcatgggt cagacaggcc     120
cctggaaaag gcctcgaatg ggtgtcggct atctccggat cgggggggatc tacttactac     180 gccgactccg tgaagggccg gttcactatc tcgagggaca actccaagaa tacgctgtac     240
ttgcaaatga actccctgcg cgccgaggat accgcggtgt attactgcgc caaggacttc     300
agctcacgcc ggtggtacct tgagtactgg ggacagggaa cccttgtcac cgtgtccagc     360
ggtggcggcg aagcggcgg gggcggatcc ggtggcgggg gctcagagct cacccaggac     420
cccgctgtgt ccgtggcctt gggacagacc gtgcgcatca catgccaggg cgatagcctg     480
cggagctatt acgcctcgtg gtaccagcag aagcctggtc aagcgccggt cctggtcatc     540 tacgaaaga caaccgcccc gtccggaatt ccagacaggt tcagcggatc cagctcgggg     600
aacaccgcct cactgactat caccggagca caggccgaag atgaagccga ctactactgc     660
```

-continued

```
aactccctgg agcggattgg atacctgagc tacgtgtttg gtggcggcac gaagctcacc      720
gtgctgggaa gcggtggatc aaacccaatt tgcaagggat gcctgagctg tagcaaggac      780
aacggatgtt cacggtgcca gcaaaagctg ttttccttcc tccggcggga aggaatgcgg      840
cagtacggcg aatgtctcca ctcctgcccc tcggggtatt acggacaccg cgcgcctgac      900
atgaaccgat gcgccagatg ccggatcgag aactgcgata gctgccgcag caaggacgcc      960
tgcactaagt gcaaagtcgg cttctacctt caccggggca gatgttttga cgaatgcccg     1020
gatggcttcg ccccgctgga ggagactatg gaatgcgtgg agggcggaga ctacaaggac     1080
gacgatgaca agggctccca ccatcaccac catcatcacc ac                        1122
```

<210> SEQ ID NO 52
<211> LENGTH: 374
<212> TYPE: PRT
<213> ORGANISM: Artificial Sequence
<220> FEATURE:
<223> OTHER INFORMATION: Made in Lab - fusion construct

<400> SEQUENCE: 52

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
        195                 200                 205

Gly Ala Gln Ala Glu Asp Glu Ala Asp Tyr Tyr Cys Asn Ser Leu Glu
    210                 215                 220

Arg Ile Gly Tyr Leu Ser Tyr Val Phe Gly Gly Thr Lys Leu Thr
225                 230                 235                 240

Val Leu Gly Ser Gly Gly Ser Asn Pro Ile Cys Lys Gly Cys Leu Ser
                245                 250                 255

Cys Ser Lys Asp Asn Gly Cys Ser Arg Cys Gln Gln Lys Leu Phe Phe
            260                 265                 270

Phe Leu Arg Arg Glu Gly Met Arg Gln Tyr Gly Glu Cys Leu His Ser
```

-continued

```
                275                 280                 285
Cys Pro Ser Gly Tyr Tyr Gly His Arg Ala Pro Asp Met Asn Arg Cys
    290                 295                 300

Ala Arg Cys Arg Ile Glu Asn Cys Asp Ser Cys Arg Ser Lys Asp Ala
305                 310                 315                 320

Cys Thr Lys Cys Lys Val Gly Phe Tyr Leu His Arg Gly Arg Cys Phe
                325                 330                 335

Asp Glu Cys Pro Asp Gly Phe Ala Pro Leu Glu Glu Thr Met Glu Cys
            340                 345                 350

Val Glu Gly Gly Asp Tyr Lys Asp Asp Asp Lys Gly Ser His His
                355                 360                 365

His His His His His His
    370
```

<210> SEQ ID NO 53
<211> LENGTH: 1119
<212> TYPE: DNA
<213> ORGANISM: Artificial Sequence
<220> FEATURE:
<223> OTHER INFORMATION: Made in Lab - fusion construct

<400> SEQUENCE: 53

```
caggtccagt tggtggaatc cggagggggt ttggtccagc ctggtggaag cctgcgcctc    60
tcatgcgccg ctagcggatt caccttctcc cgatacggca tgcattgggt cagacaggca   120
cccggaaaag gactcgaatg ggtgtcgggc atttcctcga tcgggtcaaa cacctattac   180
gccgactccg tgaagggacg gttcaccatt agccgggata acagcaagaa cactctgtac   240
ttgcaaatga actccctgcg ggctgaggac accgccgtgt actactgtgc gcggtggtac   300
aagacctata ttgacgtctg gggacagggt accctcgtga ccgtgtcatc cggtggtgga   360
ggatccggag gcggaggaag cggaggaggg ggttcagaca tcgaactcac ccagcccccg   420
tcagtgtccg tggcccctgg acagactgcg cgcatctcct gctccggcga caacctgggg   480
aagaaatacg tgtactggta ccagcagaag ccaggtcaag cccctgtgct ggtcatctac   540
ggcgacgacg aaaggccgtc aggcatccca gagcgcttct ccggctccaa ctccgggaat   600
actgccaccc ttaccatttc cggaacccag gccgaggatg aagcggatta ctattgcgcg   660
agctacgata gcagccacat cctgatcgtg tttggaggcg gtactaagct gaccgtgctg   720
ggaagcggtg gatcaaaccc aatttgcaag ggatgcctga gctgtagcaa ggacaacgga   780
tgttcacggt gccagcaaaa gctgtttttc ttcctccggc gggaaggaat gcggcagtac   840
ggcgaatgtc tccactcctg ccctcgggg tattacggac acgaagcgcc tgacatgaac   900
cgatgcgcca gatgccggat cgagaactgc gatagctgcc gcagcaagga cgcctgcact   960
aagtgcaaag tcggcttcta ccttcaccgg ggcagatgtt ttgacgaatg cccggatggc  1020
ttcgccccgc tggaggagac tatggaatgc gtggagggcg agactacaa ggacgacgat  1080
gacaagggct cccaccatca ccaccatcat caccactag                        1119
```

<210> SEQ ID NO 54
<211> LENGTH: 372
<212> TYPE: PRT
<213> ORGANISM: Artificial Sequence
<220> FEATURE:
<223> OTHER INFORMATION: Made in Lab - fusion construct

<400> SEQUENCE: 54

Gln Val Gln Leu Val Glu Ser Gly Gly Gly Leu Val Gln Pro Gly Gly

```
  1               5                    10                   15
Ser Leu Arg Leu Ser Cys Ala Ala Ser Gly Phe Thr Phe Ser Arg Tyr
                 20                  25                  30

Gly Met His Trp Val Arg Gln Ala Pro Gly Lys Gly Leu Glu Trp Val
                 35                  40                  45

Ser Gly Ile Ser Ser Ile Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Tyr Lys Thr Tyr Ile Asp Val Trp Gly Gln Gly Thr Leu
                100                 105                 110

Val Thr Val Ser Ser Gly Gly Gly Gly Ser Gly Gly Gly Ser Gly
                115                 120                 125

Gly Gly Gly Ser Asp Ile Glu Leu Thr Gln Pro Pro Ser Val Ser Val
130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
                180                 185                 190

Phe Ser Gly Ser Asn Ser Gly Asn Thr Ala Thr Leu Thr Ile Ser Gly
                195                 200                 205

Thr Gln Ala Glu Asp Glu Ala Asp Tyr Tyr Cys Ala Ser Tyr Asp Ser
210                 215                 220

Ser His Ile Leu Ile Val Phe Gly Gly Gly Thr Lys Leu Thr Val Leu
225                 230                 235                 240

Gly Ser Gly Gly Ser Asn Pro Ile Cys Lys Gly Cys Leu Ser Cys Ser
                245                 250                 255

Lys Asp Asn Gly Cys Ser Arg Cys Gln Gln Lys Leu Phe Phe Phe Leu
                260                 265                 270

Arg Arg Glu Gly Met Arg Gln Tyr Gly Glu Cys Leu His Ser Cys Pro
                275                 280                 285

Ser Gly Tyr Tyr Gly His Glu Ala Pro Asp Met Asn Arg Cys Ala Arg
                290                 295                 300

Cys Arg Ile Glu Asn Cys Asp Ser Cys Arg Ser Lys Asp Ala Cys Thr
305                 310                 315                 320

Lys Cys Lys Val Gly Phe Tyr Leu His Arg Gly Arg Cys Phe Asp Glu
                325                 330                 335

Cys Pro Asp Gly Phe Ala Pro Leu Glu Glu Thr Met Glu Cys Val Glu
                340                 345                 350

Gly Gly Asp Tyr Lys Asp Asp Asp Lys Gly Ser His His His His
                355                 360                 365

His His His His
    370

<210> SEQ ID NO 55
<211> LENGTH: 1125
<212> TYPE: DNA
<213> ORGANISM: Artificial Sequence
<220> FEATURE:
<223> OTHER INFORMATION: Made in Lab - Fusion construct
```

<400> SEQUENCE: 55

```
gaagtgcagc tgctggaatc cggggcgga ctggtgcaac ccgggggatc cctcagactg    60
tcctgtgccg catcgggttt cactttctcc tcctacgcga tgtcatgggt cagacaggcc   120
cctggaaaag gcctcgaatg ggtgtcggct atctccggat cggggggatc tacttactac   180
gccgactccg tgaagggccg gttcactatc tcgagggaca actccaagaa taccctgtac   240
ttgcaaatga actccctgcg cgccgaggat accgcggtgt attactgcgc aaggacttc    300
agctcacgcc ggtggtacct tgagtactgg ggacaggaa cccttgtcac cgtgtccagc    360
ggtggcggcg aagcggcgg gggcggatcc ggtggcgggg gctcagagct cacccaggac    420
cccgctgtgt ccgtggcctt gggacagacc gtgcgcatca catgccaggg cgatagcctg    480
cggagctatt acgcctcgtg gtaccagcag aagcctggtc aagcgccggt cctggtcatc    540
tacggaaaga caaccgccc gtccggaatt ccagacaggt tcagcggatc cagctcgggg     600
aacaccgcct cactgactat caccggagca caggccaag atgaagccga ctactactgc     660
aactccctgg agcggattgg atacctgagc tacgtgtttg gtggcggcac gaagctcacc    720
gtgctgggaa gcgtggatc aaacccaatt gcaagggat gcctgagctg tagcaaggac    780
aacgatgtt cacggtgcca gcaaaagctg ttttctcc tccggcggga aggaatgcgg      840
cagtacggcg aatgtctcca ctcctgcccc cgggtatt acggacacga agcgcctgac     900
atgaaccgat gcgccagatg ccggatcgag aactgcgata gctgccgcag caaggacgcc    960
tgcactaagt gcaaagtcgg cttctacctt caccggggca gatgttttga cgaatgcccg    1020
gatggcttcg ccccgctgga ggagactatg gaatgcgtgg agggcggaga ctacaaggac   1080
gacgatgaca agggctccca ccatcaccac catcatcacc actag                   1125
```

<210> SEQ ID NO 56
<211> LENGTH: 374
<212> TYPE: PRT
<213> ORGANISM: Artificial Sequence
<220> FEATURE:
<223> OTHER INFORMATION: Made in Lab - fusion construct

<400> SEQUENCE: 56

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160
```

```
Arg Ser Tyr Tyr Ala Ser Trp Tyr Gln Gln Lys Pro Gly Gln Ala Pro
            165                 170                 175

Val Leu Val Ile Tyr Gly Lys Asn Asn Arg Pro Ser Gly Ile Pro Asp
        180                 185                 190

Arg Phe Ser Gly Ser Ser Gly Asn Thr Ala Ser Leu Thr Ile Thr
        195                 200                 205

Gly Ala Gln Ala Glu Asp Glu Ala Asp Tyr Tyr Cys Asn Ser Leu Glu
        210                 215                 220

Arg Ile Gly Tyr Leu Ser Tyr Val Phe Gly Gly Thr Lys Leu Thr
225                 230                 235                 240

Val Leu Gly Ser Gly Ser Asn Pro Ile Cys Lys Gly Cys Leu Ser
            245                 250                 255

Cys Ser Lys Asp Asn Gly Cys Ser Arg Cys Gln Gln Lys Leu Phe Phe
            260                 265                 270

Phe Leu Arg Arg Glu Gly Met Arg Gln Tyr Gly Glu Cys Leu His Ser
        275                 280                 285

Cys Pro Ser Gly Tyr Tyr Gly His Glu Ala Pro Asp Met Asn Arg Cys
        290                 295                 300

Ala Arg Cys Arg Ile Glu Asn Cys Asp Ser Cys Arg Ser Lys Asp Ala
305                 310                 315                 320

Cys Thr Lys Cys Lys Val Gly Phe Tyr Leu His Arg Gly Arg Cys Phe
            325                 330                 335

Asp Glu Cys Pro Asp Gly Phe Ala Pro Leu Glu Glu Thr Met Glu Cys
            340                 345                 350

Val Glu Gly Gly Asp Tyr Lys Asp Asp Asp Lys Gly Ser His His
            355                 360                 365

His His His His His His
        370

<210> SEQ ID NO 57
<211> LENGTH: 1134
<212> TYPE: DNA
<213> ORGANISM: Artificial Sequence
<220> FEATURE:
<223> OTHER INFORMATION: Made in Lab - fusion construct

<400> SEQUENCE: 57
caagtgcaac tccaacaaag cggtcccgag ttggtccgac ccggcgtcag tgtgaaaatc       60
tcatgcaagg ggtccgggta taccttcact gactatgcaa tgcactgggt aaagcagagc      120
cacgccaagt ccttggagtg gatcggaggc attagtacct acttcggacg caccaactac      180
aatcaaaaat ttaagggtcg cgcaaccatg actgtagata atcatcaag taccgcgtac      240 atggaattgg ctagactgac ttctgaagat tccgcgctgt attactgtgc tgcggtttg       300 tctggcaact atgttatgga ttactggggg caagggacca gcgtcacggt gtcctctggc      360
ggaggcgggt ccggggggggg tggttctggc ggaggcggat ccgatatagt tctgtttcaa      420
tcccctgcga gcctggcggt aagtttggga cagagagcca cgatttcctg ccgagcgagt      480
gaaagcgtag acgactacgg caattctttc atgcactggt atcaacagaa gccaggccaa      540
ccgccgaagc tgcttatcta tcgcgcgtcc aatttggagt cagggatccc tgcacgattt      600
tcaggttctg gaagtaggac agactttaca cttacgataa accccgtgga agcggatgac      660
gtcgcaacct actattgtca acaaagcaat gaagcaccac taccttcgg aggtggcact       720 aaattggaaa ttaggggaag cggtggatca aacccaattt gcaagggatg cctgagctgt      780
```

-continued

```
agcaaggaca acggatgttc acggtgccag caaaagctgt ttttcttcct ccggcgggaa      840
ggaatgcggc agtacggcga atgtctccac tcctgcccct cggggtatta cggacacgaa      900
gcgcctgaca tgaaccgatg cgccagatgc cggatcgaga actgcgatag ctgccgcagc      960
aaggacgcct gcactaagtg caaagtcggc ttctaccttc accggggcag atgttttgac     1020
gaatgcccgg atggcttcgc cccgctggag gagactatgg aatgcgtgga gggcggagac     1080
tacaaggacg acgatgacaa gggctcccac catcaccacc atcatcacca ctag           1134
```

<210> SEQ ID NO 58
<211> LENGTH: 377
<212> TYPE: PRT
<213> ORGANISM: Artificial Sequence
<220> FEATURE:
<223> OTHER INFORMATION: Made in Lab - fusion construct

<400> SEQUENCE: 58

```
Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Gly Ile Ser Thr Tyr Phe Gly Arg Thr Asn Tyr Asn Gln Lys Phe
    50                  55                  60

Lys Gly Arg Ala Thr Met Thr Val Asp Lys Ser Ser Thr Ala Tyr
65                  70                  75                  80

Met Glu Leu Ala Arg Leu Thr Ser Glu Asp Ser Ala Leu Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser Gly Gly Gly Ser Gly Gly Gly Gly
        115                 120                 125

Ser Gly Gly Gly Gly Ser Asp Ile Val Leu Phe Gln Ser Pro Ala Ser
    130                 135                 140

Leu Ala Val Ser Leu Gly Gln Arg Ala Thr Ile Ser Cys Arg Ala Ser
145                 150                 155                 160

Glu Ser Val Asp Asp Tyr Gly Asn Ser Phe Met His Trp Tyr Gln Gln
                165                 170                 175

Lys Pro Gly Gln Pro Pro Lys Leu Leu Ile Tyr Arg Ala Ser Asn Leu
            180                 185                 190

Glu Ser Gly Ile Pro Ala Arg Phe Ser Gly Ser Gly Ser Arg Thr Asp
        195                 200                 205

Phe Thr Leu Thr Ile Asn Pro Val Glu Ala Asp Val Ala Thr Tyr
    210                 215                 220

Tyr Cys Gln Gln Ser Asn Glu Ala Pro Pro Thr Phe Gly Gly Gly Thr
225                 230                 235                 240

Lys Leu Glu Ile Arg Gly Ser Gly Gly Ser Asn Pro Ile Cys Lys Gly
                245                 250                 255

Cys Leu Ser Cys Ser Lys Asp Asn Gly Cys Ser Arg Cys Gln Gln Lys
            260                 265                 270

Leu Phe Phe Phe Leu Arg Arg Glu Gly Met Arg Gln Tyr Gly Glu Cys
        275                 280                 285

Leu His Ser Cys Pro Ser Gly Tyr Tyr Gly His Glu Ala Pro Asp Met
    290                 295                 300
```

Asn Arg Cys Ala Arg Cys Arg Ile Glu Asn Cys Asp Ser Cys Arg Ser
305                 310                 315                 320

Lys Asp Ala Cys Thr Lys Cys Lys Val Gly Phe Tyr Leu His Arg Gly
            325                 330                 335

Arg Cys Phe Asp Glu Cys Pro Asp Gly Phe Ala Pro Leu Glu Glu Thr
                340                 345                 350

Met Glu Cys Val Glu Gly Gly Asp Tyr Lys Asp Asp Asp Asp Lys Gly
        355                 360                 365

Ser His His His His His His His
    370                 375

<210> SEQ ID NO 59
<211> LENGTH: 1119
<212> TYPE: DNA
<213> ORGANISM: Artificial Sequence
<220> FEATURE:
<223> OTHER INFORMATION: Made in Lab - Fusion construct

<400> SEQUENCE: 59
caggtccagt tggtggaatc cggagggggt tggtccagc ctggtggaag cctgcgcctc    60
tcatgcgccg ctagcggatt caccttctcc cgatacggca tgcattgggt cagacaggca   120
cccggaaaag gactcgaatg ggtgtcgggc atttcctcga tcgggtcaaa cacctattac   180
gccgactccg tgaagggacg gttcaccatt agcgggata cagcaagaa cactctgtac   240 ttgcaaatga actccctgcg gctgaggac accgccgtgt actactgtgc gcggtggtac   300
aagacctata ttgacgtctg gggacagggt accctcgtga ccgtgtcatc cggtggtgga   360
ggatccggag gcggaggaag cggaggaggg ggttcagaca tcgaactcac ccagccccg   420 tcagtgtccg tggcccctgg acagactgcg cgcatctcct gctccggcga caacctgggg   480
aagaaatacg tgtactggta ccagcagaag ccaggtcaag cccctgtgct ggtcatctac   540
ggcgacgacg aaaggccgtc aggcatccca gagcgcttct ccggctccaa ctccgggaat   600
actgccaccc ttaccatttc cggaacccag gccgaggatg aagcggatta ctattgcgcg   660
agctacgata gcagccacat cctgatcgtg tttggaggcg gtactaagct gaccgtgctg   720
ggaagcggtg gatcaaaccc aatttgcaag ggatgcctga ctgtagcaa ggacaacgga   780 tgttcacggt gccagcaaaa gctgtttttc ttcctccggc gggaaggaat gcggcagtac   840
ggcgaatgtc tccactcctg cccctcgggg tattacggac acgaagcgcc tgacatgaac   900
cgatgcgcca atgccggat cgagaactgc gatagctgcc gcagcaagga cgcctgcact   960
aagtgcaaag tcggcttcta ccttcacgaa ggcagatgtt ttgacgaatg cccggatggc  1020
ttcgccccgc tggaggagac tatggaatgc gtggagggcg agactacaa ggacgacgat  1080 gacaagggct cccaccatca ccaccatcat caccactag                        1119

<210> SEQ ID NO 60
<211> LENGTH: 372
<212> TYPE: PRT
<213> ORGANISM: Artificial Sequence
<220> FEATURE:
<223> OTHER INFORMATION: Made in Lab - fusion construct

<400> SEQUENCE: 60

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
         35                  40                  45

Ser Gly Ile Ser Ser Ile Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Tyr Lys Thr Tyr Ile Asp Val Trp Gly Gln Gly Thr Leu
             100                 105                 110

Val Thr Val Ser Ser Gly Gly Gly Ser Gly Gly Gly Ser Gly
             115                 120                 125

Gly Gly Gly Ser Asp Ile Glu Leu Thr Gln Pro Pro Ser Val Ser Val
130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                 165                 170                 175

Leu Val Ile Tyr Gly Asp Asp Glu Arg Pro Ser Gly Ile Pro Glu Arg
             180                 185                 190

Phe Ser Gly Ser Asn Ser Gly Asn Thr Ala Thr Leu Thr Ile Ser Gly
         195                 200                 205

Thr Gln Ala Glu Asp Glu Ala Asp Tyr Tyr Cys Ala Ser Tyr Asp Ser
     210                 215                 220

Ser His Ile Leu Ile Val Phe Gly Gly Gly Thr Lys Leu Thr Val Leu
225                 230                 235                 240

Gly Ser Gly Gly Ser Asn Pro Ile Cys Lys Gly Cys Leu Ser Cys Ser
                 245                 250                 255

Lys Asp Asn Gly Cys Ser Arg Cys Gln Gln Lys Leu Phe Phe Phe Leu
             260                 265                 270

Arg Arg Glu Gly Met Arg Gln Tyr Gly Glu Cys Leu His Ser Cys Pro
         275                 280                 285

Ser Gly Tyr Tyr Gly His Glu Ala Pro Asp Met Asn Arg Cys Ala Arg
290                 295                 300

Cys Arg Ile Glu Asn Cys Asp Ser Cys Arg Ser Lys Asp Ala Cys Thr
305                 310                 315                 320

Lys Cys Lys Val Gly Phe Tyr Leu His Glu Gly Arg Cys Phe Asp Glu
                 325                 330                 335

Cys Pro Asp Gly Phe Ala Pro Leu Glu Glu Thr Met Glu Cys Val Glu
             340                 345                 350

Gly Gly Asp Tyr Lys Asp Asp Asp Lys Gly Ser His His His His
         355                 360                 365

His His His His
     370

<210> SEQ ID NO 61
<211> LENGTH: 1125
<212> TYPE: DNA
<213> ORGANISM: Artificial Sequence
<220> FEATURE:
<223> OTHER INFORMATION: Made in Lab - fusion construct

<400> SEQUENCE: 61
gaagtgcagc tgctggaatc cggggggcgga ctggtgcaac cgggggggatc cctcagactg      60 tcctgtgccg catcgggttt cactttctcc tcctacgcga tgtcatgggt cagacaggcc     120

```
cctggaaaag gcctcgaatg ggtgtcggct atctccggat cggggggatc tacttactac    180
gccgactccg tgaagggccg gttcactatc tcgaggaca actccaagaa tacccctgtac   240
ttgcaaatga actccctgcg cgccgaggat accgcggtgt attactgcgc caaggacttc   300
agctcacgcc ggtggtacct tgagtactgg ggacaggga ccttgtcac cgtgtccagc    360
ggtggcggcg aagcggcgg gggcggatcc ggtggcgggg gctcagagct cacccaggac    420
cccgctgtgt ccgtggcctt gggacagacc gtgcgcatca catgccaggg cgatagcctg   480
cggagctatt acgcctcgtg gtaccagcag aagcctggtc aagcgccggt cctggtcatc   540
tacgaaaga caaccgccc gtccggaatt ccagacaggt tcagcggatc cagctcgggg    600
aacaccgcct cactgactat caccggagca caggccgaag atgaagccga ctactactgc   660
aactccctgg agcggattgg atacctgagc tacgtgtttg gtggcggcac gaagctcacc   720
gtgctgggaa gcggtggatc aaacccaatt tgcaagggat gcctgagctg tagcaaggac   780
aacgatgtt cacggtgcca gcaaaagctg ttttcttcc tccggcggga aggaatgcgg    840
cagtacggcg aatgtctcca ctcctgcccc tcggggtatt acggacacga agcgcctgac   900
atgaaccgat gcgccagatg ccggatcgag aactgcgata gctgccgcag caaggacgcc   960
tgcactaagt gcaaagtcgg cttctacctt cacgaaggca gatgttttga cgaatgcccg  1020
gatggcttcg ccccgctgga ggagactatg gaatgcgtgg agggcggaga ctacaaggac  1080
gacgatgaca agggctccca ccatcaccac catcatcacc actag              1125
```

<210> SEQ ID NO 62
<211> LENGTH: 374
<212> TYPE: PRT
<213> ORGANISM: Artificial Sequence
<220> FEATURE:
<223> OTHER INFORMATION: Made in Lab - fusion construct

<400> SEQUENCE: 62

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
```

```
                    180                 185                 190
Arg Phe Ser Gly Ser Ser Ser Gly Asn Thr Ala Ser Leu Thr Ile Thr
            195                 200                 205

Gly Ala Gln Ala Glu Asp Glu Ala Asp Tyr Tyr Cys Asn Ser Leu Glu
        210                 215                 220

Arg Ile Gly Tyr Leu Ser Tyr Val Phe Gly Gly Thr Lys Leu Thr
225                 230                 235                 240

Val Leu Gly Ser Gly Gly Ser Asn Pro Ile Cys Lys Gly Cys Leu Ser
                245                 250                 255

Cys Ser Lys Asp Asn Gly Cys Ser Arg Cys Gln Gln Lys Leu Phe Phe
            260                 265                 270

Phe Leu Arg Arg Glu Gly Met Arg Gln Tyr Gly Glu Cys Leu His Ser
        275                 280                 285

Cys Pro Ser Gly Tyr Tyr Gly His Glu Ala Pro Asp Met Asn Arg Cys
    290                 295                 300

Ala Arg Cys Arg Ile Glu Asn Cys Asp Ser Cys Arg Ser Lys Asp Ala
305                 310                 315                 320

Cys Thr Lys Cys Lys Val Gly Phe Tyr Leu His Glu Gly Arg Cys Phe
                325                 330                 335

Asp Glu Cys Pro Asp Gly Phe Ala Pro Leu Glu Glu Thr Met Glu Cys
            340                 345                 350

Val Glu Gly Gly Asp Tyr Lys Asp Asp Asp Lys Gly Ser His His
        355                 360                 365

His His His His His His
        370

<210> SEQ ID NO 63
<211> LENGTH: 1134
<212> TYPE: DNA
<213> ORGANISM: Artificial Sequence
<220> FEATURE:
<223> OTHER INFORMATION: Made in Lab - fusion construct

<400> SEQUENCE: 63
caagtgcaac tccaacaaag cggtcccgag ttggtccgac ccggcgtcag tgtgaaaatc     60
tcatgcaagg ggtccgggta taccttcact gactatgcaa tgcactgggt aaagcagagc    120
cacgccaagt ccttggagtg gatcggaggc attagtacct acttcggacg caccaactac    180
aatcaaaaat ttaagggtcg cgcaaccatg actgtagata atcatcaag taccgcgtac    240 atggaattgg ctagactgac ttctgaagat tccgcgctgt attactgtgc tcgcggtttg    300
tctggcaact atgttatgga ttactgggg caagggacca gcgtcacggt gtcctctggc    360
ggaggcgggt ccgggggggg tggttctggc ggaggcggat ccgatatagt tctgtttcaa    420
tcccctgcga gcctggcggt aagtttggga cagagagcca cgatttcctg ccgagcgagt    480
gaaagcgtag acgactacgg caattctttc atgcactggt atcaacagaa gccaggccaa    540
ccgccgaagc tgcttatcta tcgcgcgtcc aatttggagt cagggatccc tgcacgattt    600
tcaggttctg gaagtaggac agactttaca cttacgataa accccgtgga agcggatgac    660
gtcgcaacct actattgtca acaaagcaat gaagcaccac ctaccttcgg aggtggcact    720
aaattggaaa ttaggggaag cggtggatca aacccaattt gcaagggatg cctgagctgt    780
agcaaggaca acggatgttc acggtgccag caaaagctgt tttcttcct ccggcgggaa    840 ggaatgcggc agtacggcga atgtctccac tcctgccct cggggtatta cggacacgaa    900
gcgcctgaca tgaaccgatg cgccagatgc cggatcgaga actgcgatag ctgccgcagc    960
```

```
aaggacgcct gcactaagtg caaagtcggc ttctaccttc acgaaggcag atgttttgac    1020
gaatgcccgg atggcttcgc cccgctggag gagactatgg aatgcgtgga gggcggagac    1080
tacaaggacg acgatgacaa gggctcccac catcaccacc atcatcacca ctag          1134
```

<210> SEQ ID NO 64
<211> LENGTH: 377
<212> TYPE: PRT
<213> ORGANISM: Artificial Sequence
<220> FEATURE:
<223> OTHER INFORMATION: Made in Lab - fusion construct

<400> SEQUENCE: 64

```
Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Gly Ile Ser Thr Tyr Phe Gly Arg Thr Asn Tyr Asn Gln Lys Phe
    50                  55                  60

Lys Gly Arg Ala Thr Met Thr Val Asp Lys Ser Ser Thr Ala Tyr
65                  70                  75                  80

Met Glu Leu Ala Arg Leu Thr Ser Glu Asp Ser Ala Leu Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser Gly Gly Gly Ser Gly Gly Gly Gly
        115                 120                 125

Ser Gly Gly Gly Gly Ser Asp Ile Val Leu Phe Gln Ser Pro Ala Ser
    130                 135                 140

Leu Ala Val Ser Leu Gly Gln Arg Ala Thr Ile Ser Cys Arg Ala Ser
145                 150                 155                 160

Glu Ser Val Asp Asp Tyr Gly Asn Ser Phe Met His Trp Tyr Gln Gln
                165                 170                 175

Lys Pro Gly Gln Pro Pro Lys Leu Leu Ile Tyr Arg Ala Ser Asn Leu
            180                 185                 190

Glu Ser Gly Ile Pro Ala Arg Phe Ser Gly Ser Gly Ser Arg Thr Asp
        195                 200                 205

Phe Thr Leu Thr Ile Asn Pro Val Glu Ala Asp Asp Val Ala Thr Tyr
    210                 215                 220

Tyr Cys Gln Gln Ser Asn Glu Ala Pro Pro Thr Phe Gly Gly Gly Thr
225                 230                 235                 240

Lys Leu Glu Ile Arg Gly Ser Gly Gly Ser Asn Pro Ile Cys Lys Gly
                245                 250                 255

Cys Leu Ser Cys Ser Lys Asp Asn Gly Cys Ser Arg Cys Gln Gln Lys
            260                 265                 270

Leu Phe Phe Phe Leu Arg Arg Glu Gly Met Arg Gln Tyr Gly Glu Cys
        275                 280                 285

Leu His Ser Cys Pro Ser Gly Tyr Tyr Gly His Glu Ala Pro Asp Met
    290                 295                 300

Asn Arg Cys Ala Arg Cys Arg Ile Glu Asn Cys Asp Ser Cys Arg Ser
305                 310                 315                 320

Lys Asp Ala Cys Thr Lys Cys Lys Val Gly Phe Tyr Leu His Glu Gly
                325                 330                 335
```

```
Arg Cys Phe Asp Glu Cys Pro Asp Gly Phe Ala Pro Leu Glu Glu Thr
            340                 345                 350

Met Glu Cys Val Glu Gly Gly Asp Tyr Lys Asp Asp Asp Lys Gly
            355                 360                 365

Ser His His His His His His His
            370                 375

<210> SEQ ID NO 65
<211> LENGTH: 1119
<212> TYPE: DNA
<213> ORGANISM: Artificial Sequence
<220> FEATURE:
<223> OTHER INFORMATION: Made in Lab - fusion construct

<400> SEQUENCE: 65
caggtccagt tggtggaatc cggagggggt tggtccagc  ctggtggaag cctgcgcctc        60
tcatgcgccg ctagcggatt caccttctcc cgatacggca tgcattgggt cagacaggca       120
cccggaaaag gactcgaatg ggtgtcgggc atttcctcga tcgggtcaaa cacctattac       180
gccgactccg tgaagggacg gttcaccatt agccgggata acagcaagaa cactctgtac       240
ttgcaaatga actccctgcg ggctgaggac accgccgtgt actactgtgc gcggtggtac       300
aagacctata ttgacgtctg gggacagggt accctcgtga ccgtgtcatc cggtggtgga       360
ggatccggag gcggaggaag cggaggaggg ggttcagaca tcgaactcac ccagcccccg       420
tcagtgtccg tggcccctgg acagactgcg cgcatctcct gctccggcga caacctgggg       480
aagaaatacg tgtactggta ccagcagaag ccaggtcaag cccctgtgct ggtcatctac       540
ggcgacgacg aaaggccgtc aggcatccca gagcgcttct ccggctccaa ctccgggaat       600
actgccaccc ttaccatttc cggaacccag gccgaggatg aagcggatta ctattgcgcg       660
agctacgata gcagccacat cctgatcgtg tttggaggcg gtactaagct gaccgtgctg       720
ggaagcggtg gatcaaaccc aatttgcaag ggatgcctga ctgtagcaa  ggacaacgga       780
tgttcacggt gccagcaaga gctgttttc  ttcctccggc gggaaggaat gcggcagtac       840
ggcgaatgtc tccactcctg cccctcgggg tattacggac acgaagcgcc tgacatgaac       900
cgatgcgcca atgccggat  cgagaactgc gatagctgcc gcagcaagga cgcctgcact       960
aagtgcaaag tcggcttcta ccttcacgaa ggcagatgtt ttgacgaatg cccggatggc      1020
ttcgccccgc tggaggagac tatggaatgc gtggagggcg gagactacaa ggacgacgat      1080
gacaagggct cccaccatca ccaccatcat caccactag                             1119

<210> SEQ ID NO 66
<211> LENGTH: 372
<212> TYPE: PRT
<213> ORGANISM: Artificial Sequence
<220> FEATURE:
<223> OTHER INFORMATION: Made in Lab - fusion construct

<400> SEQUENCE: 66

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60
```

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240

Gly Ser Gly Gly Ser Asn Pro Ile Cys Lys Gly Cys Leu Ser Cys Ser
                245                 250                 255

Lys Asp Asn Gly Cys Ser Arg Cys Gln Gln Leu Phe Phe Leu
            260                 265                 270

Arg Arg Glu Gly Met Arg Gln Tyr Gly Glu Cys Leu His Ser Cys Pro
        275                 280                 285

Ser Gly Tyr Tyr Gly His Glu Ala Pro Asp Met Asn Arg Cys Ala Arg
    290                 295                 300

Cys Arg Ile Glu Asn Cys Asp Ser Cys Arg Ser Lys Asp Ala Cys Thr
305                 310                 315                 320

Lys Cys Lys Val Gly Phe Tyr Leu His Glu Gly Arg Cys Phe Asp Glu
                325                 330                 335

Cys Pro Asp Gly Phe Ala Pro Leu Glu Glu Thr Met Glu Cys Val Glu
            340                 345                 350

Gly Gly Asp Tyr Lys Asp Asp Asp Lys Gly Ser His His His His
        355                 360                 365

His His His His
    370

<210> SEQ ID NO 67
<211> LENGTH: 1125
<212> TYPE: DNA
<213> ORGANISM: Artificial Sequence
<220> FEATURE:
<223> OTHER INFORMATION: Made in Lab - Fusion construct

<400> SEQUENCE: 67
gaagtgcagc tgctggaatc cggggcgga ctggtgcaac cgggggatc cctcagactg      60 tcctgtgccg catcgggttt cactttctcc tcctacgcga tgtcatgggt cagacaggcc     120
cctggaaaag gcctcgaatg ggtgtcggct atctccggat cggggggatc tacttactac     180
gccgactccg tgaagggccg gttcactatc tcgagggaca actccaagaa taccctgtac     240

```
ttgcaaatga actccctgcg cgccgaggat accgcggtgt attactgcgc caaggacttc      300
agctcacgcc ggtggtacct tgagtactgg ggacagggaa cccttgtcac cgtgtccagc      360
ggtggcggcg gaagcggcgg gggcggatcc ggtggcgggg gctcagagct cacccaggac      420
cccgctgtgt ccgtggcctt gggacagacc gtgcgcatca catgccaggg cgatagcctg      480
cggagctatt acgcctcgtg gtaccagcag aagcctggtc aagcgccggt cctggtcatc      540
tacggaaaga acaaccgccc gtccggaatt ccagacaggt tcagcggatc cagctcgggg      600
aacaccgcct cactgactat caccggagca caggccgaag atgaagccga ctactactgc      660
aactccctgg agcggattgg atacctgagc tacgtgtttg gtggcggcac gaagctcacc      720
gtgctgggaa gcggtggatc aaacccaatt tgcaaggat gcctgagctg tagcaaggac      780 aacgatgtt cacggtgcca gcaagagctg ttttcttcc tccggcggga aggaatgcgg      840
cagtacggcg aatgtctcca ctcctgcccc tcggggtatt acgacacga agcgcctgac      900 atgaaccgat cgccagatg ccggatcgag aactgcgata gctgccgcag caaggacgcc      960
tgcactaagt gcaaagtcgg cttctacctt cacgaaggca atgttttga cgaatgcccg     1020 gatggcttcg ccccgctgga ggagactatg gaatgcgtgg agggcggaga ctacaaggac     1080
gacgatgaca agggctccca ccatcaccac catcatcacc actag                      1125
```

<210> SEQ ID NO 68
<211> LENGTH: 374
<212> TYPE: PRT
<213> ORGANISM: Artificial Sequence
<220> FEATURE:
<223> OTHER INFORMATION: Made in Lab - fusion construct

<400> SEQUENCE: 68

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Arg Arg Trp Tyr Leu Glu Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
        195                 200                 205
```

Gly Ala Gln Ala Glu Asp Glu Ala Asp Tyr Tyr Cys Asn Ser Leu Glu
210                 215                 220

Arg Ile Gly Tyr Leu Ser Tyr Val Phe Gly Gly Thr Lys Leu Thr
225                 230                 235                 240

Val Leu Gly Ser Gly Ser Asn Pro Ile Cys Lys Gly Cys Leu Ser
            245                 250                 255

Cys Ser Lys Asp Asn Gly Cys Ser Arg Cys Gln Gln Glu Leu Phe Phe
            260                 265                 270

Phe Leu Arg Arg Glu Gly Met Arg Gln Tyr Gly Glu Cys Leu His Ser
            275                 280                 285

Cys Pro Ser Gly Tyr Tyr Gly His Glu Ala Pro Asp Met Asn Arg Cys
    290                 295                 300

Ala Arg Cys Arg Ile Glu Asn Cys Asp Ser Cys Arg Ser Lys Asp Ala
305                 310                 315                 320

Cys Thr Lys Cys Lys Val Gly Phe Tyr Leu His Glu Gly Arg Cys Phe
            325                 330                 335

Asp Glu Cys Pro Asp Gly Phe Ala Pro Leu Glu Glu Thr Met Glu Cys
            340                 345                 350

Val Glu Gly Gly Asp Tyr Lys Asp Asp Asp Asp Lys Gly Ser His His
            355                 360                 365

His His His His His His
        370

<210> SEQ ID NO 69
<211> LENGTH: 1134
<212> TYPE: DNA
<213> ORGANISM: Artificial Sequence
<220> FEATURE:
<223> OTHER INFORMATION: Made in Lab - fusion construct

<400> SEQUENCE: 69
caagtgcaac tccaacaaag cggtcccgag ttggtccgac ccggcgtcag tgtgaaaatc        60
tcatgcaagg ggtccgggta taccttcact gactatgcaa tgcactgggt aaagcagagc      120
cacgccaagt ccttggagtg gatcggaggc attagtacct acttcggacg caccaactac      180
aatcaaaaat ttaagggtcg cgcaaccatg actgtagata atcatcaag taccgcgtac       240 atggaattgg ctagactgac ttctgaagat tccgcgctgt attactgtgc tcgcggtttg      300
tctggcaact atgttatgga ttactggggg caagggacca gcgtcacggt gtcctctggc      360
ggaggcgggt ccgggggggg tggttctggc ggaggcggat ccgatatagt tctgttccaa      420
tcccctgcga gcctggcggt aagtttggga cagagagcca cgatttcctg ccgagcgagt      480
gaaagcgtag acgactacgg caattctttc atgcactggt atcaacagaa gccaggccaa      540
ccgccgaagc tgcttatcta tcgcgcgtcc aatttggagt cagggatccc tgcacgattt      600
tcaggttctg gaagtaggac agactttaca cttacgataa accccgtgga agcggatgac      660
gtcgcaacct actattgtca acaaagcaat gaagcaccac ctaccttcgg aggtggcact      720
aaaattggaa attaggggaag cggtggatca aacccaattt gcaagggatg cctgagctgt      780
agcaaggaca acggatgttc acggtgccag caagagctgt tttcttcct ccggcgggaa      840 ggaatgcggc agtacggcga atgtctccac tcctgcccct cggggtatta cggacacgaa      900
gcgcctgaca tgaaccgatg cgccagatgc cggatcgaga actgcgatag ctgccgcagc      960
aaggacgcct gcactaagtg caaagtcggc ttctaccttc acgaaggcag atgttttgac     1020
gaatgcccgg atggcttcgc cccgctggag gagactatgg aatgcgtgga gggcggagac     1080
tacaaggacg acgatgacaa gggctcccac catcaccacc atcatcacca ctag       1134

<210> SEQ ID NO 70
<211> LENGTH: 377
<212> TYPE: PRT
<213> ORGANISM: Artificial Sequence
<220> FEATURE:
<223> OTHER INFORMATION: Made in Lab - fusion construct

<400> SEQUENCE: 70

```
Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Gly Ile Ser Thr Tyr Phe Gly Arg Thr Asn Tyr Asn Gln Lys Phe
    50                  55                  60

Lys Gly Arg Ala Thr Met Thr Val Asp Lys Ser Ser Thr Ala Tyr
65                  70                  75                  80

Met Glu Leu Ala Arg Leu Thr Ser Glu Asp Ser Ala Leu Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser Gly Gly Gly Ser Gly Gly Gly
        115                 120                 125

Ser Gly Gly Gly Ser Asp Ile Val Leu Phe Gln Ser Pro Ala Ser
130                 135                 140

Leu Ala Val Ser Leu Gly Gln Arg Ala Thr Ile Ser Cys Arg Ala Ser
145                 150                 155                 160

Glu Ser Val Asp Asp Tyr Gly Asn Ser Phe Met His Trp Tyr Gln Gln
                165                 170                 175

Lys Pro Gly Gln Pro Pro Lys Leu Leu Ile Tyr Arg Ala Ser Asn Leu
            180                 185                 190

Glu Ser Gly Ile Pro Ala Arg Phe Ser Gly Ser Gly Ser Arg Thr Asp
        195                 200                 205

Phe Thr Leu Thr Ile Asn Pro Val Glu Ala Asp Val Ala Thr Tyr
210                 215                 220

Tyr Cys Gln Gln Ser Asn Glu Ala Pro Pro Thr Phe Gly Gly Gly Thr
225                 230                 235                 240

Lys Leu Glu Ile Arg Gly Ser Gly Gly Ser Asn Pro Ile Cys Lys Gly
                245                 250                 255

Cys Leu Ser Cys Ser Lys Asp Asn Gly Cys Ser Arg Cys Gln Gln Glu
            260                 265                 270

Leu Phe Phe Phe Leu Arg Arg Glu Gly Met Arg Gln Tyr Gly Glu Cys
        275                 280                 285

Leu His Ser Cys Pro Ser Gly Tyr Tyr Gly His Glu Ala Pro Asp Met
    290                 295                 300

Asn Arg Cys Ala Arg Cys Arg Ile Glu Asn Cys Asp Ser Cys Arg Ser
305                 310                 315                 320

Lys Asp Ala Cys Thr Lys Cys Lys Val Gly Phe Tyr Leu His Glu Gly
                325                 330                 335

Arg Cys Phe Asp Glu Cys Pro Asp Gly Phe Ala Pro Leu Glu Glu Thr
            340                 345                 350

Met Glu Cys Val Glu Gly Gly Asp Tyr Lys Asp Asp Asp Lys Gly
```

```
                355                 360                 365
Ser His His His His His His His
    370                 375

<210> SEQ ID NO 71
<211> LENGTH: 645
<212> TYPE: DNA
<213> ORGANISM: Artificial Sequence
<220> FEATURE:
<223> OTHER INFORMATION: Made in Lab

<400> SEQUENCE: 71
gacatcgagc tcacccagga ccccgctgtg tccgtggcct tgggacagac cgtgcgcatc      60
acatgccagg gcgatagcct gcggagctat tacgcctcgt ggtaccagca gaagcctggt     120
caagcgccgg tcctggtcat ctacggaaag aacaaccgcc cgtccggaat tccagacagg     180
ttcagcggat ccagctcggg gaacaccgcc tcactgacta tcaccggagc acaggccgaa     240
gatgaagccg actactactg caactccctg gagcggattg gatacctgag ctacgtgttt     300
ggtggcggta ccaagcttac cgtcctaggt cagcccaagg ctgcccccct ggtcactctg     360
ttcccgccct cctctgagga gcttcaagcc aacaaggcca cactggtgtg tctcataagt     420
gacttctacc cgggagccgt gacagtggcc tggaaggcag atagcagccc cgtcaaggcg     480
ggagtggaga ccaccacacc ctccaaacaa agcaacaaca gtacgcggc cagcagctat      540 ctgagcctga cgcctgagca gtggaagtcc cacagaagct acagctgcca ggtcacgcat     600
gaagggagca ccgtggagaa gacagtggcc cctacagaat gttca                    645

<210> SEQ ID NO 72
<211> LENGTH: 215
<212> TYPE: PRT
<213> ORGANISM: Artificial Sequence
<220> FEATURE:
<223> OTHER INFORMATION: Made in Lab

<400> SEQUENCE: 72

Asp Ile Glu Leu Thr Gln Asp Pro Ala Val Ser Val Ala Leu Gly Gln
1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Leu Glu Arg Ile Gly Tyr Leu
                85                  90                  95

Ser Tyr Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175
```

```
Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 73
<211> LENGTH: 1707
<212> TYPE: DNA
<213> ORGANISM: Artificial Sequence
<220> FEATURE:
<223> OTHER INFORMATION: Made in Lab

<400> SEQUENCE: 73
```

| | | | | | |
|---|---|---|---|---|---|
| aacccaattt | gcaagggatg | cctgagctgt | agcaaggaca | acggatgttc | acggtgccag | 60 |
| caaaagctgt | ttttcttcct | ccggcgggaa | ggaatgcggc | agtacggcga | atgtctccac | 120 |
| tcctgcccct | cggggtatta | cggacaccgc | gcgcctgaca | tgaaccgatg | cgccagatgc | 180 |
| cggatcgaga | actgcgatag | ctgccgcagc | aaggacgcct | gcactaagtg | caaagtcggc | 240 |
| ttctaccttc | accggggcag | atgttttgac | gaatgcccgg | atggcttcgc | ccgctggag | 300 |
| gagactatgg | aatgcgtgga | gggtggtggt | ggctcgggag | gaggaggctc | cggtggcggt | 360 |
| ggcagcgaag | tgcagctgct | ggaatccggg | gcggactgg | tgcaacccgg | ggatccctc | 420 |
| agactgtcct | gtgccgcatc | gggtttcact | ttctcctcct | acgcgatgtc | atgggtcaga | 480 |
| caggcccctg | gaaaaggcct | cgaatgggtg | tcggctatct | ccggatcggg | gggatctact | 540 |
| tactacgccg | actccgtgaa | gggccggttc | actatctcga | gggacaactc | caagaatacc | 600 |
| ctgtacttgc | aaatgaactc | cctgcgcgcc | gaggataccg | cggtgtatta | ctgcgccaag | 660 |
| gacttcagct | cacgccggtg | gtaccttgag | tactggggac | agggaaccct | tgtcaccgtg | 720 |
| tcgagtgcta | gcaccaaggg | cccatcggtc | ttccccctgg | cgccctgctc | caggagcacc | 780 |
| tccgagagca | cagcggccct | gggctgcctg | gtcaaggact | acttccccga | accggtgacg | 840 |
| gtgtcgtgga | actcaggcgc | tctgaccagc | ggcgtgcaca | ccttcccagc | tgtcctacag | 900 |
| tcctcaggac | tctactccct | cagcagcgtg | gtgaccgtgc | cctccagcaa | cttcggcacc | 960 |
| cagacctaca | cctgcaacgt | agatcacaag | cccagcaaca | ccaaggtgga | caagacagtt | 1020 |
| gagcgcaaat | gttgtgtcga | gtgcccaccg | tgcccagcac | cacctgtggc | aggaccgtca | 1080 |
| gtcttcctct | tccccccaaa | acccaaggac | accctcatga | tctcccggac | ccctgaggtc | 1140 |
| acgtgcgtgg | tggtggacgt | gagccacgaa | gaccccgagg | tccagttcaa | ctggtacgtg | 1200 |
| gacggcgtgg | aggtgcataa | tgccaagaca | aagccacggg | aggagcagtt | caacagcacg | 1260 |
| ttccgtgtgg | tcagcgtcct | caccgttgtg | caccaggact | ggctgaacgg | caaggagtac | 1320 |
| aagtgcaagg | tctccaacaa | aggcctccca | gcccccatcg | agaaaaccat | ctccaaaacc | 1380 |
| aaagggcagc | cccgagaacc | acaggtgtac | accctgcccc | catcccggga | ggagatgacc | 1440 |
| aagaaccagg | tcagcctgac | ctgcctggtc | aaaggcttct | accccagcga | catcgccgtg | 1500 |
| gagtgggaga | gcaatgggca | gccggagaac | aactacaaga | ccacgcctcc | catgctggac | 1560 |
| tccgacggct | ccttcttcct | ctacagcaag | ctcaccgtgg | acaagagcag | gtggcagcag | 1620 |
| gggaacgtct | tctcatgctc | cgtgatgcat | gaggctctgc | acaaccacta | cacgcagaag | 1680 |
| agcctctccc | tgtctccggg | taaatga | | | | 1707 |

-continued

```
<210> SEQ ID NO 74
<211> LENGTH: 568
<212> TYPE: PRT
<213> ORGANISM: Artificial Sequence
<220> FEATURE:
<223> OTHER INFORMATION: Made in Lab

<400> SEQUENCE: 74

Asn Pro Ile Cys Lys Gly Cys Leu Ser Cys Ser Lys Asp Asn Gly Cys
1               5                   10                  15

Ser Arg Cys Gln Gln Lys Leu Phe Phe Leu Arg Arg Glu Gly Met
            20                  25                  30

Arg Gln Tyr Gly Glu Cys Leu His Ser Cys Pro Ser Gly Tyr Tyr Gly
        35                  40                  45

His Arg Ala Pro Asp Met Asn Arg Cys Ala Arg Cys Arg Ile Glu Asn
    50                  55                  60

Cys Asp Ser Cys Arg Ser Lys Asp Ala Cys Thr Lys Cys Lys Val Gly
65                  70                  75                  80

Phe Tyr Leu His Arg Gly Arg Cys Phe Asp Glu Cys Pro Asp Gly Phe
                85                  90                  95

Ala Pro Leu Glu Glu Thr Met Glu Cys Val Glu Gly Gly Gly Ser
            100                 105                 110

Gly Gly Gly Gly Ser Gly Gly Gly Ser Glu Val Gln Leu Leu Glu
        115                 120                 125

Ser Gly Gly Gly Leu Val Gln Pro Gly Gly Ser Leu Arg Leu Ser Cys
130                 135                 140

Ala Ala Ser Gly Phe Thr Phe Ser Ser Tyr Ala Met Ser Trp Val Arg
145                 150                 155                 160

Gln Ala Pro Gly Lys Gly Leu Glu Trp Val Ser Ala Ile Ser Gly Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Lys Asp Phe Ser Ser
    210                 215                 220

Arg Arg Trp Tyr Leu Glu Tyr Trp Gly Gln Gly Thr Leu Val Thr Val
225                 230                 235                 240

Ser Ser Ala Ser Thr Lys Gly Pro Ser Val Phe Pro Leu Ala Pro Cys
                245                 250                 255

Ser Arg Ser Thr Ser Glu Ser Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Asn Phe Gly Thr
305                 310                 315                 320

Gln Thr Tyr Thr Cys Asn Val Asp His Lys Pro Ser Asn Thr Lys Val
                325                 330                 335

Asp Lys Thr Val Glu Arg Lys Cys Cys Val Glu Cys Pro Pro Cys Pro
            340                 345                 350

Ala Pro Pro Val Ala Gly Pro Ser Val Phe Leu Phe Pro Pro Lys Pro
        355                 360                 365

Lys Asp Thr Leu Met Ile Ser Arg Thr Pro Glu Val Thr Cys Val Val
```

```
                370                 375                 380
Val Asp Val Ser His Glu Asp Pro Glu Val Gln Phe Asn Trp Tyr Val
385                 390                 395                 400

Asp Gly Val Glu Val His Asn Ala Lys Thr Lys Pro Arg Glu Glu Gln
                405                 410                 415

Phe Asn Ser Thr Phe Arg Val Val Ser Val Leu Thr Val Val His Gln
                420                 425                 430

Asp Trp Leu Asn Gly Lys Glu Tyr Lys Cys Lys Val Ser Asn Lys Gly
            435                 440                 445

Leu Pro Ala Pro Ile Glu Lys Thr Ile Ser Lys Thr Lys Gly Gln Pro
        450                 455                 460

Arg Glu Pro Gln Val Tyr Thr Leu Pro Pro Ser Arg Glu Glu Met Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Met Leu Asp Ser Asp Gly Ser Phe Phe Leu Tyr
        515                 520                 525

Ser Lys Leu Thr Val Asp Lys Ser Arg Trp Gln Gln Gly Asn Val Phe
    530                 535                 540

Ser Cys Ser Val Met His Glu Ala Leu His Asn His Tyr Thr Gln Lys
545                 550                 555                 560

Ser Leu Ser Leu Ser Pro Gly Lys
                565

<210> SEQ ID NO 75
<211> LENGTH: 1008
<212> TYPE: DNA
<213> ORGANISM: Artificial Sequence
<220> FEATURE:
<223> OTHER INFORMATION: Made in Lab - fusion construct

<400> SEQUENCE: 75
gacatcgaac tcacccagcc cccgtcagtg tccgtggccc ctggacagac tgcgcgcatc    60
tcctgctccg gcgacaacct ggggaagaaa tacgtgtact ggtaccagca gaagccaggt   120
caagcccctg tgctggtcat ctacggcgac gacgaaaggc cgtcaggcat cccagagcgc   180
ttctccggct ccaactccgg gaatactgcc acccttacca tttccggaac ccaggccgag   240
gatgaagcgg attactattg cgcgagctac gatagcagcc acatcctgat cgtgtttgga   300
ggcggtacca agcttaccgt cctaggtcag cccaaggctg cccctcggt cactctgttc   360 ccgcccctcct ctgaggagct tcaagccaac aaggccacac tggtgtgtct cataagtgac   420
ttctacccgg agccgtgac agtggcctgg aaggcagata gcagcccgt caaggcggga   480 gtggagacca ccacaccctc caaacaaagc aacaacaagt acgcggccag cagctatctg   540
agcctgacgc ctgagcagtg gaagtcccac agaagctaca gctgccaggt cacgcatgaa   600
gggagcaccg tggagaagac agtggcccct acagaatgtt caggtggtgg tggctcggga   660
ggaggaggct ccggtggcgg tggcagcaac ccaatttgca agggatgcct gagctgtagc   720
aaggacaacg gatgttcacg gtgccagcaa aagctgtttt tcttcctccg gcgggaagga   780
atgcggcagt acggcgaatg tctccactcc tgcccctcgg ggtattacgg acaccgcgcg   840
cctgacatga accgatgcgc cagatgccgg atcgagaact gcgatagctg ccgcagcaag   900
gacgcctgca ctaagtgcaa agtcggcttc taccttcacc ggggcagatg ttttgacgaa   960
```

```
                tgcccggatg gcttcgcccc gctggaggag actatggaat gcgtggag              1008
```

<210> SEQ ID NO 76
<211> LENGTH: 336
<212> TYPE: PRT
<213> ORGANISM: Artificial Sequence
<220> FEATURE:
<223> OTHER INFORMATION: Made in Lab

<400> SEQUENCE: 76

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Lys Lys Tyr Val
            20                  25                  30

Tyr Trp Tyr Gln Gln Lys Pro Gly Gln Ala Pro Val Leu Val Ile Tyr
        35                  40                  45

Gly Asp Asp Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ser Tyr Asp Ser Ser His Ile Leu
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Gly Gly Ser Gly Gly Gly Gly Ser
    210                 215                 220

Gly Gly Gly Gly Ser Asn Pro Ile Cys Lys Gly Cys Leu Ser Cys Ser
225                 230                 235                 240

Lys Asp Asn Gly Cys Ser Arg Cys Gln Gln Lys Leu Phe Phe Phe Leu
                245                 250                 255

Arg Arg Glu Gly Met Arg Gln Tyr Gly Glu Cys Leu His Ser Cys Pro
            260                 265                 270

Ser Gly Tyr Tyr Gly His Arg Ala Pro Asp Met Asn Arg Cys Ala Arg
        275                 280                 285

Cys Arg Ile Glu Asn Cys Asp Ser Cys Arg Ser Lys Asp Ala Cys Thr
    290                 295                 300

Lys Cys Lys Val Gly Phe Tyr Leu His Arg Gly Arg Cys Phe Asp Glu
305                 310                 315                 320

Cys Pro Asp Gly Phe Ala Pro Leu Glu Glu Thr Met Glu Cys Val Glu
                325                 330                 335
```

<210> SEQ ID NO 77
<211> LENGTH: 1011

<212> TYPE: DNA
<213> ORGANISM: Artificial Sequence
<220> FEATURE:
<223> OTHER INFORMATION: Made in Lab - fusion construct

<400> SEQUENCE: 77

```
gacatcgagc tcacccagga ccccgctgtg tccgtggcct gggacagac cgtgcgcatc      60
acatgccagg gcgatagcct gcggagctat acgcctcgt ggtaccagca gaagcctggt     120
caagcgccgg tcctggtcat ctacggaaag aacaaccgcc cgtccggaat accagacagg    180
ttcagcggat ccagctcggg gaacaccgcc tcactgacta tcaccggagc acaggccgaa    240
gatgaagccg actactactg caactccctg gagcggattg gatacctgag ctacgtgttt    300
ggtggcggta ccaagcttac cgtcctaggt cagcccaagg ctgcccctc ggtcactctg     360
ttcccgccct cctctgagga gcttcaagcc aacaaggcca cactggtgtg tctcataagt    420
gacttctacc cgggagccgt gacagtggcc tggaaggcag atagcagccc cgtcaaggcg    480
ggagtggaga ccaccacacc ctccaaacaa agcaacaaca gtacgcggc cagcagctat     540
ctgagcctga cgcctgagca gtggaagtcc cacagaagct acagctgcca ggtcacgcat    600
gaagggagca ccgtggagaa gacagtggcc cctacagaat gttcaggtgg tggtggctcg    660
ggaggaggag gctccggtgg cgtggcagc aacccaattt gcaagggatg cctgagctgt     720
agcaaggaca acgatgttc acggtgccag caaaagctgt ttttcttcct ccggcgggaa     780
ggaatgcggc agtacggcga atgtctccac tcctgcccct cggggtatta cggacaccgc    840
gcgcctgaca tgaaccgatg cgccagatgc cggatcgaga actgcgatag ctgccgcagc    900
aaggacgcct gcactaagtg caaagtcggc ttctaccttc accggggcag atgttttgac    960
gaatgcccgg atggcttcgc cccgctggag gagactatgg aatgcgtgga g           1011
```

<210> SEQ ID NO 78
<211> LENGTH: 337
<212> TYPE: PRT
<213> ORGANISM: Artificial Sequence
<220> FEATURE:
<223> OTHER INFORMATION: Made in Lab

<400> SEQUENCE: 78

```
Asp Ile Glu Leu Thr Gln Asp Pro Ala Val Ser Val Ala Leu Gly Gln
1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Leu Glu Arg Ile Gly Tyr Leu
                85                  90                  95

Ser Tyr Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
```

145                 150                 155                 160
Gly Val Glu Thr Thr Thr Pro Ser Lys Gln Ser Asn Asn Lys Tyr Ala
                    165                 170                 175
Ala Ser Ser Tyr Leu Ser Leu Thr Pro Glu Gln Trp Lys Ser His Arg
                180                 185                 190
Ser Tyr Ser Cys Gln Val Thr His Glu Gly Ser Thr Val Glu Lys Thr
            195                 200                 205
Val Ala Pro Thr Glu Cys Ser Gly Gly Gly Ser Gly Gly Gly
        210                 215                 220
Ser Gly Gly Gly Ser Asn Pro Ile Cys Lys Gly Cys Leu Ser Cys
225                 230                 235                 240
Ser Lys Asp Asn Gly Cys Ser Arg Cys Gln Gln Lys Leu Phe Phe Phe
                245                 250                 255
Leu Arg Arg Glu Gly Met Arg Gln Tyr Gly Glu Cys Leu His Ser Cys
                260                 265                 270
Pro Ser Gly Tyr Tyr Gly His Arg Ala Pro Asp Met Asn Arg Cys Ala
            275                 280                 285
Arg Cys Arg Ile Glu Asn Cys Asp Ser Cys Arg Ser Lys Asp Ala Cys
        290                 295                 300
Thr Lys Cys Lys Val Gly Phe Tyr Leu His Arg Gly Arg Cys Phe Asp
305                 310                 315                 320
Glu Cys Pro Asp Gly Phe Ala Pro Leu Glu Glu Thr Met Glu Cys Val
                325                 330                 335
Glu

<210> SEQ ID NO 79
<211> LENGTH: 1341
<212> TYPE: DNA
<213> ORGANISM: Artificial Sequence
<220> FEATURE:
<223> OTHER INFORMATION: Made in Lab

<400> SEQUENCE: 79

```
gaagtgcagc tgctggaatc cggggggcgga ctggtgcaac ccggggggatc cctcagactg      60
tcctgtgccg catcgggttt cactttctcc tcctacgcga tgtcatgggt cagacaggcc     120
cctggaaaag gcctcgaatg ggtgtcggct atctccggat cggggggatc tacttactac     180
gccgactccg tgaagggccg gttcactatc tcgaggaca actccaagaa taccctgtac     240
ttgcaaatga actccctgcg cgccgaggat accgcggtgt attactgcgc caaggacttc     300
agctcacgcc ggtggtacct tgagtactgg ggacagggaa cccttgtcac cgtgtcgagt     360
gctagcacca agggcccatc ggtcttcccc ctggcgccct gctccaggag cacctccgag     420
agcacagcgg ccctgggctg cctggtcaag gactacttcc ccgaaccggt gacggtgtcg     480
tggaactcag gcgctctgac cagcggcgtg cacaccttcc cagctgtcct acagtcctca     540
ggactctact ccctcagcag cgtggtgacc gtgccctcca gcaacttcgg cacccagacc     600
tacacctgca acgtagatca caagcccagc aacaccaagg tggacaagac agttgagcgc     660
aaatgttgtg tcgagtgccc accgtgccca gcaccacctg tggcaggacc gtcagtcttc     720
ctcttccccc caaaacccaa ggacaccctc atgatctccc ggacccctga ggtcacgtgc     780
gtggtggtgg acgtgagcca cgaagacccc gaggtccagt tcaactggta cgtggacggc     840
gtggaggtgc ataatgccaa gacaaagcca cgggaggagc agttcaacag cacgttccgt     900
gtggtcagcg tcctcaccgt tgtgcaccag gactggctga acggcaagga gtacaagtgc     960
```

-continued

```
aaggtctcca acaaaggcct cccagccccc atcgagaaaa ccatctccaa aaccaaaggg    1020
cagccccgag aaccacaggt gtacaccctg cccccatccc gggaggagat gaccaagaac    1080
caggtcagcc tgacctgcct ggtcaaaggc ttctacccca gcgacatcgc cgtggagtgg    1140
gagagcaatg ggcagccgga gaacaactac aagaccacgc ctcccatgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaatg a                                              1341
```

<210> SEQ ID NO 80
<211> LENGTH: 446
<212> TYPE: PRT
<213> ORGANISM: Artificial Sequence
<220> FEATURE:
<223> OTHER INFORMATION: Made in Lab

<400> SEQUENCE: 80

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Arg Arg Trp Tyr Leu Glu Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
```

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
            325                 330                 335

Lys Thr Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 81
<211> LENGTH: 1020
<212> TYPE: DNA
<213> ORGANISM: Artificial Sequence
<220> FEATURE:
<223> OTHER INFORMATION: Made in Lab - fusion construct

<400> SEQUENCE: 81
gatatagttc tgtttcaatc ccctgcgagc ctggcggtaa gtttgggaca gagagccacg        60
atttcctgcc gagcgagtga aagcgtagac gactacggca attctttcat gcactggtat       120
caacagaagc caggccaacc gccgaagctg cttatctatc gcgcgtccaa tttggagtca       180
gggatccctg cacgattttc aggttctgga agtaggacag actttacact tacgataaac       240
cccgtggaag cggatgacgt cgcaacctac tattgtcaac aaagcaatga agcaccacct       300
accttcggag gtggcactaa attggaaatt aaacgtacgg tggctgcacc atctgtcttc       360
atcttcccgc catctgatga gcagttgaaa tctggaactg cctctgttgt gtgcctgctg       420
aataacttct atcccagaga ggccaaagta cagtggaagg tggataacgc cctccaatcg       480
ggtaactccc aggagagtgt cacagagcag gacagcaagg acagcaccta cagcctcagc       540
agcaccctga cgctgagcaa agcagactac gagaaacaca agtctacgc ctgcgaagtc       600 acccatcagg cctgagctc gcccgtcaca aagagcttca caggggaga gtgtggtggt       660 ggtggctcgg gaggaggagg ctccggtggc ggtggcagca cccaatttg caagggatgc       720 ctgagctgta gcaaggacaa cggatgttca cggtgccagc aaaagctgtt tttcttcctc       780
cggcgggaag aatgcggca gtacggcgaa tgtctccact cctgccctc ggggtattac       840 ggacaccgcg cgcctgacat gaaccgatgc gccagatgcc ggatcgagaa ctgcgatagc       900
tgccgcagca aggacgcctg cactaagtgc aaagtcggct tctaccttca ccggggcaga       960
tgttttgacg aatgcccgga tggcttcgcc ccgctggagg agactatgga atgcgtggag      1020

<210> SEQ ID NO 82
<211> LENGTH: 340
<212> TYPE: PRT
<213> ORGANISM: Artificial Sequence
<220> FEATURE:

<223> OTHER INFORMATION: Made in Lab

<400> SEQUENCE: 82

Asp Ile Val Leu Phe Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Ala Pro Pro Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Ser Gly
    210                 215                 220

Gly Gly Gly Ser Gly Gly Gly Ser Asn Pro Ile Cys Lys Gly Cys
225                 230                 235                 240

Leu Ser Cys Ser Lys Asp Asn Gly Cys Ser Arg Cys Gln Gln Lys Leu
                245                 250                 255

Phe Phe Phe Leu Arg Arg Glu Gly Met Arg Gln Tyr Gly Glu Cys Leu
            260                 265                 270

His Ser Cys Pro Ser Gly Tyr Tyr Gly His Arg Ala Pro Asp Met Asn
        275                 280                 285

Arg Cys Ala Arg Cys Arg Ile Glu Asn Cys Asp Ser Cys Arg Ser Lys
    290                 295                 300

Asp Ala Cys Thr Lys Cys Lys Val Gly Phe Tyr Leu His Arg Gly Arg
305                 310                 315                 320

Cys Phe Asp Glu Cys Pro Asp Gly Phe Ala Pro Leu Glu Glu Thr Met
                325                 330                 335

Glu Cys Val Glu
            340

<210> SEQ ID NO 83
<211> LENGTH: 1707
<212> TYPE: DNA
<213> ORGANISM: Artificial Sequence
<220> FEATURE:
<223> OTHER INFORMATION: Made in Lab - fusion construct

<400> SEQUENCE: 83

```
aacccaattt gcaagggatg cctgagctgt agcaaggaca acggatgttc acggtgccag      60
caaaagctgt ttttcttcct ccggcgggaa ggaatgcggc agtacggcga atgtctccac     120
tcctgcccct cggggtatta cggacaccgc gcgcctgaca tgaaccgatg cgccagatgc     180
cggatcgaga actgcgatag ctgccgcagc aaggacgcct gcactaagtg caaagtcggc     240
ttctaccttc accggggcag atgttttgac gaatgcccgg atggcttcgc cccgctggag     300
gagactatgg aatgcgtgga gggtggtggt ggctcgggag gaggaggctc cggtggcggt     360
ggcagccagg tccagttggt ggaatccgga ggggtttgg tccagcctgg tggaagcctg      420
cgcctctcat cgccgctag cggattcacc ttctcccgat acggcatgca ttgggtcaga      480
caggcacccg aaaaggact cgaatgggtg tcgggcattt cctcgatcgg gtcaaacacc      540
tattacgccg actccgtgaa gggacggttc accattagcc gggataacag caagaacact     600
ctgtacttgc aaatgaactc cctgcgggct gaggacaccg ccgtgtacta ctgtgcgcgg     660
tggtacaaga cctatattga cgtctgggga cagggtaccc tcgtgaccgt gtcgagtgct     720
agcaccaagg gcccatcggt cttccccctg gcaccctcct ccaagagcac ctctggggc     780
acagcggccc tgggctgcct ggtcaaggac tacttcccg aaccggtgac ggtgtcgtgg      840
aactcaggcg ccctgaccag cggcgtgcac accttcccgg ctgtcctaca gtcctcagga     900
ctctactccc tcagcagcgt ggtgaccgtg ccctccagca gcttgggcac ccagacctac     960
atctgcaacg tgaatcacaa gcccagcaac accaaggtgg acaagaaagt tgagcccaaa    1020
tcttgtgaca aaactcacac atgcccaccg tgcccagcac ctgaactcct ggggggaccg    1080
tcagtcttcc tcttccccc aaaacccaag acaccctca tgatctcccg acccctgag       1140
gtcacatgcg tggtggtgga cgtgagccac gaagaccctg aggtcaagtt caactggtac    1200
gtggacggcg tggaggtgca taatgccaag acaaagccgc gggaggagca gtacggcagc    1260
acgtaccgtg tggtcagcgt cctcaccgtc ctgcaccagg actggctgaa tggcaaggag    1320
tacaagtgca aggtctccaa caaagccctc ccagccccca tcgagaaaac catctccaaa    1380
gccaaagggc agccccgaga accacaggtg tacaccctgc ccccatcccg ggaggagatg    1440
accaagaacc aggtcagcct gacctgcctg gtcaaaggct tctatcccag cgacatcgcc    1500
gtggagtggg agagcaatgg gcagccggag aacaactaca agaccacgcc tcccgtgctg    1560
gactccgacg gctccttctt cctctacagc aagctcaccg tggacaagag caggtggcag    1620
caggggaacg tcttctcatg ctccgtgatg catgaggctc tgcacaacca ctacacgcag    1680
aagagcctct ccctgtctcc gggtaaa                                        1707
```

<210> SEQ ID NO 84
<211> LENGTH: 569
<212> TYPE: PRT
<213> ORGANISM: Artificial Sequence
<220> FEATURE:
<223> OTHER INFORMATION: Made in Lab

<400> SEQUENCE: 84

Asn Pro Ile Cys Lys Gly Cys Leu Ser Cys Ser Lys Asp Asn Gly Cys
1               5                   10                  15

Ser Arg Cys Gln Gln Lys Leu Phe Phe Phe Leu Arg Arg Glu Gly Met
            20                  25                  30

Arg Gln Tyr Gly Glu Cys Leu His Ser Cys Pro Ser Gly Tyr Tyr Gly
        35                  40                  45

His Arg Ala Pro Asp Met Asn Arg Cys Ala Arg Cys Arg Ile Glu Asn

```
            50                  55                  60
Cys Asp Ser Cys Arg Ser Lys Asp Ala Cys Thr Lys Cys Lys Val Gly
65                  70                  75                  80

Phe Tyr Leu His Arg Gly Arg Cys Phe Asp Glu Cys Pro Asp Gly Phe
                85                  90                  95

Ala Pro Leu Glu Glu Thr Met Glu Cys Val Gly Gly Gly Gly Gly Ser
            100                 105                 110

Gly Gly Gly Gly Ser Gly Gly Gly Ser Gln Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Phe Thr Phe Ser Arg Tyr Gly Met His Trp Val Arg
145                 150                 155                 160

Gln Ala Pro Gly Lys Gly Leu Glu Trp Val Ser Gly Ile Ser Ser Ile
                165                 170                 175

Gly Ser Asn Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
            195                 200                 205

Arg Ala Glu Asp Thr Ala Val Tyr Tyr Cys Ala Arg Trp Tyr Lys Thr
210                 215                 220

Tyr Ile Asp Val Trp Gly Gln Gly Thr Leu Val Thr Val Ser Ser Ala
225                 230                 235                 240

Ser Thr Lys Gly Pro Ser Val Phe Pro Leu Ala Pro Ser Ser Lys Ser
                245                 250                 255

Thr Ser Gly Gly Thr Ala Ala Leu Gly Cys Leu Val Lys Asp Tyr Phe
            260                 265                 270

Pro Glu Pro Val Thr Val Ser Trp Asn Ser Gly Ala Leu Thr Ser Gly
            275                 280                 285

Val His Thr Phe Pro Ala Val Leu Gln Ser Ser Gly Leu Tyr Ser Leu
            290                 295                 300

Ser Ser Val Val Thr Val Pro Ser Ser Ser Leu Gly Thr Gln Thr Tyr
305                 310                 315                 320

Ile Cys Asn Val Asn His Lys Pro Ser Asn Thr Lys Val Asp Lys Lys
                325                 330                 335

Val Glu Pro Lys Ser Cys Asp Lys Thr His Thr Cys Pro Pro Cys Pro
            340                 345                 350

Ala Pro Glu Leu Leu Gly Gly Pro Ser Val Phe Leu Phe Pro Pro Lys
            355                 360                 365

Pro Lys Asp Thr Leu Met Ile Ser Arg Thr Pro Glu Val Thr Cys Val
370                 375                 380

Val Val Asp Val Ser His Glu Asp Pro Glu Val Lys Phe Asn Trp Tyr
385                 390                 395                 400

Val Asp Gly Val Glu Val His Asn Ala Lys Thr Lys Pro Arg Glu Glu
                405                 410                 415

Gln Tyr Gly Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
            435                 440                 445

Ala Leu Pro Ala Pro Ile Glu Lys Thr Ile Ser Lys Ala Lys Gly Gln
            450                 455                 460

Pro Arg Glu Pro Gln Val Tyr Thr Leu Pro Pro Ser Arg Glu Glu Met
465                 470                 475                 480
```

```
Thr Lys Asn Gln Val Ser Leu Thr Cys Leu Val Lys Gly Phe Tyr Pro
                485                 490                 495
Ser Asp Ile Ala Val Glu Trp Glu Ser Asn Gly Gln Pro Glu Asn Asn
            500                 505                 510
Tyr Lys Thr Thr Pro Pro Val Leu Asp Ser Asp Gly Ser Phe Phe Leu
        515                 520                 525
Tyr Ser Lys Leu Thr Val Asp Lys Ser Arg Trp Gln Gln Gly Asn Val
    530                 535                 540
Phe Ser Cys Ser Val Met His Glu Ala Leu His Asn His Tyr Thr Gln
545                 550                 555                 560
Lys Ser Leu Ser Leu Ser Pro Gly Lys
                565

<210> SEQ ID NO 85
<211> LENGTH: 1716
<212> TYPE: DNA
<213> ORGANISM: Artificial Sequence
<220> FEATURE:
<223> OTHER INFORMATION: Made in Lab - fusion construct

<400> SEQUENCE: 85 aacccaatttt gcaagggatg cctgagctgt agcaaggaca acggatgttc acggtgccag      60
caaaagctgt ttttcttcct ccggcgggaa ggaatgcggc agtacggcga atgtctccac     120
tcctgcccct cggggtatta cggacaccgc gcgcctgaca tgaaccgatg cgccagatgc     180
cggatcgaga actgcgatag ctgccgcagc aaggacgcct gcactaagtg caaagtcggc     240
ttctaccttc accggggcag atgttttgac gaatgcccgg atggcttcgc cccgctggag     300
gagactatgg aatgcgtgga gggtggtggt ggctcgggag gaggaggctc cggtggcggt     360
ggcagcgaag tgcagctgct ggaatccggg ggcggactgg tgcaacccgg ggatccctc      420
agactgtcct gtgccgcatc gggtttcact ttctcctcct acgcgatgtc atgggtcaga     480
caggcccctg gaaaaggcct cgaatgggtg tcggctatct ccggatcggg gggatctact     540
tactacgccg actccgtgaa gggccggttc actatctcga gggacaactc caagaatacc     600
ctgtacttgc aaatgaactc cctgcgcgcc gaggatacc  cggtgtatta ctgcgccaag     660
gacttcagct cacgccggtg gtaccttgag tactggggac agggaaccct tgtcaccgtg     720
tcgagtgcta gcaccaaggg cccatcggtc ttccccctgg cacctcctc  caagagcacc     780
tctggggggca gcgggcccct gggctgcctg gtcaaggact acttccccga accggtgacg     840
gtgtcgtgga actcaggcgc cctgaccagc ggcgtgcaca ccttcccggc tgtcctacag     900
tcctcaggac tctactccct cagcagcgtg gtgaccgtgc cctccagcag cttgggcacc     960
cagacctaca tctgcaacgt gaatcacaag cccagcaaca ccaaggtgga caagaaagtt    1020
gagcccaaat cttgtgacaa aactcacaca tgcccaccgt gcccagcacc tgaactcctg    1080
gggggaccgt cagtcttcct cttccccca  aaacccaagg acaccctcat gatctcccgg    1140
acccctgagg tcacatgcgt ggtggtggac gtgagccacg aagaccctga ggtcaagttc    1200
aactggtacg tggacggcgt ggaggtgcat aatgccaaga caaagccgcg ggaggagcag    1260
tacggcagca cgtaccgtgt ggtcagcgtc ctcaccgtcc tgcaccagga ctggctgaat    1320
ggcaaggagt acaagtgcaa ggtctccaac aaagccctcc cagcccccat cgagaaaacc    1380
atctccaaag ccaaagggca gccccgagaa ccacaggtgt acaccctgcc cccatcccgg    1440
gaggagatga ccaagaacca ggtcagcctg acctgcctgg tcaaaggctt ctatcccagc    1500
```

-continued

```
gacatcgccg tggagtggga gagcaatggg cagccggaga caactacaa gaccacgcct   1560 cccgtgctgg actccgacgg ctccttcttc ctctacagca agctcaccgt ggacaagagc   1620
aggtggcagc aggggaacgt cttctcatgc tccgtgatgc atgaggctct gcacaaccac   1680
tacacgcaga gagcctctc cctgtctccg ggtaaa                              1716
```

<210> SEQ ID NO 86
<211> LENGTH: 572
<212> TYPE: PRT
<213> ORGANISM: Artificial Sequence
<220> FEATURE:
<223> OTHER INFORMATION: Made in Lab

<400> SEQUENCE: 86

```
Asn Pro Ile Cys Lys Gly Cys Leu Ser Cys Ser Lys Asp Asn Gly Cys
1               5                   10                  15

Ser Arg Cys Gln Gln Lys Leu Phe Phe Phe Leu Arg Arg Glu Gly Met
            20                  25                  30

Arg Gln Tyr Gly Glu Cys Leu His Ser Cys Pro Ser Gly Tyr Tyr Gly
        35                  40                  45

His Arg Ala Pro Asp Met Asn Arg Cys Ala Arg Cys Arg Ile Glu Asn
    50                  55                  60

Cys Asp Ser Cys Arg Ser Lys Asp Ala Cys Thr Lys Cys Lys Val Gly
65                  70                  75                  80

Phe Tyr Leu His Arg Gly Arg Cys Phe Asp Glu Cys Pro Asp Gly Phe
                85                  90                  95

Ala Pro Leu Glu Glu Thr Met Glu Cys Val Glu Gly Gly Gly Ser
            100                 105                 110

Gly Gly Gly Gly Ser Gly Gly Gly Ser Glu Val Gln Leu Leu Glu
        115                 120                 125

Ser Gly Gly Gly Leu Val Gln Pro Gly Gly Ser Leu Arg Leu Ser Cys
130                 135                 140

Ala Ala Ser Gly Phe Thr Phe Ser Ser Tyr Ala Met Ser Trp Val Arg
145                 150                 155                 160

Gln Ala Pro Gly Lys Gly Leu Glu Trp Val Ser Ala Ile Ser Gly Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Lys Asp Phe Ser Ser
    210                 215                 220

Arg Arg Trp Tyr Leu Glu Tyr Trp Gly Gln Gly Thr Leu Val Thr Val
225                 230                 235                 240

Ser Ser Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
        275                 280                 285

Thr Ser Gly Val His Thr Phe Pro Ala Val Leu Gln Ser Ser Gly Leu
    290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
```

```
                    325                 330                 335
Asp Lys Lys Val Glu Pro Lys Ser Cys Asp Lys Thr His Thr Cys Pro
            340                 345                 350

Pro Cys Pro Ala Pro Glu Leu Leu Gly Gly Pro Ser Val Phe Leu Phe
        355                 360                 365

Pro Pro Lys Pro Lys Asp Thr Leu Met Ile Ser Arg Thr Pro Glu Val
    370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Gly Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
        515                 520                 525

Phe Phe Leu Tyr Ser Lys Leu Thr Val Asp Lys Ser Arg Trp Gln Gln
    530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570
```

<210> SEQ ID NO 87
<211> LENGTH: 1713
<212> TYPE: DNA
<213> ORGANISM: Artificial Sequence
<220> FEATURE:
<223> OTHER INFORMATION: Made in Lab - fusion construct

<400> SEQUENCE: 87

```
aacccaattt gcaagggatg cctgagctgt agcaaggaca acggatgttc acggtgccag    60
caaaagctgt ttttcttcct ccggcgggaa ggaatgcggc agtacggcga atgtctccac   120
tcctgccccct cggggtatta cggacaccgc gcgcctgaca tgaaccgatg cgccagatgc   180
cggatcgaga actgcgatag ctgccgcagc aaggacgcct gcactaagtg caaagtcggc   240
ttctaccttc accggggcag atgttttgac gaatgcccgg atggcttcgc ccgctggag   300
gagactatgg aatgcgtgga gggtggtggt ggctcgggag gaggaggctc cggtggcggt   360
ggcagccaag tgcaactcca acaaagcggt cccgagttgg tccgacccgg cgtcagtgtg   420
aaaatctcat gcaagggggtc cgggtatacc ttcactgact atgcaatgca ctgggtaaag   480
cagagccacg ccaagtcctt ggagtggatc ggaggcatta gtacctactt cggacgcacc   540
aactacaatc aaaaatttaa gggtcgcgca accatgactg tagataaatc atcaagtacc   600
gcgtacatgg aattggctag actgacttct gaagattccg cgctgtatta ctgtgctcgc   660
```

-continued

```
ggtttgtctg gcaactatgt tatggattac tgggggcaag ggaccagcgt cacggtgtcg      720
agtgctagca ccaagggccc atcggtcttc cccctggcac cctcctccaa gagcacctct      780
gggggcacag cggccctggg ctgcctggtc aaggactact tccccgaacc ggtgacggtg      840
tcgtggaact caggcgccct gaccagcggc gtgcacacct tcccggctgt cctacagtcc      900
tcaggactct actccctcag cagcgtggtg accgtgccct ccagcagctt gggcacccag      960
acctacatct gcaacgtgaa tcacaagccc agcaacacca aggtggacaa gaaagttgag     1020
cccaaatctt gtgacaaaac tcacacatgc ccaccgtgcc cagcacctga actcctgggg     1080
ggaccgtcag tcttcctctt ccccccaaaa cccaaggaca ccctcatgat ctcccggacc     1140
cctgaggtca catgcgtggt ggtggacgtg agccacgaag accctgaggt caagttcaac     1200
tggtacgtgg acggcgtgga ggtgcataat gccaagacaa agccgcggga ggagcagtac     1260
ggcagcacgt accgtgtggt cagcgtcctc accgtcctgc accaggactg gctgaatggc     1320
aaggagtaca agtgcaaggt ctccaacaaa gccctcccag cccccatcga gaaaaccatc     1380
tccaaagcca agggcagccc cgagaaccca ggtgtacacc cctgccccca tcccgggag     1440 gagatgacca agaaccaggt cagcctgacc tgcctggtca aaggcttcta tcccagcgac     1500
atcgccgtgg agtgggagag caatgggcag ccggagaaca actacaagac cacgcctccc     1560
gtgctggact ccgacggctc cttcttcctc tacagcaagc tcaccgtgga caagagcagg     1620
tggcagcagg ggaacgtctt ctcatgctcc gtgatgcatg aggctctgca caaccactac     1680
acgcagaaga gcctctccct gtctccgggt aaa                                  1713
```

<210> SEQ ID NO 88
<211> LENGTH: 571
<212> TYPE: PRT
<213> ORGANISM: Artificial Sequence
<220> FEATURE:
<223> OTHER INFORMATION: Made in Lab

<400> SEQUENCE: 88

```
Asn Pro Ile Cys Lys Gly Cys Leu Ser Cys Ser Lys Asp Asn Gly Cys
1               5                   10                  15

Ser Arg Cys Gln Gln Lys Leu Phe Phe Phe Leu Arg Arg Glu Gly Met
            20                  25                  30

Arg Gln Tyr Gly Glu Cys Leu His Ser Cys Pro Ser Gly Tyr Tyr Gly
        35                  40                  45

His Arg Ala Pro Asp Met Asn Arg Cys Ala Arg Cys Arg Ile Glu Asn
    50                  55                  60

Cys Asp Ser Cys Arg Ser Lys Asp Ala Cys Thr Lys Cys Lys Val Gly
65                  70                  75                  80

Phe Tyr Leu His Arg Gly Arg Cys Phe Asp Glu Cys Pro Asp Gly Phe
                85                  90                  95

Ala Pro Leu Glu Glu Thr Met Glu Cys Val Glu Gly Gly Gly Ser
            100                 105                 110

Gly Gly Gly Gly Ser Gly Gly Gly Ser Gln Val Gln Leu Gln Gln
        115                 120                 125

Ser Gly Pro Glu Leu Val Arg Pro Gly Val Ser Val Lys Ile Ser Cys
    130                 135                 140

Lys Gly Ser Gly Tyr Thr Phe Thr Asp Tyr Ala Met His Trp Val Lys
145                 150                 155                 160

Gln Ser His Ala Lys Ser Leu Glu Trp Ile Gly Gly Ile Ser Thr Tyr
                165                 170                 175
```

-continued

Phe Gly Arg Thr Asn Tyr Asn Gln Lys Phe Lys Gly Arg Ala Thr Met
            180                 185                 190

Thr Val Asp Lys Ser Ser Thr Ala Tyr Met Glu Leu Ala Arg Leu
        195                 200                 205

Thr Ser Glu Asp Ser Ala Leu Tyr Tyr Cys Ala Arg Gly Leu Ser Gly
    210                 215                 220

Asn Tyr Val Met Asp Tyr Trp Gly Gln Gly Thr Ser Val Thr Val Ser
225                 230                 235                 240

Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Gly Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 89
<211> LENGTH: 1341
<212> TYPE: DNA

<213> ORGANISM: Artificial Sequence
<220> FEATURE:
<223> OTHER INFORMATION: Made in Lab

<400> SEQUENCE: 89

```
caggtccagt tggtggaatc cggagggggt ttggtccagc ctggtggaag cctgcgcctc      60
tcatgcgccg ctagcggatt caccttctcc cgatacggca tgcattgggt cagacaggca     120
cccggaaaag gactcgaatg ggtgtcgggc atttcctcga tcgggtcaaa cacctattac     180
gccgactccg tgaagggacg gttcaccatt agccgggata cagcaagaa cactctgtac      240
ttgcaaatga actccctgcg ggctgaggac accgccgtgt actactgtgc gcggtggtac     300
aagacctata ttgacgtctg gggacagggt accctcgtga ccgtgtcgag tgctagcacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacgg cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                               1341
```

<210> SEQ ID NO 90
<211> LENGTH: 447
<212> TYPE: PRT
<213> ORGANISM: Artificial Sequence
<220> FEATURE:
<223> OTHER INFORMATION: Made in Lab

<400> SEQUENCE: 90

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Gly Met His Trp Val Arg Gln Ala Pro Gly Lys Gly Leu Glu Trp Val
         35                  40                  45

Ser Gly Ile Ser Ser Ile Gly Ser Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95
```

Ala Arg Trp Tyr Lys Thr Tyr Ile Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Gly Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 91
<211> LENGTH: 1347
<212> TYPE: DNA
<213> ORGANISM: Artificial Sequence
<220> FEATURE:
<223> OTHER INFORMATION: Made in Lab

<400> SEQUENCE: 91
caagtgcaac tccaacaaag cggtcccgag ttggtccgac ccggcgtcag tgtgaaaatc    60

| | |
|---|---|
| tcatgcaagg ggtccgggta taccttcact gactatgcaa tgcactgggt aaagcagagc | 120 |
| cacgccaagt ccttggagtg gatcggaggc attagtacct acttcggacg caccaactac | 180 |
| aatcaaaaat ttaagggtcg cgcaaccatg actgtagata atcatcaag taccgcgtac | 240 |
| atggaattgg ctagactgac ttctgaagat tccgcgctgt attactgtgc tcgcggtttg | 300 |
| tctggcaact atgttatgga ttactggggg caagggacca gcgtcacggt gtcgagtgct | 360 |
| agcaccaagg gcccatcggt cttccccctg gcaccctcct ccaagagcac ctctgggggc | 420 |
| acagcggccc tgggctgcct ggtcaaggac tacttccccg aaccggtgac ggtgtcgtgg | 480 |
| aactcaggcg ccctgaccag cggcgtgcac accttcccgg ctgtcctaca gtcctcagga | 540 |
| ctctactccc tcagcagcgt ggtgaccgtg ccctccagca gcttgggcac ccagacctac | 600 |
| atctgcaacg tgaatcacaa gcccagcaac accaaggtgg acaagaaagt tgagcccaaa | 660 |
| tcttgtgaca aaactcacac atgcccaccg tgcccagcac ctgaactcct ggggggaccg | 720 |
| tcagtcttcc tcttcccccc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacggcagc | 900 |
| acgtaccgtg tggtcagcgt cctcaccgtc ctgcaccagg actggctgaa tggcaaggag | 960 |
| tacaagtgca aggtctccaa caaagccctc ccagccccca tcgagaaaac catctccaaa | 1020 |
| gccaaagggc agccccgaga accacaggtg tacaccctgc ccccatcccg ggaggagatg | 1080 |
| accaagaacc aggtcagcct gacctgcctg gtcaaaggct tctatccag cgacatcgcc | 1140 |
| gtggagtggg agagcaatgg gcagccggag aacaactaca agaccacgcc tcccgtgctg | 1200 |
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaa | 1347 |

<210> SEQ ID NO 92
<211> LENGTH: 449
<212> TYPE: PRT
<213> ORGANISM: Artificial Sequence
<220> FEATURE:
<223> OTHER INFORMATION: Made in Lab

<400> SEQUENCE: 92

```
Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Gly Ile Ser Thr Tyr Phe Gly Arg Thr Asn Tyr Asn Gln Lys Phe
    50                  55                  60

Lys Gly Arg Ala Thr Met Thr Val Asp Lys Ser Ser Thr Ala Tyr
65                  70                  75                  80

Met Glu Leu Ala Arg Leu Thr Ser Glu Asp Ser Ala Leu Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gly Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 93
<211> LENGTH: 1350
<212> TYPE: DNA
<213> ORGANISM: Artificial Sequence
<220> FEATURE:
<223> OTHER INFORMATION: Made in Lab

<400> SEQUENCE: 93
gaagtgcagc tgctggaatc cggggggcgga ctggtgcaac cggggggatc cctcagactg      60
tcctgtgccg catcgggttt cactttctcc tcctacgcga tgtcatgggt cagacaggcc     120
cctggaaaag gcctcgaatg ggtgtcggct atctccggat cggggggatc tacttactac     180
gccgactccg tgaagggccg gttcactatc tcgagggaca actccaagaa taccctgtac     240
```

```
ttgcaaatga actccctgcg cgccgaggat accgcggtgt attactgcgc caaggacttc        300
agctcacgcc ggtggtacct tgagtactgg ggacagggaa cccttgtcac cgtgtcgagt        360
gctagcacca agggcccatc ggtcttcccc ctggcaccct cctccaagag cacctctggg        420
ggcacagcgg ccctgggctg cctggtcaag gactacttcc ccgaaccggt gacggtgtcg        480
tggaactcag gcgccctgac cagcggcgtg cacaccttcc cggctgtcct acagtcctca        540
ggactctact ccctcagcag cgtggtgacc gtgccctcca gcagcttggg cacccagacc        600
tacatctgca acgtgaatca caagcccagc aacaccaagg tggacaagaa agttgagccc        660
aaatcttgtg acaaaactca cacatgccca ccgtgcccag cacctgaact cctgggggga        720
ccgtcagtct tcctcttccc cccaaaaccc aaggacaccc tcatgatctc ccggacccct        780
gaggtcacat gcgtggtggt ggacgtgagc cacgaagacc ctgaggtcaa gttcaactgg        840
tacgtggacg gcgtggaggt gcataatgcc aagacaaagc cgcgggagga gcagtacggc        900
agcacgtacc gtgtggtcag cgtcctcacc gtcctgcacc aggactggct gaatggcaag        960
gagtacaagt gcaaggtctc caacaaagcc ctcccagccc ccatcgagaa aaccatctcc        1020
aaagccaaag ggcagccccg agaaccacag gtgtacaccc tgcccccatc ccgggaggag        1080
atgaccaaga accaggtcag cctgacctgc ctggtcaaag cttctatcc cagcgacatc         1140 gccgtggagt gggagagcaa tgggcagccg gagaacaact acaagaccac gcctcccgtg        1200
ctggactccg acggctcctt cttcctctac agcaagctca ccgtggacaa gagcaggtgg        1260
cagcagggga acgtcttctc atgctccgtg atgcatgagg ctctgcacaa ccactacacg        1320
cagaagagcc tctccctgtc tccgggtaaa                                         1350
```

<210> SEQ ID NO 94
<211> LENGTH: 450
<212> TYPE: PRT
<213> ORGANISM: Artificial Sequence
<220> FEATURE:
<223> OTHER INFORMATION: Made in Lab

<400> SEQUENCE: 94

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                       165                 170                 175
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Gly Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 95
<211> LENGTH: 1119
<212> TYPE: DNA
<213> ORGANISM: Artificial Sequence
<220> FEATURE:
<223> OTHER INFORMATION: Made in Lab - fusion construct

<400> SEQUENCE: 95
caggtccagt tggtggaatc cggaggggt  ttggtccagc tggtggaag  cctgcgcctc      60 tcatgcgccg ctagcggatt caccttctcc cgatacggca tgcattgggt cagacaggca     120
cccggaaaag gactcgaatg ggtgtcgggc atttcctcga tcgggtcaaa cacctattac     180
gccgactccg tgaagggacg gttcaccatt agccgggata cagcaagaa  cactctgtac     240 ttgcaaatga actccctgcg ggctgaggac accgccgtgt actactgtgc gcggtggtac     300
aagacctata ttgacgtctg gggacagggt accctcgtga ccgtgtcatc cggtggtgga     360
ggatccggag gcggaggaag cggaggaggg ggttcagaca tcgaactcac ccagccccg      420
```

```
tcagtgtccg tggccnctgg acagactgcg cgcatctcct gctccggcga caacctgggg    480
aagaaatacg tgtactggta ccagcagaag ccaggtcaag cccctgtgct ggtcatctac    540
ggcgacgacg aaaggccgtc aggcatccca gagcgcttct ccggctccaa ctccgggaat    600
actgccaccc ttaccatttc cggaacccag gccgaggatg aagcggatta ctattgcgcg    660
agctacgata gcagccacat cctgatcgtg tttggaggcg gtactaagct gaccgtgctg    720
ggaagcggtg gatcacaggc ctgtgccaaa ggctgtgagc tctgctctga agtcaacggc    780
tgcctcaagt gctcacccaa gctgttcatc ctgctggaga ggaacgacat ccgccaggtg    840
ggcgtctgct tgccgtcctg cccacctgga tacttcgacg cccgcaaccc cgacatgaac    900
aagtgcatca aatgcaagat cgagcactgt gaggcctgct tcagccataa cttctgcacc    960
aagtgtaagg agggcttgta cctgcacaag ggccgctgct atccagcttg tcccgagggc   1020
tcctcagctg ccaatggcac catggagtgc agtagtggcg agactacaa ggacgacgat   1080
gacaagggct cccaccatca ccaccatcat caccactag                          1119
```

<210> SEQ ID NO 96
<211> LENGTH: 372
<212> TYPE: PRT
<213> ORGANISM: Artificial Sequence
<220> FEATURE:
<223> OTHER INFORMATION: Made in Lab - fusion construct

<400> SEQUENCE: 96

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240
```

Gly Ser Gly Gly Ser Gln Ala Cys Ala Lys Gly Cys Glu Leu Cys Ser
            245                 250                 255

Glu Val Asn Gly Cys Leu Lys Cys Ser Pro Lys Leu Phe Ile Leu Leu
        260                 265                 270

Glu Arg Asn Asp Ile Arg Gln Val Gly Val Cys Leu Pro Ser Cys Pro
    275                 280                 285

Pro Gly Tyr Phe Asp Ala Arg Asn Pro Asp Met Asn Lys Cys Ile Lys
290                 295                 300

Cys Lys Ile Glu His Cys Glu Ala Cys Phe Ser His Asn Phe Cys Thr
305                 310                 315                 320

Lys Cys Lys Glu Gly Leu Tyr Leu His Lys Gly Arg Cys Tyr Pro Ala
                325                 330                 335

Cys Pro Glu Gly Ser Ser Ala Ala Asn Gly Thr Met Glu Cys Ser Ser
            340                 345                 350

Gly Gly Asp Tyr Lys Asp Asp Asp Asp Lys Gly Ser His His His His
        355                 360                 365

His His His His
    370

<210> SEQ ID NO 97
<211> LENGTH: 1116
<212> TYPE: DNA
<213> ORGANISM: Artificial Sequence
<220> FEATURE:
<223> OTHER INFORMATION: Made in Lab - fusion construct

<400> SEQUENCE: 97

```
caggtccagt tggtggaatc cggagggggt ttggtccagc ctggtggaag cctgcgcctc      60
tcatgcgccg ctagcggatt caccttctcc cgatacggca tgcattgggt cagacaggca     120
cccggaaaag gactcgaatg ggtgtcgggc atttcctcga tcgggtcaaa cacctattac     180
gccgactccg tgaagggacg gttcaccatt agcgggata cagcaagaa cactctgtac      240
ttgcaaatga actccctgcg ggctgaggac accgccgtgt actactgtgc gcggtggtac     300
aagacctata ttgacgtctg gggacagggt accctcgtga ccgtgtcatc cggtggtgga     360
ggatccggag gcggaggaag cggaggaggg ggttcagaca tcgaactcac ccagccccg     420
tcagtgtccg tggcccctgg acagactgcg cgcatctcct gctccggcga caacctgggg     480
aagaaatacg tgtactggta ccagcagaag ccaggtcaag cccctgtgct ggtcatctac     540
ggcgacgacg aaaggccgtc aggcatccca gagcgcttct ccggctccaa ctccgggaat     600
actgccaccc ttaccatttc cggaacccag gccgaggatg aagcggatta ctattgcgcg     660
agctacgata gcagccacat cctgatcgtg tttggaggcg gtactaagct gaccgtgctg     720
ggaagcggtg gatcacaagg ctgccaagga ggctgtgcaa catgctcaga ttacaatgga     780
tgtttgtcat gtaagcccag actatttttt gctctggaaa gaattggcat gaagcagatt     840
ggagtatgtc tctcttcatg tccaagtgga tattatggaa ctcgatatcc agatataaat     900
aagtgtacaa aatgcaaagc tgactgtgat acctgtttca caaaaattt ctgcacaaaa     960
tgtaaaagtg gattttactt acaccttgga aagtgccttg caattgccc agaagggttg    1020
gaagccaaca ccatactat ggagtgtgtc agtggcggag actacaagga cgacgatgac    1080
aagggctccc accatcacca ccatcatcac cactag                              1116
```

<210> SEQ ID NO 98
<211> LENGTH: 371

```
<212> TYPE: PRT
<213> ORGANISM: Artificial Sequence
<220> FEATURE:
<223> OTHER INFORMATION: Made in Lab - fusion construct

<400> SEQUENCE: 98

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Pro Pro Ser Val Ser Val
130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240

Gly Ser Gly Gly Ser Gln Gly Cys Gln Gly Gly Cys Ala Thr Cys Ser
                245                 250                 255

Asp Tyr Asn Gly Cys Leu Ser Cys Lys Pro Arg Leu Phe Phe Ala Leu
            260                 265                 270

Glu Arg Ile Gly Met Lys Gln Ile Gly Val Cys Leu Ser Ser Cys Pro
        275                 280                 285

Ser Gly Tyr Tyr Gly Thr Arg Tyr Pro Asp Ile Asn Lys Cys Thr Lys
    290                 295                 300

Cys Lys Ala Asp Cys Asp Thr Cys Phe Asn Lys Asn Phe Cys Thr Lys
305                 310                 315                 320

Cys Lys Ser Gly Phe Tyr Leu His Leu Gly Lys Cys Leu Asp Asn Cys
                325                 330                 335

Pro Glu Gly Leu Glu Ala Asn Asn His Thr Met Glu Cys Val Ser Gly
            340                 345                 350

Gly Asp Tyr Lys Asp Asp Asp Lys Gly Ser His His His His
        355                 360                 365

His His His
    370
```

<210> SEQ ID NO 99
<211> LENGTH: 1116
<212> TYPE: DNA
<213> ORGANISM: Artificial Sequence
<220> FEATURE:
<223> OTHER INFORMATION: Made in Lab - fusion construct

<400> SEQUENCE: 99

```
caggtccagt tggtggaatc cggagggggt ttggtccagc ctggtggaag cctgcgcctc    60
tcatgcgccg ctagcggatt caccttctcc cgatacggca tgcattgggt cagacaggca   120
cccggaaaag gactcgaatg ggtgtcgggc atttcctcga tcgggtcaaa cacctattac   180
gccgactccg tgaagggacg gttcaccatt agccgggata acagcaagaa cactctgtac   240
ttgcaaatga actccctgcg ggctgaggac accgccgtgt actactgtgc gcggtggtac   300
aagacctata ttgacgtctg gggacagggt accctcgtga ccgtgtcatc cggtggtgga   360
ggatccggag gcggaggaag cggaggaggg ggttcagaca tcgaactcac ccagcccccg   420
tcagtgtccg tggcccctgg acagactgcg cgcatctcct gctccggcga caacctgggg   480
aagaaatacg tgtactggta ccagcagaag ccaggtcaag cccctgtgct ggtcatctac   540
ggcgacgacg aaaggccgtc aggcatccca gagcgcttct ccggctccaa ctccgggaat   600
actgccaccc ttaccatttc cggaacccag gccgaggatg aagcggatta ctattgcgcg   660
agctacgata gcagccacat cctgatcgtg tttggaggcg gtactaagct gaccgtgctg   720
ggaagcggtg gatcagggggg caactgcaca ggctgtatca tctgctcaga ggagaacggc   780
tgttccacct gccagcagag gctcttcctg ttcatccgcc gggaaggcat ccgccagtac   840
ggcaagtgcc tgcacgactg tccccctggg tacttcggca tccgcggcca ggaggtcaac   900
aggtgcaaaa aatgtgggc cacttgtgag agctgcttca gccaggactt ctgcatccgg   960
tgcaagaggc agttttactt gtacaagggg aagtgtctgc caacctgccc gccgggcact  1020
ttggcccacc agaacacacg ggagtgccag ggggcggag actacaagga cgacgatgac  1080
aagggctccc accatcacca ccatcatcac cactag                            1116
```

<210> SEQ ID NO 100
<211> LENGTH: 371
<212> TYPE: PRT
<213> ORGANISM: Artificial Sequence
<220> FEATURE:
<223> OTHER INFORMATION: Made in Lab - fusion construct

<400> SEQUENCE: 100

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110
```

Val Thr Val Ser Ser Gly Gly Gly Ser Gly Gly Gly Ser Gly
            115                 120                 125

Gly Gly Gly Ser Asp Ile Glu Leu Thr Gln Pro Pro Ser Val Ser Val
            130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
            195                 200                 205

Thr Gln Ala Glu Asp Glu Ala Asp Tyr Tyr Cys Ala Ser Tyr Asp Ser
            210                 215                 220

Ser His Ile Leu Ile Val Phe Gly Gly Gly Thr Lys Leu Thr Val Leu
225                 230                 235                 240

Gly Ser Gly Gly Ser Gly Gly Asn Cys Thr Gly Cys Ile Ile Cys Ser
                245                 250                 255

Glu Glu Asn Gly Cys Ser Thr Cys Gln Gln Arg Leu Phe Leu Phe Ile
            260                 265                 270

Arg Arg Glu Gly Ile Arg Gln Tyr Gly Lys Cys Leu His Asp Cys Pro
            275                 280                 285

Pro Gly Tyr Phe Gly Ile Arg Gly Gln Glu Val Asn Arg Cys Lys Lys
            290                 295                 300

Cys Gly Ala Thr Cys Glu Ser Cys Phe Ser Gln Asp Phe Cys Ile Arg
305                 310                 315                 320

Cys Lys Arg Gln Phe Tyr Leu Tyr Lys Gly Lys Cys Leu Pro Thr Cys
                325                 330                 335

Pro Pro Gly Thr Leu Ala His Gln Asn Thr Arg Glu Cys Gln Gly Gly
            340                 345                 350

Gly Asp Tyr Lys Asp Asp Asp Lys Gly Ser His His His His
            355                 360                 365

His His His
    370

<210> SEQ ID NO 101
<211> LENGTH: 1116
<212> TYPE: DNA
<213> ORGANISM: Artificial Sequence
<220> FEATURE:
<223> OTHER INFORMATION: Made in Lab - fusion construct

<400> SEQUENCE: 101
caggtccagt tggtggaatc cggaggggt ttggtccagc ctggtggaag cctgcgcctc      60
tcatgcgccg ctagcggatt caccttctcc cgatacggca tgcattgggt cagacaggca    120
cccggaaaag gactcgaatg ggtgtcgggc atttcctcga tcgggtcaaa cacctattac    180
gccgactccg tgaagggacg gttcaccatt agccgggata cagcaagaa cactctgtac    240 ttgcaaatga actccctgcg ggctgaggac accgccgtgt actactgtgc gcggtggtac    300
aagacctata ttgacgtctg gggacaggt accctcgtga ccgtgtcatc cggtggtgga    360
ggatccggag gcggaggaag cggaggaggg ggttcagaca tcgaactcac ccagccccg    420 tcagtgtccg tggcccctgg acagactgcg cgcatctcct gctccggcga caacctgggg    480
aagaaatacg tgtactggta ccagcagaag ccaggtcaag cccctgtgct ggtcatctac    540

-continued

```
ggcgacgacg aaaggccgtc aggcatccca gagcgcttct ccggctccaa ctccgggaat    600
actgccaccc ttaccatttc cggaacccag gccgaggatg aagcggatta ctattgcgcg    660
agctacgata gcagccacat cctgatcgtg tttggaggcg gtactaagct gaccgtgctg    720
ggaagcggtg gatcacaagg ctgccaagga ggctgtgcaa catgctcaga ttacaatgga    780
tgtttgtcat gtaagcccag actatttttt gctctggaaa gaattggcat gaagcagatt    840
ggagtatgtc tctcttcatg tccaagtgga tattatggaa ctcgatatcc agatataaat    900
aagtgtacaa aatgcaaagc tgactgtgat acctgtgcca acaaaaatgc ctgcacaaaa    960
tgtaaaagtg gattttactt acaccttgga aagtgccttg caattgccca gaaagggttg   1020
gaagccaaca accatactat ggagtgtgtc agtggcggag actacaagga cgacgatgac   1080
aagggctccc accatcacca ccatcatcac cactag                             1116
```

<210> SEQ ID NO 102
<211> LENGTH: 371
<212> TYPE: PRT
<213> ORGANISM: Artificial Sequence
<220> FEATURE:
<223> OTHER INFORMATION: Made in Lab - fusion construct

<400> SEQUENCE: 102

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240

Gly Ser Gly Gly Ser Gln Gly Cys Gln Gly Gly Cys Ala Thr Cys Ser
                245                 250                 255

Asp Tyr Asn Gly Cys Leu Ser Cys Lys Pro Arg Leu Phe Phe Ala Leu
```

```
                  260                 265                 270
Glu Arg Ile Gly Met Lys Gln Ile Gly Val Cys Leu Ser Ser Cys Pro
            275                 280                 285

Ser Gly Tyr Tyr Gly Thr Arg Tyr Pro Asp Ile Asn Lys Cys Thr Lys
        290                 295                 300

Cys Lys Ala Asp Cys Asp Thr Cys Ala Asn Lys Asn Ala Cys Thr Lys
305                 310                 315                 320

Cys Lys Ser Gly Phe Tyr Leu His Leu Gly Lys Cys Leu Asp Asn Cys
                325                 330                 335

Pro Glu Gly Leu Glu Ala Asn Asn His Thr Met Glu Cys Val Ser Gly
            340                 345                 350

Gly Asp Tyr Lys Asp Asp Asp Lys Gly Ser His His His His His His
        355                 360                 365

His His His
        370

<210> SEQ ID NO 103
<211> LENGTH: 1116
<212> TYPE: DNA
<213> ORGANISM: Artificial Sequence
<220> FEATURE:
<223> OTHER INFORMATION: Made in Lab - fusion construct

<400> SEQUENCE: 103
caggtccagt tggtggaatc cggagggggt tggtccagc ctggtggaag cctgcgcctc       60
tcatgcgccg ctagcggatt caccttctcc cgatacggca tgcattgggt cagacaggca      120
cccggaaaag gactcgaatg ggtgtcgggc atttcctcga tcgggtcaaa cacctattac      180
gccgactccg tgaagggacg gttcaccatt agccgggata cagcaagaa cactctgtac      240 ttgcaaatga actccctgcg ggctgaggac accgccgtgt actactgtgc gcggtggtac      300
aagacctata ttgacgtctg gggacagggt accctcgtga ccgtgtcatc cggtggtgga      360
ggatccggag gcggaggaag cggaggaggg ggttcagaca tcgaactcac ccagccccg      420 tcagtgtccg tggcccctgg acagactgcg cgcatctcct gctccggcga caacctgggg      480
aagaaatacg tgtactggta ccagcagaag ccaggtcaag cccctgtgct ggtcatctac      540
ggcgacgacg aaaggccgtc aggcatccca gagcgcttct ccggctccaa ctccgggaat      600
actgccaccc ttaccatttc cggaacccag gccgaggatg aagcggatta ctattgcgcg      660
agctacgata gcagccacat cctgatcgtg tttggaggcg gtactaagct gaccgtgctg      720
ggaagcggtg gatcacaagg ctgccaagga ggctgtgcaa catgctcaga ttacaatgga      780
tgtttgtcat gtaagcccag actatttttt gctctggaaa gaattggcat gaagcagatt      840
ggagtatgtc tctcttcatg tccaagtgga tattatggaa ctcgatatcc agatataaat      900
aagtgtacaa aatgcaaagc tgactgtgat acctgtcgca caaaaatgc ctgcacaaaa      960 tgtaaaagtg gattttactt acaccttgga aagtgccttg acaattgccc agaagggttg     1020
gaagccaaca accatactat ggagtgtgtc agtggcggag actacaagga cgacgatgac     1080
aagggctccc accatcacca ccatcatcac cactag                              1116

<210> SEQ ID NO 104
<211> LENGTH: 371
<212> TYPE: PRT
<213> ORGANISM: Artificial Sequence
<220> FEATURE:
<223> OTHER INFORMATION: Made in Lab - fusion construct
```

<400> SEQUENCE: 104

| | | | | | | | | | | | | | | |
|---|---|---|---|---|---|---|---|---|---|---|---|---|---|---|
|Gln|Val|Gln|Leu|Val|Glu|Ser|Gly|Gly|Gly|Leu|Val|Gln|Pro|Gly|Gly|
|1| | |5| | | | |10| | | | |15| | |
|Ser|Leu|Arg|Leu|Ser|Cys|Ala|Ala|Ser|Gly|Phe|Thr|Phe|Ser|Arg|Tyr|
| | | |20| | | | |25| | | | |30| | |
|Gly|Met|His|Trp|Val|Arg|Gln|Ala|Pro|Gly|Lys|Gly|Leu|Glu|Trp|Val|
| | |35| | | | |40| | | | |45| | | |
|Ser|Gly|Ile|Ser|Ser|Ile|Gly|Ser|Asn|Thr|Tyr|Tyr|Ala|Asp|Ser|Val|
| |50| | | | |55| | | | |60| | | | |
|Lys|Gly|Arg|Phe|Thr|Ile|Ser|Arg|Asp|Asn|Ser|Lys|Asn|Thr|Leu|Tyr|
|65| | | | |70| | | | |75| | | | |80|
|Leu|Gln|Met|Asn|Ser|Leu|Arg|Ala|Glu|Asp|Thr|Ala|Val|Tyr|Tyr|Cys|
| | | | |85| | | | |90| | | | |95| |
|Ala|Arg|Trp|Tyr|Lys|Thr|Tyr|Ile|Asp|Val|Trp|Gly|Gln|Gly|Thr|Leu|
| | | |100| | | | |105| | | | |110| | |
|Val|Thr|Val|Ser|Ser|Gly|Gly|Gly|Gly|Ser|Gly|Gly|Gly|Gly|Ser|Gly|
| | | |115| | | | |120| | | | |125| | |
|Gly|Gly|Gly|Ser|Asp|Ile|Glu|Leu|Thr|Gln|Pro|Pro|Ser|Val|Ser|Val|
| |130| | | | |135| | | | |140| | | | |
|Ala|Pro|Gly|Gln|Thr|Ala|Arg|Ile|Ser|Cys|Ser|Gly|Asp|Asn|Leu|Gly|
|145| | | | |150| | | | |155| | | | |160|
|Lys|Lys|Tyr|Val|Tyr|Trp|Tyr|Gln|Gln|Lys|Pro|Gly|Gln|Ala|Pro|Val|
| | | |165| | | | |170| | | | |175| | |
|Leu|Val|Ile|Tyr|Gly|Asp|Asp|Glu|Arg|Pro|Ser|Gly|Ile|Pro|Glu|Arg|
| | | |180| | | | |185| | | | |190| | |
|Phe|Ser|Gly|Ser|Asn|Ser|Gly|Asn|Thr|Ala|Thr|Leu|Thr|Ile|Ser|Gly|
| | |195| | | | |200| | | | |205| | | |
|Thr|Gln|Ala|Glu|Asp|Glu|Ala|Asp|Tyr|Tyr|Cys|Ala|Ser|Tyr|Asp|Ser|
| |210| | | | |215| | | | |220| | | | |
|Ser|His|Ile|Leu|Ile|Val|Phe|Gly|Gly|Gly|Thr|Lys|Leu|Thr|Val|Leu|
|225| | | | |230| | | | |235| | | | |240|
|Gly|Ser|Gly|Gly|Ser|Gln|Gly|Cys|Gln|Gly|Gly|Cys|Ala|Thr|Cys|Ser|
| | | |245| | | | |250| | | | |255| | |
|Asp|Tyr|Asn|Gly|Cys|Leu|Ser|Cys|Lys|Pro|Arg|Leu|Phe|Phe|Ala|Leu|
| | | |260| | | | |265| | | | |270| | |
|Glu|Arg|Ile|Gly|Met|Lys|Gln|Ile|Gly|Val|Cys|Leu|Ser|Ser|Cys|Pro|
| | |275| | | | |280| | | | |285| | | |
|Ser|Gly|Tyr|Tyr|Gly|Thr|Arg|Tyr|Pro|Asp|Ile|Asn|Lys|Cys|Thr|Lys|
| |290| | | | |295| | | | |300| | | | |
|Cys|Lys|Ala|Asp|Cys|Asp|Thr|Cys|Arg|Asn|Lys|Asn|Ala|Cys|Thr|Lys|
|305| | | | |310| | | | |315| | | | |320|
|Cys|Lys|Ser|Gly|Phe|Tyr|Leu|His|Leu|Gly|Lys|Cys|Leu|Asp|Asn|Cys|
| | | |325| | | | |330| | | | |335| | |
|Pro|Glu|Gly|Leu|Glu|Ala|Asn|Asn|His|Thr|Met|Glu|Cys|Val|Ser|Gly|
| | |340| | | | |345| | | | |350| | | |
|Gly|Asp|Tyr|Lys|Asp|Asp|Asp|Asp|Lys|Gly|Ser|His|His|His|His|His|
| | |355| | | | |360| | | | |365| | | |
|His|His|His| | | | | | | | | | | | | |
| |370| | | | | | | | | | | | | | |

<210> SEQ ID NO 105
<211> LENGTH: 1122
<212> TYPE: DNA
<213> ORGANISM: Artificial Sequence
<220> FEATURE:
<223> OTHER INFORMATION: Made in Lab - fusion construct

<400> SEQUENCE: 105

```
gaagtgcagc tgctggaatc cgggggcgga ctggtgcaac ccgggggatc cctcagactg      60
tcctgtgccg catcgggttt cactttctcc tcctacgcga tgtcatgggt cagacaggcc     120
cctggaaaag gcctcgaatg ggtgtcggct atctccggat cgggggggatc tacttactac    180
gccgactccg tgaagggccg gttcactatc tcgaggaca actccaagaa tacccctgtac    240
ttgcaaatga actccctgcg cgccgaggat accgcggtgt attactgcgc caaggacttc    300
agctcacgcc ggtggtacct tgagtactgg ggacagggaa cccttgtcac cgtgtccagc    360
ggtggcggcg gaagcggcgg gggcggatcc ggtggcgggg gctcagagct cacccaggac    420
cccgctgtgt ccgtggcctt gggacagacc gtgcgcatca catgccaggg cgatagcctg    480
cggagctatt acgcctcgtg gtaccagcag aagcctggtc aagcgccggt cctggtcatc    540
tacgaaaga caaccgccc gtccggaatt ccagacaggt tcagcggatc cagctcgggg    600
aacaccgcct cactgactat caccggagca caggccgaag atgaagccga ctactactgc    660
aactccctgg agcggattgg atacctgagc tacgtgtttg gtggcggcac gaagctcacc    720
gtgctgggaa gcggtggatc acaaggctgc caaggaggct gtgcaacatg ctcagattac    780
aatggatgtt tgtcatgtaa gcccagacta ttttttgctc tggaaagaat tggcatgaag    840
cagattggag tatgtctctc ttcatgtcca agtggatatt atggaactcg atatccagat    900
ataaataagt gtacaaaatg caaagctgac tgtgatacct gtgccaacaa aaatgcctgc    960
acaaaatgta aagtggatt ttacttacac cttggaaagt gccttgacaa ttgcccagaa   1020
gggttggaag ccaacaacca tactatggag tgtgtcagtg cggagactaa caaggacgac   1080
gatgacaagg gctcccacca tcaccaccat catcaccact ag                      1122
```

<210> SEQ ID NO 106
<211> LENGTH: 373
<212> TYPE: PRT
<213> ORGANISM: Artificial Sequence
<220> FEATURE:
<223> OTHER INFORMATION: Made in Lab - fusion construct

<400> SEQUENCE: 106

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Leu Thr Gln Asp Pro Ala Val Ser
    130                 135                 140
```

```
Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
            165                 170                 175

Val Leu Val Ile Tyr Gly Lys Asn Asn Arg Pro Ser Gly Ile Pro Asp
        180                 185                 190

Arg Phe Ser Gly Ser Ser Ser Gly Asn Thr Ala Ser Leu Thr Ile Thr
    195                 200                 205

Gly Ala Gln Ala Glu Asp Glu Ala Asp Tyr Tyr Cys Asn Ser Leu Glu
210                 215                 220

Arg Ile Gly Tyr Leu Ser Tyr Val Phe Gly Gly Gly Thr Lys Leu Thr
225                 230                 235                 240

Val Leu Gly Ser Gly Gly Ser Gln Gly Cys Gln Gly Gly Cys Ala Thr
                245                 250                 255

Cys Ser Asp Tyr Asn Gly Cys Leu Ser Cys Lys Pro Arg Leu Phe Phe
            260                 265                 270

Ala Leu Glu Arg Ile Gly Met Lys Gln Ile Gly Val Cys Leu Ser Ser
        275                 280                 285

Cys Pro Ser Gly Tyr Tyr Gly Thr Arg Tyr Pro Asp Ile Asn Lys Cys
    290                 295                 300

Thr Lys Cys Lys Ala Asp Cys Asp Thr Cys Ala Asn Lys Asn Ala Cys
305                 310                 315                 320

Thr Lys Cys Lys Ser Gly Phe Tyr Leu His Leu Gly Lys Cys Leu Asp
                325                 330                 335

Asn Cys Pro Glu Gly Leu Glu Ala Asn Asn His Thr Met Glu Cys Val
            340                 345                 350

Ser Gly Gly Asp Tyr Lys Asp Asp Asp Lys Gly Ser His His His His
        355                 360                 365

His His His His His
    370

<210> SEQ ID NO 107
<211> LENGTH: 1122
<212> TYPE: DNA
<213> ORGANISM: Artificial Sequence
<220> FEATURE:
<223> OTHER INFORMATION: Made in Lab - fusion construct

<400> SEQUENCE: 107
gaagtgcagc tgctggaatc cggggggcgga ctggtgcaac cgggggggatc cctcagactg    60 tcctgtgccg catcgggttt cactttctcc tcctacgcga tgtcatgggt cagacaggcc   120
cctggaaaag gcctcgaatg ggtgtcggct atctccggat cggggggatc tacttactac   180
gccgactccg tgaagggccg gttcactatc tcgagggaca actccaagaa taccctgtac   240
ttgcaaatga actccctgcg cgccgaggat accgcggtgt attactgcgc caaggacttc   300
agctcacgcc ggtggtacct tgagtactgg ggacagggaa cccttgtcac cgtgtccagc   360
ggtggcggcg gaagcggcgg gggcggatcc ggtgcggggg gctcagagct cacccaggac   420
cccgctgtgt ccgtggcctt gggacagacc gtgcgcatca catgccaggg cgatagcctg   480
cggagctatt acgcctcgtg gtaccagcag aagcctggtc aagcgccggt cctggtcatc   540
tacggaaaga caaccgccc gtccggaatt ccagacaggt tcagcggatc cagctcgggg   600
aacaccgcct cactgactat caccggagca caggccgaag atgaagccga ctactactgc   660
aactccctgg agcggattgg atacctgagc tacgtgtttg gtggcggcac gaagctcacc   720
```

```
gtgctgggaa gcggtggatc acaaggctgc caaggaggct gtgcaacatg ctcagattac      780
aatggatgtt tgtcatgtaa gcccagacta tttttgctc tggaaagaat tggcatgaag       840
cagattggag tatgtctctc ttcatgtcca agtggatatt atggaactcg atatccagat     900
ataaataagt gtacaaaatg caaagctgac tgtgatacct gtcgcaacaa aaatgcctgc     960
acaaaatgta aaagtggatt ttacttacac cttggaaagt gccttgacaa ttgcccagaa    1020
gggttggaag ccaacaacca tactatggag tgtgtcagtg gcggagacta caaggacgac    1080
gatgacaagg gctcccacca tcaccaccat catcaccact ag                       1122
```

<210> SEQ ID NO 108
<211> LENGTH: 373
<212> TYPE: PRT
<213> ORGANISM: Artificial Sequence
<220> FEATURE:
<223> OTHER INFORMATION: Made in Lab - fusion construct

<400> SEQUENCE: 108

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Gly Asn Thr Ala Ser Leu Thr Ile Thr
        195                 200                 205

Gly Ala Gln Ala Glu Asp Glu Ala Asp Tyr Tyr Cys Asn Ser Leu Glu
    210                 215                 220

Arg Ile Gly Tyr Leu Ser Tyr Val Phe Gly Gly Thr Lys Leu Thr
225                 230                 235                 240

Val Leu Gly Ser Gly Gly Ser Gln Gly Cys Gln Gly Cys Ala Thr
                245                 250                 255

Cys Ser Asp Tyr Asn Gly Cys Leu Ser Cys Lys Pro Arg Leu Phe Phe
            260                 265                 270

Ala Leu Glu Arg Ile Gly Met Lys Gln Ile Gly Val Cys Leu Ser Ser
        275                 280                 285
```

```
Cys Pro Ser Gly Tyr Tyr Gly Thr Arg Tyr Pro Asp Ile Asn Lys Cys
        290                 295                 300

Thr Lys Cys Lys Ala Asp Cys Asp Thr Cys Arg Asn Lys Asn Ala Cys
305                 310                 315                 320

Thr Lys Cys Lys Ser Gly Phe Tyr Leu His Leu Gly Lys Cys Leu Asp
                325                 330                 335

Asn Cys Pro Glu Gly Leu Glu Ala Asn Asn His Thr Met Glu Cys Val
            340                 345                 350

Ser Gly Gly Asp Tyr Lys Asp Asp Asp Lys Gly Ser His His His
        355                 360                 365

His His His His His
        370

<210> SEQ ID NO 109
<211> LENGTH: 1131
<212> TYPE: DNA
<213> ORGANISM: Artificial Sequence
<220> FEATURE:
<223> OTHER INFORMATION: Made in Lab - fusion construct

<400> SEQUENCE: 109
caagtgcaac tccaacaaag cggtcccgag ttggtccgac ccggcgtcag tgtgaaaatc     60
tcatgcaagg ggtccgggta taccttcact gactatgcaa tgcactgggt aaagcagagc    120
cacgccaagt ccttggagtg gatcggaggc attagtacct acttcggacg caccaactac    180
aatcaaaaat ttaagggtcg cgcaaccatg actgtagata aatcatcaag taccgcgtac    240
atggaattgg ctagactgac ttctgaagat tccgcgctgt attactgtgc tcgcggtttg    300
tctggcaact atgttatgga ttactggggg caagggacca gcgtcacggt gtcctctggc    360
ggaggcgggt ccggggggg tggttctggc ggaggcggat ccgatatagt tctgtttcaa    420
tcccctgcga gcctggcggt aagtttggga cagagagcca cgatttcctg ccgagcgagt    480
gaaagcgtag acgactacgg caattctttc atgcactggt atcaacagaa gccaggccaa    540
ccgccgaagc tgcttatcta tcgcgcgtcc aatttggagt cagggatccc tgcacgattt    600
tcaggttctg gaagtaggac agactttaca cttacgataa accccgtgga agcggatgac    660
gtcgcaacct actattgtca acaaagcaat gaagcaccac ctaccttcgg aggtggcact    720
aaattggaaa ttaggggaag cggtggatca caaggctgcc aaggaggctg tgcaacatgc    780
tcagattaca atggatgttt gtcatgtaag cccagactat tttttgctct ggaaagaatt    840
ggcatgaagc agattggagt atgtctctct tcatgtccaa gtggatatta tggaactcga    900
tatccagata taaataagtg tacaaaatgc aaagctgact gtgatacctg tgccaacaaa    960
aatgcctgca caaatgtaa agtggatttt acttacacc ttggaaagtg ccttgacaat   1020
tgcccagaag ggttggaagc caacaaccat actatggagt gtgtcagtgg cggagactac   1080
aaggacgacg atgacaaggg ctcccaccat caccaccatc atcaccacta g            1131

<210> SEQ ID NO 110
<211> LENGTH: 376
<212> TYPE: PRT
<213> ORGANISM: Artificial Sequence
<220> FEATURE:
<223> OTHER INFORMATION: Made in Lab - fusion construct

<400> SEQUENCE: 110

Gln Val Gln Leu Gln Gln Ser Gly Pro Glu Leu Val Arg Pro Gly Val
1               5                   10                  15
```

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Gly Ile Ser Thr Tyr Phe Gly Arg Thr Asn Tyr Asn Gln Lys Phe
    50                  55                  60

Lys Gly Arg Ala Thr Met Thr Val Asp Lys Ser Ser Thr Ala Tyr
65                  70                  75                  80

Met Glu Leu Ala Arg Leu Thr Ser Glu Asp Ser Ala Leu Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser Gly Gly Gly Ser Gly Gly Gly
        115                 120                 125

Ser Gly Gly Gly Ser Asp Ile Val Leu Phe Gln Ser Pro Ala Ser
    130                 135                 140

Leu Ala Val Ser Leu Gly Gln Arg Ala Thr Ile Ser Cys Arg Ala Ser
145                 150                 155                 160

Glu Ser Val Asp Asp Tyr Gly Asn Ser Phe Met His Trp Tyr Gln Gln
                165                 170                 175

Lys Pro Gly Gln Pro Pro Lys Leu Leu Ile Tyr Arg Ala Ser Asn Leu
            180                 185                 190

Glu Ser Gly Ile Pro Ala Arg Phe Ser Gly Ser Gly Ser Arg Thr Asp
        195                 200                 205

Phe Thr Leu Thr Ile Asn Pro Val Glu Ala Asp Val Ala Thr Tyr
    210                 215                 220

Tyr Cys Gln Gln Ser Asn Glu Ala Pro Pro Thr Phe Gly Gly Gly Thr
225                 230                 235                 240

Lys Leu Glu Ile Arg Gly Ser Gly Ser Gln Gly Cys Gln Gly Gly
                245                 250                 255

Cys Ala Thr Cys Ser Asp Tyr Asn Gly Cys Leu Ser Cys Lys Pro Arg
            260                 265                 270

Leu Phe Phe Ala Leu Glu Arg Ile Gly Met Lys Gln Ile Gly Val Cys
        275                 280                 285

Leu Ser Ser Cys Pro Ser Gly Tyr Tyr Gly Thr Arg Tyr Pro Asp Ile
    290                 295                 300

Asn Lys Cys Thr Lys Cys Lys Ala Asp Cys Asp Thr Cys Ala Asn Lys
305                 310                 315                 320

Asn Ala Cys Thr Lys Cys Lys Ser Gly Phe Tyr Leu His Leu Gly Lys
                325                 330                 335

Cys Leu Asp Asn Cys Pro Glu Gly Leu Glu Ala Asn Asn His Thr Met
            340                 345                 350

Glu Cys Val Ser Gly Gly Asp Tyr Lys Asp Asp Asp Lys Gly Ser
        355                 360                 365

His His His His His His His
    370                 375

<210> SEQ ID NO 111
<211> LENGTH: 1131
<212> TYPE: DNA
<213> ORGANISM: Artificial Sequence
<220> FEATURE:
<223> OTHER INFORMATION: Made in Lab - fusion construct

<400> SEQUENCE: 111

```
caagtgcaac tccaacaaag cggtcccgag ttggtccgac ccggcgtcag tgtgaaaatc      60
tcatgcaagg ggtccgggta taccttcact gactatgcaa tgcactgggt aaagcagagc     120
cacgccaagt ccttggagtg gatcggaggc attagtacct acttcggacg caccaactac    180
aatcaaaaat ttaagggtcg cgcaaccatg actgtagata aatcatcaag taccgcgtac    240
atggaattgg ctagactgac ttctgaagat tccgcgctgt attactgtgc tcgcggtttg    300
tctggcaact atgttatgga ttactggggg caagggacca gcgtcacggt gtcctctggc    360
ggaggcgggt ccggggggg tggttctggc ggaggcggat ccgatatagt tctgtttcaa     420
tcccctgcga gcctggcggt aagtttggga cagagagcca cgatttcctg ccgagcgagt    480
gaaagcgtag acgactacgg caattctttc atgcactggt atcaacagaa gccaggccaa    540
ccgccgaagc tgcttatcta tcgcgcgtcc aatttggagt cagggatccc tgcacgattt    600
tcaggttctg gaagtaggac agactttaca cttacgataa accccgtgga agcggatgac    660
gtcgcaacct actattgtca acaaagcaat gaagcaccac ctaccttcgg aggtggcact    720
aaattggaaa ttaggggaag cggtggatca caaggctgcc aaggaggctg tgcaacatgc    780
tcagattaca atggatgttt gtcatgtaag cccagactat tttttgctct ggaaagaatt    840
ggcatgaagc agattggagt atgtctctct tcatgtccaa gtggatatta tggaactcga    900
tatccagata taaataagtg tacaaaatgc aaagctgact gtgatacctg tcgcaacaaa    960
aatgcctgca caaatgtaa aagtggattt tacttcacacc ttgaaagtg ccttgacaat    1020
tgcccagaag ggttggaagc caacaaccat actatggagt gtgtcagtgg cggagactac   1080
aaggacgacg atgacaaggg ctcccaccat caccaccatc atcaccacta g            1131
```

<210> SEQ ID NO 112
<211> LENGTH: 376
<212> TYPE: PRT
<213> ORGANISM: Artificial Sequence
<220> FEATURE:
<223> OTHER INFORMATION: Made in Lab - fusion construct

<400> SEQUENCE: 112

```
Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Gly Ile Ser Thr Tyr Phe Gly Arg Thr Asn Tyr Asn Gln Lys Phe
    50                  55                  60

Lys Gly Arg Ala Thr Met Thr Val Asp Lys Ser Ser Ser Thr Ala Tyr
65                  70                  75                  80

Met Glu Leu Ala Arg Leu Thr Ser Glu Asp Ser Ala Leu Tyr Tyr Cys
                85                  90                  95

Ala Arg Gly Leu Ser Gly Asn Tyr Val Met Asp Tyr Trp Gly Gln Gly
            100                 105                 110

Thr Ser Val Thr Val Ser Ser Gly Gly Gly Gly Ser Gly Gly Gly Gly
        115                 120                 125

Ser Gly Gly Gly Gly Ser Asp Ile Val Leu Phe Gln Ser Pro Ala Ser
    130                 135                 140

Leu Ala Val Ser Leu Gly Gln Arg Ala Thr Ile Ser Cys Arg Ala Ser
145                 150                 155                 160

Glu Ser Val Asp Asp Tyr Gly Asn Ser Phe Met His Trp Tyr Gln Gln
```

```
                165                 170                 175
Lys Pro Gly Gln Pro Pro Lys Leu Leu Ile Tyr Arg Ala Ser Asn Leu
            180                 185                 190

Glu Ser Gly Ile Pro Ala Arg Phe Ser Gly Ser Gly Ser Arg Thr Asp
        195                 200                 205

Phe Thr Leu Thr Ile Asn Pro Val Glu Ala Asp Asp Val Ala Thr Tyr
    210                 215                 220

Tyr Cys Gln Gln Ser Asn Glu Ala Pro Pro Thr Phe Gly Gly Gly Thr
225                 230                 235                 240

Lys Leu Glu Ile Arg Gly Ser Gly Gly Ser Gln Gly Cys Gln Gly Gly
                245                 250                 255

Cys Ala Thr Cys Ser Asp Tyr Asn Gly Cys Leu Ser Cys Lys Pro Arg
                260                 265                 270

Leu Phe Phe Ala Leu Glu Arg Ile Gly Met Lys Gln Ile Gly Val Cys
                275                 280                 285

Leu Ser Ser Cys Pro Ser Gly Tyr Tyr Gly Thr Arg Tyr Pro Asp Ile
            290                 295                 300

Asn Lys Cys Thr Lys Cys Lys Ala Asp Cys Asp Thr Cys Arg Asn Lys
305                 310                 315                 320

Asn Ala Cys Thr Lys Cys Lys Ser Gly Phe Tyr Leu His Leu Gly Lys
                325                 330                 335

Cys Leu Asp Asn Cys Pro Glu Gly Leu Glu Ala Asn Asn His Thr Met
                340                 345                 350

Glu Cys Val Ser Gly Gly Asp Tyr Lys Asp Asp Asp Lys Gly Ser
            355                 360                 365

His His His His His His His
    370                 375

<210> SEQ ID NO 113
<211> LENGTH: 1116
<212> TYPE: DNA
<213> ORGANISM: Artificial Sequence
<220> FEATURE:
<223> OTHER INFORMATION: Made in Lab - fusion construct

<400> SEQUENCE: 113
caggtccagt tggtggaatc cggagggggt tggtccagc ctggtggaag cctgcgcctc      60
tcatgcgccg ctagcggatt caccttctcc cgatacggca tgcattgggt cagacaggca     120
cccggaaaag gactcgaatg ggtgtcgggc atttcctcga tcgggtcaaa cacctattac     180
gccgactccg tgaagggacg gttcaccatt agccgggata cagcaagaa cactctgtac     240 ttgcaaatga actccctgcg ggctgaggac accgccgtgt actactgtgc gcggtggtac     300
aagacctata ttgacgtctg gggacagggt accctcgtga ccgtgtcatc cggtggtgga     360
ggatccggag gcggaggaag cggaggaggg ggttcagaca tcgaactcac ccagccccg     420 tcagtgtccg tggcccctgg acagactgcg cgcatctcct gctccggcga caacctgggg     480
aagaaatacg tgtactggta ccagcagaag ccaggtcaag cccctgtgct ggtcatctac     540
ggcgacgacg aaaggccgtc aggcatccca gagcgcttct ccggctccaa ctccggggat     600
actgccaccc ttaccatttc cggaacccag gccgaggatg aagcggatta ctattgcgcg     660
agctacgata gcagccacat cctgatcgtg tttggaggcg gtactaagct gaccgtgctg     720
ggaagcggtg gatcacaagg ctgccaagga ggctgtgcaa catgctcaga ttacaatgga     780
tgtttgtcat gtaagcccag actatttttt gctctggaaa gaattggcat gaagcagatt     840
```

```
ggagtatgtc tctcttcatg tccaagtgga tattatggaa ctcgatatcc agatataaat    900
aagtgtacaa aatgcaaagc tgactgtgat acctgtcgca acaaaaatcg ctgcacaaaa    960
tgtaaaagtg gattttactt acaccttgga aagtgccttg acaattgccc agaagggttg   1020
gaagccaaca accatactat ggagtgtgtc agtggcggag actacaagga cgacgatgac   1080
aagggctccc accatcacca ccatcatcac cactag                             1116
```

<210> SEQ ID NO 114  
<211> LENGTH: 371  
<212> TYPE: PRT  
<213> ORGANISM: Artificial Sequence  
<220> FEATURE:  
<223> OTHER INFORMATION: Made in Lab - fusion construct

<400> SEQUENCE: 114

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Ser Gly Gly Gly Ser Gly
        115                 120                 125

Gly Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240

Gly Ser Gly Gly Ser Gln Gly Cys Gln Gly Gly Cys Ala Thr Cys Ser
                245                 250                 255

Asp Tyr Asn Gly Cys Leu Ser Cys Lys Pro Arg Leu Phe Phe Ala Leu
            260                 265                 270

Glu Arg Ile Gly Met Lys Gln Ile Gly Val Cys Leu Ser Ser Cys Pro
        275                 280                 285

Ser Gly Tyr Tyr Gly Thr Arg Tyr Pro Asp Ile Asn Lys Cys Thr Lys
    290                 295                 300

Cys Lys Ala Asp Cys Asp Thr Cys Arg Asn Lys Asn Arg Cys Thr Lys
305                 310                 315                 320
```

Cys Lys Ser Gly Phe Tyr Leu His Leu Gly Lys Cys Leu Asp Asn Cys
            325                 330                 335

Pro Glu Gly Leu Glu Ala Asn Asn His Thr Met Glu Cys Val Ser Gly
            340                 345                 350

Gly Asp Tyr Lys Asp Asp Asp Lys Gly Ser His His His His
            355                 360                 365

His His His
    370

<210> SEQ ID NO 115
<211> LENGTH: 1116
<212> TYPE: DNA
<213> ORGANISM: Artificial Sequence
<220> FEATURE:
<223> OTHER INFORMATION: Made in Lab - fusion construct

<400> SEQUENCE: 115

| | | |
|---|---|---|
| caggtccagt tggtggaatc cggaggggggt ttggtccagc ctggtggaag cctgcgcctc | 60 |
| tcatgcgccg ctagcggatt caccttctcc cgatacggca tgcattgggt cagacaggca | 120 |
| cccggaaaag gactcgaatg ggtgtcgggc atttcctcga tcgggtcaaa cacctattac | 180 |
| gccgactccg tgaagggacg gttcaccatt agccgggata cagcaagaa cactctgtac | 240 |
| ttgcaaatga actccctgcg ggctgaggac accgccgtgt actactgtgc gcggtggtac | 300 |
| aagacctata ttgacgtctg gggacagggt accctcgtga ccgtgtcatc cggtggtgga | 360 |
| ggatccggag gcggaggaag cggaggaggg ggttcagaca tcgaactcac ccagcccccg | 420 |
| tcagtgtccg tggcccctgg acagactgcg cgcatctcct gctccggcga caacctgggg | 480 |
| aagaaatacg tgtactggta ccagcagaag ccaggtcaag cccctgtgct ggtcatctac | 540 |
| ggcgacgacg aaaggccgtc aggcatccca gagcgcttct ccggctccaa ctccgggaat | 600 |
| actgccaccc ttaccatttc cggaacccag gccgaggatg aagcggatta ctattgcgcg | 660 |
| agctacgata gcagccacat cctgatcgtg tttggaggcg gtactaagct gaccgtgctg | 720 |
| ggaagcggtg gatcacaagg ctgccaagga ggctgtgcaa catgctcaga ttacaatgga | 780 |
| tgtttgtcat gtaagcccag actatttttt gctctgaaaa gaattggcat gaagcagatt | 840 |
| ggagtatgtc tctcttcatg tccaagtgga tattatggaa ctcgatatcc agatataaat | 900 |
| aagtgtacaa aatgcaaagc tgactgtgat acctgtgaaa caaaaatga atgcacaaaa | 960 |
| tgtaaaagtg gattttactt acaccttgga aagtgccttg acaattgccc agaagggttg | 1020 |
| gaagccaaca accatactat ggagtgtgtc agtggcggag actacaagga cgacgatgac | 1080 |
| aagggctccc accatcacca ccatcatcac cactag | 1116 |

<210> SEQ ID NO 116
<211> LENGTH: 371
<212> TYPE: PRT
<213> ORGANISM: Artificial Sequence
<220> FEATURE:
<223> OTHER INFORMATION: Made in Lab - fusion construct

<400> SEQUENCE: 116

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Ser Gly Gly Gly Ser Gly
        115                 120                 125

Gly Gly Gly Ser Asp Ile Glu Leu Thr Gln Pro Pro Ser Val Ser Val
130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
210                 215                 220

Ser His Ile Leu Ile Val Phe Gly Gly Gly Thr Lys Leu Thr Val Leu
225                 230                 235                 240

Gly Ser Gly Gly Ser Gln Gly Cys Gln Gly Cys Ala Thr Cys Ser
                245                 250                 255

Asp Tyr Asn Gly Cys Leu Ser Cys Lys Pro Arg Leu Phe Phe Ala Leu
            260                 265                 270

Glu Arg Ile Gly Met Lys Gln Ile Gly Val Cys Leu Ser Ser Cys Pro
        275                 280                 285

Ser Gly Tyr Tyr Gly Thr Arg Tyr Pro Asp Ile Asn Lys Cys Thr Lys
290                 295                 300

Cys Lys Ala Asp Cys Asp Thr Cys Glu Asn Lys Asn Glu Cys Thr Lys
305                 310                 315                 320

Cys Lys Ser Gly Phe Tyr Leu His Leu Gly Lys Cys Leu Asp Asn Cys
                325                 330                 335

Pro Glu Gly Leu Glu Ala Asn Asn His Thr Met Glu Cys Val Ser Gly
            340                 345                 350

Gly Asp Tyr Lys Asp Asp Asp Lys Gly Ser His His His His
        355                 360                 365

His His His
    370

<210> SEQ ID NO 117
<211> LENGTH: 1116
<212> TYPE: DNA
<213> ORGANISM: Artificial Sequence
<220> FEATURE:
<223> OTHER INFORMATION: Made in Lab - fusion construct

<400> SEQUENCE: 117
caggtccagt tggtggaatc cggaggggggt ttggtccagc ctggtggaag cctgcgcctc    60
tcatgcgccg ctagcggatt caccttctcc cgatacggca tgcattgggt cagacaggca   120
cccggaaaag gactcgaatg ggtgtcgggc atttcctcga tcgggtcaaa cacctattac   180

```
gccgactccg tgaagggacg gttcaccatt agccgggata acagcaagaa cactctgtac      240
ttgcaaatga actccctgcg ggctgaggac accgccgtgt actactgtgc gcggtggtac      300
aagacctata ttgacgtctg gggacagggt accctcgtga ccgtgtcatc cggtggtgga      360
ggatccggag gcgaggaag  cggaggaggg ggttcagaca tcgaactcac ccagcccccg      420
tcagtgtccg tggcccctgg acagactgcg cgcatctcct gctccggcga caacctgggg      480
aagaaatacg tgtactggta ccagcagaag ccaggtcaag cccctgtgct ggtcatctac      540
ggcgacgacg aaaggccgtc aggcatccca gagcgcttct ccggctccaa ctccgggaat      600
actgccaccc ttaccatttc cggaacccag gccgaggatg aagcggatta ctattgcgcg      660
agctacgata gcagccacat cctgatcgtg tttggaggcg gtactaagct gaccgtgctg      720
ggaagcggtg gatcacaagg ctgccaagga ggctgtgcaa catgctcaga ttacaatgga      780
tgtttgtcat gtaagcccag actatttttt gctctggaaa gaattggcat gaagcagatt      840
ggagtatgtc tctcttcatg tccaagtgga tattatggaa ctcgatatcc agatataaat      900
aagtgtacaa aatgcaaagc tgactgtgat acctgtcgca acaaaatga  atgcacaaaa      960 tgtaaaagtg gattttactt acaccttgga aagtgccttg caattgccc  agaagggttg      1020 gaagccaaca accatactat ggagtgtgtc agtggcggag actacaagga cgacgatgac      1080
aagggctccc accatcacca ccatcatcac cactag                                1116
```

<210> SEQ ID NO 118
<211> LENGTH: 371
<212> TYPE: PRT
<213> ORGANISM: Artificial Sequence
<220> FEATURE:
<223> OTHER INFORMATION: Made in Lab - fusion construct

<400> SEQUENCE: 118

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190
```

Phe Ser Gly Ser Asn Ser Gly Asn Thr Ala Thr Leu Thr Ile Ser Gly
            195                 200                 205

Thr Gln Ala Glu Asp Glu Ala Asp Tyr Tyr Cys Ala Ser Tyr Asp Ser
        210                 215                 220

Ser His Ile Leu Ile Val Phe Gly Gly Gly Thr Lys Leu Thr Val Leu
225                 230                 235                 240

Gly Ser Gly Gly Ser Gln Gly Cys Gln Gly Gly Cys Ala Thr Cys Ser
                245                 250                 255

Asp Tyr Asn Gly Cys Leu Ser Cys Lys Pro Arg Leu Phe Phe Ala Leu
            260                 265                 270

Glu Arg Ile Gly Met Lys Gln Ile Gly Val Cys Leu Ser Ser Cys Pro
        275                 280                 285

Ser Gly Tyr Tyr Gly Thr Arg Tyr Pro Asp Ile Asn Lys Cys Thr Lys
    290                 295                 300

Cys Lys Ala Asp Cys Asp Thr Cys Arg Asn Lys Asn Glu Cys Thr Lys
305                 310                 315                 320

Cys Lys Ser Gly Phe Tyr Leu His Leu Gly Lys Cys Leu Asp Asn Cys
                325                 330                 335

Pro Glu Gly Leu Glu Ala Asn Asn His Thr Met Glu Cys Val Ser Gly
            340                 345                 350

Gly Asp Tyr Lys Asp Asp Asp Lys Gly Ser His His His His His His
        355                 360                 365

His His His
    370

<210> SEQ ID NO 119
<211> LENGTH: 1116
<212> TYPE: DNA
<213> ORGANISM: Artificial Sequence
<220> FEATURE:
<223> OTHER INFORMATION: Made in Lab - fusion construct

<400> SEQUENCE: 119
caggtccagt tggtggaatc cggagggggt tggtccagc ctggtggaag cctgcgcctc      60
tcatgcgccg ctagcggatt caccttctcc cgatacggca tgcattgggt cagacaggca     120
cccggaaaag gactcgaatg ggtgtcgggc atttcctcga tcgggtcaaa cacctattac     180
gccgactccg tgaagggacg gttcaccatt agccgggata cagcaagaa cactctgtac     240 ttgcaaatga actccctgcg ggctgaggac accgccgtgt actactgtgc gcggtggtac     300
aagacctata ttgacgtctg gggacagggt accctcgtga ccgtgtcatc cggtggtgga     360
ggatccggag gcggaggaag cggaggaggg ggttcagaca tcgaactcac ccagccccg      420 tcagtgtccg tggcccctgg acagactgcg cgcatctcct gctccggcga caacctgggg     480
aagaaatacg tgtactggta ccagcagaag ccaggtcaag cccctgtgct ggtcatctac     540
ggcgacgacg aaaggccgtc aggcatccca gagcgcttct ccggctccaa ctccgggaat     600
actgccaccc ttaccatttc cggaacccag gccgaggatg aagcggatta ctattgcgcg     660
agctacgata gcagccacat cctgatcgtg tttggaggcg gtactaagct gaccgtgctg     720
ggaagcggtg gatcacaagg ctgccaagga ggctgtgcaa catgctcaga ttacaatgga     780
tgtttgtcat gtaagcccag actattttt gctctggaaa gaattggcat gaagcagatt     840
ggagtatgtc tctcttcatg tccaagtgga tattatggaa ctcgatatcc agatataaat     900
aagtgtacaa aatgcaaagc tgactgtgat acctgtgaaa acaaaaatgc ctgcacaaaa     960
tgtaaaagtg gattttactt acaccttgga aagtgccttg acaattgccc agaagggttg    1020

```
gaagccaaca accatactat ggagtgtgtc agtggcggag actacaagga cgacgatgac    1080
aagggctccc accatcacca ccatcatcac cactag                              1116
```

<210> SEQ ID NO 120
<211> LENGTH: 371
<212> TYPE: PRT
<213> ORGANISM: Artificial Sequence
<220> FEATURE:
<223> OTHER INFORMATION: Made in Lab - fusion construct

<400> SEQUENCE: 120

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Glu Leu Thr Gln Pro Pro Ser Val Ser Val
    130                 135                 140

Ala Pro Gly Gln Thr Ala Arg Ile Ser Cys Ser Gly Asp Asn Leu Gly
145                 150                 155                 160

Lys Lys Tyr Val Tyr Trp Tyr Gln Gln Lys Pro Gly Gln Ala Pro Val
                165                 170                 175

Leu Val Ile Tyr Gly Asp Asp Glu Arg Pro Ser Gly Ile Pro Glu Arg
            180                 185                 190

Phe Ser Gly Ser Asn Ser Gly Asn Thr Ala Thr Leu Thr Ile Ser Gly
        195                 200                 205

Thr Gln Ala Glu Asp Glu Ala Asp Tyr Tyr Cys Ala Ser Tyr Asp Ser
    210                 215                 220

Ser His Ile Leu Ile Val Phe Gly Gly Gly Thr Lys Leu Thr Val Leu
225                 230                 235                 240

Gly Ser Gly Gly Ser Gln Gly Cys Gln Gly Gly Cys Ala Thr Cys Ser
                245                 250                 255

Asp Tyr Asn Gly Cys Leu Ser Cys Lys Pro Arg Leu Phe Phe Ala Leu
            260                 265                 270

Glu Arg Ile Gly Met Lys Gln Ile Gly Val Cys Leu Ser Ser Cys Pro
        275                 280                 285

Ser Gly Tyr Tyr Gly Thr Arg Tyr Pro Asp Ile Asn Lys Cys Thr Lys
    290                 295                 300

Cys Lys Ala Asp Cys Asp Thr Cys Glu Asn Lys Asn Ala Cys Thr Lys
305                 310                 315                 320

Cys Lys Ser Gly Phe Tyr Leu His Leu Gly Lys Cys Leu Asp Asn Cys
                325                 330                 335

Pro Glu Gly Leu Glu Ala Asn Asn His Thr Met Glu Cys Val Ser Gly
```

```
                 340                 345                 350
Gly Asp Tyr Lys Asp Asp Asp Lys Gly Ser His His His His
        355                 360                 365
His His His
    370
```

<210> SEQ ID NO 121
<211> LENGTH: 1116
<212> TYPE: DNA
<213> ORGANISM: Artificial Sequence
<220> FEATURE:
<223> OTHER INFORMATION: Made in Lab - fusion construct

<400> SEQUENCE: 121

```
caggtccagt tggtggaatc cggagggggt ttggtccagc ctggtggaag cctgcgcctc    60
tcatgcgccg ctagcggatt caccttctcc cgatacggca tgcattgggt cagacaggca   120
cccggaaaag gactcgaatg ggtgtcgggc atttcctcga tcgggtcaaa cacctattac   180
gccgactccg tgaagggacg gttcaccatt agccggata acagcaagaa cactctgtac   240
ttgcaaatga actccctgcg ggctgaggac accgccgtgt actactgtgc gcggtggtac   300
aagacctata ttgacgtctg gggacagggt accctcgtga ccgtgtcatc cggtggtgga   360
ggatccggag gcggaggaag cggaggaggg ggttcagaca tcgaactcac ccagcccccg   420
tcagtgtccg tggcccctgg acagactgcg cgcatctcct gctccggcga acctggggg   480
aagaaatacg tgtactggta ccagcagaag ccaggtcaag cccctgtgct ggtcatctac   540
ggcgacgacg aaaggccgtc aggcatccca gagcgcttct ccggctccaa ctccgggaat   600
actgccaccc ttaccatttc cggaacccag gccgaggatg aagcggatta ctattgcgcg   660
agctacgata gcagccacat cctgatcgtg tttggaggcg gtactaagct gaccgtgctg   720
ggaagcggtg gatcacaagg ctgccaagga ggctgtgcaa catgctcaga ttacaatgga   780
tgtttgtcat gtaagcccga actattttt gctctggaaa gaattggcat gaagcagatt   840
ggagtatgtc tctcttcatg tccaagtgga tattatggaa ctgaatatcc agatatagct   900
aagtgtacaa atgcaaagc tgactgtgat acctgtcgca acaaaaatgc ctgcacaaaa   960
tgtaaaagtg gatttactt acaccttgga aagtgccttg caattgccc agaagggttg  1020
gaagccaaca accatactat ggagtgtgtc agtggcggag actacaagga cgacgatgac  1080
aagggctccc accatcacca ccatcatcac cactag                           1116
```

<210> SEQ ID NO 122
<211> LENGTH: 371
<212> TYPE: PRT
<213> ORGANISM: Artificial Sequence
<220> FEATURE:
<223> OTHER INFORMATION: Made in Lab - fusion construct

<400> SEQUENCE: 122

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                        85                  90                  95
Ala Arg Trp Tyr Lys Thr Tyr Ile Asp Val Trp Gly Gln Gly Thr Leu
                100                 105                 110
Val Thr Val Ser Ser Gly Gly Gly Gly Ser Gly Gly Gly Gly Ser Gly
                115                 120                 125
Gly Gly Gly Ser Asp Ile Glu Leu Thr Gln Pro Pro Ser Val Ser Val
            130                 135                 140
Ala Pro Gly Gln Thr Ala Arg Ile Ser Cys Ser Gly Asp Asn Leu Gly
145                 150                 155                 160
Lys Lys Tyr Val Tyr Trp Tyr Gln Gln Lys Pro Gly Gln Ala Pro Val
                165                 170                 175
Leu Val Ile Tyr Gly Asp Asp Glu Arg Pro Ser Gly Ile Pro Glu Arg
                180                 185                 190
Phe Ser Gly Ser Asn Ser Gly Asn Thr Ala Thr Leu Thr Ile Ser Gly
                195                 200                 205
Thr Gln Ala Glu Asp Glu Ala Asp Tyr Tyr Cys Ala Ser Tyr Asp Ser
            210                 215                 220
Ser His Ile Leu Ile Val Phe Gly Gly Gly Thr Lys Leu Thr Val Leu
225                 230                 235                 240
Gly Ser Gly Gly Ser Gln Gly Cys Gln Gly Cys Ala Thr Cys Ser
                245                 250                 255
Asp Tyr Asn Gly Cys Leu Ser Cys Lys Pro Glu Leu Phe Phe Ala Leu
            260                 265                 270
Glu Arg Ile Gly Met Lys Gln Ile Gly Val Cys Leu Ser Ser Cys Pro
            275                 280                 285
Ser Gly Tyr Tyr Gly Thr Glu Tyr Pro Asp Ile Ala Lys Cys Thr Lys
            290                 295                 300
Cys Lys Ala Asp Cys Asp Thr Cys Arg Asn Lys Asn Ala Cys Thr Lys
305                 310                 315                 320
Cys Lys Ser Gly Phe Tyr Leu His Leu Gly Lys Cys Leu Asp Asn Cys
                325                 330                 335
Pro Glu Gly Leu Glu Ala Asn Asn His Thr Met Glu Cys Val Ser Gly
            340                 345                 350
Gly Asp Tyr Lys Asp Asp Asp Lys Gly Ser His His His His
            355                 360                 365
His His His
        370

<210> SEQ ID NO 123
<211> LENGTH: 1122
<212> TYPE: DNA
<213> ORGANISM: Artificial Sequence
<220> FEATURE:
<223> OTHER INFORMATION: Made in Lab - fusion construct

<400> SEQUENCE: 123
gaagtgcagc tgctggaatc cggggggcgga ctggtgcaac ccggggggatc cctcagactg      60 tcctgtgccg catcgggttt cactttctcc tcctacgcga tgtcatgggt cagacaggcc     120
cctggaaaag gcctcgaatg ggtgtcggct atctccggat cggggggatc tacttactac     180
gccgactccg tgaagggccg gttcactatc tcgaggaca actccaagaa tacccctgtac     240 ttgcaaatga actccctgcg cgccgaggat accgcggtgt attactgcgc caaggacttc     300
```

```
agctcacgcc ggtggtacct tgagtactgg ggacagggaa cccttgtcac cgtgtccagc    360
ggtggcggcg gaagcggcgg gggcggatcc ggtggcgggg gctcagagct cacccaggac    420
cccgctgtgt ccgtggcctt gggacagacc gtgcgcatca catgccaggg cgatagcctg    480
cggagctatt acgcctcgtg gtaccagcag aagcctggtc aagcgccggt cctggtcatc    540
tacggaaaga acaaccgccc gtccggaatt ccagacaggt tcagcggatc cagctcgggg    600
aacaccgcct cactgactat caccggagca caggccgaag atgaagccga ctactactgc    660
aactccctgg agcggattgg atacctgagc tacgtgtttg gtggcggcac gaagctcacc    720
gtgctgggaa gcgtggatc acaaggctgc caaggaggct gtgcaacatg ctcagattac    780
aatggatgtt tgtcatgtaa gcccagacta ttttttgctc tggaaagaat tggcatgaag    840
cagattggag tatgtctctc ttcatgtcca agtggatatt atggaactcg atatccagat    900
ataaataagt gtacaaaatg caaagctgac tgtgatacct gtcgcaacaa aaatcgctgc    960
acaaaatgta aaagtggatt ttacttacac cttggaaagt gccttgacaa ttgcccagaa   1020
gggttggaag ccaacaacca tactatggag tgtgtcagtg gcgagactaa caaggacgac   1080
gatgacaagg gctcccacca tcaccaccat catcaccact ag                      1122
```

<210> SEQ ID NO 124
<211> LENGTH: 373
<212> TYPE: PRT
<213> ORGANISM: Artificial Sequence
<220> FEATURE:
<223> OTHER INFORMATION: Made in Lab - fusion construct

<400> SEQUENCE: 124

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
        195                 200                 205

Gly Ala Gln Ala Glu Asp Glu Ala Asp Tyr Tyr Cys Asn Ser Leu Glu
    210                 215                 220
```

```
Arg Ile Gly Tyr Leu Ser Tyr Val Phe Gly Gly Thr Lys Leu Thr
225                 230                 235                 240

Val Leu Gly Ser Gly Ser Gln Gly Cys Gln Gly Cys Ala Thr
            245                 250                 255

Cys Ser Asp Tyr Asn Gly Cys Leu Ser Cys Lys Pro Arg Leu Phe Phe
        260                 265                 270

Ala Leu Glu Arg Ile Gly Met Lys Gln Ile Gly Val Cys Leu Ser Ser
        275                 280                 285

Cys Pro Ser Gly Tyr Tyr Gly Thr Arg Tyr Pro Asp Ile Asn Lys Cys
        290                 295                 300

Thr Lys Cys Lys Ala Asp Cys Asp Thr Cys Arg Asn Lys Asn Arg Cys
305                 310                 315                 320

Thr Lys Cys Lys Ser Gly Phe Tyr Leu His Leu Gly Lys Cys Leu Asp
            325                 330                 335

Asn Cys Pro Glu Gly Leu Glu Ala Asn Asn His Thr Met Glu Cys Val
            340                 345                 350

Ser Gly Gly Asp Tyr Lys Asp Asp Asp Asp Lys Gly Ser His His His
            355                 360                 365

His His His His His
    370
```

<210> SEQ ID NO 125
<211> LENGTH: 1122
<212> TYPE: DNA
<213> ORGANISM: Artificial Sequence
<220> FEATURE:
<223> OTHER INFORMATION: Made in Lab - fusion construct

<400> SEQUENCE: 125

```
gaagtgcagc tgctggaatc cggggggcgga ctggtgcaac cgggggggatc cctcagactg    60
tcctgtgccg catcgggttt cactttctcc tcctacgcga tgtcatgggt cagacaggcc   120
cctggaaaag gcctcgaatg ggtgtcggct atctccggat cgggggggatc tacttactac   180
gccgactccg tgaagggccg gttcactatc tcgaggaca actccaagaa tacccctgtac   240
ttgcaaatga actccctgcg cgccgaggat accgcgtgt attactgcgc caaggacttc   300
agctcacgcc ggtggtacct tgagtactgg ggacagggaa cccttgtcac cgtgtccagc   360
ggtggcggcg aagcggcgg gggcggatcc ggtggcgggg gctcagagct cacccaggac   420
cccgctgtgt ccgtggcctt gggacagacc gtgcgcatca catgccaggg cgatagcctg   480
cggagctatt acgcctcgtg gtaccagcag aagcctggtc aagcgccggt cctggtcatc   540
tacggaaaga caaccgccc gtccggaatt ccagacaggt tcagcggatc cagctcgggg   600
aacaccgcct cactgactat caccggagca caggccgaag atgaagccga ctactactgc   660
aactccctgg agcggattgg atacctgagc tacgtgtttg gtggcggcac gaagctcacc   720
gtgctgggaa gcgtggatc acaaggctgc caaggaggct gtgcaacatg ctcagattac   780
aatggatgtt tgtcatgtaa gcccagacta ttttttgctc tggaaagaat tggcatgaag   840
cagattggag tatgtctctc ttcatgtcca agtggatatt atggaactcg atatccagat   900
ataaataagt gtacaaaatg caagctgac tgtgataacct gtgaaaacaa aaatgaatgc   960
acaaaatgta aagtggatt ttacttacac cttggaaagt gccttgacaa ttgcccagaa  1020
gggttggaag ccaacaacca tactatggag tgtgtcagtg gcggagacta caaggacgac  1080
gatgacaagg gctcccacca tcaccaccat catcaccact ag                     1122
```

<210> SEQ ID NO 126
<211> LENGTH: 373
<212> TYPE: PRT
<213> ORGANISM: Artificial Sequence
<220> FEATURE:
<223> OTHER INFORMATION: Made in Lab - fusion construct

<400> SEQUENCE: 126

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
        195                 200                 205

Gly Ala Gln Ala Glu Asp Glu Ala Asp Tyr Tyr Cys Asn Ser Leu Glu
    210                 215                 220

Arg Ile Gly Tyr Leu Ser Tyr Val Phe Gly Gly Gly Thr Lys Leu Thr
225                 230                 235                 240

Val Leu Gly Ser Gly Ser Gln Gly Cys Gln Gly Cys Ala Thr
                245                 250                 255

Cys Ser Asp Tyr Asn Gly Cys Leu Ser Cys Lys Pro Arg Leu Phe Phe
                260                 265                 270

Ala Leu Glu Arg Ile Gly Met Lys Gln Ile Gly Val Cys Leu Ser Ser
            275                 280                 285

Cys Pro Ser Gly Tyr Tyr Gly Thr Arg Tyr Pro Asp Ile Asn Lys Cys
        290                 295                 300

Thr Lys Cys Lys Ala Asp Cys Asp Thr Cys Glu Asn Lys Asn Glu Cys
305                 310                 315                 320

Thr Lys Cys Lys Ser Gly Phe Tyr Leu His Leu Gly Lys Cys Leu Asp
                325                 330                 335

Asn Cys Pro Glu Gly Leu Glu Ala Asn Asn His Thr Met Glu Cys Val
            340                 345                 350

Ser Gly Gly Asp Tyr Lys Asp Asp Asp Lys Gly Ser His His His
        355                 360                 365
```

His His His His His
    370

<210> SEQ ID NO 127
<211> LENGTH: 1122
<212> TYPE: DNA
<213> ORGANISM: Artificial Sequence
<220> FEATURE:
<223> OTHER INFORMATION: Made in Lab - fusion construct

<400> SEQUENCE: 127

```
gaagtgcagc tgctggaatc cggggggcgga ctggtgcaac ccgggggatc cctcagactg      60
tcctgtgccg catcgggttt cactttctcc tcctacgcga tgtcatgggt cagacaggcc     120
cctggaaaag gcctcgaatg ggtgtcggct atctccggat cggggggatc tacttactac     180
gccgactccg tgaagggccg gttcactatc tcgaggaca actccaagaa tacccctgtac     240
ttgcaaatga actccctgcg cgccgaggat accgcggtgt attactgcgc caaggacttc     300
agctcacgcc ggtggtacct tgagtactgg ggacagggaa cccttgtcac cgtgtccagc     360
ggtggcggcg gaagcggcgg gggcggatcc ggtggcgggg gctcagagct cacccaggac     420
cccgctgtgt ccgtggcctt gggacagacc gtgcgcatca catgccaggg cgatagcctg     480
cggagctatt acgcctcgtg gtaccagcag aagcctggtc aagcgccggt cctggtcatc     540
tacggaaaga caaccgccc gtccggaatt ccagacaggt tcagcggatc cagctcgggg     600
aacaccgcct cactgactat caccggagca caggccgaag atgaagccga ctactactgc     660
aactccctgg agcggattgg atacctgagc tacgtgtttg gtggcggcac gaagctcacc     720
gtgctgggaa gcggtggatc acaaggctgc caaggaggct gtgcaacatg ctcagattac     780
aatggatgtt tgtcatgtaa gcccagacta ttttttgctc tggaaagaat tggcatgaag     840
cagattggag tatgtctctc ttcatgtcca agtggatatt atggaactcg atatccagat     900
ataaataagt gtacaaaatg caaagctgac tgtgataccct gtcgcaacaa aaatgaatgc     960
acaaaatgta aaagtggatt ttacttacac cttggaaagt gccttgacaa ttgcccagaa    1020
gggttggaag ccaacaacca tactatggag tgtgtcagtg gcggagacta caaggacgac    1080
gatgacaagg gctcccacca tcaccaccat catcaccact ag                        1122
```

<210> SEQ ID NO 128
<211> LENGTH: 373
<212> TYPE: PRT
<213> ORGANISM: Artificial Sequence
<220> FEATURE:
<223> OTHER INFORMATION: Made in Lab - fusion construct

<400> SEQUENCE: 128

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
        195                 200                 205

Gly Ala Gln Ala Glu Asp Glu Ala Asp Tyr Tyr Cys Asn Ser Leu Glu
    210                 215                 220

Arg Ile Gly Tyr Leu Ser Tyr Val Phe Gly Gly Gly Thr Lys Leu Thr
225                 230                 235                 240

Val Leu Gly Ser Gly Gly Ser Gln Gly Cys Gln Gly Gly Cys Ala Thr
                245                 250                 255

Cys Ser Asp Tyr Asn Gly Cys Leu Ser Cys Lys Pro Arg Leu Phe Phe
            260                 265                 270

Ala Leu Glu Arg Ile Gly Met Lys Gln Ile Gly Val Cys Leu Ser Ser
        275                 280                 285

Cys Pro Ser Gly Tyr Tyr Gly Thr Arg Tyr Pro Asp Ile Asn Lys Cys
    290                 295                 300

Thr Lys Cys Lys Ala Asp Cys Asp Thr Cys Arg Asn Lys Asn Glu Cys
305                 310                 315                 320

Thr Lys Cys Lys Ser Gly Phe Tyr Leu His Leu Gly Lys Cys Leu Asp
                325                 330                 335

Asn Cys Pro Glu Gly Leu Glu Ala Asn Asn His Thr Met Glu Cys Val
            340                 345                 350

Ser Gly Gly Asp Tyr Lys Asp Asp Asp Asp Lys Gly Ser His His His
        355                 360                 365

His His His His His
    370

<210> SEQ ID NO 129
<211> LENGTH: 1122
<212> TYPE: DNA
<213> ORGANISM: Artificial Sequence
<220> FEATURE:
<223> OTHER INFORMATION: Made in Lab - fusion construct

<400> SEQUENCE: 129
gaagtgcagc tgctggaatc cggggggcgga ctggtgcaac ccggggggatc cctcagactg      60 tcctgtgccg catcgggttt cactttctcc tcctacgcga tgtcatgggt cagacaggcc     120
cctggaaaag gcctcgaatg ggtgtcggct atctccggat cggggggatc tacttactac     180
gccgactccg tgaagggccg gttcactatc tcgaggaca actccaagaa taccctgtac     240
ttgcaaatga actccctgcg cgccgaggat accgcggtgt attactgcgc caaggacttc     300
agctcacgcc ggtggtacct tgagtactgg ggacagggaa cccttgtcac cgtgtccagc     360
ggtggcggcg aagcggcgg gggcggatcc ggtggcgggg gctcagagct cacccaggac     420
cccgctgtgt ccgtggcctt gggacagacc gtgcgcatca catgccaggg cgatagcctg     480

```
cggagctatt acgcctcgtg gtaccagcag aagcctggtc aagcgccggt cctggtcatc    540 tacgaaaga acaaccgccc gtccggaatt ccagacaggt tcagcggatc cagctcgggg    600
aacaccgcct cactgactat caccggagca caggccgaag atgaagccga ctactactgc    660
aactccctgg agcggattgg atacctgagc tacgtgtttg gtggcggcac gaagctcacc    720
gtgctgggaa gcggtggatc acaaggctgc caaggaggct gtgcaacatg ctcagattac    780
aatggatgtt tgtcatgtaa gcccagacta ttttttgctc tggaaagaat tggcatgaag    840
cagattggag tatgtctctc ttcatgtcca agtggatatt atggaactcg atatccagat    900
ataaataagt gtacaaaatg caaagctgac tgtgatacct gtgaaaacaa aaatgcctgc    960
acaaaatgta aagtggatt ttacttacac cttggaaagt gccttgacaa ttgcccagaa    1020
gggttggaag ccaacaacca tactatggag tgtgtcagtg gcggagacta caaggacgac    1080
gatgacaagg gctcccacca tcaccaccat catcaccact ag                       1122
```

<210> SEQ ID NO 130
<211> LENGTH: 373
<212> TYPE: PRT
<213> ORGANISM: Artificial Sequence
<220> FEATURE:
<223> OTHER INFORMATION: Made in Lab - fusion construct

<400> SEQUENCE: 130

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Gly Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Gly Asn Thr Ala Ser Leu Thr Ile Thr
            195                 200                 205

Gly Ala Gln Ala Glu Asp Glu Ala Asp Tyr Tyr Cys Asn Ser Leu Glu
        210                 215                 220

Arg Ile Gly Tyr Leu Ser Tyr Val Phe Gly Gly Thr Lys Leu Thr
225                 230                 235                 240

Val Leu Gly Ser Gly Gly Ser Gln Gly Cys Gln Gly Gly Cys Ala Thr
```

245                 250                 255
Cys Ser Asp Tyr Asn Gly Cys Leu Ser Cys Lys Pro Arg Leu Phe Phe
            260                 265                 270

Ala Leu Glu Arg Ile Gly Met Lys Gln Ile Gly Val Cys Leu Ser Ser
            275                 280                 285

Cys Pro Ser Gly Tyr Tyr Gly Thr Arg Tyr Pro Asp Ile Asn Lys Cys
            290                 295                 300

Thr Lys Cys Lys Ala Asp Cys Asp Thr Cys Glu Asn Lys Asn Ala Cys
305                 310                 315                 320

Thr Lys Cys Lys Ser Gly Phe Tyr Leu His Leu Gly Lys Cys Leu Asp
                325                 330                 335

Asn Cys Pro Glu Gly Leu Glu Ala Asn Asn His Thr Met Glu Cys Val
            340                 345                 350

Ser Gly Gly Asp Tyr Lys Asp Asp Asp Lys Gly Ser His His His His
            355                 360                 365

His His His His His
        370

<210> SEQ ID NO 131
<211> LENGTH: 1122
<212> TYPE: DNA
<213> ORGANISM: Artificial Sequence
<220> FEATURE:
<223> OTHER INFORMATION: Made in Lab - fusion construct

<400> SEQUENCE: 131
gaagtgcagc tgctggaatc cggggggcgga ctggtgcaac ccgggggatc cctcagactg      60
tcctgtgccg catcgggttt cactttctcc tcctacgcga tgtcatgggt cagacaggcc     120
cctggaaaag gcctcgaatg ggtgtcggct atctccggat cggggggatc tacttactac     180
gccgactccg tgaagggccg gttcactatc tcgagggaca actccaagaa taccctgtac     240
ttgcaaatga actccctgcg cgccgaggat accgcggtgt attactgcgc caaggacttc     300
agctcacgcc ggtggtacct tgagtactgg ggacagggaa ccctcgtcac cgtgtccagc     360
ggtggcggcg gaagcggcgg gggcggatcc ggtggcgggg gctcagagct cacccaggac     420
cccgctgtgt ccgtggcctt gggacagacc gtgcgcatca catgccaggg cgatagcctg     480
cggagctatt acgcctcgtg gtaccagcag aagcctggtc aagcgccggt cctggtcatc     540
tacggaaaga caaccgccc gtccggaatt ccagacaggt tcagcggatc cagctcgggg     600
aacaccgcct cactgactat cacggagca caggccgaag atgaagccga ctactactgc     660
aactccctgg agcggattgg atacctgagc tacgtgtttg gtggcggcac gaagctcacc     720
gtgctgggaa gcgtggatc acaaggctgc caaggaggct gtgcaacatg ctcagattac     780
aatggatgtt tgtcatgtaa gcccgaacta ttttttgctc tggaaagaat tggcatgaag     840
cagattggag tatgtctctc ttcatgtcca agtggatatt atggaactga atatccagat     900
atagctaagt gtacaaaatg caaagctgac tgtgatacct gtcgcaacaa aaatgcctgc     960
acaaaatgta aaagtggatt ttacttacac cttggaaagt gccttgacaa ttgcccagaa    1020
gggttggaag ccaacaacca tactatggag tgtgtcagtg gcggagacta caaggacgac    1080
gatgacaagg gctcccacca tcaccaccat catcaccact ag                       1122

<210> SEQ ID NO 132
<211> LENGTH: 373
<212> TYPE: PRT
<213> ORGANISM: Artificial Sequence

```
<220> FEATURE:
<223> OTHER INFORMATION: Made in Lab - fusion construct

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Glu Leu Thr Gln Asp Pro Ala Val Ser
    130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
        195                 200                 205

Gly Ala Gln Ala Glu Asp Glu Ala Asp Tyr Tyr Cys Asn Ser Leu Glu
    210                 215                 220

Arg Ile Gly Tyr Leu Ser Tyr Val Phe Gly Gly Gly Thr Lys Leu Thr
225                 230                 235                 240

Val Leu Gly Ser Gly Gly Ser Gln Gly Cys Gln Gly Cys Ala Thr
                245                 250                 255

Cys Ser Asp Tyr Asn Gly Cys Leu Ser Cys Lys Pro Glu Leu Phe Phe
            260                 265                 270

Ala Leu Glu Arg Ile Gly Met Lys Gln Ile Gly Val Cys Leu Ser Ser
        275                 280                 285

Cys Pro Ser Gly Tyr Tyr Gly Thr Glu Tyr Pro Asp Ile Ala Lys Cys
    290                 295                 300

Thr Lys Cys Lys Ala Asp Cys Asp Thr Cys Arg Asn Lys Asn Ala Cys
305                 310                 315                 320

Thr Lys Cys Lys Ser Gly Phe Tyr Leu His Leu Gly Lys Cys Leu Asp
                325                 330                 335

Asn Cys Pro Glu Gly Leu Glu Ala Asn Asn His Thr Met Glu Cys Val
            340                 345                 350

Ser Gly Gly Asp Tyr Lys Asp Asp Asp Lys Gly Ser His His His
        355                 360                 365

His His His His His
    370

<210> SEQ ID NO 133
```

<211> LENGTH: 642
<212> TYPE: DNA
<213> ORGANISM: Artificial Sequence
<220> FEATURE:
<223> OTHER INFORMATION: Made in Lab

<400> SEQUENCE: 133

```
gacatcgaac tcacccagcc cccgtcagtg tccgtggccc ctggacagac tgcgcgcatc      60
tcctgctccg gcgacaacct ggggaagaaa tacgtgtact ggtaccagca gaagccaggt     120
caagcccctg tgctggtcat ctacggcgac gacgaaaggc cgtcaggcat cccagagcgc     180
ttctccggct ccaactccgg gaatactgcc acccttacca tttccggaac ccaggccgag     240
gatgaagcgg attactattg cgcgagctac gatagcagcc acatcctgat cgtgtttgga     300
ggcggtacca agcttaccgt cctaggtcag cccaaggctg cccccctcggt cactctgttc     360
ccgccctcct ctgaggagct tcaagccaac aaggccacac tggtgtgtct cataagtgac     420
ttctacccgg gagccgtgac agtggcctgg aaggcagata gcagcccgt caaggcggga     480
gtggagacca ccacaccctc caaacaaagc aacaacaagt acgcggccaa gagctatctg     540
agcctgacgc tgagcagtg gaagtcccac agaagctaca gctgccaggt cacgcatgaa     600
gggagcaccg tggagaagac agtggcccct acagaatgtt ca                       642
```

<210> SEQ ID NO 134
<211> LENGTH: 214
<212> TYPE: PRT
<213> ORGANISM: Artificial Sequence
<220> FEATURE:
<223> OTHER INFORMATION: Made in Lab

<400> SEQUENCE: 134

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Lys Lys Tyr Val
            20                  25                  30

Tyr Trp Tyr Gln Gln Lys Pro Gly Gln Ala Pro Val Leu Val Ile Tyr
        35                  40                  45

Gly Asp Asp Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ser Tyr Asp Ser Ser His Ile Leu
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Lys Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205
```

Ala Pro Thr Glu Cys Ser
    210

<210> SEQ ID NO 135
<211> LENGTH: 642
<212> TYPE: DNA
<213> ORGANISM: Artificial Sequence
<220> FEATURE:
<223> OTHER INFORMATION: Made in Lab

<400> SEQUENCE: 135

```
gatatcgagc tgacccagcc tccttccgtg tctgtgtctc ctggccagac cgcctccatc      60
acctgttctg gcgattccct gggctcctac tacgtgcact ggtatcagca gaagcccggc     120
caggctcctg tgctggtcat ctacagaaac aagcagcggc ccagcggcat ccctgagaga     180
ttctctggct ccaactccgg caacaccgcc acactgacca tctctggaac ccaggctgag     240
gacgaggccg actactactg ccagacctac gactggatgt actcctccag agtgttcggc     300
ggaggcacca gctgacagt tctgggacag cctaaggccg ctccttctgt gaccctgttt     360
cctccatcct ccgaggaact gcaggccaac aaggctaccc tcgtgtgcct gatctccgac     420
ttttaccctg gcgctgtgac cgtggcttgg aagggcgata gttctcctgt gaaggccggc     480
gtggaaacca ccacacctag caagcagtcc aacaacaaat acgccgccga atcctacctg     540
tctctgaccc ctgaacagtg gaagtcccac cggtcctaca gctgccaagt gacccatgag     600
ggctccaccg tggaaaagac agtggcccct accgagtgct cc                       642
```

<210> SEQ ID NO 136
<211> LENGTH: 214
<212> TYPE: PRT
<213> ORGANISM: Artificial Sequence
<220> FEATURE:
<223> OTHER INFORMATION: Made in Lab

<400> SEQUENCE: 136

Asp Ile Glu Leu Thr Gln Pro Pro Ser Val Ser Val Ser Pro Gly Gln
1               5                   10                  15

Thr Ala Ser Ile Thr Cys Ser Gly Asp Ser Leu Gly Ser Tyr Tyr Val
            20                  25                  30

His Trp Tyr Gln Gln Lys Pro Gly Gln Ala Pro Val Leu Val Ile Tyr
        35                  40                  45

Arg Asn Lys Gln Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Trp Met Tyr Ser Ser
                85                  90                  95

Arg Val Phe Gly Gly Gly Thr Lys Leu Thr Val Leu Gly Gln Pro Lys
            100                 105                 110

Ala Ala Pro Ser Val Thr Leu Phe Pro Pro Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Gly Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Glu Ser Tyr Leu Ser Leu Thr Pro Glu Gln Trp Lys Ser His Arg Ser

```
            180             185             190
Tyr Ser Cys Gln Val Thr His Glu Gly Ser Thr Val Glu Lys Thr Val
            195             200             205
Ala Pro Thr Glu Cys Ser
        210

<210> SEQ ID NO 137
<211> LENGTH: 2046
<212> TYPE: DNA
<213> ORGANISM: Artificial Sequence
<220> FEATURE:
<223> OTHER INFORMATION: Made in Lab - fusion construct

<400> SEQUENCE: 137
gaagtgcagc tggtggaatc tggcggcgga cttgtgaaac ctggcggctc tctgagactg      60
tcttgtgccg cttctggctt caccttctcc gactacggca tccactgggt ccgacaggca     120
cctggcaaag gactggaatg ggtcggacgg atcaagtcca agaccgatgg cggcatcacc     180
gagtatgctg cccctgtgaa gggcagattc accatctctc gggacgactc caagaacacc     240
ctgtacctgc agatgaactc cctgaaaacc gaggacaccg ccgtgtacta ctgcgccaga     300
gccatctact acctggaagc cttcgatgtg tggggccagg gcacactggt taccgtgtcc     360
tctgcttcca ccaagggacc ctctgtgttc cctctggctc cttccagcaa gtctacctct     420
ggcggaacag ctgctctggg ctgcctggtc aaggactact tcctgagccc tgtgaccgtg     480
tcttggaact ctggcgctct gacatccggc gtgcacacct tccagctgt gctgcaatcc     540 tccggcctgt actctctgaa gtccgtcgtg accgtgcctt ctagctctct gggcacccag     600
acctacatct gcaatgtgaa ccacaagcct tccaacacca aggtggacaa gagagtggaa     660
cccaagtcct gcgtggtggg tggctcggga ggaggaggct ccgtggcgg tggcagccag     720 gtccagttgg tggaatccgg aggggtttg gtccagcctg gtggaagcct cgcctctca     780 tgcgccgcta gcggattcac cttctcccga tacggcatgc attgggtcag acaggcaccc     840
ggaaaaggac tcgaatgggt gtcgggcatt tcctcgatcg ggtcaaacac ctattacgcc     900
gactccgtga agggacggtt caccattagc cgggataaca gcaagaacac tctgtacttg     960
caaatgaact ccctgcgggc tgaggacacc gccgtgtact actgtgcgcg gtggtacaag    1020
acctatattg acgtctgggg acagggtacc ctcgtgaccg tgtcgagtgc tagcaccaag    1080
ggcccatcgg tcttcccct ggcgccctgc tccaggagca cctccgagag cacagcggcc    1140
ctgggctgcc tggtcaagga ctacttcccc gaaccggtga cggtgtcgtg gaactcaggc    1200
gctctgacca gcggcgtgca caccttccca gctgtcctac agtcctcagg actctactcc    1260
ctcgaaagcg tggtgaccgt gccctccagc aacttcggca cccagaccta cacctgcaac    1320
gtagatcaca gcccagcaa caccaaggtg gacaagacag ttgagcgcaa atgttgtgtc    1380
gagtgcccac cgtgcccagc accacctgtg gcaggaccgt cagtcttcct cttcccccca    1440
aaacccaagg acaccctcat gatctcccgg acccctgagg tcacgtgcgt ggtggtggac    1500
gtgagccacg aagaccccga ggtccagttc aactggtacg tggacggcgt ggaggtgcat    1560
aatgccaaga caaagccacg ggaggagcag ttcaacagca cgttccgtgt ggtcagcgtc    1620
ctcaccgttg tgcaccagga ctggctgaac ggcaaggagt acaagtgcaa ggtctccaac    1680
aaaggcctcc cagcccccat cgagaaaacc atctccaaaa ccaaagggca gccccgagaa    1740
ccacaggtgt acaccctgcc cccatcccgg gaggagatga ccaagaacca ggtcagcctg    1800
acctgcctgg tcaaaggctt ctaccccagc gacatcgccg tggagtggga gagcaatggg    1860
```

```
cagccggaga acaactacaa gaccacgcct cccatgctgg actccgacgg ctccttcttc   1920
ctctacagca agctcaccgt ggacaagagc aggtggcagc aggggaacgt cttctcatgc   1980
tccgtgatgc atgaggctct gcacaaccac tacacgcaga agagcctctc cctgtctccg   2040
ggtaaa                                                              2046
```

<210> SEQ ID NO 138
<211> LENGTH: 682
<212> TYPE: PRT
<213> ORGANISM: Artificial Sequence
<220> FEATURE:
<223> OTHER INFORMATION: Made in Lab - fusion construct

<400> SEQUENCE: 138

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Gly Ile His Trp Val Arg Gln Ala Pro Gly Lys Gly Leu Glu Trp Val
         35                  40                  45

Gly Arg Ile Lys Ser Lys Thr Asp Gly Gly Ile Thr Glu Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Lys Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Gly Gly Gly Gly Ser Gly Gly Gly Gly Ser Gly Gly Gly Gly Ser Gln
225                 230                 235                 240

Val Gln Leu Val Glu Ser Gly Gly Gly Leu Val Gln Pro Gly Gly Ser
                245                 250                 255

Leu Arg Leu Ser Cys Ala Ala Ser Gly Phe Thr Phe Ser Arg Tyr Gly
            260                 265                 270

Met His Trp Val Arg Gln Ala Pro Gly Lys Gly Leu Glu Trp Val Ser
        275                 280                 285

Gly Ile Ser Ser Ile Gly Ser Asn Thr Tyr Tyr Ala Asp Ser Val Lys
    290                 295                 300

Gly Arg Phe Thr Ile Ser Arg Asp Asn Ser Lys Asn Thr Leu Tyr Leu
305                 310                 315                 320
```

Gln Met Asn Ser Leu Arg Ala Glu Asp Thr Ala Val Tyr Tyr Cys Ala
            325                 330                 335

Arg Trp Tyr Lys Thr Tyr Ile Asp Val Trp Gly Gln Gly Thr Leu Val
            340                 345                 350

Thr Val Ser Ser Ala Ser Thr Lys Gly Pro Ser Val Phe Pro Leu Ala
            355                 360                 365

Pro Cys Ser Arg Ser Thr Ser Glu Ser Thr Ala Ala Leu Gly Cys Leu
370                 375                 380

Val Lys Asp Tyr Phe Pro Glu Pro Val Thr Val Ser Trp Asn Ser Gly
385                 390                 395                 400

Ala Leu Thr Ser Gly Val His Thr Phe Pro Ala Val Leu Gln Ser Ser
            405                 410                 415

Gly Leu Tyr Ser Leu Glu Ser Val Val Thr Val Pro Ser Ser Asn Phe
            420                 425                 430

Gly Thr Gln Thr Tyr Thr Cys Asn Val Asp His Lys Pro Ser Asn Thr
            435                 440                 445

Lys Val Asp Lys Thr Val Glu Arg Lys Cys Cys Val Glu Cys Pro Pro
450                 455                 460

Cys Pro Ala Pro Pro Val Ala Gly Pro Ser Val Phe Leu Phe Pro Pro
465                 470                 475                 480

Lys Pro Lys Asp Thr Leu Met Ile Ser Arg Thr Pro Glu Val Thr Cys
            485                 490                 495

Val Val Val Asp Val Ser His Glu Asp Pro Glu Val Gln Phe Asn Trp
            500                 505                 510

Tyr Val Asp Gly Val Glu Val His Asn Ala Lys Thr Lys Pro Arg Glu
            515                 520                 525

Glu Gln Phe Asn Ser Thr Phe Arg Val Val Ser Val Leu Thr Val Val
530                 535                 540

His Gln Asp Trp Leu Asn Gly Lys Glu Tyr Lys Cys Lys Val Ser Asn
545                 550                 555                 560

Lys Gly Leu Pro Ala Pro Ile Glu Lys Thr Ile Ser Lys Thr Lys Gly
            565                 570                 575

Gln Pro Arg Glu Pro Gln Val Tyr Thr Leu Pro Pro Ser Arg Glu Glu
            580                 585                 590

Met Thr Lys Asn Gln Val Ser Leu Thr Cys Leu Val Lys Gly Phe Tyr
            595                 600                 605

Pro Ser Asp Ile Ala Val Glu Trp Glu Ser Asn Gly Gln Pro Glu Asn
610                 615                 620

Asn Tyr Lys Thr Thr Pro Pro Met Leu Asp Ser Asp Gly Ser Phe Phe
625                 630                 635                 640

Leu Tyr Ser Lys Leu Thr Val Asp Lys Ser Arg Trp Gln Gln Gly Asn
            645                 650                 655

Val Phe Ser Cys Ser Val Met His Glu Ala Leu His Asn His Tyr Thr
            660                 665                 670

Gln Lys Ser Leu Ser Leu Ser Pro Gly Lys
            675                 680

<210> SEQ ID NO 139
<211> LENGTH: 645
<212> TYPE: DNA
<213> ORGANISM: Artificial Sequence
<220> FEATURE:
<223> OTHER INFORMATION: Made in Lab

<400> SEQUENCE: 139

```
gacatcgagc tcacccagga ccccgctgtg tccgtggcct tgggacagac cgtgcgcatc    60
acatgccagg gcgatagcct gcggagctat tacgcctcgt ggtaccagca gaagcctggt   120
caagcgccgg tcctggtcat ctacggaaag aacaaccgcc cgtccggaat tccagacagg   180
ttcagcggat ccagctcggg gaacaccgcc tcactgacta tcaccggagc acaggccgaa   240
gatgaagccg actactactg caactccctg agcggattgg atacctgag ctacgtgttt    300
ggtggcggta ccaagcttac cgtcctaggt cagcccaagg ctgccccctc ggtcactctg   360
ttcccgccct cctctgagga gcttcaagcc aacaaggcca cactggtgtg tctcataagt   420
gacttctacc cgggagccgt gacagtggcc tggaaggcag atagcagccc cgtcaaggcg   480
ggagtggaga ccaccacacc ctccaaacaa agcaacaaca agtacgcggc caagagctat   540
ctgagcctga cgcctgagca gtggaagtcc cacagaagct acagctgcca ggtcacgcat   600
gaagggagca ccgtggagaa gacagtggcc cctacagaat gttca              645
```

<210> SEQ ID NO 140
<211> LENGTH: 215
<212> TYPE: PRT
<213> ORGANISM: Artificial Sequence
<220> FEATURE:
<223> OTHER INFORMATION: Made in Lab

<400> SEQUENCE: 140

Asp Ile Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Leu Glu Arg Ile Gly Tyr Leu
                85                  90                  95

Ser Tyr Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Lys Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 141
<211> LENGTH: 2055
<212> TYPE: DNA
<213> ORGANISM: Artificial Sequence
<220> FEATURE:
<223> OTHER INFORMATION: Made in Lab - fusion construct

<400> SEQUENCE: 141

```
gaagtgcagc tggtggaatc tggcggcgga cttgtgaaac ctggcggctc tctgagactg      60
tcttgtgccg cttctggctt caccttctcc gactacggca tccactgggt ccgacaggca     120
cctggcaaag gactggaatg ggtcggacgg atcaagtcca agaccgatgg cggcatcacc     180
gagtatgctg cccctgtgaa gggcagattc accatctctc gggacgactc caagaacacc     240
ctgtacctgc agatgaactc cctgaaaacc gaggacaccg ccgtgtacta ctgcgccaga     300
gccatctact acctggaagc cttcgatgtg tggggccagg gcacactggt taccgtgtcc     360
tctgcttcca ccaagggacc ctctgtgttc cctctggctc cttccagcaa gtctacctct     420
ggcggaacag ctgctctggg ctgcctggtc aaggactact tcctgagccc tgtgaccgtg     480
tcttggaact ctggcgctct gacatccggc gtgcacacct tccagctgt gctgcaatcc     540
tccggcctgt actctctgaa gtccgtcgtg accgtgcctt ctagctctct gggcacccag     600
acctacatct gcaatgtgaa ccacaagcct tccaacacca aggtggacaa gagagtggaa     660
cccaagtcct gcgtggtggg tggctcggga ggaggaggct ccggtggcgg tggcagcgaa     720
gtgcagctgc tggaatccgg gggcggactg gtgcaacccg ggggatccct cagactgtcc     780
tgtgccgcat cgggtttcac tttctcctcc tacgcgatgt catgggtcag acaggccct     840
ggaaaaggcc tcgaatgggt gtcggctatc tccggatcgg ggggatctac ttactacgcc     900
gactccgtga agggccggtt cactatctcg agggacaact ccaagaatac cctgtacttg     960
caaatgaact ccctgcgcgc cgaggatacc gcggtgtatt actgcgccaa ggacttcagc    1020
tcacgccggt ggtaccttga gtactgggga cagggaaccc ttgtcaccgt gtcgagtgct    1080
agcaccaagg gcccatcggt cttccccctg gcgccctgct ccaggagcac ctccgagagc    1140
acagcggccc tgggctgcct ggtcaaggac tacttcccg aaccggtgac ggtgtcgtgg    1200
aactcaggcg ctctgaccag cggcgtgcac accttcccag ctgtcctaca gtcctcagga    1260
ctctactccc tcgaaagcgt ggtgaccgtg ccctccagca acttcggcac ccagacctac    1320
acctgcaacg tagatcacaa gcccagcaac accaaggtgg acaagacagt tgagcgcaaa    1380
tgttgtgtcg agtgcccacc gtgcccagca ccacctgtgg caggaccgtc agtcttcctc    1440
ttccccccaa aacccaagga caccctcatg atctcccgga cccctgaggt cacgtgcgtg    1500
gtggtggacg tgagccacga agaccccgag gtccagttca actggtacgt ggacggcgtg    1560
gaggtgcata atgccaagac aaagccacgg gaggagcagt tcaacagcac gttccgtgtg    1620
gtcagcgtcc tcaccgttgt gcaccaggac tggctgaacg gcaaggagta caagtgcaag    1680
gtctccaaca aaggcctccc agccccatc gagaaaacca tctccaaaac caagggcag    1740
ccccgagaac acaggtgta cccctgccc catcccggg aggagatgac caagaaccag    1800
gtcagcctga cctgcctggt caaaggcttc taccccagcg acatcgccgt ggagtgggag    1860
agcaatgggc agccggagaa caactacaag accacgcctc ccatgctgga ctccgacggc    1920
tccttcttcc tctacagcaa gctcaccgtg gacaagagca ggtggcagca ggggaacgtc    1980
ttctcatgct ccgtgatgca tgaggctctg cacaaccact acacgcagaa gagcctctcc    2040
ctgtctccgg gtaaa                                                    2055
```

<210> SEQ ID NO 142
<211> LENGTH: 685
<212> TYPE: PRT

<213> ORGANISM: Artificial Sequence
<220> FEATURE:
<223> OTHER INFORMATION: Made in Lab - fusion construct

<400> SEQUENCE: 142

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Gly Arg Ile Lys Ser Lys Thr Asp Gly Gly Ile Thr Glu Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ala Ile Tyr Tyr Leu Glu Ala Phe Asp Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Lys Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Gly Gly Gly Gly Ser Gly Gly Gly Ser Gly Gly Gly Gly Ser Glu
225                 230                 235                 240

Val Gln Leu Leu Glu Ser Gly Gly Gly Leu Val Gln Pro Gly Gly Ser
                245                 250                 255

Leu Arg Leu Ser Cys Ala Ala Ser Gly Phe Thr Phe Ser Ser Tyr Ala
            260                 265                 270

Met Ser Trp Val Arg Gln Ala Pro Gly Lys Gly Leu Glu Trp Val Ser
        275                 280                 285

Ala Ile Ser Gly Ser Gly Gly Ser Thr Tyr Tyr Ala Asp Ser Val Lys
290                 295                 300

Gly Arg Phe Thr Ile Ser Arg Asp Asn Ser Lys Asn Thr Leu Tyr Leu
305                 310                 315                 320

Gln Met Asn Ser Leu Arg Ala Glu Asp Thr Ala Val Tyr Tyr Cys Ala
                325                 330                 335

Lys Asp Phe Ser Ser Arg Arg Trp Tyr Leu Glu Tyr Trp Gly Gln Gly
            340                 345                 350

Thr Leu Val Thr Val Ser Ser Ala Ser Thr Lys Gly Pro Ser Val Phe
        355                 360                 365

Pro Leu Ala Pro Cys Ser Arg Ser Thr Ser Glu Ser Thr Ala Ala Leu
370                 375                 380

Gly Cys Leu Val Lys Asp Tyr Phe Pro Glu Pro Val Thr Val Ser Trp
```

```
                385                 390                 395                 400
            Asn Ser Gly Ala Leu Thr Ser Gly Val His Thr Phe Pro Ala Val Leu
                            405                 410                 415
            Gln Ser Ser Gly Leu Tyr Ser Leu Glu Ser Val Val Thr Val Pro Ser
                        420                 425                 430
            Ser Asn Phe Gly Thr Gln Thr Tyr Thr Cys Asn Val Asp His Lys Pro
                    435                 440                 445
            Ser Asn Thr Lys Val Asp Lys Thr Val Glu Arg Lys Cys Cys Val Glu
                450                 455                 460
            Cys Pro Pro Cys Pro Ala Pro Pro Val Ala Gly Pro Ser Val Phe Leu
            465                 470                 475                 480
            Phe Pro Pro Lys Pro Lys Asp Thr Leu Met Ile Ser Arg Thr Pro Glu
                            485                 490                 495
            Val Thr Cys Val Val Val Asp Val Ser His Glu Asp Pro Glu Val Gln
                        500                 505                 510
            Phe Asn Trp Tyr Val Asp Gly Val Glu Val His Asn Ala Lys Thr Lys
                    515                 520                 525
            Pro Arg Glu Glu Gln Phe Asn Ser Thr Phe Arg Val Val Ser Val Leu
                530                 535                 540
            Thr Val Val His Gln Asp Trp Leu Asn Gly Lys Glu Tyr Lys Cys Lys
            545                 550                 555                 560
            Val Ser Asn Lys Gly Leu Pro Ala Pro Ile Glu Lys Thr Ile Ser Lys
                            565                 570                 575
            Thr Lys Gly Gln Pro Arg Glu Pro Gln Val Tyr Thr Leu Pro Pro Ser
                        580                 585                 590
            Arg Glu Glu Met Thr Lys Asn Gln Val Ser Leu Thr Cys Leu Val Lys
                    595                 600                 605
            Gly Phe Tyr Pro Ser Asp Ile Ala Val Glu Trp Glu Ser Asn Gly Gln
                610                 615                 620
            Pro Glu Asn Asn Tyr Lys Thr Thr Pro Pro Met Leu Asp Ser Asp Gly
            625                 630                 635                 640
            Ser Phe Phe Leu Tyr Ser Lys Leu Thr Val Asp Lys Ser Arg Trp Gln
                            645                 650                 655
            Gln Gly Asn Val Phe Ser Cys Ser Val Met His Glu Ala Leu His Asn
                        660                 665                 670
            His Tyr Thr Gln Lys Ser Leu Ser Leu Ser Pro Gly Lys
                    675                 680                 685

<210> SEQ ID NO 143
<211> LENGTH: 654
<212> TYPE: DNA
<213> ORGANISM: Artificial Sequence
<220> FEATURE:
<223> OTHER INFORMATION: Made in lab

<400> SEQUENCE: 143
gatatagttc tgtttcaatc ccctgcgagc ctggcggtaa gtttgggaca gagagccacg    60
atttcctgcc gagcgagtga aagcgtagac gactacggca attctttcat gcactggtat   120
caacagaagc caggccaacc gccgaagctg cttatctatc gcgcgtccaa tttggagtca   180
gggatccctg cacgattttc aggttctgga agtaggacag actttacact tacgataaac   240
cccgtggaag cggatgacgt cgcaacctac tattgtcaac aaagcaatga agcaccacct   300
accttcggag gtggcactaa attggaaatt aaacgtacgg tggctgcacc atctgtcttc   360
atcttcccgc catctgatga gcagttgaaa tctggaactg cctctgttgt gtgcctgctg   420
```

```
aataacttct atcccagaga ggccaaagta cagtggaagg tggataacgc cctccaatcg    480
ggtaactccc aggagagtgt cacagagcag gacagcaagg acagcaccta cagcctcaag    540
agcaccctga cgctgagcaa agcagactac gagaaacaca agtctacgc ctgcgaagtc     600 acccatcagg gcctgagctc gcccgtcaca aagagcttca cagggagaga gtgt           654
```

<210> SEQ ID NO 144
<211> LENGTH: 218
<212> TYPE: PRT
<213> ORGANISM: Artificial Sequence
<220> FEATURE:
<223> OTHER INFORMATION: Made in Lab

<400> SEQUENCE: 144

```
Asp Ile Val Leu Phe Gln Ser Pro Ala Ser Leu Ala Val Ser Leu Gly
1               5                   10                  15

Gln Arg Ala Thr Ile Ser Cys Arg Ala Ser Glu Ser Val Asp Asp Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Ala Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Lys Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 145
<211> LENGTH: 2052
<212> TYPE: DNA
<213> ORGANISM: Artificial Sequence
<220> FEATURE:
<223> OTHER INFORMATION: Made in Lab - fusion construct

<400> SEQUENCE: 145

```
gaagtgcagc tggtggaatc tggcggcgga cttgtgaaac tggcggctc tctgagactg     60 tcttgtgccg cttctggctt caccttctcc gactacggca tccactgggt ccgacaggca    120
cctggcaaag gactggaatg ggtcggacgg atcaagtcca agaccgatgg cggcatcacc    180
gagtatgctg cccctgtgaa gggcagattc accatctctc gggacgactc caagaacacc    240
```

```
ctgtacctgc agatgaactc cctgaaaacc gaggacaccg ccgtgtacta ctgcgccaga      300
gccatctact acctggaagc cttcgatgtg tggggccagg gcacactggt taccgtgtcc      360
tctgcttcca ccaagggacc ctctgtgttc cctctggctc cttccagcaa gtctacctct      420
ggcggaacag ctgctctggg ctgcctggtc aaggactact tcctgagcc tgtgaccgtg       480
tcttggaact ctggcgctct gacatccggc gtgcacacct ttccagctgt gctgcaatcc      540
tccggcctgt actctctgaa gtccgtcgtg accgtgcctt ctagctctct gggcacccag      600
acctacatct gcaatgtgaa ccacaagcct tccaacacca aggtggacaa gagagtggaa      660
cccaagtcct gcgtggtggt ggctcgggga ggaggaggct ccggtggcgg tggcagccaa      720
gtgcaactcc aacaaagcgg tcccgagttg gtccgacccg gcgtcagtgt gaaaatctca      780
tgcaaggggt ccgggtatac cttcactgac tatgcaatgc actgggtaaa gcagagccac      840
gccaagtcct tggagtggat cggaggcatt agtacctact cggacgcac caactacaat      900
caaaaattta aggtcgcgc aaccatgact gtagataaat catcaagtac cgcgtacatg      960
gaattggcta gactgactc tgaagattcc gcgctgtatt actgtgctcg cggtttgtct     1020
ggcaactatg ttatggatta ctgggggcaa gggaccagcg tcacggtgtc gagtgctagc     1080
accaagggcc catcggtctt cccccctggcg ccctgctcca ggagcacctc cgagagcaca     1140
gcggccctgg gctgcctggt caaggactac ttccccgaac cggtgacggt gtcgtggaac     1200
tcaggcgctc tgaccagcgg cgtgcacacc ttcccagctg tcctacagtc ctcaggactc     1260
tactccctcg aaagcgtggt gaccgtgccc tccagcaact tcggcaccca gacctacacc     1320
tgcaacgtag atcacaagcc cagcaacacc aaggtggaca gacagttga gcgcaaatgt      1380
tgtgtcgagt gcccaccgtg cccagcacca cctgtggcag gaccgtcagt cttcctcttc     1440
cccccaaaac ccaaggacac cctcatgatc tcccggaccc ctgaggtcac gtgcgtggtg     1500
gtggacgtga gccacgaaga ccccgaggtc cagttcaact ggtacgtgga cggcgtggag     1560
gtgcataatg ccaagacaaa gccacgggag gagcagttca acagcacgtt ccgtgtggtc     1620
agcgtcctca ccgttgtgca ccaggactgg ctgaacggca aggagtacaa gtgcaaggtc     1680
tccaacaaag gcctcccagc cccatcgag aaaaccatct ccaaaaccaa agggcagccc     1740
cgagaaccac aggtgtacac cctgcccca tcccgggagg agatgaccaa gaaccaggtc     1800
agcctgacct gcctggtcaa aggcttctac cccagcgaca tcgccgtgga gtgggagagc     1860
aatgggcagc cggagaacaa ctacaagacc acgcctccca tgctggactc cgacggctcc     1920
ttcttcctct acagcaagct caccgtggac aagagcaggt ggcagcaggg gaacgtcttc     1980
tcatgctccg tgatgcatga ggctctgcac aaccactaca cgcagaagag cctctccctg     2040
tctccgggta aa                                                         2052
```

<210> SEQ ID NO 146
<211> LENGTH: 684
<212> TYPE: PRT
<213> ORGANISM: Artificial Sequence
<220> FEATURE:
<223> OTHER INFORMATION: Made in Lab - fusion construct

<400> SEQUENCE: 146

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
```

-continued

```
                35                  40                  45
Gly Arg Ile Lys Ser Lys Thr Asp Gly Gly Ile Thr Glu Tyr Ala Ala
             50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Arg Ala Ile Tyr Tyr Leu Glu Ala Phe Asp Val Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Gly Gly Gly Gly Ser Gly Gly Gly Gly Ser Gly Gly Gly Gly Ser Gln
225                 230                 235                 240

Val Gln Leu Gln Gln Ser Gly Pro Glu Leu Val Arg Pro Gly Val Ser
                245                 250                 255

Val Lys Ile Ser Cys Lys Gly Ser Gly Tyr Thr Phe Thr Asp Tyr Ala
            260                 265                 270

Met His Trp Val Lys Gln Ser His Ala Lys Ser Leu Glu Trp Ile Gly
        275                 280                 285

Gly Ile Ser Thr Tyr Phe Gly Arg Thr Asn Tyr Asn Gln Lys Phe Lys
290                 295                 300

Gly Arg Ala Thr Met Thr Val Asp Lys Ser Ser Ser Thr Ala Tyr Met
305                 310                 315                 320

Glu Leu Ala Arg Leu Thr Ser Glu Asp Ser Ala Leu Tyr Tyr Cys Ala
                325                 330                 335

Arg Gly Leu Ser Gly Asn Tyr Val Met Asp Tyr Trp Gly Gln Gly Thr
            340                 345                 350

Ser Val Thr Val Ser Ser Ala Ser Thr Lys Gly Pro Ser Val Phe Pro
        355                 360                 365

Leu Ala Pro Cys Ser Arg Ser Thr Ser Glu Ser Thr Ala Ala Leu Gly
    370                 375                 380

Cys Leu Val Lys Asp Tyr Phe Pro Glu Pro Val Thr Val Ser Trp Asn
385                 390                 395                 400

Ser Gly Ala Leu Thr Ser Gly Val His Thr Phe Pro Ala Val Leu Gln
                405                 410                 415

Ser Ser Gly Leu Tyr Ser Leu Glu Ser Val Val Thr Val Pro Ser Ser
            420                 425                 430

Asn Phe Gly Thr Gln Thr Tyr Thr Cys Asn Val Asp His Lys Pro Ser
        435                 440                 445

Asn Thr Lys Val Asp Lys Thr Val Glu Arg Lys Cys Cys Val Glu Cys
    450                 455                 460
```

Pro Pro Cys Pro Ala Pro Val Ala Gly Pro Ser Val Phe Leu Phe
465                 470                 475                 480

Pro Pro Lys Pro Lys Asp Thr Leu Met Ile Ser Arg Thr Pro Glu Val
                485                 490                 495

Thr Cys Val Val Val Asp Val Ser His Glu Asp Pro Glu Val Gln Phe
            500                 505                 510

Asn Trp Tyr Val Asp Gly Val Glu Val His Asn Ala Lys Thr Lys Pro
        515                 520                 525

Arg Glu Glu Gln Phe Asn Ser Thr Phe Arg Val Val Ser Val Leu Thr
    530                 535                 540

Val Val His Gln Asp Trp Leu Asn Gly Lys Glu Tyr Lys Cys Lys Val
545                 550                 555                 560

Ser Asn Lys Gly Leu Pro Ala Pro Ile Glu Lys Thr Ile Ser Lys Thr
                565                 570                 575

Lys Gly Gln Pro Arg Glu Pro Gln Val Tyr Thr Leu Pro Pro Ser Arg
            580                 585                 590

Glu Glu Met Thr Lys Asn Gln Val Ser Leu Thr Cys Leu Val Lys Gly
        595                 600                 605

Phe Tyr Pro Ser Asp Ile Ala Val Glu Trp Glu Ser Asn Gly Gln Pro
    610                 615                 620

Glu Asn Asn Tyr Lys Thr Thr Pro Pro Met Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
    675                 680

<210> SEQ ID NO 147
<211> LENGTH: 651
<212> TYPE: DNA
<213> ORGANISM: Artificial Sequence
<220> FEATURE:
<223> OTHER INFORMATION: Made in lab

<400> SEQUENCE: 147
cagagcgtgc tgacccagcc gccgagcgcg agcggcaccc cgggccagcg cgtgaccatt    60
agctgcaccg gcagcagcag caacattggc gcgggctatg tggtgcattg gtatcagcag    120
ctgccgggca ccgcgccgaa actgctgatt tatgataaca caaaacgccc gagcggcgtg    180
ccggatcgct ttagcggcag caaaagcggc accagcgcga gcctggcgat tagcggcctg    240
gcgagcgaag atgaagcgga ttattattgc gcggcgtggg atgatcgcct gaacggcccg    300
gtgtttggcg gcggcaccaa actgaccgtg ctgggtcagc ccaaggctgc cccctcggtc    360
actctgttcc cgccctcctc tgaggagctt caagccaaca ggccacact ggtgtgtctc    420 ataagtgact tctacccggg agccgtgaca gtggcctgga aggcagatag cagccccgtc    480
aaggcgggag tggagaccac cacaccctcc aaacaaagca acaacaagta cgcggccagc    540
agctatctga gcctgacgcc tgagcagtgg aagtcccaca aagctacag ctgccaggtc    600 acgcatgaag ggagcaccgt ggagaagaca gtggccccta cagaatgttc a            651

<210> SEQ ID NO 148
<211> LENGTH: 217
<212> TYPE: PRT

<213> ORGANISM: Artificial Sequence
<220> FEATURE:
<223> OTHER INFORMATION: Made in Lab

<400> SEQUENCE: 148

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Ala Ser Glu Asp Glu Ala Asp Tyr Tyr Cys Ala Ala Trp Asp Asp Arg
                85                  90                  95

Leu Asn Gly Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215
```

<210> SEQ ID NO 149
<211> LENGTH: 1707
<212> TYPE: DNA
<213> ORGANISM: Artificial Sequence
<220> FEATURE:
<223> OTHER INFORMATION: Made in Lab - fusion construct

<400> SEQUENCE: 149

| | | | | | |
|---|---|---|---|---|---|
| aacccaattt | gcaagggatg | cctgagctgt | agcaaggaca | acggatgttc | acggtgccag | 60 |
| caaaagctgt | ttttcttcct | ccggcgggaa | ggaatgcggc | agtacggcga | atgtctccac | 120 |
| tcctgcccct | cggggtatta | cggacaccgc | gcgcctgaca | tgaaccgatg | cgccagatgc | 180 |
| cggatcgaga | actgcgatag | ctgccgcagc | aaggacgcct | gcactaagtg | caaagtcggc | 240 |
| ttctaccttc | accggggcag | atgttttgac | gaatgcccgg | atggcttcgc | cccgctggag | 300 |
| gagactatgg | aatgcgtgga | gggtggtggt | ggctcgggag | gaggaggctc | cggtggcggt | 360 |
| ggcagcgaag | tgcagctgct | ggaaagcggc | ggcggcctgg | tgcagccggg | cggcagcctg | 420 |
| cgcctgagct | gcgcggcgag | cggctttacc | tttagcaacg | cgtggatgag | ctgggtgcgc | 480 |
| caggcgccgg | gcaaaggcct | ggaatgggtg | agctatatta | gcagcagcgg | cagcaccatt | 540 |
| tattatgcgg | atagcgtgaa | aggccgcttt | accattagcc | gcgataacag | caaaaacacc | 600 |
| ctgtatctgc | agatgaacag | cctgcgcgcg | gaagataccg | cggtgtatta | ttgcgcgcgc | 660 |

```
gaaggcctgt gggcgtttga ttattggggc cagggcaccc tggtgaccgt gaccagcgct    720
agcaccaagg gcccatcggt cttccccctg cacccctcct ccaagagcac ctctgggggc    780
acagcggccc tgggctgcct ggtcaaggac tacttccccg aaccggtgac ggtgtcgtgg    840
aactcaggcg ccctgaccag cggcgtgcac accttcccgg ctgtcctaca gtcctcagga    900
ctctactccc tcagcagcgt ggtgaccgtg ccctccagca gcttgggcac ccagacctac    960
atctgcaact gaatcacaa gcccagcaac accaaggtgg acaagaaagt tgagcccaaa   1020
tcttgtgaca aaactcacac atgcccaccg tgcccagcac ctgaagccgc ggggggaccg   1080
tcagtcttcc tcttcccccc aaaacccaag gacaccctca tgatctcccg gacccctgag   1140
gtcacatgcg tggtggtgga cgtgagccac gaagaccctg aggtcaagtt caactggtac   1200
gtggacggcg tggaggtgca taatgccaag acaaagccgc gggaggagca gtacaacagc   1260
acgtaccgtg tggtcagcgt cctcaccgtc ctgcaccagg actggctgaa tggcaaggag   1320
tacaagtgca aggtctccaa caaagccctc ggagccccca tcgagaaaac catctccaaa   1380
gccaaagggc agccccgaga accacaggtg tacaccctgc ccccatcccg ggaggagatg   1440
accaagaacc aggtcagcct gacctgcctg gtcaaaggct tctatcccag cgacatcgcc   1500
gtggagtggg agagcaatgg gcagccggag aacaactaca agaccacgcc tcccgtgctg   1560
gactccgacg gctccttctt cctctacagc aagctcaccg tggacaagag caggtggcag   1620
caggggaacg tcttctcatg ctccgtgatg catgaggctc tgcacaacca ctacacgcag   1680
aagagcctct ccctgtctcc gggtaaa                                      1707

<210> SEQ ID NO 150
<211> LENGTH: 569
<212> TYPE: PRT
<213> ORGANISM: Artificial Sequence
<220> FEATURE:
<223> OTHER INFORMATION: Made in Lab - fusion construct

<400> SEQUENCE: 150

Asn Pro Ile Cys Lys Gly Cys Leu Ser Cys Ser Lys Asp Asn Gly Cys
1               5                   10                  15

Ser Arg Cys Gln Gln Lys Leu Phe Phe Phe Leu Arg Arg Glu Gly Met
            20                  25                  30

Arg Gln Tyr Gly Glu Cys Leu His Ser Cys Pro Ser Gly Tyr Tyr Gly
        35                  40                  45

His Arg Ala Pro Asp Met Asn Arg Cys Ala Arg Cys Arg Ile Glu Asn
    50                  55                  60

Cys Asp Ser Cys Arg Ser Lys Asp Ala Cys Thr Lys Cys Lys Val Gly
65                  70                  75                  80

Phe Tyr Leu His Arg Gly Arg Cys Phe Asp Glu Cys Pro Asp Gly Phe
                85                  90                  95

Ala Pro Leu Glu Glu Thr Met Glu Cys Val Glu Gly Gly Gly Gly Ser
            100                 105                 110

Gly Gly Gly Gly Ser Gly Gly Gly Gly Ser Glu Val Gln Leu Leu Glu
        115                 120                 125

Ser Gly Gly Gly Leu Val Gln Pro Gly Gly Ser Leu Arg Leu Ser Cys
    130                 135                 140

Ala Ala Ser Gly Phe Thr Phe Ser Asn Ala Trp Met Ser Trp Val Arg
145                 150                 155                 160

Gln Ala Pro Gly Lys Gly Leu Glu Trp Val Ser Tyr Ile Ser Ser Ser
                165                 170                 175
```

```
Gly Ser Thr Ile Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Glu Gly Leu Trp
210                 215                 220

Ala Phe Asp Tyr Trp Gly Gln Gly Thr Leu Val Thr Val Ser Ala
225                 230                 235                 240

Ser Thr Lys Gly Pro Ser Val Phe Pro Leu Ala Pro Ser Ser Lys Ser
                245                 250                 255

Thr Ser Gly Gly Thr Ala Ala Leu Gly Cys Leu Val Lys Asp Tyr Phe
            260                 265                 270

Pro Glu Pro Val Thr Val Ser Trp Asn Ser Gly Ala Leu Thr Ser Gly
        275                 280                 285

Val His Thr Phe Pro Ala Val Leu Gln Ser Ser Gly Leu Tyr Ser Leu
    290                 295                 300

Ser Ser Val Val Thr Val Pro Ser Ser Ser Leu Gly Thr Gln Thr Tyr
305                 310                 315                 320

Ile Cys Asn Val Asn His Lys Pro Ser Asn Thr Lys Val Asp Lys Lys
                325                 330                 335

Val Glu Pro Lys Ser Cys Asp Lys Thr His Thr Cys Pro Pro Cys Pro
            340                 345                 350

Ala Pro Glu Ala Ala Gly Gly Pro Ser Val Phe Leu Phe Pro Pro Lys
        355                 360                 365

Pro Lys Asp Thr Leu Met Ile Ser Arg Thr Pro Glu Val Thr Cys Val
    370                 375                 380

Val Val Asp Val Ser His Glu Asp Pro Glu Val Lys Phe Asn Trp Tyr
385                 390                 395                 400

Val Asp Gly Val Glu Val His Asn Ala Lys Thr Lys Pro Arg Glu Glu
                405                 410                 415

Gln Tyr Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
        435                 440                 445

Ala Leu Gly Ala Pro Ile Glu Lys Thr Ile Ser Lys Ala Lys Gly Gln
    450                 455                 460

Pro Arg Glu Pro Gln Val Tyr Thr Leu Pro Pro Ser Arg Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
        515                 520                 525

Tyr Ser Lys Leu Thr Val Asp Lys Ser Arg Trp Gln Gln Gly Asn Val
    530                 535                 540

Phe Ser Cys Ser Val Met His Glu Ala Leu His Asn His Tyr Thr Gln
545                 550                 555                 560

Lys Ser Leu Ser Leu Ser Pro Gly Lys
                565

<210> SEQ ID NO 151
<211> LENGTH: 648
```

-continued

```
<212> TYPE: DNA
<213> ORGANISM: Artificial Sequence
<220> FEATURE:
<223> OTHER INFORMATION: Made in lab

<400> SEQUENCE: 151
gagatagtgc ttacgcaaag cccagcccctt atggcggcgt cacctgggga aaaagtgacc      60
atcacgtgtt cagtgtcctc atcaatatca agtagtaatc tccactggta ccagcaaaag     120
tccgggacga gccccaagcc gtggatctac ggaaccagta atcttgccag cggagtacca     180
gtacggtttt ccggctccgg ctcaggaacc agctactcac ttacgattag cacgatggag     240
gctgaggacg cggctactta ttattgccag cagtggtcct cctacccgct tacattcggt     300
gcgggaacca aacttgaatt gaagcgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgttag                  648

<210> SEQ ID NO 152
<211> LENGTH: 215
<212> TYPE: PRT
<213> ORGANISM: Artificial Sequence
<220> FEATURE:
<223> OTHER INFORMATION: Made in Lab

<400> SEQUENCE: 152

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ile Ser Ser Ser
            20                  25                  30

Asn Leu His Trp Tyr Gln Gln Lys Ser Gly Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Thr Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Ala Gly Thr Lys Leu Glu Leu Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
```

<210> SEQ ID NO 153
<211> LENGTH: 1728
<212> TYPE: DNA
<213> ORGANISM: Artificial Sequence
<220> FEATURE:
<223> OTHER INFORMATION: Made in Lab - fusion construct

<400> SEQUENCE: 153

```
aacccaattt gcaagggatg cctgagctgt agcaaggaca acggatgttc acggtgccag      60
caaaagctgt ttttcttcct ccggcgggaa ggaatgcggc agtacggcga atgtctccac     120
tcctgcccct cggggtatta cggacaccgc gcgcctgaca tgaaccgatg cgccagatgc     180
cggatcgaga actgcgatag ctgccgcagc aaggacgcct gcactaagtg caaagtcggc     240
ttctaccttc accggggcag atgttttgac gaatgcccgg atggcttcgc cccgctggag     300
gagactatgg aatgcgtgga gggtggtggt ggctcgggag gaggaggctc cggtggcggt     360
ggcagcgagg ttcaactcca acaaagtggc actgtgcttg ccagaccagg tgcgagtgta     420
aaaatgtctt gcaaagcgag cggatatact ttcgcgagct attggattca ttgggttaaa     480
caaaggcctg acagggggct ggaatggatt ggaagcatat accccggcaa ctccgacacc     540
acctataacc agaaatttaa aggtaaagca aaactcaccg tcgtcacatc agctagtagt     600
gcatacatgg aactctccag tcttacgaac gaggattccg ctgtttacta ctgtactgaa     660
ccaacctact acagttatga tgattactat gctatggact actggggtca gggcacgtcc     720
gttaccgtgt cttctgctag caccaagggc ccatcggtct tccccctggc accctcctcc     780
aagagcacct ctggggggcac agcggccctg gctgcctggt caaggactac ttcccccgaa     840
ccggtgacgg tgtcgtggaa ctcaggcgcc ctgaccagcg gcgtgcacac cttcccggct     900
gtcctacagt cctcaggact ctactccctc agcagcgtgg tgaccgtgcc ctccagcagc     960
ttgggcaccc agacctacat ctgcaacgtg aatcacaagc ccagcaacac caaggtggac    1020
aagaaagttg agcccaaatc ttgtgacaaa actcacacat gcccaccgtg cccagcacct    1080
gaagccgcgg ggggaccgtc agtcttcctc ttccccccaa aacccaagga caccctcatg    1140
atctcccgga cccctgaggt cacatgcgtg gtggtggacg tgagccacga agaccctgag    1200
gtcaagttca actggtacgt ggacggcgtg gaggtgcata atgccaagac aaagccgcgg    1260
gaggagcagt acaacagcac gtaccgtgtg gtcagcgtcc tcaccgtcct gcaccaggac    1320
tggctgaatg gcaaggagta caagtgcaag gtctccaaca aagccctcgg agcccccatc    1380
gagaaaacca tctccaaagc caaagggcag ccccgagaac acaggtgta caccctgccc    1440
ccatcccggg aggagatgac caagaaccag gtcagcctga cctgcctggt caaaggcttc    1500
tatcccagcg acatcgccgt ggagtgggag agcaatgggc agccggagaa caactacaag    1560
accacgcctc ccgtgctgga ctccgacggc tccttcttcc tctacagcaa gctcaccgtg    1620
gacaagagca ggtggcagca ggggaacgtc ttctcatgct ccgtgatgca tgaggctctg    1680
cacaaccact acacgcagaa gagcctctcc ctgtctccgg gtaaatga               1728
```

<210> SEQ ID NO 154
<211> LENGTH: 575
<212> TYPE: PRT
<213> ORGANISM: Artificial Sequence
<220> FEATURE:
<223> OTHER INFORMATION: Made in Lab - fusion construct

<400> SEQUENCE: 154

-continued

```
Asn Pro Ile Cys Lys Gly Cys Leu Ser Cys Ser Lys Asp Asn Gly Cys
1               5                   10                  15

Ser Arg Cys Gln Gln Lys Leu Phe Phe Leu Arg Arg Glu Gly Met
            20                  25                  30

Arg Gln Tyr Gly Glu Cys Leu His Ser Cys Pro Ser Gly Tyr Tyr Gly
            35                  40                  45

His Arg Ala Pro Asp Met Asn Arg Cys Ala Arg Cys Arg Ile Glu Asn
        50                  55                  60

Cys Asp Ser Cys Arg Ser Lys Asp Ala Cys Thr Lys Cys Lys Val Gly
65                  70                  75                  80

Phe Tyr Leu His Arg Gly Arg Cys Phe Asp Cys Pro Asp Gly Phe
                85                  90                  95

Ala Pro Leu Glu Glu Thr Met Glu Cys Val Glu Gly Gly Gly Ser
            100                 105                 110

Gly Gly Gly Gly Ser Gly Gly Gly Ser Glu Val Gln Leu Gln Gln
            115                 120                 125

Ser Gly Thr Val Leu Ala Arg Pro Gly Ala Ser Val Lys Met Ser Cys
    130                 135                 140

Lys Ala Ser Gly Tyr Thr Phe Ala Ser Tyr Trp Ile His Trp Val Lys
145                 150                 155                 160

Gln Arg Pro Gly Gln Gly Leu Glu Trp Ile Gly Ser Ile Tyr Pro Gly
            165                 170                 175

Asn Ser Asp Thr Thr Tyr Asn Gln Lys Phe Lys Gly Lys Ala Lys Leu
            180                 185                 190

Thr Val Val Thr Ser Ala Ser Ser Ala Tyr Met Glu Leu Ser Ser Leu
        195                 200                 205

Thr Asn Glu Asp Ser Ala Val Tyr Tyr Cys Thr Glu Pro Thr Tyr Tyr
    210                 215                 220

Ser Tyr Asp Asp Tyr Tyr Ala Met Asp Tyr Trp Gly Gln Gly Thr Ser
225                 230                 235                 240

Val Thr Val Ser Ser Ala Ser Thr Lys Gly Pro Ser Val Phe Pro Leu
            245                 250                 255

Ala Pro Ser Ser Lys Ser Thr Ser Gly Gly Thr Ala Ala Leu Gly Cys
            260                 265                 270

Leu Val Lys Asp Tyr Phe Pro Glu Pro Val Thr Val Ser Trp Asn Ser
            275                 280                 285

Gly Ala Leu Thr Ser Gly Val His Thr Phe Pro Ala Val Leu Gln Ser
        290                 295                 300

Ser Gly Leu Tyr Ser Leu Ser Ser Val Val Thr Val Pro Ser Ser Ser
305                 310                 315                 320

Leu Gly Thr Gln Thr Tyr Ile Cys Asn Val Asn His Lys Pro Ser Asn
            325                 330                 335

Thr Lys Val Asp Lys Lys Val Glu Pro Lys Ser Cys Asp Lys Thr His
            340                 345                 350

Thr Cys Pro Pro Cys Pro Ala Pro Glu Ala Ala Gly Gly Pro Ser Val
            355                 360                 365

Phe Leu Phe Pro Pro Lys Pro Lys Asp Thr Leu Met Ile Ser Arg Thr
            370                 375                 380

Pro Glu Val Thr Cys Val Val Asp Val Ser His Glu Asp Pro Glu
385                 390                 395                 400

Val Lys Phe Asn Trp Tyr Val Asp Gly Val Glu Val His Asn Ala Lys
                405                 410                 415
```

```
Thr Lys Pro Arg Glu Glu Gln Tyr Asn Ser Thr Tyr Arg Val Val Ser
            420                 425                 430
Val Leu Thr Val Leu His Gln Asp Trp Leu Asn Gly Lys Glu Tyr Lys
        435                 440                 445
Cys Lys Val Ser Asn Lys Ala Leu Gly Ala Pro Ile Glu Lys Thr Ile
    450                 455                 460
Ser Lys Ala Lys Gly Gln Pro Arg Glu Pro Gln Val Tyr Thr Leu Pro
465                 470                 475                 480
Pro Ser Arg Glu Glu Met Thr Lys Asn Gln Val Ser Leu Thr Cys Leu
                485                 490                 495
Val Lys Gly Phe Tyr Pro Ser Asp Ile Ala Val Glu Trp Glu Ser Asn
            500                 505                 510
Gly Gln Pro Glu Asn Asn Tyr Lys Thr Thr Pro Pro Val Leu Asp Ser
        515                 520                 525
Asp Gly Ser Phe Phe Leu Tyr Ser Lys Leu Thr Val Asp Lys Ser Arg
    530                 535                 540
Trp Gln Gln Gly Asn Val Phe Ser Cys Ser Val Met His Glu Ala Leu
545                 550                 555                 560
His Asn His Tyr Thr Gln Lys Ser Leu Ser Leu Ser Pro Gly Lys
                565                 570                 575

<210> SEQ ID NO 155
<211> LENGTH: 1344
<212> TYPE: DNA
<213> ORGANISM: Artificial Sequence
<220> FEATURE:
<223> OTHER INFORMATION: Made in Lab - fusion construct

<400> SEQUENCE: 155
caggtccagt tggtggaatc cggaggggt tggtccagc ctggtggaag cctgcgcctc     60
tcatgcgccg ctagcggatt cacccttctcc cgatacggca tgcattgggt cagacaggca    120
cccggaaaag gactcgaatg ggtgtcgggc atttcctcga tcgggtcaaa cacctattac    180
gccgactccg tgaagggacg gttcaccatt agccgggata cagcaagaa cactctgtac    240
ttgcaaatga actccctgcg ggctgaggac accgccgtgt actactgtgc gcggtggtac    300
aagacctata ttgacgtctg gggacagggt accctcgtga ccgtgtcgag tgctagcacc    360
aagggcccat cggtcttccc cctggcaccc tcctccaaga gcacctctgg ggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
gacaaaactc acacatgccc accgtgccca gcacctgaag ccgcgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcggagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
```

-continued

```
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atga                                           1344
```

<210> SEQ ID NO 156
<211> LENGTH: 447
<212> TYPE: PRT
<213> ORGANISM: Artificial Sequence
<220> FEATURE:
<223> OTHER INFORMATION: Made in Lab - fusion construct

<400> SEQUENCE: 156

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ser Gly Ile Ser Ser Ile Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Tyr Lys Thr Tyr Ile Asp Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 157
<211> LENGTH: 1068
<212> TYPE: DNA
<213> ORGANISM: Artificial Sequence
<220> FEATURE:
<223> OTHER INFORMATION: Made in Lab - fusion construct

<400> SEQUENCE: 157
atcgagctga cccagcctcc ctccgtgtcc gtggcccctg gccagaccgc ccggatctcc      60
tgctccggcg acaacatcgg cagcttctac gtgcactggt atcagcagaa acctggacag     120
gcccctgtgc tggtgatcta cgacaagtcc aacggccctt ccggcatccc tgagcggttc     180
tccggctcca actccggcaa caccgccacc ctgaccatct ccggcaccca ggccgaggac     240
gaggccgact actactgcca gtcctacgcc aacaccctgt ccctggtgtt tggcggcgga     300
acaaagctga ccgtgctggg caccacggcg gcaagcggga gcagtggcgg aagttcttcg     360
ggcgcagagg tgcagctggt cgagtctggc ggcggactgg tgcagcctgg cggctccctg     420
agactgtcct gcgccgcctc cggcttcacc ttctcccact acaccctgtc ctgggtgcgc     480
caggcaccag ggaagggact ggagtgggtc tccgtgatct ccggcgacgg ctcctacacc     540
tactacgccg actccgtgaa gggccggttc accatctcct ccgacaactc caagaacacc     600
ctgtacctgc agatgaactc tctgagagcc gaggacaccg ccgtgtacta ctgcgcccgg     660
aacttcatca gtacgtgttt cgccaactgg ggccagggca ccctggtgac cgtgtccggc     720
ggctccggat ccgggaagat gtaccatacc aagggacaag agggctccgt gtgcttgaga     780
tccagcgact gtgccagcgg actgtgctgc ctaggcactt tctggagcaa gatctgcaaa     840
cccgtgctga aggagggtca agtctgcacc aagcacaggc ggaagggatc ccatggactg     900
gagatcttcc aacggtgcta ctgtggagag ggcctgagct gccggattca aaggaccac      960 catcaggcct caaactcctc ccggctccac acttgccagc ccacggcgg cgactacaag     1020 gatgacgacg ataaggggtc gcaccaccat catcaccacc accactag                 1068

<210> SEQ ID NO 158
<211> LENGTH: 355
<212> TYPE: PRT
<213> ORGANISM: Artificial Sequence
<220> FEATURE:
<223> OTHER INFORMATION: Made in Lab - fusion construct

<400> SEQUENCE: 158

Ile Glu Leu Thr Gln Pro Pro Ser Val Ser Val Ala Pro Gly Gln Thr
```

```
  1               5                   10                  15
Ala Arg Ile Ser Cys Ser Gly Asp Asn Ile Gly Ser Phe Tyr Val His
             20                  25                  30

Trp Tyr Gln Gln Lys Pro Gly Gln Ala Pro Val Leu Val Ile Tyr Asp
             35                  40                  45

Lys Ser Asn Arg Pro Ser Gly Ile Pro Glu Arg Phe Ser Gly Ser Asn
 50                  55                  60

Ser Gly Asn Thr Ala Thr Leu Thr Ile Ser Gly Thr Gln Ala Glu Asp
 65                  70                  75                  80

Glu Ala Asp Tyr Tyr Cys Gln Ser Tyr Ala Asn Thr Leu Ser Leu Val
                 85                  90                  95

Phe Gly Gly Gly Thr Lys Leu Thr Val Leu Gly Thr Thr Ala Ala Ser
                 100                 105                 110

Gly Ser Ser Gly Ser Ser Gly Ala Glu Val Gln Leu Val Glu
                 115                 120                 125

Ser Gly Gly Gly Leu Val Gln Pro Gly Gly Ser Leu Arg Leu Ser Cys
 130                 135                 140

Ala Ala Ser Gly Phe Thr Phe Ser His Tyr Thr Leu Ser Trp Val Arg
145                  150                 155                 160

Gln Ala Pro Gly Lys Gly Leu Glu Trp Val Ser Val Ile Ser Gly Asp
             165                 170                 175

Gly Ser Tyr Thr Tyr Tyr Ala Asp Ser Val Lys Gly Arg Phe Thr Ile
             180                 185                 190

Ser Ser Asp Asn Ser Lys Asn Thr Leu Tyr Leu Gln Met Asn Ser Leu
             195                 200                 205

Arg Ala Glu Asp Thr Ala Val Tyr Tyr Cys Ala Arg Asn Phe Ile Lys
210                  215                 220

Tyr Val Phe Ala Asn Trp Gly Gln Gly Thr Leu Val Thr Val Ser Gly
225                  230                 235                 240

Gly Ser Gly Ser Gly Lys Met Tyr His Thr Lys Gly Gln Glu Gly Ser
                 245                 250                 255

Val Cys Leu Arg Ser Ser Asp Cys Ala Ser Gly Leu Cys Cys Ala Arg
             260                 265                 270

His Phe Trp Ser Lys Ile Cys Lys Pro Val Leu Lys Glu Gly Gln Val
             275                 280                 285

Cys Thr Lys His Arg Arg Lys Gly Ser His Gly Leu Glu Ile Phe Gln
 290                 295                 300

Arg Cys Tyr Cys Gly Glu Gly Leu Ser Cys Arg Ile Gln Lys Asp His
305                  310                 315                 320

His Gln Ala Ser Asn Ser Ser Arg Leu His Thr Cys Gln Arg His Gly
             325                 330                 335

Gly Asp Tyr Lys Asp Asp Asp Lys Gly Ser His His His His
             340                 345                 350

His His His
        355

<210> SEQ ID NO 159
<211> LENGTH: 4
<212> TYPE: PRT
<213> ORGANISM: Artificial Sequence
<220> FEATURE:
<223> OTHER INFORMATION: Synthesized peptide linker

<400> SEQUENCE: 159

Gly Gly Gly Gly
```

```
<210> SEQ ID NO 160
<211> LENGTH: 5
<212> TYPE: PRT
<213> ORGANISM: Artificial Sequence
<220> FEATURE:
<223> OTHER INFORMATION: Synthesized peptide linker

<400> SEQUENCE: 160

Gly Gly Gly Gly Gly
1               5

<210> SEQ ID NO 161
<211> LENGTH: 6
<212> TYPE: PRT
<213> ORGANISM: Artificial Sequence
<220> FEATURE:
<223> OTHER INFORMATION: Synthesized peptide linker

<400> SEQUENCE: 161

Gly Gly Gly Gly Gly Gly
1               5

<210> SEQ ID NO 162
<211> LENGTH: 7
<212> TYPE: PRT
<213> ORGANISM: Artificial Sequence
<220> FEATURE:
<223> OTHER INFORMATION: Synthesized peptide linker

<400> SEQUENCE: 162

Gly Gly Gly Gly Gly Gly Gly
1               5

<210> SEQ ID NO 163
<211> LENGTH: 8
<212> TYPE: PRT
<213> ORGANISM: Artificial Sequence
<220> FEATURE:
<223> OTHER INFORMATION: Synthesized peptide linker

<400> SEQUENCE: 163

Gly Gly Gly Gly Gly Gly Gly Gly
1               5

<210> SEQ ID NO 164
<211> LENGTH: 5
<212> TYPE: PRT
<213> ORGANISM: Artificial Sequence
<220> FEATURE:
<223> OTHER INFORMATION: Synthesized peptide linker

<400> SEQUENCE: 164

Gly Gly Gly Gly Ser
1               5

<210> SEQ ID NO 165
<211> LENGTH: 4
<212> TYPE: PRT
<213> ORGANISM: Artificial Sequence
<220> FEATURE:
<223> OTHER INFORMATION: Synthesized peptide linker

<400> SEQUENCE: 165

Gly Ala Gly Ala
1
```

<210> SEQ ID NO 166
<211> LENGTH: 6
<212> TYPE: PRT
<213> ORGANISM: Artificial Sequence
<220> FEATURE:
<223> OTHER INFORMATION: Synthesized peptide linker

<400> SEQUENCE: 166

Gly Ala Gly Ala Gly Ala
1               5

<210> SEQ ID NO 167
<211> LENGTH: 8
<212> TYPE: PRT
<213> ORGANISM: Artificial Sequence
<220> FEATURE:
<223> OTHER INFORMATION: Synthesized peptide linker

<400> SEQUENCE: 167

Gly Ala Gly Ala Gly Ala Gly Ala
1               5

<210> SEQ ID NO 168
<211> LENGTH: 4
<212> TYPE: PRT
<213> ORGANISM: Artificial Sequence
<220> FEATURE:
<223> OTHER INFORMATION: Synthesized peptide linker

<400> SEQUENCE: 168

Ala Ala Ala Ala
1

<210> SEQ ID NO 169
<211> LENGTH: 5
<212> TYPE: PRT
<213> ORGANISM: Artificial Sequence
<220> FEATURE:
<223> OTHER INFORMATION: Synthesized peptide linker

<400> SEQUENCE: 169

Ala Ala Ala Ala Ala
1               5

<210> SEQ ID NO 170
<211> LENGTH: 6
<212> TYPE: PRT
<213> ORGANISM: Artificial Sequence
<220> FEATURE:
<223> OTHER INFORMATION: Synthesized peptide linker

<400> SEQUENCE: 170

Ala Ala Ala Ala Ala Ala
1               5

<210> SEQ ID NO 171
<211> LENGTH: 7
<212> TYPE: PRT
<213> ORGANISM: Artificial Sequence
<220> FEATURE:
<223> OTHER INFORMATION: Synthesized peptide linker

<400> SEQUENCE: 171

Ala Ala Ala Ala Ala Ala Ala
1               5

<210> SEQ ID NO 172
<211> LENGTH: 8
<212> TYPE: PRT
<213> ORGANISM: Artificial Sequence
<220> FEATURE:
<223> OTHER INFORMATION: Synthesized peptide linker

<400> SEQUENCE: 172

Ala Ala Ala Ala Ala Ala Ala Ala
1               5

<210> SEQ ID NO 173
<211> LENGTH: 6
<212> TYPE: PRT
<213> ORGANISM: Artificial Sequence
<220> FEATURE:
<223> OTHER INFORMATION: Synthesized peptide linker

<400> SEQUENCE: 173

Gly Gly Gly Gly Gly Lys
1               5

<210> SEQ ID NO 174
<211> LENGTH: 7
<212> TYPE: PRT
<213> ORGANISM: Artificial Sequence
<220> FEATURE:
<223> OTHER INFORMATION: Synthesized peptide linker

<400> SEQUENCE: 174

Gly Gly Gly Gly Gly Lys Arg
1               5

<210> SEQ ID NO 175
<211> LENGTH: 8
<212> TYPE: PRT
<213> ORGANISM: Artificial Sequence
<220> FEATURE:
<223> OTHER INFORMATION: Synthesized peptide linker

<400> SEQUENCE: 175

Gly Gly Gly Lys Gly Gly Gly Gly
1               5

<210> SEQ ID NO 176
<211> LENGTH: 10
<212> TYPE: PRT
<213> ORGANISM: Artificial Sequence
<220> FEATURE:
<223> OTHER INFORMATION: Heavy chain CDR1 sequence

<400> SEQUENCE: 176

Gly Phe Thr Phe Ser His Tyr Thr Leu Ser
1               5                   10

<210> SEQ ID NO 177
<211> LENGTH: 17
<212> TYPE: PRT
<213> ORGANISM: Artificial Sequence
<220> FEATURE:
<223> OTHER INFORMATION: Heavy chain CDR2 sequence

<400> SEQUENCE: 177

Val Ile Ser Gly Asp Gly Ser Tyr Thr Tyr Tyr Ala Asp Ser Val Lys
1               5                   10                  15

Gly

<210> SEQ ID NO 178
<211> LENGTH: 9
<212> TYPE: PRT
<213> ORGANISM: Artificial Sequence
<220> FEATURE:
<223> OTHER INFORMATION: Heavy chain CDR3 sequence

<400> SEQUENCE: 178

Asn Phe Ile Lys Tyr Val Phe Ala Asn
1               5

<210> SEQ ID NO 179
<211> LENGTH: 11
<212> TYPE: PRT
<213> ORGANISM: Artificial Sequence
<220> FEATURE:
<223> OTHER INFORMATION: Light chain CDR1 sequence

<400> SEQUENCE: 179

Ser Gly Asp Lys Leu Gly Lys Lys Tyr Ala Ser
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Light chain CDR1 sequence

<400> SEQUENCE: 180

Ser Gly Asp Asn Ile Gly Ser Phe Tyr Val His
1               5                   10

<210> SEQ ID NO 181
<211> LENGTH: 8
<212> TYPE: PRT
<213> ORGANISM: Artificial Sequence
<220> FEATURE:
<223> OTHER INFORMATION: Light chain CDR2 sequence

<400> SEQUENCE: 181

Glu Lys Asp Asn Arg Pro Ser Gly
1               5

<210> SEQ ID NO 182
<211> LENGTH: 8
<212> TYPE: PRT
<213> ORGANISM: Artificial Sequence
<220> FEATURE:
<223> OTHER INFORMATION: Light chain CDR2 sequence

<400> SEQUENCE: 182

Asp Lys Ser Asn Arg Pro Ser Gly
1               5

<210> SEQ ID NO 183
<211> LENGTH: 9
<212> TYPE: PRT
<213> ORGANISM: Artificial Sequence
<220> FEATURE:
<223> OTHER INFORMATION: Light chain CDR3 sequence

<400> SEQUENCE: 183

Ser Ser Phe Ala Gly Asn Ser Leu Glu
1               5

```
<210> SEQ ID NO 184
<211> LENGTH: 8
<212> TYPE: PRT
<213> ORGANISM: Artificial Sequence
<220> FEATURE:
<223> OTHER INFORMATION: Light chain CDR3 sequence

<400> SEQUENCE: 184

Gln Ser Tyr Ala Asn Thr Leu Ser
1               5

<210> SEQ ID NO 185
<211> LENGTH: 90
<212> TYPE: PRT
<213> ORGANISM: Homo sapiens

<400> SEQUENCE: 185

Lys Met Tyr His Thr Lys Gly Gln Glu Gly Ser Val Cys Leu Arg Ser
1               5                   10                  15

Ser Asp Cys Ala Ser Gly Leu Cys Cys Ala Arg His Phe Trp Ser Lys
            20                  25                  30

Ile Cys Lys Pro Val Leu Lys Glu Gly Gln Val Cys Thr Lys His Arg
        35                  40                  45

Arg Lys Gly Ser His Gly Leu Glu Ile Phe Gln Arg Cys Tyr Cys Gly
    50                  55                  60

Glu Gly Leu Ser Cys Arg Ile Gln Lys Asp His His Gln Ala Ser Asn
65                  70                  75                  80

Ser Ser Arg Leu His Thr Cys Gln Arg His
                85                  90

<210> SEQ ID NO 186
<211> LENGTH: 88
<212> TYPE: PRT
<213> ORGANISM: Homo sapiens

<400> SEQUENCE: 186

Lys Met Ser His Ile Lys Gly His Glu Gly Asp Pro Cys Leu Arg Ser
1               5                   10                  15

Ser Asp Cys Ile Glu Gly Phe Cys Cys Ala Arg His Phe Trp Thr Lys
            20                  25                  30

Ile Cys Lys Pro Val Leu His Gln Gly Glu Val Cys Thr Lys Gln Arg
        35                  40                  45

Lys Lys Gly Ser His Gly Leu Glu Ile Phe Gln Arg Cys Asp Cys Ala
    50                  55                  60

Lys Gly Leu Ser Cys Lys Val Trp Lys Asp Ala Thr Tyr Ser Ser Lys
65                  70                  75                  80

Ala Arg Leu His Val Cys Gln Lys
                85
```

TISSUE-SPECIFIC WNT SIGNAL ENHANCING MOLECULES AND USES THEREOF

CROSS-REFERENCE TO RELATED APPLICATIONS

This application claims the benefit of International PCT Application No. PCT/US2018/015595, filed Jan. 26, 2018; which claims priority to U.S. Provisional Application No. 62/450,804, filed on Jan. 26, 2017, and U.S. Provisional Application No. 62/487,135, filed on Apr. 19, 2017, all of which are incorporated by reference herein in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is SRZN_03_02US_ST25.txt. The text file is 409,384 bytes, was created on Aug. 30, 2021, and is being submitted electronically via EFS-Web.

FIELD OF THE INVENTION

The present disclosure relates to tissue-specific Wnt signal enhancing molecules, e.g., fusion proteins, comprising a domain that binds an E3 ubiquitin ligase, ZNRF3 or RNF43, and a tissue-specific cell surface receptor binding domain, as well as related methods of using the tissue-specific Wnt signal enhancing molecules to mediate tissue-specific internalization or sequestration of the E3 ligases, ZNRF3/RNF43, thus stabilizing Wnt receptors and enhancing Wnt signaling in a tissue-specific manner, and to treat and prevent a variety of diseases and disorders.

BACKGROUND OF THE INVENTION

Wnt ("Wingless-related integration site" or "Wingless and Int-1" or "Wingless-Int") ligands and their signals play key roles in the control of development, homeostasis and regeneration of many essential organs and tissues, including bone, liver, skin, stomach, intestine, kidney, central nervous system, mammary gland, taste bud, ovary, cochlea and many other tissues (reviewed, e.g., by Clevers, Loh, and Nusse, 2014; 346:1248012). Modulation of Wnt signaling pathways has potential for treatment of degenerative diseases and tissue injuries. To achieve this goal, it is desirous to develop strategies to modulate Wnt signaling activity in a tissue-specific or cell type-specific manner to avoid unwanted effects. One of the challenges for modulating Wnt signaling as a therapeutic is the existence of multiple Wnt ligands and Wnt receptors, Frizzled 1-10 (Fzd1-10), with many tissues expressing multiple and overlapping Fzds. Canonical Wnt signals also involve Low-density lipoprotein (LDL) receptor-related protein 5 (LRP5) or Low-density lipoprotein (LDL) receptor-related protein 6 (LRP6) as co-receptors, which are broadly expressed in various tissues, in addition to Fzds.

R-spondins 1-4 are a family of ligands that amplify Wnt signals. Each of the R-spondins work through a receptor complex that contains Zinc and Ring Finger 3 (ZNRF3) or Ring Finger Protein 43 (RNF43) on one end and a Leucine-rich repeat-containing G-protein coupled receptor 4-6 (LGR4-6) on the other (reviewed, e.g., by Knight and Hankenson 2014, Matrix Biology; 37: 157-161). R-spondins might also work through additional mechanisms of action. ZNRF3 and RNF43 are two membrane-bound E3 ligases specifically targeting Wnt receptors (Fzd1-10 and LRP5 or LRP6) for degradation. Binding of an R-spondin to ZNRF3/RNF43 and LGR4-6 causes clearance or sequestration of the ternary complex, which removes E3 ligases from Wnt receptors and stabilizes Wnt receptors, resulting in enhanced Wnt signals. Each R-spondin contains two Furin domains (1 and 2), with Furin domain 1 binding to ZNRF3/RNF43, and Furin domain 2 binding to LGR4-6. Fragments of R-spondins containing Furin domains 1 and 2 are sufficient for amplifying Wnt signaling. While R-spondin effects depend on Wnt signals, since both LGR4-6 and ZNRF3/RNF43 are widely expressed in various tissues, the effects of R-spondins are not tissue-specific.

There is clearly a need in the art for tissue-specific Wnt signal enhancing molecules for the treatment and prevention of specific diseases and disorders. The present invention addresses this need by providing compositions and methods useful for enhancing Wnt activity in a tissue-specific manner.

SUMMARY OF THE INVENTION

The present invention relates to tissue-specific Wnt signal enhancing molecules and uses thereof, e.g., in increasing Wnt signaling in a target tissue and treating disease and conditions that would benefit from increased Wnt signaling.

In one embodiment, the present invention provides a tissue-specific Wnt signal enhancing molecule, or a pharmaceutically acceptable salt thereof, comprising a first domain that specifically binds one or more transmembrane E3 ubiquitin ligases selected from ZNRF3 and RNF43, and a second domain that specifically binds a tissue-specific cell surface molecule, wherein the molecule increases Wnt signaling in a tissue comprising the tissue-specific cell surface molecule. In certain embodiments, the tissue is selected from the group consisting of: bone tissue, liver tissue, skin tissue, stomach tissue, intestine tissue, oral mucosa tissue, kidney tissue, central nervous system tissue, mammary gland tissue, taste bud tissue, ovary tissue, inner ear tissue (including cochlear and vestibular tissues), hair follicles, pancreas tissue, retina tissue, vascular tissue, cornea tissue, heart tissue and lung tissue. In various embodiments, either or both of the first domain and the second domain are polypeptides, antibodies, small molecules, natural ligands, non-natural ligands, or variants thereof.

In particular embodiments of Wnt signal enhancing molecules, the first domain comprises a first polypeptide sequence and/or the second domain comprises a second polypeptide sequence. In particular embodiments, the molecule is a fusion protein comprising the first polypeptide sequence and the second polypeptide sequence. In certain embodiments, the first polypeptide sequence comprises an R-Spondin sequence or a fragment or variant thereof. In particular embodiments, the R-spondin is an R-spondin-1, an R-spondin-2, an R-spondin-3, or an R-spondin-4, e.g., a human R-spondin-1-4. In certain embodiments, the first polypeptide suequence comprises an R-spondin Furin domain 1 or a fragment or variant thereof. In particular embodiments, the first polypeptide sequence is a wild-type sequence or a modified sequence. In addition, the first polypeptide sequence could have increased, similar, or reduced binding to LGR4-6 as compared to the corresponding native full length R-spondin. In some embodiments, the Rspondin or the R-spondin Furin domain 1 has at least 50%, at least 60%, at least 70%, at least 80%, at least 90%, or at least 95% identity to any of the R-spondins or R-spondin Furin 1 domains present in SEQ ID NOs:1-4. In certain embodiments, the second polypeptide sequence is polypeptide, an antibody or fragment or variant thereof, or a ligand or fragment or variant thereof.

In certain illustrative embodiments of the tissue-specific Wnt signal enhancing molecules disclosed herein: the tissue is bone tissue, and the cell surface receptor is parathyroid hormone receptor 1 (PTH1R); the tissue is liver tissue, and the cell surface receptor is asialoglycoprotein receptor 1 (ASGR1), asialoglycoprotein receptor 2 (ASGR2), transferrin receptor 2 (TFR2) or solute carrier family 10 member 1 (SLC10A1); or the tissue is oral mucous tissue, and the cell surface receptor is LY6/PLAUR Domain Containing 3 (LYPD3) or Desmoglein 3 (DSG3).

In certain illustrative embodiments of the tissue-specific Wnt signal enhancing molecules disclosed herein: the cell surface molecule is a PTH1, and the second polypeptide sequence specifically binds PTH1R; the cell surface molecule is ASGR1, and the second polypeptide sequence specifically binds ASGR1; the cell surface molecule is ASGR2, and the second polypeptide sequence specifically binds ASGR2; the cell surface molecule is SLC10A1, and the second polypeptide sequence specifically binds SLC10A1; the cell surface molecule is TFR2, and the second polypeptide sequence specifically binds TFR2; the cell surface molecule is LYPD3, and the second polypeptide sequence specifically binds LYPD3; or the cell surface molecule is DSG3, and the second polypeptide sequence specifically binds DSG3, wherein the second polypeptide is an antibody or fragment thereof, a small molecule, or a ligand, or fragment or variant thereof, of the cell surface molecule.

In particular embodiments of the tissue-specific Wnt signal enhancing molecules described herein, the first domain and the second domain are joined by a linker moiety. In certain embodiments, the linker moiety is a peptidyl linker sequence. In particular embodiments, the peptidyl linker sequence comprises one or more amino acids selected from the group consisting of: Glycine, Asparagine, Serine, Threonine and Alanine In particular embodiments, the tissue-specific Wnt signal enhancing molecules described herein consist of a single polypeptide, e.g., a fusion protein comprising the first domain and the second domain. In certain embodiments, the tissue-specific Wnt signal enhancing moelcules described herein comprise two or more polypeptides, such as dimers or multimers comprising two or more fusion proteins, each comprising the first domain and the second domain, wherein the two or more polypeptides are linked, e.g., through a linker moiety or via a bond between amino acid residues in each of the two or more polypepitdes, e.g., an intermolecular disulfide bond between cysteine residues. In particular embodiments, the tissue-specific Wnt signal enhancing molecules described herein comprise two or more polypeptide sequences. For example, a tissue-specific Wnt signal enhancing molecule may comprise antibody heavy and light chains (or antigen-binding fragments thereof) that constitute either the first domain or the second domain, wherein the other domain (i.e., the second domain or first domain) is linked to the antibody heavy chain or light chain, either as a fusion protein or via a linker moiety. In particular embodiments, the other domain is linked to the N-terminus of the heavy chain, the C-terminus of the heavy chain, the N-terminus of the light chain, or the C-terminus of the light chain. Such structures may be referred to herein as appended IgG scaffolds or formats.

In a related embodiment, the present invention includes a nucleic acid sequence encoding for a tissue-specific Wnt signal enhancing fusion protein disclosed herein or a subunit thereof, e.g., an antibody heavy chain or light chain having an appended or fused first domain or second domain. In a further related embodiment, the present invention includes a vector comprising the nucleic acid sequence. In some embodiments, the vector is an expression vector comprising a promoter sequence operatively linked to the nucleic acid sequence, e.g., in a manner suitable for expression in bacterial or eukaryotic cells. In another embodiment, the vector is engineered for in vitro translation and modification of functional mRNA. In a further related embodiment, the present invention includes a host cell comprising the vector. In yet another further related embodiment, the present invention includes a process for producing a tissue-specific Wnt signal enhancing fusion protein described herein, comprising culturing the host cell under conditions wherein the fusion polypeptide is expressed by the expression vector. In some embodiments, the process further comprises the step of isolating the fusion polypeptide that is produced.

In another embodiment, the present invention provides a pharmaceutical composition comprising a tissue-specific Wnt signal enhancing molecule described herein, or a pharmaceutically acceptable salt thereof, and a pharmaceutically acceptable diluent, adjuvant or carrier.

In another embodiment, the present invention provides a pharmaceutical composition comprising a polynucleotide comprising a nucleic acid sequence encoding a tissue-specific Wnt signal enhancing molecule described herein, or a pharmaceutically acceptable salt thereof, and a pharmaceutically acceptable diluent, adjuvant or carrier. In particular embodiments, the nucleic acid sequence comprises DNA or mRNA, optionally a modified mRNA.

In another embodiment, the present invention provides a pharmaceutical composition comprising a vector comprising a nucleic acid sequence encoding a tissue-specific Wnt signal enhancing molecule, or a pharmaceutically acceptable salt thereof, and a pharmaceutically acceptable diluent, adjuvant or carrier. In particular embodiments, the vector comprises a promoter operatively linked to the nucleic acid sequence, which drives expression of the tissue-specific Wnt signal enhancing molecule. In certain embodiments, the vector is an expression vector or a viral vector.

In another embodiment, the present invention provides a pharmaceutical composition comprising a polynucleotide comprising a nucleic acid sequence encoding a Wnt polypeptide, a Norrin polypeptide, or a Wnt signaling agonist (e.g., natural or engineered), or a pharmaceutically acceptable salt thereof, and a pharmaceutically acceptable diluent, adjuvant or carrier. In particular embodiments, the nucleic acid sequence comprises DNA or mRNA, optionally a modified mRNA.

In another embodiment, the present invention provides a pharmaceutical composition comprising a vector comprising a nucleic acid sequence encoding a Wnt polypeptide, a Norrin polypeptide, or a Wnt signaling agonist (e.g., natural or engineered), or a pharmaceutically acceptable salt thereof, and a pharmaceutically acceptable diluent, adjuvant or carrier. In particular embodiments, the vector comprises a promoter operatively linked to the nucleic acid sequence, which drives expression of the Wnt polypeptide, a Norrin polypeptide, or a Wnt signaling agonist. In certain embodiments, the vector is an expression vector or a viral vector.

In another embodiment, the present invention provides a pharmaceutical composition comprising: a tissue-specific Wnt signal enhancing molecule described herein, or a pharmaceutically acceptable salt thereof; a Wnt polypeptide, a Norrin polypeptide, or a Wnt signaling agonist, or a pharmaceutically acceptable salt thereof; and a pharmaceutically acceptable diluent, adjuvant or carrier.

In another embodiment, the present invention provides a pharmaceutical composition comprising: a polynucleotide comprising a nucleic acid sequence encoding a tissue-specific Wnt signal enhancing molecule described herein, or a pharmaceutically acceptable salt thereof; a polynucleotide comprising a nucleic acid sequence encoding a Wnt polypeptide, a Norrin polypeptide, or a Wnt signaling agonist, or a pharmaceutically acceptable salt thereof; and a pharmaceutically acceptable diluent, adjuvant or carrier. In particular embodiments, the nucleic acid sequence comprises DNA or mRNA, optionally a modified mRNA.

In another embodiment, the present invention provides a pharmaceutical composition comprising: a vector comprising a nucleic acid sequence encoding a tissue-specific Wnt signal enhancing molecule, or a pharmaceutically acceptable salt thereof; a vector comprising a nucleic acid sequence encoding a Wnt polypeptide, a Norrin polypeptide, or a Wnt signaling agonist, or a pharmaceutically acceptable salt thereof; and a pharmaceutically acceptable diluent, adjuvant or carrier. In particular embodiments, the vector comprises a promoter operatively linked to the nucleic acid sequence, which drives expression of the tissue-specific Wnt signal enhancing molecule. In certain embodiments, the vector is an expression vector or a viral vector.

In a further embodiment, the present invention includes a method for increasing Wnt signaling in a target tissue, comprising contacting the target tissue with a tissue-specific Wnt signal enhancing molecule described herein, wherein the second domain specifically binds a cell-specific surface molecule on the target tissue, and wherein the tissue-specific Wnt signal enhancing molecule binds the target tissue and sequesters or increases endocytosis of one or more transmembrane E3 ubiquitin ligase selected from ZNRF3 and RNF43 in the target tissue.

In certain embodiments of any of the methods described herein: the tissue is bone tissue, and the cell surface molecule is PTH1R; the tissue is liver tissue, and the cell surface molecule is ASGR1, ASGR2, TFR2, or SLC10A1; or the tissue is oral mucous tissue and the cell surface receptor is LYPD3 or DSG3. In particular embodiments, the target tissue or cell is contacted with a polynucleotide comprising a nucleic acid sequence encoding the tissue-specific Wnt signal enhancing molecule, or a vector comprising a nucleic acid sequence encoding the tissue-specific Wnt signal enhancing molecule, e.g., an expression vector or viral vector.

In a further embodiment, the present invention includes a method for increasing Wnt signaling in a target tissue, comprising contacting the target tissue with a Wnt polypeptide, a Norrin polypeptide, or a Wnt signaling agonist, or a pharmaceutically acceptable salt thereof. In particular embodiments, the target tissue or cell is contacted with a polynucleotide comprising a nucleic acid sequence encoding the Wnt polypeptide, a Norrin polypeptide, or a Wnt signaling agonist, or a pharmaceutically acceptable salt thereof, or a vector comprising a nucleic acid sequence encoding the Wnt polypeptide, a Norrin polypeptide, or a Wnt signaling agonist, or a pharmaceutically acceptable salt thereof, e.g., an expression vector or viral vector.

In a further embodiment, the present invention includes a method for increasing Wnt signaling in a target tissue, comprising contacting the target tissue with: a tissue-specific Wnt signal enhancing molecule described herein, wherein the second domain specifically binds a cell-specific surface molecule on the target tissue, and wherein the tissue-specific Wnt signal enhancing molecule binds the target tissue and sequesters or increases endocytosis of one or more transmembrane E3 ubiquitin ligase selected from ZNRF3 and RNF43 in the target tissue, and a Wnt polypeptide, a Norrin polypeptide, or a Wnt signaling agonist, or a pharmaceutically acceptable salt thereof. In particular embodiments, the target tissue or cell is contacted with a polynucleotide comprising a nucleic acid sequence encoding the tissue-specific Wnt signal enhancing molecule and a nucleic acid encoding the Wnt polypeptide, a Norrin polypeptide, or a Wnt signaling agonist. In other embodiments, the target tissue or cell is contacted with a vector comprising a nucleic acid sequence encoding the tissue-specific Wnt signal enhancing molecule and a vector encoding the Wnt polypeptide, a Norrin polypeptide, or a Wnt signaling agonist.

In yet another related embodiment, the present invention includes a method for treating or preventing a disease or condition in a subject in need thereof, wherein the disease or condition is associated with reduced Wnt signaling or would benefit from increased Wnt signaling, comprising providing to the subject an effective amount of a pharmaceutical composition comprising the tissue-specific Wnt signal enhancing molecule, or a pharmaceutically acceptable salt thereof, either alone or in combination with a Wnt, Norrin, or a Wnt activating/mimetic molecule. In particular embodiments, the method is performed using a pharmaceutical composition comprising a polynucleotide comprising a nucleic acid sequence encoding the tissue-specific Wnt signal enhancing molecule (e.g., a DNA or mRNA), or a vector comprising a nucleic acid sequence encoding the tissue-specific Wnt signal enhancing molecule (e.g., an expression vector or viral vector), alone or in combination with a pharmaceutical composition comprising a polynucleotide comprising a nucleic acid sequence encoding the Wnt polypeptide, a Norrin polypeptide, or a Wnt signaling agonist molecule (e.g., a DNA or mRNA), or a vector comprising a nucleic acid sequence encoding the Wnt polypeptide, a Norrin polypeptide, or a Wnt signaling agonist molecule (e.g., an expression vector or viral vector).

In yet another related embodiment, the present invention includes a method for treating or preventing a disease or condition in a subject in need thereof, wherein the disease or condition is associated with reduced Wnt signaling or would benefit from increased Wnt signaling, comprising providing to the subject an effective amount of a pharmaceutical composition comprising a Wnt polypeptide, a Norrin polypeptide, or a Wnt signaling agonist molecule. In particular embodiments, the method is performed using a pharmaceutical composition comprising a polynucleotide comprising a nucleic acid sequence encoding the Wnt polypeptide, a Norrin polypeptide, or a Wnt signaling agonist molecule (e.g., a DNA or mRNA), or a vector comprising a nucleic acid sequence encoding the Wnt polypeptide, a Norrin polypeptide, or a Wnt signaling agonist molecule (e.g., an expression vector or viral vector).

In particular embodiments of any of the methods of treatment described herein, the disease or disorder is a disease or disorder of a tissue selected from the group consisting of: bone tissue, liver tissue, skin tissue, stomach tissue, intestine tissue, oral mucosa tissue, kidney tissue, central nervous system tissue, mammary gland tissue, taste bud tissue, ovary tissue, inner ear tissue (including cochlear and vestibular tissues), hair follicles, pancreas tissue, retina tissue, vascular tissue, cornea tissue, heart tissue, and lung tissue. In certain illustrative embodiments, the disease or disorder is: a disease or disorder of bone tissue, and the cell surface receptor is PTH1R; or a disease or disorder of liver tissue, and the cell surface receptor is ASGR1, ASGR2, TFR2, or SLC10A1; or a disease or disorder of oral mucous tissue, and the cell surface receptor is LYPD3 or DSG3. In certain illustrative embodiments, the disease or condition is selected from the group consisting of: bone fractures, osteoporosis, osteoporotic fractures, spinal fusion, osseointegration of orthopedic devices, tendon-bone integration, tooth growth and regeneration, dental implantation, periodontal diseases, maxillofacial reconstruction, osteonecrosis of the jaw, alopecia, hearing loss, vestibular hypofunction, macular degeneration, vitreoretinopathy, diseases of retinal degeneration, diabetic retinopathy, Fuchs' dystrophy, stroke, traumatic brain injury, Alzheimer's disease, multiple sclerosis, spinal cord injuries, oral mucositis, intestinal mucositis, short bowel syndrome, inflammatory bowel diseases (IBD), metabolic syndrome, diabetes, pancreatitis, exocrine pancreatic insufficiency, wound healing, diabetic foot ulcers, coronary artery disease, acute kidney injuries, chronic kidney diseases, chronic obstructive pulmonary diseases (COPD), idiopathic pulmonary fibrosis, acute liver failure, acute alcoholic liver injuries, chronic liver diseases with hepatitis C virus (HCV), HCV patients post-antiviral drug therapies, chronic liver diseases with hepatitis B virus (HBV), HBV patients post-antiviral drug therapies, chronic alcoholic liver diseases, non-alcoholic fatty liver diseases and non-alcoholic steatohepatitis (NASH), cirrhosis, and chronic liver insufficiencies of all causes. In particular embodiments of any of the methods of treatment or prevention described herein, the pharmaceutical composition is provided systemically, parenterally, orally, intramuscularly, locally, or topically. In particular embodiments, the subject is a mammal, optionally a human.

BRIEF DESCRIPTION OF THE DRAWINGS

Features of the disclosure are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 4 shows an alignment of all four human R-spondin proteins (Rspo1 (SEQ ID NO:1); Rspo2 (SEQ ID NO:2); Rspo3 (SEQ ID NO:3); and Rspo4 (SEQ ID NO:4), with the Furin domain 1 (Fu1) and 2 (Fu2) shaded in light and dark shading, respectively. The Fu1 domain generally corresponds to: about amino acid residues 38-94 of SEQ ID NO:1; about amino acid residues 37-93 of SEQ ID NO:2; about amino acid residues 39-95 of SEQ ID NO:3; and about amino acid residues 32-88 of SEQ ID NO:4. The Fu2 domain generally corresponds to: about amino acid residues 97-144 of SEQ ID NO:1; about amino acid residues 96-143 of SEQ ID NO:2; about amino acid residues 98-144 of SEQ ID NO:3; and about amino acid residues 91-137 of SEQ ID NO:4.

FIGS. 5A-5D demonstrate cell-specific up-regulation of Wnt-signaling by an illustrative tissue-specific Wnt signal enhancing fusion protein. FIG. 5A provides a scheme of three constructs tested. From top to bottom: (1) anti-GFP fused to a functional human Rspo2 fragment (SEQ ID NO6; encoding DNA provided in SEQ ID NO:5), which contains the wild-type Fu1 and Fu2 domains (amino acid residues 37-143); (2) anti-GFP fused to human Rspo2 with point mutations in Fu2 domain (F105A/F109A) (SEQ ID NO:8; encoding DNA provided in SEQ ID NO:7), abolishing its binding to LGR proteins; and (3) one antibody binding to the human liver/hepatocyte-specific surface receptor ASGR1 fused to the same Rspo2 mutant construct (SEQ ID NO:10; encoding DNA provided in SEQ ID NO:9). FIG. 5B shows a quantitative-PCR analysis of ASGR1/2 and ZNRF3/RNF43 expression in the human liver carcinoma Huh-7 cells and the human epidermoid carcinoma A431 cells, representing liver and non-liver cells, respectively. The top graph shows the relevant expression level compared to GAPDH control in the same cell line. The bottom graph shows a comparison with the relative levels in Huh-7 set as 1. FIG. 5C shows the results of a reporter assay monitoring Wnt enhancing activity in Huh-7 cells. The graph shows the results of a Super Top Flash (STF) reporter assay monitoring Wnt signaling activity. The cells contained a luciferase gene controlled by a Wnt-responsive promoter. The cells were transiently transfected by plasmids expressing the designed fusion proteins as specified. Wnt3a-conditioned media was added to comprise 10% of the total media volume three hours after transfection. Forty hours post-transfection, the cells were assayed for luciferase activity. The luciferase activity was normalized to mock transfection (no DNA). The bottom of the figure shows a Western blot of the fusion proteins. All fusion proteins contained a signal peptide at the N-terminus for secretion (that was cleaved off in the process of protein maturation) and a FLAG tag at the C-terminus for detection. The antibodies were in the form of single-chain variable fragments (scFv). 10 µl of the culture supernatant was analyzed by Western blot using the anti-FLAG monoclonal antibody, M2, using culture supernatant harvested just prior to the luciferase assay.

FIG. 5D shows the results of a reporter assay monitoring Wnt enhancing activity in A431 cells. The experimental setup is the same as described in FIG. 5C, except for that the cells were co-transfected with vectors expressing either human TFR2 or human ASGR1.

FIGS. 6A-6C provides graphs showing the effect of additional combinations of Rspo2 mutations on basal and targeted activity. FIG. 6A focuses on several indicated residues within the Fu1 domain critical for the Rspo2 interaction with the E3 ligases, and show the effects of these mutations in combination with the F105A/F109A double mutation. FIG. 6B shows the effects of alleviating the double mutation in the LGR-binding Fu2 domain into the indicated single point mutations. FIG. 6C provides an example of an additional mutation in the phenylamine 105 (F105R) residue of Fu2 domain, as an alternative to the F105A/F109A double mutation, as a method to reduce the interaction with LGR proteins. As shown in FIGS. 6A-6C, F105R mutation, together with F109A mutation, may reduce the basal level, without significantly compromising the targeted activity. In FIG. 6C, the targeting domain is anti-human TFR1, which is further described in FIGS. 7A and 7B. Huh-7 cells were transfected with specified constructs and assayed as described in the description of FIGS. 5A-5D.

FIGS. 7A-B provides another example by targeting a second receptor, human TFR1. FIG. 7A shows a reporter assay based on transient transfection of Huh-7 cells. FIG. 7B shows the same assay in A431 cells. The Western blots are images from the same membrane detecting the FLAG tag of the fusion proteins. More procedural details can be found in the description of FIGS. 5A-5D.

FIG. 8A shows Coomassie-stained gel images of proteins composed of specified targeting domain and the mutant Rspo2 as the action domain. Left is protein standard in kD. FIG. 8B compares the STF activity, in Huh-7 cells, of the ASGR1-targeting Rspo2 (F105A/F109A) or (F109) mutant fusion proteins with a negative control (the anti-GFP construct; left) and a positive control (Rspo2, right), which corresponds to human Rspo2 Fu1 and Fu2 domains (S36-E143), with a His-tag at the C-terminus. FIG. 8C provides a comparison of three targeted proteins and the Rspo2 positive control on three different cell lines: human liver carcinoma Huh-7, human colorectal adenocarcinoma HT29, and mouse normal liver FL83B. The ASGR1 antibody may cross-react with mouse ASGR1 while the TFR1 antibody is human-specific. All three cell lines have the reporter gene integrated, and were treated by the proteins at specified concentration for ~18 hours at the presence of 10% Wnt3a conditioned media. For each dosage tested, data from Huh-7 cells are on the left, data from HT29 cells are in the middle, and data from FL83B cells are on the right.

FIGS. 14A-14E show results obtained using illustrative scaffolds of appended IgG. Mutant Rspo2 was covalently attached to the N-terminus of heavy chain (N-HC), N-terminus of light chain (N-LC), or C-terminus of light chain (C-LC), as sketched on the right of FIG. 14A. Two types of IgGs were analyzed: IgG2 (wild-type, FIGS. 14A-C) or IgG1 (with a N297G "effector-less" mutation, FIGS. 14D-E). Targeting antibodies were anti-human ASGR1 and TFR1, and the control antibody was anti-GFP. The STF activities of purified proteins were tested in Huh-7 (hASGR1+/hTFR1+; FIG. 14A and FIG. 14D), 293 (hASGR1-/hTFR1+; FIG. 14B and FIG. 14E), and FL83B (mouse cell line, hASGR1-/hTFR1-; FIG. 14C) cell lines at the presence of 30% Wnt3a conditioned media. Rspo2 was used as the positive control. Negative control was a treatment by 30% Wnt3a conditioned media only ("Wnt only").

FIGS. 15A-15C provide results from a comparison of all four human R-spondins, showing the targeted Wnt signal-enhancing activity in selected cell lines. FIG. 15A compares the Wnt signal enhancing activity of the Fu1-Fu2 domains of wild-type human Rspo 1-4 fused to anti-GFP (in scFv format) in human Huh-7 (left) or HEK293T (right) cells. FIG. 15B demonstrates the enhancement of (targeted) activity of human Rspo2 mutants (F105A/F109A, "AA", or F105R/F109A, "RA") when fused to anti-ASGR1 or anti-TFR1, in Huh-7 (hASGR1+/hTFR1+) or HEK293T (hASGR1-/hTFR1+) cells, with fusions to anti-GFP as controls for the basal, untargeted activity. FIG. 15C demonstrates the enhancement of (targeted) activity of human Rspo3 mutants when fused to anti-ASGR1 or anti-TFR1, in Huh-7 or HEK293T cells, in contrast to the anti-GFP fusion controls. 30% Wnt3a conditioned media was supplied in the STF assay. Rspo2 was used as positive control. Negative control was a treatment by 30% Wnt3a conditioned media only ("Wnt only").

FIGS. 16A-16C provide non-limiting examples of Rspo3 mutations that can be used to construct tissue-specific Wnt signaling enhancers. FIG. 16A lists the mutations tested. These mutant Rspo3 (Fu1-Fu2) domains were fused to the anti-ASGR1 or anti-GFP scFv, and the activity of purified proteins were tested in Huh-7 cells by STF assay at the presence of 30% Wnt3a conditioned media. The results were summarized in FIG. 16B (for the anti-GFP controls) and FIG. 16C (for the anti-ASGR1 targeted constructs). Rspo2 and wild-type Rspo3 (Fu1-Fu2 domain) fused to anti-GFP were used as positive controls in the assay.

FIGS. 17A and 17B demonstrate examples of Wnt signal enhancing molecule design where the action domain is composed of an E3 ligase binder that is structurally independent of the Rspo scaffold. FIG. 17A illustrates the structures of the functional molecules tested, which are composed of a Fab against human ZNRF3 covalently attached to the N-terminus of heavy chains of IgG2 against human ASGR1 or TFR1 (or anti-GFP as the negative control). FIG. 17B shows the STF results using human liver Huh-7 cells. The assay was performed at the presence of 30% Wnt conditioned media and Rspo2 was used as a positive reference.

FIG. 18A shows a Q-PCR analysis of LYPD3, DSG3, ZNRF3 and RNF43 gene expression in three different cell lines. CAL27 and SCC25 are squamous cell carcinoma cell lines originally from human tongue and A431 is the epidermoid carcinoma cell line from human skin. The top graph shows the relative expression level of each gene compared to ACTB gene control and bottom graph shows a comparison with the relative levels of each gene in CAL27 set as 1. FIG. 18B shows the results of a STF reporter assay monitoring the Wnt signal enhancing activity in CAL27, SCC25 and A431 cells of the specified proteins after treatment for 1618 hours at the presence of 30% Wnt3a condition media. The proteins were constructed by fusing Rspo2 (F105R/F109A) mutant to the N-terminus of heavy chain of monoclonal antibodies against human LYPD3, human DSG3, and GFP. Rspo2 was used as a reference.

FIG. 19A shows the experimental scheme. 8-week old mice were first injected with AAV vector containing hASGR1 coding sequence to introduce ectopic expression of hASGR1 in livers. Seven days later, the mice were treated with test and control proteins in groups of eight. Eight hours later mice were euthanized and liver samples were taken for quantitative-PCR analysis of gene expression. FIG. 19B shows the expression levels of ectopic hASGR1 in mice livers. The doses of treatments were: anti-GFP (at 1 mg/kg), Rspo2 (at 0.46 mg/kg), anti-GFP-Rspo2(F105R/F109A) (at 1 mg/kg), or anti-ASGR1-Rspo2(F105R/F109A) (at 1 mg/kg), respectively, either alone (left four groups) or in combination with a Wnt agonist protein (18R5-Dkk1c, Janda et al., 2017 Nature) at 3 mg/kg (right 4 groups). FIG. 19C shows the induction of the Wnt signaling target gene Axing in response to the treatment.

DETAILED DESCRIPTION OF THE INVENTION

Figure 1:
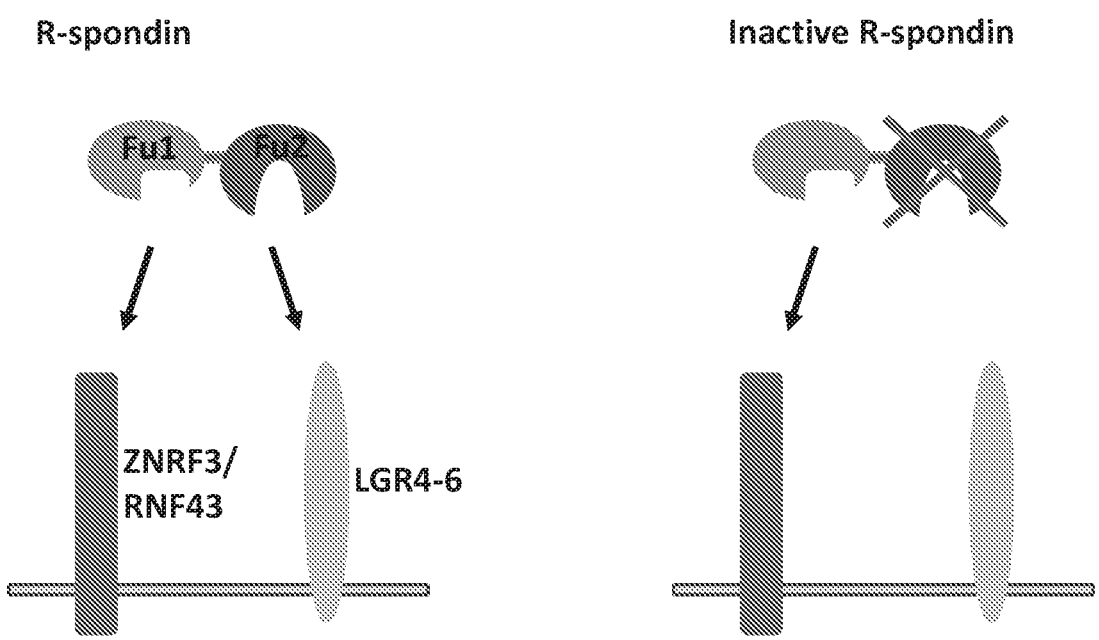
FIG. 1 provides diagrams depicting the binding of R-spondin to ZNRF3/RNF43 and LGR4-6. The left diagram shows wild-type R-spondin binding both ZNRF3/RNF43 and LGR4-6, and the right diagram shows an inactive R-spondin mutant lacking a Furin domain 2 (or with Furin domain 2 mutated) capable of binding to ZNRF3/RNF43 but incapable of or compromised for binding to LGR4-6.

The present disclosure provides tissue-specific Wnt signal enhancing molecules, where in certain embodiments, the molecules: 1) selectively bind to a tissue- or cell-specific cell surface receptor; 2) mediate internalization or sequestration of ZNRF3/RNF43 in the targeted tissue or cell type; and 3) enhance Wnt signaling in a tissue-specific manner. In certain embodiments, the molecules are fusion proteins. In certain embodiments, the molecules are antibodies having an additional appended binding domain. Also provided are pharmaceutical compositions and methods for the use of any of the compositions disclosed herein for enhancing, i.e., increasing, Wnt signaling in a targeted tissue or cell type, e.g., for the treatment or prophylaxis of a disease or disorder. These and other objects, advantages, and features of the invention will become apparent to those persons skilled in the art upon reading the details of the compositions and methods as more fully described below.

Definitions

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors, liposomes, and other gene delivery vehicles.

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif, USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970)

Of interest is the BestFit program using the local homology algorithm of Smith and Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters: Mismatch Penalty: 1.00; Gap Penalty: 1.00; Gap Size Penalty: 0.33; and Joining Penalty: 30.0.

"Recombinant," as applied to a polynucleotide means that the polynucleotide is the product of various combinations of cloning, restriction or ligation steps, and other procedures that result in a construct that is distinct from a polynucleotide found in nature.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a gene product of interest, and is used for effecting the expression of the gene product in an intended target cell. An expression vector also comprises control elements operatively linked to the encoding region to facilitate expression of the gene product in the target. The combination of control elements and a gene or genes to which they are operably linked for expression is sometimes referred to as an "expression cassette," a large number of which are known and available in the art or can be readily constructed from components that are available in the art.

As used herein, the terms "polypeptide," "peptide," and "protein" refer to polymers of amino acids of any length. The terms also encompass an amino acid polymer that has been modified; for example, to include disulfide bond formation, glycosylation, lipidation, phosphorylation, or conjugation with a labeling component.

As used herein, the term "antibody" means an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Thus, it is used in the broadest sense and specifically covers monoclonal antibodies (including full-length monoclonal antibodies), polyclonal antibodies, human antibodies, humanized antibodies, chimeric antibodies, nanobodies, diabodies, multispecific antibodies (e.g., bispecific antibodies), and antibody fragments including but not limited to scFv, Fab, and $Fab_2$, so long as they exhibit the desired biological activity.

"Antibody fragments" comprise a portion of an intact antibody, for example, the antigen-binding or variable region of the intact antibody. Examples of antibody fragments include Fab, Fab', $F(ab')_2$, and Fv fragments; diabodies; linear antibodies (e.g., Zapata et al., Protein Eng. 8(10): 1057-1062 (1995)); single-chain antibody molecules (e.g., scFv); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

By "comprising," it is meant that the recited elements are required in, for example, the composition, method, kit, etc., but other elements may be included to form the, for example, composition, method, kit etc. within the scope of the claim. For example, an expression cassette "comprising" a gene encoding a therapeutic polypeptide operably linked to a promoter is an expression cassette that may include other elements in addition to the gene and promoter, e.g. polyadenylation sequence, enhancer elements, other genes, linker domains, etc.

By "consisting essentially of," it is meant a limitation of the scope of the, for example, composition, method, kit, etc., described to the specified materials or steps that do not materially affect the basic and novel characteristic(s) of the, for example, composition, method, kit, etc. For example, an expression cassette "consisting essentially of" a gene encoding a therapeutic polypeptide operably linked to a promoter and a polyadenylation sequence may include additional sequences, e.g. linker sequences, so long as they do not materially affect the transcription or translation of the gene. As another example, a variant, or mutant, polypeptide fragment "consisting essentially of" a recited sequence has the amino acid sequence of the recited sequence plus or minus about 10 amino acid residues at the boundaries of the sequence based upon the full length naïve polypeptide from which it was derived, e.g. 10, 9, 8, 7, 6, 5, 4, 3, 2 or 1 residue less than the recited bounding amino acid residue, or 1, 2, 3, 4, 5, 6, 7, 8, 9, or 10 residues more than the recited bounding amino acid residue.

By "consisting of" it is meant the exclusion from the composition, method, or kit of any element, step, or ingredient not specified in the claim. For example, a polypeptide or polypeptide domain "consisting of" a recited sequence contains only the recited sequence.

An "expression vector" as used herein encompasses a vector, e.g. plasmid, minicircle, viral vector, liposome, and the like as discussed herein or as known in the art, comprising a polynucleotide which encodes a gene product of interest, and is used for effecting the expression of a gene product in an intended target cell. An expression vector also comprises control elements operatively linked to the encoding region to facilitate expression of the gene product in the target. The combination of control elements, e.g. promoters, enhancers, UTRs, miRNA targeting sequences, etc., and a gene or genes to which they are operably linked for expression is sometimes referred to as an "expression cassette." Many such control elements are known and available in the art or can be readily constructed from components that are available in the art.

A "promoter" as used herein encompasses a DNA sequence that directs the binding of RNA polymerase and thereby promotes RNA synthesis, i.e., a minimal sequence sufficient to direct transcription. Promoters and corresponding protein or polypeptide expression may be ubiquitous, meaning strongly active in a wide range of cells, tissues and species or cell-type specific, tissue-specific, or species specific. Promoters may be "constitutive," meaning continually active, or "inducible," meaning the promoter can be activated or deactivated by the presence or absence of biotic or abiotic factors. Also included in the nucleic acid constructs or vectors of the invention are enhancer sequences that may or may not be contiguous with the promoter sequence. Enhancer sequences influence promoter-dependent gene expression and may be located in the 5' or 3' regions of the native gene.

The term "native" or "wild-type" as used herein refers to a nucleotide sequence, e.g. gene, or gene product, e.g. RNA or protein, that is present in a wild-type cell, tissue, organ or organism. The term "variant" as used herein refers to a mutant of a reference polynucleotide or polypeptide sequence, for example a native polynucleotide or polypeptide sequence, i.e. having less than 100% sequence identity with the reference polynucleotide or polypeptide sequence. Put another way, a variant comprises at least one amino acid difference (e.g., amino acid substitution, amino acid insertion, amino acid deletion) relative to a reference polynucleotide sequence, e.g. a native polynucleotide or polypeptide sequence. For example, a variant may be a polynucleotide having a sequence identity of 50% or more, 60% or more, or 70% or more with a full length native polynucleotide sequence, e.g. an identity of 75% or 80% or more, such as 85%, 90%, or 95% or more, for example, 98% or 99% identity with the full length native polynucleotide sequence. As another example, a variant may be a polypeptide having a sequence identity of 70% or more with a full length native polypeptide sequence, e.g. an identity of 75% or 80% or more, such as 85%, 90%, or 95% or more, for example, 98% or 99% identity with the full length native polypeptide sequence. Variants may also include variant fragments of a reference, e.g. native, sequence sharing a sequence identity of 70% or more with a fragment of the reference, e.g. native, sequence, e.g. an identity of 75% or 80% or more, such as 85%, 90%, or 95% or more, for example, 98% or 99% identity with the native sequence.

As used herein, the terms "biological activity" and "biologically active" refer to the activity attributed to a particular biological element in a cell. For example, the "biological activity" of an R-spondin, or fragment or variant thereof refers to the ability to enhance Wnt signals. As another example, the biological activity of a polypeptide or functional fragment or variant thereof refers to the ability of the polypeptide or functional fragment or variant thereof to carry out its native functions of, e.g., binding, enzymatic activity, etc. As a third example, the biological activity of a gene regulatory element, e.g. promoter, enhancer, Kozak sequence, and the like, refers to the ability of the regulatory element or functional fragment or variant thereof to regulate, i.e. promote, enhance, or activate the translation of, respectively, the expression of the gene to which it is operably linked.

The terms "administering" or "introducing" or "providing", as used herein, refer to delivery of a composition to a cell, to cells, tissues and/or organs of a subject, or to a subject. Such administering or introducing may take place in vivo, in vitro or ex vivo.

The terms "treatment", "treating" and the like are used herein to generally mean obtaining a desired pharmacologic and/or physiologic effect. The effect may be prophylactic in terms of completely or partially preventing a disease or symptom thereof, e.g. reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The various compositions and methods of the invention are described below. Although particular compositions and methods are exemplified herein, it is understood that any of a number of alternative compositions and methods are applicable and suitable for use in practicing the invention. It will also be understood that an evaluation of the expression constructs and methods of the invention may be carried out using procedures standard in the art.

The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

All publications mentioned herein are incorporated herein by reference to disclose and describe the methods and/or materials in connection with which the publications are cited. It is understood that the present disclosure supersedes any disclosure of an incorporated publication to the extent there is a contradiction.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless otherwise indicated, all terms used herein have the same meaning as they would to one skilled in the art and the practice of the present invention will employ, conventional techniques of microbiology and recombinant DNA technology, which are within the knowledge of those of skill of the art.

Tissue-Specific Wnt Signal Enhancing Molecules

In certain aspects, the present disclosure provides novel tissue-specific Wnt signal enhancing molecules capable of enhancing Wnt activity in a tissue- or cell-specific manner. In certain embodiments, the tissue-specific Wnt signal enhancing molecules are bi-functional molecules comprising a first domain that binds to one or more ZNRF3 and/or RNF43 ligases, and a second domain that binds to one or more targeted tissue or cell type in a tissue- or cell-specific manner. Each of the first domain and the second domain may be any moiety capable of binding to the ligase complex or targeted tissue or cell, respectively. For example, each of the first domain and the second domain may be, but are not limited to, a moiety selected from: a polypeptide (e.g., an antibody or antigen-binding fragment thereof or a peptide or polypeptide different from an antibody), a small molecule, and a natural ligand or a variant, fragment or derivative thereof. In certain embodiments, the natural ligand is a polypeptide, a small molecule, an ion, an amino acid, a lipid, or a sugar molecule. The first domain and the second domain may be the same type of moiety as each other, or they may be different types of moieties. In certain embodiments, the tissue-specific Wnt signal enhancing molecules bind to a tissue- or cell-specific cell surface receptor. In particular embodiments, the tissue-specific Wnt signal enhancing molecules increase or enhance Wnt signaling by at least 50%, at least two-fold, at least three-fold, at least five-fold, at least ten-fold, at least twenty-fold, at least thirty-fold, at least forty-fold, or at least fifty-fold, e.g., as compared to a negative control.

In particular embodiments, the tissue-specific Wnt signal enhancing molecules are fusion proteins comprising a first polypeptide sequence that binds to ZNRF3/RNF43 and a second polypeptide sequence that binds to one or more targeted tissue or cell type in a tissue- or cell-specific manner. In certain embodiments, the tissue-specific Wnt signal enhancing molecules comprise two or more polypeptides, such as dimers or multimers comprising two or more fusion proteins, each comprising the first domain and the second domain, wherein the two or more polypeptides are linked, e.g., through a linker moiety or via a bond between amino acid residues in each of the two or more polypepitdes, e.g., an intermolecular disulfide bond between cysteine residues. In particular embodiments, a tissue-specific Wnt signal enhancing molecule is an antibody comprising antibody heavy and light chains (or antigen-binding fragments thereof) that constitute either the first domain or the second domain, wherein the other domain (i.e., the second domain or first domain) is linked to the antibody heavy chain or light chain, either as a fusion protein or via a linker moiety. In particular embodiments, the other domain is linked to the N-terminus of the heavy chain, the C-terminus of the heavy chain, the N-terminus of the light chain, or the C-terminus of the light chain. Such structures may be referred to herein as appended IgG scaffolds or formats. For example, a tissue-specific Wnt signal enhancing molecule can be an antibody that binds ZNRF3/RNF43, wherein a binding domain that binds a tissue- or cell-specific receptor is fused or appended to either the heavy chain or light chain of the antibody that binds ZNRF3/RNF43. In another example, a tissue-specific Wnt signal enhancing molecule can be an antibody that binds a tissue- or cell-specific receptor, wherein a binding domain that binds ZNRF3/RNF43 is fused or appended to either the heavy chain or light chain of the antibody that binds the tissue- or cell-specific receptor.

In certain embodiments, the tissue-specific Wnt signal enhancing molecules comprise a first domain ("action domain") that binds ZNRF3/RNF43 and a second domain ("targeting domain") that binds a tissue- or cell-specific receptor, e.g., with high affinity. In certain embodiments, each of these two domains has substantially reduced activity or is inactive in enhancing Wnt signals by itself. However, when the tissue-specific Wnt signal enhancing molecules engage with target tissues that express the tissue-specific receptor, E3 ligases ZNRF3/RNF43 are recruited to a ternary complex with the tissue-specific receptors, leading them to be sequestered, and/or cleared from the cell surface via receptor-mediated endocytosis. The net result is to enhance Wnt signals in a tissue-specific manner.

In certain embodiments, the action domain is a binder to ZNRF3/RNF43 E3 ligases, and it can be designed based on R-spondins, e.g., R-spondins-1-4, including but not limited to human R-spondins-1-4. In certain embodiments, the action domain is an R-spondin, e.g., a wild-type R-spondin-1-4, optionally a human R-spondin-1-4, or a variant or fragment thereof. In particular embodiments, it is a variant of any of R-spondins-1-4 having at least 80%, at least 85%, at least 90%, at least 95%, at least 98%, or at least 99% sequence identity to the corresponding wild-type R-spondin-1-4 sequence. In certain embodiments, the action domain comprises or consists of a Furin domain 1 of an R-spondin, e.g., any of R-spondons 1-4, which bind ZNRF3/RNF43. Extended versions of Furin domain 1 (including, but not limited to, those with a mutated Furin domain 2 that no longer binds to LGR4-6 or has reduced binding to LGR4-6) or engineered antibodies or any other derivatives or any engineered polypeptides different from antibodies that are able to bind specifically to ZNRF3/RNF43 can also be used. In certain embodiments, the action domain comprises one or more Furin domain 1 of an R-spondin. In certain embodiments, it does not comprise a Furin domain 2 of an R-spondin, or it comprises a modified or variant Furin domain 2 of an R-spondin, e.g., a Furin domain 2 with reduced activity as compared to the wild-type Furin domain 2. In certain embodiments, an action domain comprises a Furin domain 1 but not a Furin domain 2 of R-spondin. In certain embodiments, an action domain comprises two or more Furin domain 1 or multimers of a Furin domain 1. The action doman may comprise one or more wild-type Furin domain 1 of an R-spondin. In particular embodiments, the action domain comprises a modified or variant Furin domain 1 of an R-spondin that has increased activity, e.g., binding to ZNRF3/RNF43, as compared to the wild-type Furin domain 1. Variants having increased binding to ZNRF3/RNF43 may be identified, e.g., by screening a phage or yeast display library comprising variants of an R-spondin Furin domain 1. Peptides or polypeptides unrelated to R-spondin Furin domain 1 but with increased binding to ZNRF3/RNF43 may also be identified through screening. Action domains may further comprise additional moieties or polypeptide sequences, e.g., additional amino acid residues to stabilize the structure of the action domain or tissue-specific Wnt signal enhancing molecule in which it is present.

In certain embodiments, the targeting domain specifically binds to a cell-specific surface molecule, e.g., a cell-specific surface receptor, and can be, e.g., natural ligands, antibodies, or synthetic chemicals. In particular embodiments, the cell-specific surface molecule is preferentially expressed on a target organ, tissue or cell type, e.g., an organ, tissue or cell type in which it is desirous to enhance Wnt signaling, e.g., to treat or prevent a disease or disorder. In particular embodiments, the cell-specific surface molecule has increased or enhanced expression on a target organ, tissue or cell type, e.g., an organ, tissue or cell type in which it is desirous to enhance Wnt signaling, e.g., to treat or prevent a disease or disorder, e.g., as compared to one or more other non-targeted organs, tissues or cell types. In certain embodiments, the cell-specific surface molecule is preferentially expressed on the surface of the target organ, tissue or cell type as compared to one or more other organ, tissue or cell types, respectively. For example, in particular embodiments, a cell surface receptor is considered to be a tissue-specific or cell-specific cell surface molecule if it is expressed at levels at least two-fold, at least five-fold, at least 10-fold, at least 20-fold, at least 30-fold, at least 40-fold, at least 50-fold, at least 100-fold, at least 500-fold, or at least 1000-fold higher in the target organ, tissue or cell than it is expressed in one or more, five or more, all other organs, tissues or cells, or an average of all other organs, tissue or cells, respectively. In certain embodiments, the tissue-specific or cell-specific cell surface molecule is a cell surface receptor, e.g., a polypeptide receptor comprising a region located within the cell surface membrane and an extracellular region to which the targeting domain can bind. In various embodiments, the methods described herein may be practiced by specifically targeting cell surface molecules that are only expressed on the target tissue or a subset of tissues including the target tissue, or by specifically targeting cell surface molecules that have higher levels of expression on the target tissue as compared to all, most, or a substantial number of other tissues, e.g., higher expression on the target tissue than on at least two, at least five, at least ten, or at least twenty other tissues.

Tissue-specific and cell-specific cell surface receptors are known in the art. Examples of tissue- and cell-specific surface receptors include but are not limited to, ASGR1 (for liver specificity), ASGR2 (for liver specificity), TFR2 (for liver specificity), SLC10A1 (for liver specificity), PTH1R (for bone and kidney specificity), LYPD3 (for oral mucous specificity), DSG3 (for oral mucous specificity) etc. (see FIG. 2). Additional receptors for liver delivery are described, e.g., by Yan et al., Tumor Biology, 2015; 36:55-67.

An action domain or targeting domain, e.g., an antibody or antigen-binding fragment thereof, that "specifically binds to" or is "specific for" a particular cell surface polypeptide or receptor is one that binds to that particular polypeptide or receptor without substantially binding to any other polypeptide or polypeptide epitope. In some embodiments, the action domains and targeting domains of the present disclosure specifically bind to ZNRF3/RNF43 or a tissue-specific cell surface molecule (e.g., receptor), respectively, with dissociation constants ($K_d$) equal to or lower than 1000 nM, equal to or lower than 100 nM, equal to or lower than 10 nM, equal to or lower than 1 nM, equal to or lower than 0.5 nM, equal to or lower than 0.1 nM, equal to or lower than 0.01 nM, equal to or lower than 0.005 nM, equal to or lower than 0.001 nM, or equal to or lower than 0.0005 nM, when measured at a temperature of about 4° C., 25° C., 37° C. or 42° C. Affinities of binders, e.g., antibodies, can be readily determined using conventional techniques, for example, those described by Scatchard et al. (Ann. N. Y. Acad. Sci. USA 51:660 (1949), ELISA assays, biolayer interferometry (BLI) assays, and surface plasmon resonance (SPR) assays). Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

In certain embodiments, the action domain and/or the targeting domain of the tissue-specific Wnt signal enhancing molecule are polypeptides, whereas in other embodiments, the action domain and/or the targeting domain of the tissue-specific Wnt signaling molecule are small organic molecules. In certain embodiments, the action domain and the targeting domain of a tissue-specific Wnt signal enhancing molecule are covalently bound to each other. In certain embodiments, the action domain and the targeting domain of a tissue-specific Wnt signal enhancing fusion molecule are non-covalently bound to each other. In certain embodiments, the action domain and the targeting domain of a tissue-specific Wnt signal enhancing molecule are present within the same fusion protein. In other embodiments, the action domain is present within a first polypeptide further comprising a first binding domain, and the targeting domain is present within a second polypeptide further comprising a second binding domain, wherein the first and second binding domain bind to each other. In some embodiments, the first and second binding domain are the same or variants thereof, such as, e.g., an Fc polypeptide. In some embodiments, the first and second binding domain are different from each other. In particular embodiments, the present invention includes the use of fragments or variants of any of the targeting domains or action domains described herein, including functional fragments or variants of the reference molecule.

In certain embodiments, a tissue-specific Wnt signal enhancing molecule (e.g., a fusion protein) has a formula selected from: $R_1$-L-$R_2$, and $R_2$-L-$R_1$, wherein $R_1$ is an action domain that binds ZNRF3/RNF43, $R_2$ is a targeting domain that binds a tissue-specific cell surface receptor, and L is a linker, and wherein L may be absent or present. Each of $R_1$ and $R_2$ may be any of the various action domains and targeting domains described herein, respectively. Each of $R_1$ and $R_2$ may be any moiety capable of binding to one or more of the E3 ligases (ZNRF3 or RNF43), or targeted tissue or cell, respectively. For example, each of $R_1$ and $R_2$ may be, but are not limited to, a moiety selected from: a polypeptide (e.g., an antibody or antigen-binding fragment thereof or a peptide or polypeptide different from an antibody), a small molecule, and a natural ligand or a variant, fragment or derivative thereof. In certain embodiments, the natural ligand is a polypeptide, a small molecule, an ion, an amino acid, a lipid, or a sugar molecule. The action domain and the targeting domain (i.e., $R_1$ and $R_2$) may be the same type of moiety as each other, or they may be different types of moieties. In particular embodiments, $R_2$ is an antibody of antigen-binding fragment thereof, and in certain embodiments, $R_2$ comprises an Fc protein or analog thereof.

In certain embodiments, a tissue-specific Wnt signal enhancing molecule comprises a single molecule (e.g., polypeptide), whereas in other embodiments, a Wnt signal enhancing fusion molecule comprises two or more molecules (e.g., polypeptides) bound to each other, e.g., non-covalently bound to each other. For example, in one embodiment, a tissue specific Wnt signal enhancing fusion comprises two molecules having formulas $R_3$-$L_1$ and $R_4$-$L_2$, respectively, wherein $R_3$ is an action domain, $R_4$ is a targeting domain, and wherein the $L_1$ and $L_2$ groups bind to each other, e.g., to form a dimer. In various embodiments, the $L_1$ and $L_2$ groups are the same as each other or different from one another. One example of an $L_1$ or $L_2$ group is an Fc sequence, e.g., murine Fc2b or human Fc1, each of which is known in the art. Each of $R_3$ and $R_4$ may be any of the various action domains and targeting domains described herein, respectively. Each of $R_3$ and $R_4$ may be any moiety capable of binding to one or more of the E3 ligases (ZNRF3 and/or RNF43), or targeted tissue or cell, respectively. In particular embodiments, a tissue-specific Wnt signal enhancing molecule comprises an antibody or binding fragments thereof that binds one or more of the E3 ligases (ZNRF3 and/or RNF43), wherein the antibody heavy chain and/or the antibody light chain comprises an appended binding domain that binds a targeted tissue or cell. In particular embodiments, a tissue-specific Wnt signal enhancing molecule comprises an antibody or binding fragments thereof that binds a targeted tissue or cell, wherein the antibody heavy chain and/or the antibody light chain comprises an appended binding domain that binds one or more of the E3 ligases (ZNRF3 and/or RNF43). The appended binding domain may be directly fused to the N-terminus or C-terminus of the antibody, e.g., as a heavy chain or light chain fusion protein, or it may be appended to the heavy chain or light chain via a linker moiety, e.g., to the N-terminus, C-terminus, or an internal amino acid of the heavy chain or light chain. In certain embodiments, the antibody is an IgG.

In certain embodiments, the tissue-specific Wnt signal enhancing molecules (e.g., fusion proteins) increase Wnt signaling in a target tissue or cell type contacted with the fusion protein. In particular embodiments, Wnt signaling in the target tissue or cell type is increased by at least 50%, at least two-fold, at least three-fold, at least four-fold, at least five-fold, or at least ten-fold.

Tissue-specific Wnt signal enhancing molecules may be produced by standard methods of organic synthesis and molecular biology known and available in the art. For example, a tissue-specific Wnt signal enhancing fusion protein may be generated by fusing a targeting domain (e.g., an antibody that bind ASGR1) to an action domain (e.g., human R-spondin 2 Furin domain 1 alone, corresponding to amino acid residues N37-R95, or human R-spondin 2 Furin domain 1 followed by a Furin domain 2, in which the Furin domain 2 interaction with the LGR proteins is abolished or compromised by point mutations, e.g., F105A and F109A, singly or in combination). In certain embodiments, the targeting domain and action domain are fused by a linker, e.g., a glycine-serine linker, with either domain located at the N-terminus of the tissue-specific Wnt signal enhancing molecule. In certain embodiments, the targeting domain and action domain are fused by a protein linker (e.g., albumin). Additional ways of "fusing" the targeting domain with the action domain include, but are not limited to, "knob-in-hole" or leucine zipper mediated dimerization, for example. DNA sequences encoding the targeting domain, the action domain (and, optionally, a linker) may be genetically engineered to encode the desired fusion protein.

For tissue-specific Wnt signal enhancing fusion molecules, including antibody heavy and light chains, the DNA sequences encoding different parts of the fusion proteins may be inserted into bacterial or eukaryotic expression vectors using standard molecular cloning techniques, and expressed in appropriate host cells. The expressed fusion proteins may be purified to homogeneity using standard techniques in protein science such as affinity, ion-exchange, and size-exclusion chromatography. The present disclosure also includes functional fragments and variants of any of the polypeptide action domains, targeting domains, and fusion proteins described herein, including variants having at least 50%, at least 60%, at least 70%, at least 80%, at least 85%, at least 90%, at least 95%, at least 98% or at least 99% polypeptide sequence identity to an action domain, targeting domain, or fusion protein described herein. Such variants may comprise one or more amino acid modifications as compared to any of the sequences disclosed herein, e.g., one or more amino acid deletion, insertion or substitution. In particular embodiments, functional fragments and variants of tissue-specific Wnt signal enhancing fusion proteins have at least 5%, at least 10%, at least 20%, at least 30%, at least 40%, at least 50%, at least 60%, at least 70%, at least 80% at least 90% at least 100% or more Wnt signal enhancing activity as compared to the tissue-specific Wnt signal enhancing fusion protein from which they were derived. In certain embodiments, functional fragments and variants of polypeptide action domains have at least 5%, at least 10%, at least 20%, at least 30%, at least 40%, at least 50%, at least 60%, at least 70%, at least 80% at least 90% at least 100% or more Wnt signal enhancing activity as compared to the action domain from which they were derived (when measured in the context of the entire tissue-specific Wnt signal enhancing molecule). In certain embodiments, functional fragments and variants of targeting domains have at least 5%, at least 10%, at least 20%, at least 30%, at least 40%, at least 50%, at least 60%, at least 70%, at least 80% at least 90% at least 100% or more binding activity as compared to the targeting domain from which they were derived.

The present disclosure also includes polynucleotides or nucleic acid sequences that encode one or more tissue-specific Wnt signal enhancing molecules or components thereof, e.g., fusion proteins or variants thereof, described herein, and vectors comprising these polynucleotides, including expression vectors, and cells comprising these vectors. In certain embodiments, the polynucleotides or nucleic acid sequences are DNA or RNA. In particular embodiments, the RNA is messenger RNA (mRNA). In certain embodiments, the RNA is a modified mRNA comprising one or more modified nucleosides. Modified mRNAs comprising one or more modified nucleoside have been described as having advantages over unmodified mRNAs, including increase stability, higher expression levels and reduced immunogenicity. Non-limiting examples of modified mRNAs that may be used according to the present invention are described, e.g., in PCT Patent Application Publication Nos. WO2011/130624, WO2012/138453, WO2013052523, WO2013151666, WO2013/071047, WO2013/078199, WO2012045075, WO2014081507, WO2014093924 WO2014164253, US Patent Nos: U.S. Pat. No. 8,278,036 (describing modified mRNAs comprising pseudouridine), U.S. Pat. No. 8,691,966 (describing modified mRNAs comprising pseudouridine and/or N1-methylpseudouridine), U.S. Pat. No. 8,835,108 (describing modified mRNAs comprising 5-methylcytidine, U.S. Pat. No. 8,748, 089 (describing modified mRNAs comprising pseudouridine or 1-methylpseudouridine). In particular embodiments, the modified mRNA sequence encoding the tissue-specific Wnt signal enhancing polypeptide comprises at least one modification as compared to an unmodified A, G, U or C ribonucleoside. In particular embodiments, the at least one modified nucleosides include N1-methylpseudouridine and/or 5-methylcytidine. In particular embodiments, the modified mRNA comprises a 5' terminal cap sequence followed by a sequence encoding the tissue-specific Wnt signal enhancing polypeptide, following by a 3' tailing sequence, such as a polyA or a polyA-G sequence.

In particular embodiments, the polynucleotide is a vector, e.g., an expression vector, and the expression vector comprises a polynucleotide sequence encoding a tissue-specific Wnt signal enhancing fusion molecule (e.g., a fusion protein or one or both chains of an appended antibody) described herein operably linked to a promoter sequence, e.g., a promoter sequence that drives expression of the polynucleotide in a cell. In certain embodiments, the vector is a viral vector, e.g., a virus comprising a polynucleotide comprising an expression cassette comprising a promoter operably linked to a DNA or RNA sequence encoding the tissue-specific Wnt signal enhancing polypeptide. In particular embodiments, the expression cassette comprises 5' and/or 3' cellular or viral UTRs or the derivatives thereof.

The present disclosure also includes functional fragments and variants of the polynucleotides described herein, including variants having at least 50%, at least 60%, at least 70%, at least 80%, at least 85%, at least 90%, at least 95%, at least 98% or at least 99% polynucleotide sequence identity to a polynucleotide described herein. Such variants may comprise one or more nucleotide or nucleoside modifications as compared to any of the sequences disclosed herein, e.g., one or more nucleotide deletion, insertion or substitution. In particular embodiments, the polynucleotides described herein are codon-optimized, e.g., to enhance expression of the encoded polypeptide in a host cell. In particular embodiments, polynucleotide variants comprise one or more modified nucleotide or nucleoside.

The present disclosure also includes cells comprising a polynucleotide or vector that encodes a tissue-specific Wnt signal enhancing molecule, e.g., fusion protein, described herein. In certain embodiments, the cell is a host cell, such as, e.g., an HEK293 cell that may be used to produce tissue-specific Wnt signal enhancing fusion proteins. In preparing the subject compositions, any host cells may be employed, including but not limited to, for example, mammalian cells (e.g. 293 cells), insect cells (e.g., SF9 cells), microorganisms and yeast. In certain embodiments, the cells are heterologous or autologous to a subject treated with a tissue-specific Wnt signal enhancing polypeptide described herein. In particular embodiments, the cells were obtained from the subject and transduced with a viral vector described herein. In particular embodiments, the transduced cells are delivered to the subject for treatment.

The present disclosure also includes pharmaceutical compositions comprising one or more tissue-specific Wnt signal enhancing molecules (e.g., fusion proteins), or one or more polynucleotides or vectors comprising sequences encoding a tissue-specific Wnt signal enhancing molecule.

Wnt signaling may be measured using techniques and assays known and available in the art. In certain embodiments, an increase in Wnt signaling is determined using a cell line corresponding to a target tissue or cell type. In particular embodiments, the cell line contains a reporter plasmid with a marker gene (e.g., a luciferase gene) under the control of a Wnt signal-responsive promoter. Enhanced reporter activity of the cells in response to Wnt3a, Wnt3a conditioned media, or recombinant sources of Wnt3a, by the addition of either Furin domain 1 alone (or together with Furin domain 2, with the F105A and/or F109A point mutations) as a negative control or functional R-spondin (full length or Furin domains 1 and 2) as a positive control may be determined. Reporter activity in response to the tissue-specific Wnt signal enhancing molecules may also be determined by contacting the reporter cell line with the tissue specific Wnt signal enhancing molecule. The negative control may be substantially, significantly, or completely negative for reporter activity, and the tissue-specific Wnt signal enhancing molecule and positive control should show an increase in Wnt signaling response as an increase in reporter activity. Additional controls may include an anti-ASGR1 antibody alone (negative), a fusion protein in which an anti-GFP antibody is used in place of an anti-ASGR1 antibody (negative), and intact Furin domain 1-Furin domain 2 protein (positive). Tissue specificity of the tissue-specific Wnt signal enhancing molecule may be determined by similarly measuring the reporter activity in response to treatment with the tissue-specific Wnt signal enhancing molecule in cell types or tissues other than those targeted. In certain embodiments, reporter activity is higher in the targeted tissue bound by the tissue-specific Wnt signal enhancing molecule as compared to non-targeted tissues, e.g., at least 50%, at least two-fold, at least three-fold, at least four-fold, at least five-fold, or at least ten-fold higher.

In particular embodiments, a tissue-specific Wnt signal enhancing polypeptide comprises any combination of action domain and targeting domain, including any combination of any of the action domains and targeting domains described herein. In particular embodiments, they are joined by a linker, e.g., albumin (e.g., human serum albumin), a peptidyl linker, or a non-peptidyl linker, where the targeting and action domains are on the N- and C-termini of the linker, e.g., Fc or albumin, peptidyl linker, or non-peptidyl linker.

The tissue-specific Wnt signal enhancing molecules can also be joined to a moiety such as a polyethylene glycol (PEG), Fc, albumin, etc. as known in the art to enhance stability in vivo.

Illustrative, non-limiting examples of tissue-specific Wnt signal enhancing molecules include the following:

a) a bone tissue specific Wnt signal enhancing polypeptide comprising an action domain comprising a variant or fragment of an R-spondin (e.g., human R-spondin 2) having reduced ability to enhance Wnt signaling and a targeting domain that specifically binds PTH1R, wherein the tissue specific Wnt signal enhancing polypeptide increases Wnt signaling in bone tissue and may be used to treat a disease or condition of bone tissue;

b) a liver tissue specific Wnt signal enhancing polypeptide comprising an action domain comprising a variant or fragment of an R-spondin (e.g., human R-spondin 2) having reduced ability to enhance Wnt signaling and a targeting domain that specifically binds ASGR1, ASGR2, TFR2, or SLC10A1, wherein the tissue specific Wnt signal enhancing polypeptide increases Wnt signaling in liver tissue and may be used to treat a disease or condition of liver tissue; or c) a oral mucosal tissue specific Wnt signal enhancing polypeptide comprising an action domain comprising a variant or fragment of an R-spondin (e.g., human R-spondin 2) having reduced ability to enhance Wnt signaling and a targeting domain that specifically binds LYPDS3 or DSG3, wherein the tissue specific Wnt signal enhancing polypeptide increases Wnt signaling in oral mucosal tissue and may be used to treat a disease or condition of oral muosal tissue Illustrative, non-limiting examples of tissue-specific Wnt signal enhancing molecules include those described in the accompany Examples and sequences, including but not limited to those described in Table 1. In particular embodiments, a tissue-specific Wnt signal enhancing molecule comprises two or more polypeptide sequences disclosed herein, e.g., in the appended IgG or antibody format. Polypeptides disclosed herein include but are not limited to polypeptides comprising or consisting of a sequence having at least 80%, at least 85%, at least 90%, at least 95%, at least 98%, or at least 99% identity to any of the sequences set forth in SEQ ID NOs:1-4, 6, 8, 10, 12, 14, 16, 18, 20, 22, 24, 26, 28, 30, 32, 34, 36, 38, 40, 4244, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, or 158, and fragments thereof. In certain embodiments, the polypeptides have activity as a functional domain and/or a targeting domain.

Illustrative, non-limiting examples of polynucleotides disclosed herein include any that encode for any of the polypeptides, variants and fragments described herein, including those described above. Polynucleotides disclosed herein include but are not limited to polynucleotides comprising or consisting of a sequence having at least 80%, at least 85%, at least 90%, at least 95%, at least 98%, or at least 99% identity to any of the sequences set forth in SEQ ID NOs:5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 15, 155, and 157, and fragments thereof. In certain embodiments, the polynucleotides encode polypeptides that have activity as a functional domain and/or a targeting domain.

Action Domains

R-spondins are capable of amplifying Wnt signals. The minimal functional unit of R-spondin is composed of two Furin domains, Furin domain 1 that binds to ZNRF3/RNF43 E3 ligases, and Furin domain 2 that binds to LGR4-6, bringing together a ternary complex of R-spondin, LGR, and the E3 ligases. This results in internalization of the whole complex and removal of ZNRF3/RNF43 away from their targets of destruction. Furin domain 1 alone is not functional, but it is capable of binding to both ZNRF3 and RNF43 (see FIG. 1).

Figure 2:
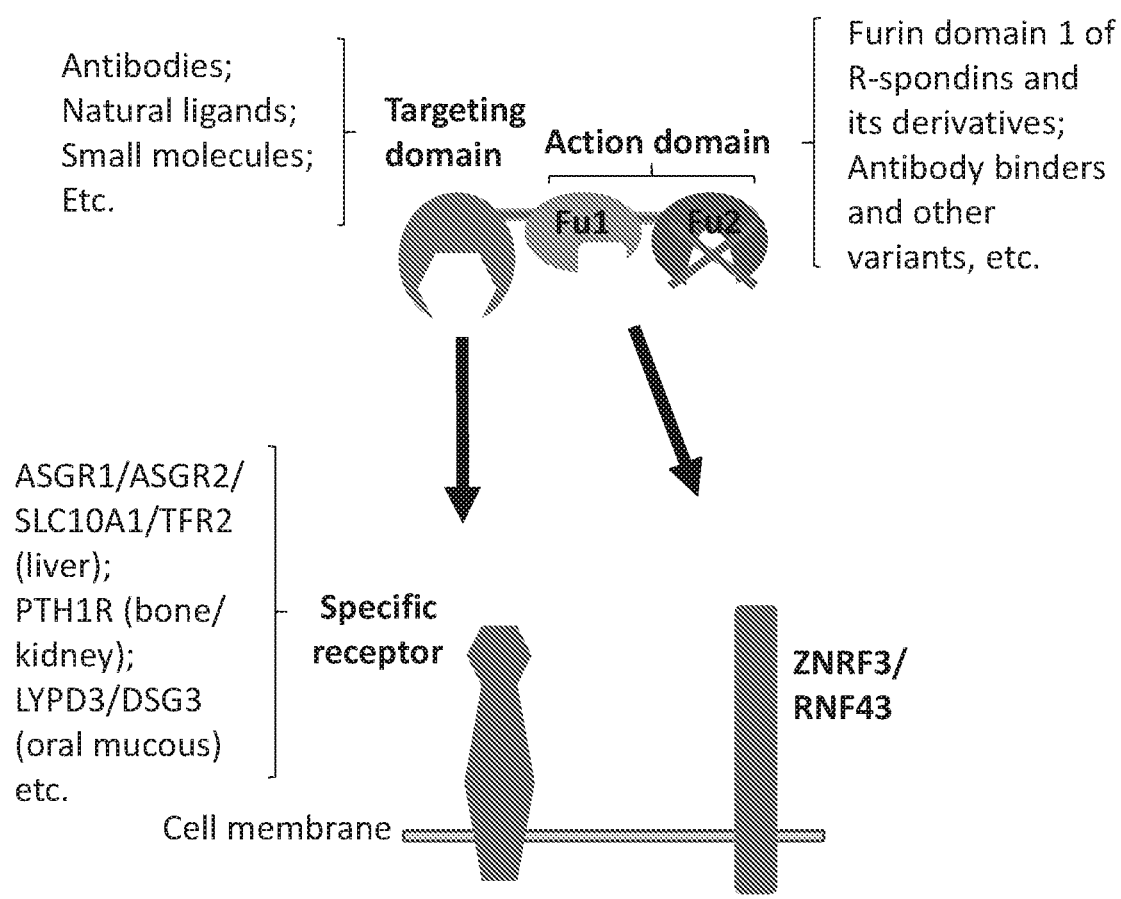
FIG. 2 provides a schematic diagram of one embodiment of a tissue-specific Wnt signal enhancing molecule disclosed herein. The molecule is a composite molecule, including but not limited to fusion proteins, comprising a "targeting domain" that binds to a tissue-specific cell surface protein and an "action domain" capable of binding to a ZNRF3 and/or RNF43.
Figure 3:
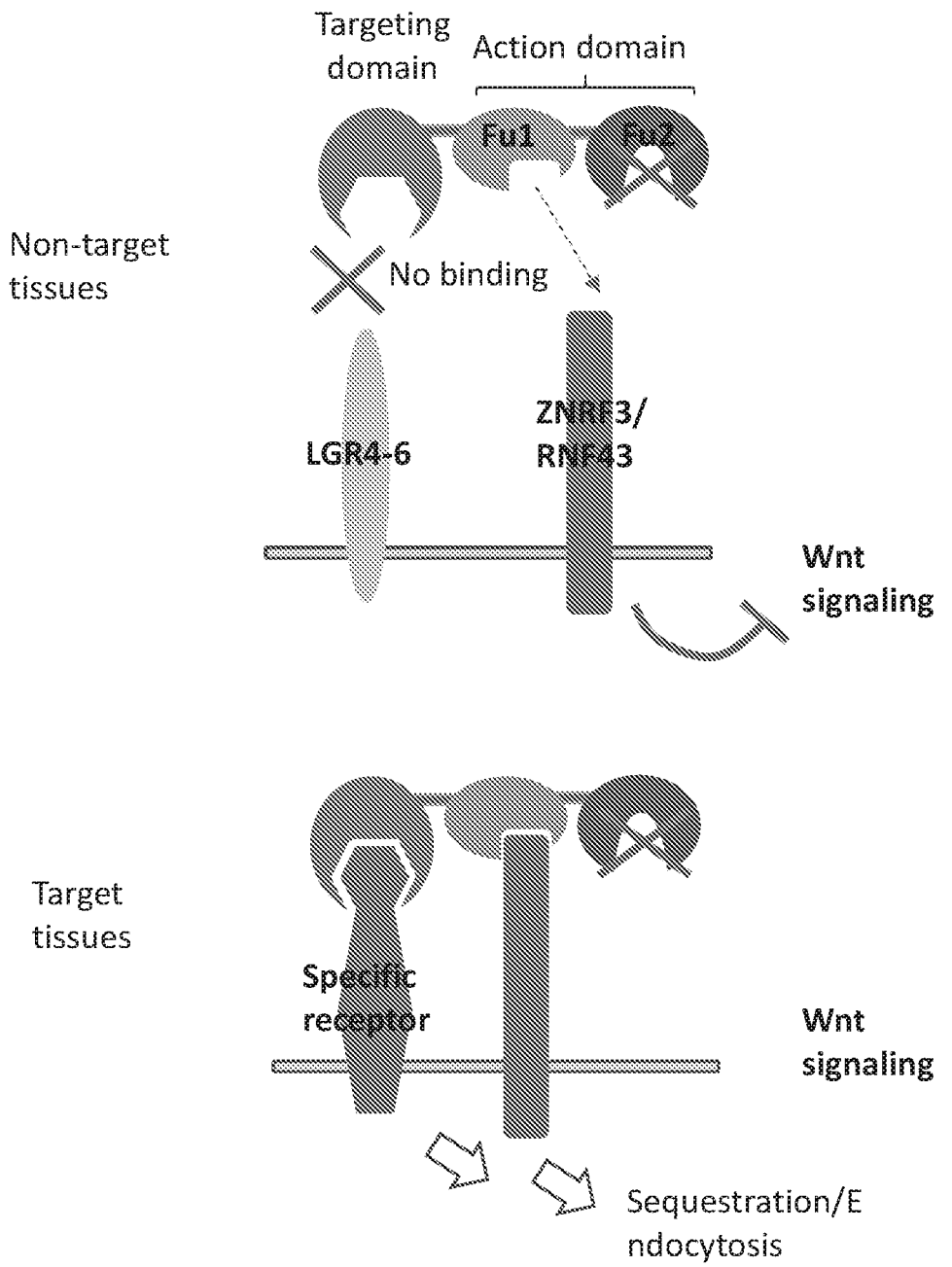
FIG. 3 provides diagrams illustrating the effect of a tissue-specific Wnt signal enhancing molecule described herein, and showing that the molecule preferentially binds to target tissues. In non-target tissues lacking the specific targeted cell surface receptor, the tissue-specific Wnt signal enhancing molecule may or may not bind to ZNRF3/RNF43, does not internalize or remove the E3 ligases, and is essentially inactive in non-target tissues (top diagram). In target tissues having the specific targeted cell surface receptor, the tissue-specific Wnt signal enhancing molecule binds to the targeted tissue via its targeting domain and the action domain binds to ZNRF3/RNF43 on the targeted tissue, and triggers the sequestration or endocytosis of ZNRF3/RNF43 in the targeted tissue (bottom diagram).
Figure 8:
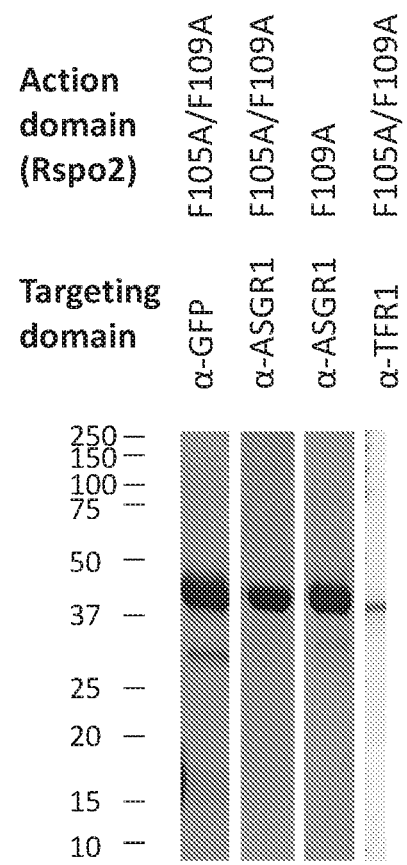
FIGS. 8A-8C shows the enhancement of Wnt signaling activity by purified proteins in which the mutant Rspo2 was fused to targeting (anti-ASGR1 or anti-TFR1) or non-targeting (control, anti-GFP) domain in the scFv form.
Figure 8:
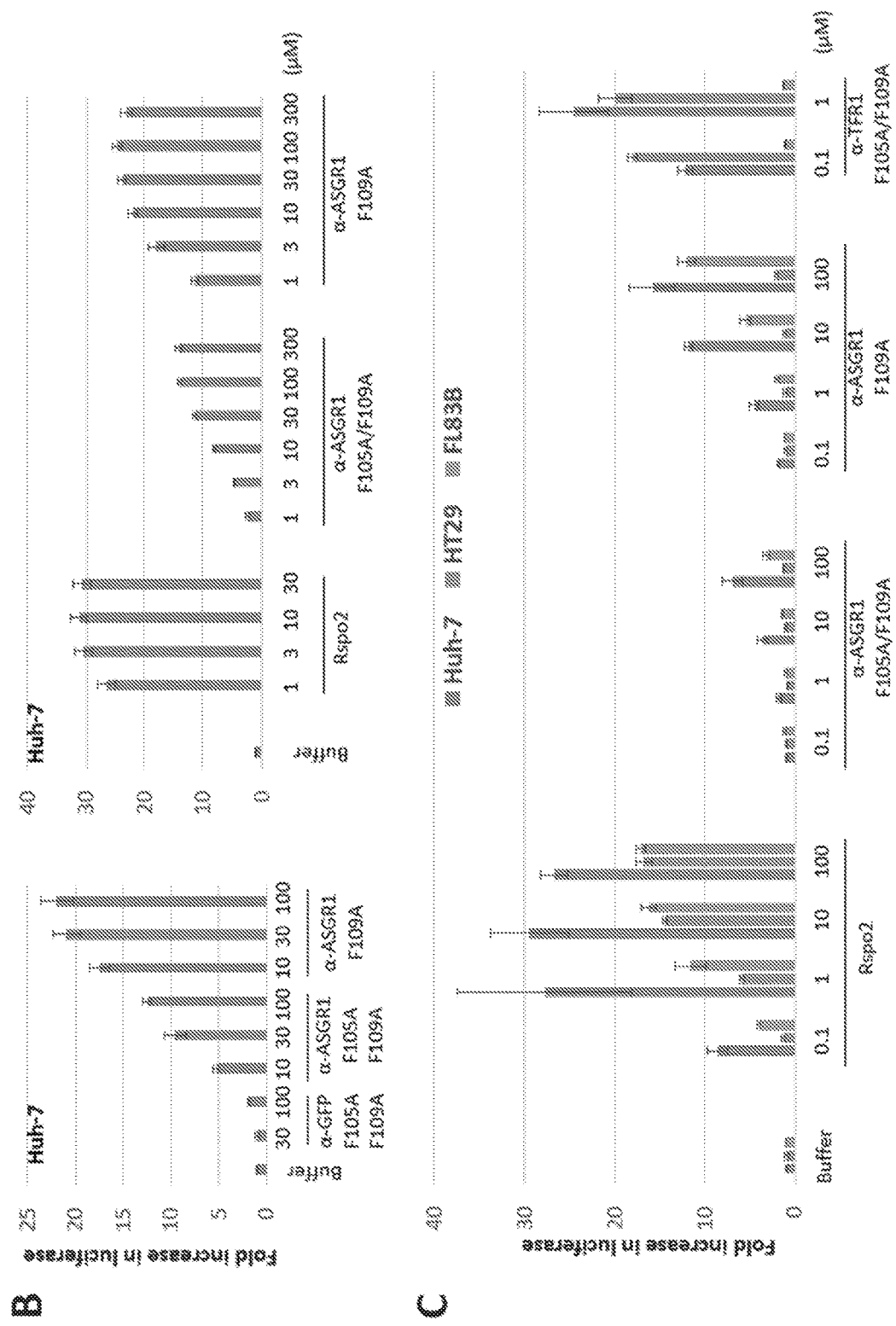

The action domain of the tissue-specific Wnt signal enhancing molecules described herein can be, but is not limited to, any functional moiety that can bind to the ZNRF3/RNF43 ligases, e.g., polypeptides or organic chemicals (see FIG. 2). In particular embodiments, the action domain, for example a polypeptide comprising the Furin domain 1 of an R-spondin, either alone or together with the targeting domain, is substantially inactive in non-target tissues, so as to minimize potential off-target effects. The action domain is fused to or bound to a targeting domain in the context of a tissue-specific Wnt signal enhancing molecule, and when the tissue-specific Wnt signal enhancing molecule engages with target tissue that express the tissue-specific receptor, E3 ligases ZNRF3/RNF43 are recruited to a ternary complex with the tissue-specific receptors, leading them to be relocated on the cell surface, sequestered, and/or cleared from the cell surface (see FIG. 3).

In certain embodiments, the action domain comprises a fragment or variant of an R-spondin polypeptide (e.g., any of R-spondins 1-4), or a functional fragment or variant thereof. In particular embodiments, the action domain comprises a fragment of a wild-type R-spondin, and in other embodiments, the action domain comprises a fragment of an R-spondin comprising one or more amino acid modifications. The R-spondin may be any R-spondin known in the art or a homolog thereof, including R-spondins from any animal species, including but not limited to mammalian species, such as human R-spondins. R-spondins have been identified and described, and their polypeptide and encoding polynucleotide sequences are known and available in the art. In particular embodiments, the R-spondin polypeptide is a human R-spondin or a homolog found in other vertebrates or non-vertebrates, e.g., a mouse R-spondin. Amino acid sequences of human R-spondin 1, human R-spondin 2, human R-spondin 3, and human R-spondin 4, and the Furin domains 1 thereof, are provided in FIG. 4 and SEQ ID NOs:1-4, respectively. Their homologues and variants are available from general database search, such as https://www.dot.ncbi.dot.nlm.dot.nih.dot.gov/protein/. The present invention includes (but is not limited to) action domains comprising or consisting of fragments and variants of any of these or other R-spondins. In various embodiments, variants of any of the R-spondin polypeptides and fragments thereof comprise one or more amino acid modifications, e.g., deletions, additions, or substitutions as compared to the wild-type R-spondin polypeptide. The modification(s) may be present in any region of the variant of R-spondin or a fragment thereof, including but not limited to a Furin domain 1 and/or a Furin domain 2. It is understood that amino acid modifications outside of the Furin domain 1 or Furin domain 2 may alter the resulting variant such that the resulting variant has reduced LGR4-6 binding activity as compared to the wild-type R-spondin or fragment thereof.

In certain embodiments, the action domain comprises or consists of an R-spondin sequence, e.g., a full length or wild-type R-spondin-1, -2, -3 or -4, optionally a human R-spondin-1, -2, -3, or -4, or a variant or fragment thereof. In particular embodiments, it is a variant of any of R-spondins-1-4 having at least 80%, at least 85%, at least 90%, at least 95%, at least 98%, or at least 99% sequence identity to the corresponding wild-type R-spondin-1-4 sequence. In certain embodiments, the action domain comprises or consists of a full length R-spondin (e.g., any of R-spondins-1-4) comprising one or more amino acid modifications, including but not limited to any of those disclosed herein. In certain embodiments, the action domain comprises or consists of a fragment of a wild-type or modified R-spondin (e.g., any of R-spondins-1-4). In particular embodiments, the fragment is able to bind to ZNRF3 and/or RNF43. In certain embodiments, the action domain comprises the Furin domain 1 of an R-spondin protein, or fragments or variants of R-spondin proteins. In certain embodiments, the action domain comprises or consists of one or more (e.g., one, two or three or more Furin domain 1 of an R-spondin protein (e.g., R-spondin-1-4), or a variant thereof having at least 85%, at least 90%, at least 95%, at lest 98% or at least 99% sequence identify to an R-spondin Furin domain 1. In certain embodiments, the action domain comprises an R-spondin Furin 1 domain or variant or fragment thereof and an R-spondin Furin 2 domain or variant or fragment thereof. In certain embodiments, the action domain comprises an antibody, or antigen binding fragment thereof, that bind ZNRF3/RNF43. In particular embodiments, the action domain specifically binds to either ZNRF3 or RNF43.

In certain embodiments, the action domain comprises one or more Furin domain 1 of an R-spondin, e.g., human R-spondin 1 or human R-spondin 2, or a variant thereof. In certain embodiments, the action domain comprises one or more Furin domain 1 of an R-spondin, but it does not comprise a Furin domain 2 of an R-spondin. In certain embodiments, the action domain comprises one or more Furin domain 1 of an R-spondin, and it comprises a modified or variant Furin domain 2 of an R-spondin, e.g., a Furin domain 2 with reduced activity as compared to the wild-type Furin domain 2. In certain embodiments, the action domain comprises an R-spondin protein having a modified or variant Furin domain 2 of an R-spondin, e.g, a Furin domain 2 with reduced activity as compared to the wild-type Furin domain 2. In certain embodiments, an action domain comprises two or more Furin domains 1, or variants thereof, or multimers of a Furin domain 1 or variant thereof. In certain embodiments, the action domain comprises a variant R-spondin Furin 1 domain comprising one or more point mutations, e.g., at amino acid residues corresponding to K58, H76, S77, R86, N91 of human R-spondin 2. In particular embodiments, the action domain comprises a modified or variant Furin domain 1 of an R-spondin that has increased activity, e.g., binding to ZNRF3/RNF43, as compared to the wild-type Furin domain 1. Action domains may further comprise additional moieties or polypeptide sequences, e.g., additional amino acid residues to stabilize the structure of the action domain or tissue-specific Wnt signal enhancing molecule in which it is present. In certain embodiments, an action domain comprises a peptide or polypeptide without obvious/strong sequence homology to R-spondins but has binding affinity to ZNRF3/RNF43 comparable to or higher than the binding affinity of R-spondins to ZNRF3/RNF43.

In certain embodiments, the action domain comprises a Furin domain 1 of an R-spondin polypeptide (e.g., a human R-spondin), or a functional fragment or variant thereof, and a modified or variant Furin domain 2 of an R-spondin polypeptide (e.g., a human R-spondin), wherein the modified Furin domain 2 has reduced binding affinity to LGR4-6 as compared to the corresponding wild-type Furin domain 2 (see FIGS. 5-7). In certain embodiments, the Furin domain 2 comprises one or more point mutations, e.g., at amino acid residues corresponding to F105 and/or F109 of human R-spondin 2. The skilled artisan can readily determine the corresponding amino acid residues in other R-spondin polypeptides by comparing their amino acid sequences to human R-spondin 2. In certain embodiments, the action domain comprises a Furin domain 1 or variant thereof and a Furin domain 2 or variant thereof, wherein the Furin domain 1 and/or Furin domain 2 comprises one or more point mutations. The one or more point mutations within the action domain (as compared to the corresponding wild-type R-spondin sequence) may occur at any amino acid residues within the Furin domain 1 and/or Furin domain 2, including but not limited to, e.g., at amino acid residues K58, H76, S77, R86, N91, F105, F109, or K121 and other residues that can be modified to reduce the binding affinity to LGR4-6. Regions of the Furin domain 1 and Furin domain 2 of human R-spondin 1 that are important for its functional activity have been identified, including conserved hydrophilic residues S48, N51, R66, R70 and Q71, and less conserved, hydrophobic residues, L46, L54, I62 and L64, which are important for binding to the E3 ligases. In addition, in the human R-spondin 1 Furin domain 1, amino acid residues K59, S78, D85, R87, N88 and N92 form a hydrophilic interaction surface with LGR5, and the FSHNF amino acid sequence has been identified as a loop important for the hydrophobic surface. In particular embodiments, action domains comprising R-spondin Furin domain 1 and/or Furin domain 2 may comprise one or more mutations within any of these regions, surfaces or amino acid residues. In particular embodiments, action domains comprising R-spondin Furin domain 1 and/or Furin domain 2 may comprise one or more mutations or other alternations beyond these regions, surfaces or amino acid residues, which indirectly compromise LGR4-6 binding by affecting the structure and/or stability of the binding surface. In certain embodiments, action domains comprising R-spondin Furin domain 1 and/ or Furin domain 2 may comprise one or more mutations at any amino acid residues, including but not limited to any of those depicted in the accompanying Examples. In particular embodiments, the modified Furin domain 2 has binding affinity to LGR4-6 less than 80%, less than 50%, less than 20%, or less than 10% the binding of the corresponding wild-type Furin domain 2, e.g., in the context of the full length R-spondin protein.

In certain embodiments, the action domain comprises a Furin domain 1 of an R-spondin polypeptide (e.g., a human R-spondin), or a functional fragment or variant thereof, and an unmodified Furin domain 2 of an R-spondin polypeptide (e.g., a human R-spondin). While in certain embodiments, a modified Furin domain 2 having reduced binding affinity to LGR4-6 as compared to the corresponding wild-type Furin domain 2 is more desirable to increase the specificity of tissue targeting, in particular embodiments, the unmodified Furin domain 2 combined with the targeting domain has improved tissue targeting over wild-type R-spondin without targeting domain, and has utility in certain contexts.

In certain emboidments, the action domain comprises a wild-type or modified R-spondin Furin domain 1, e.g., from any of R-spondin-1, -2, -3, -4, optionally human R-spondins-1, -2, -3 or -4. In particular embodiments, the action domain comprises the R-spondin Furin 1 domain and a wild-type or modified R-spondin Furin 2 domain, e.g., from any of R-spondin-1, -2, -3, -4, optionally human R-spondins-1, -2, -3 or -4. In particular embodiments, the action domain comprises the first R-spondin Furin 1 domain and a second wild-type or modified R-spondin Furin 1 domain, e.g., from any of R-spondin-1, -2, -3, -4, optionally human R-spondins-1, -2, -3 or -4. In particular embodiments, the modified Furin domain 2 has comparable binding affinity to LGR4-6 or a binding affinity to LGR4-6 of less than 80%, less than 50%, less than 20%, or less than 10% the binding of the corresponding wild-type Furin domain 2, e.g., in the context of the full length R-spondin protein.

Targeting Domains

Specific cell types and cells within specific tissue may comprise one or more cell- or tissue-specific surface molecule, such as a cell surface receptor (see FIG. 2). As used herein, the molecule is said to be cell- or tissue-specific if a greater amount of the molecule is present on the specific cell or tissue type as compared to one or more other cell or tissue types, or any other cell or tissue type. In certain embodiments, the greater amount is at least two-fold, at least five-fold, at least 10-fold, at least 20-fold, at least 50-fold, or at least 100-fold as compared to the amount in the one or more other cell or tissue types, or any other cell or tissue type. In particular embodiments, the cell-specific surface molecule has increased or enhanced expression on a target organ, tissue or cell type, e.g., an organ, tissue or cell type in which it is desirous to enhance Wnt signaling, e.g., to treat or prevent a disease or disorder, e.g., as compared to one or more other non-targeted organs, tissues or cell types. In certain embodiments, the cell-specific surface molecule is preferentially expressed on the surface of the target organ, tissue or cell type as compared to one or more other organ, tissue or cell types, respectively. For example, in particular embodiments, a cell surface receptor is considered to be a tissue-specific or cell-specific cell surface molecule if it is expressed at levels at least two-fold, at least five-fold, at least 10-fold, at least 20-fold, at least 30-fold, at least 40-fold, at least 50-fold, at least 100-fold, at least 500-fold, or at least 1000-fold higher in the target organ, tissue or cell than it is expressed in one or more, five or more, all other organs, tissues or cells, or an average of all other organs, tissue or cells, respectively. In certain embodiments, the tissue-specific or cell-specific cell surface molecule is a cell surface receptor, e.g., a polypeptide receptor comprising a region located within the cell surface membrane and an extracellular region to which the targeting domain can bind. In various embodiments, the methods described herein may be practiced by specifically targeting cell surface molecules that are only expressed on the target tissue or a subset of tissues including the target tissue, or by specifically targeting cell surface molecules that have higher levels of expression on the target tissue as compared to all, most, or a substantial number of other tissues, e.g., higher expression on the target tissue than on at least two, at least five, at least ten, or at least twenty other tissues.

In particular embodiments, the targeting domain binds to a tissue-specific surface molecule expressed on a target cell or tissue type of interest, i.e., a cell or tissue type wherein it is desired to enhance or increase Wnt signaling activity. The targeting domains that bind to each tissue-specific surface molecules can be, but are not limited to, antibodies or antigen-binding fragments thereof, peptides, natural ligands of tissue- or cell-specific receptors, or their derivatives, and synthetic small molecules, etc.

The targeted tissue bound by the targeting domain may be any tissue, e.g., any mammalian tissue or cell type. In certain embodiments, the targeted tissue may be present in any organ. In certain embodiments, the target tissue is bone tissue, liver tissue, skin tissue, stomach tissue, intestine tissue, oral mucosa tissue, kidney tissue, central nervous system tissue, mammary gland tissue, taste bud tissue, ovary tissue, inner ear tissue (including cochlear and vestibular tissues), hair follicles, pancreas tissue, retina tissue, cornea tissue, heart tissue or lung tissue, and the targeting domain binds to a tissue-specific cell surface molecule (e.g., a cell surface receptor) preferentially expressed on bone tissue, liver tissue, skin tissue, stomach tissue, intestine tissue, oral mucosa tissue, kidney tissue, central nervous system tissue, mammary gland tissue, taste bud tissue, ovary tissue, inner ear tissue (including cochlear and vestibular tissues), hair follicles, pancreas tissue, retina tissue, cornea tissue, heart tissue or lung tissue, respectively.

The targeting domain may bind to any cell type, e.g., any cell within any tissue, organ or animal, including but not limited to mammals, such as humans. In certain embodiments, the tissue-specific Wnt signal enhancing molecule binds to specific cell types, e.g., specific cell types associated with a target tissue. For example, in liver tissue, the targeting domain may bind to hepatocytes, precursors and stem cells of hepatocytes, biliary tract cells, and/or endothelial or other vascular cells. For example, in bone tissue, the targeting domain may bind osteoblasts, precursors of osteoblasts, mesenchymal stem cells, stem cells and precursor cells that give rise to bone, cartilage and/or other cells present in bone tissue. Cell types present in various tissues, including but not limited to the tissues described herein, are known in the art, and in various embodiments, the tissue-specific Wnt signal enhancing molecules described herein may bind any of them.

In various embodiments, the tissue-specific surface molecules are tissue-specific cell surface receptors. For liver, these include, but are not limited to, ASGR1, ASGR2, TFR2, SLC10A1, etc. In certain embodiments, the targeting domain is a natural ligand, or functional variant or fragment thereof, or an antibody, or antigen-binding fragment thereof, that binds ASGR1, ASGR2, TFR2, SLC10A1, LYPD3, or DSG3. For bone or kidney, such tissue-specific cell surface receptors include, but are not limited to, parathyroid hormone receptor 1 (PTH1R), etc. In certain embodiments, the targeting domain is a natural ligand, or a functional variant or fragment thereof, or an antibody, or antigen-binding fragment thereof, that binds PTH1R. For oral mucosa, such tissue-specific cell surface receptors include, but are not limited to, LYPD3 and DSG3. In certain embodiments, the targeting domain is a natural ligand, or a functional variant or fragment thereof, or an antibody, or antigen-binding fragment thereof, that binds LYPD3 or DSG3.

The asialoglycoprotein receptor (ASGPR) is comprised of ASGR1 and ASGR2 (reviewed, for example by Stockert, Morell and Ashwell, 1991, Targeted Diagnostics and Therapy 4: 41-64). This receptor is a transmembrane protein that plays a critical role in serum glycoprotein homeostasis by mediating the endocytosis and lysosomal degradation of glycoproteins with exposed terminal galactose or N-acetyl-galactosamine residues. Thus, natural and synthetic ligands of AGPR include, but are not limited to, galactosylated cholinesterase, galactose (Gal) and N-acetylgalactosamine (GalNAc), GalNAc containing molecules such as GalNAc-terminating glycoproteins, and mono-, oligo-, or poly-saccharide containing molecules or nano-particles (reviewed, for example, by D'Souza and Devarajan 2015, Journal of Controlled Release, 203:126-139).

The SLC10 family transport bile acids, sulphated solutes, and other xenobiotics in a sodium-dependent manner. The founding members, SLC10A1 (NTCP) and SLC10A2 (ASBT) function to maintain the enterohepatic circulation of bile acids. Examples of natural and synthetic ligands of SLC10A include, but are not limited to, cholate, Na(+)/bile acid, Na(+)/taurocholate, and the preS1 domain of hepatitis B virus and the fragments or variants thereof (reported, for example, by Yan et al., 2012 eLife, 1: e00049).

Transferrin receptor 2 (TFR2) is a homologue of transferrin receptor 1 (TFR1), the protein that delivers iron to cells through receptor-mediated endocytosis of diferric transferrin ($Fe_2TF$). TFR2 also binds $Fe_2TF$, but it seems to function primarily in the regulation of systemic iron homeostasis (reviewed, for example, by Worthen and Enns, 2014, Frontiers in Pharmacology 5:34). Examples of natural and synthetic ligands and binding partners of TFR2 include, but are not limited to, transferrin, such as diferric transferrin, and the hemochromatosis (HFE) protein and fragments and variants thereof.

The type 1 receptor (PTH1R) for parathyroid hormone (PTH) and PTH-related peptide (PTHrP) is highly expressed in bone and kidney (reviewed, for example, by Mannstadt, Juppner, and Gardella, 1999, American Journal of Physiology 277: F665-F675). Natural and synthetic ligands of parathyroid hormone receptor 1 (PTH1R) include, but are not limited to, PTH, PTHrP, and fragments and variants thereof.

Ly6/PLAUR domain-containing protein 3 (LYPD3) is a GPI-anchored protein exhibiting highly specific expression in stratified squamous epithelium found in tissues such as oral mucosa, skin and esophagus. LYPD3 expression was also seen unregulated in migrating keratinocytes during wound healing as well as various cancers(reviewed, e.g., by Jacobsen, Kriegbaum, Santoni-Rugiu and Ploug, 2014, World Journal of Clinical Oncology, 5(4):621-32). Even though LYPD3 expression has been reported, its exact function remains unclear, since animals lacking LYPD3 gene are viable, fertile and no obvious defect in development of squamous epithelia. Various molecules have been identified as binding partners of LYPD3. Laminin1, laminin5, and galectin-3 associate with LYPD3 to promote cell migration (Paret, Bourouba, Beer, Miyazaki, Schnölzer, Fiedler and Zoller. International Journal of Cancer. 2005 Jul. 10; 115(5):724-33). Anterior gradient 2, AGR2, interacts with LYPD3 and promotes cancer growth, metastasis and resistance to therapy in pancreatic ductal adenocarcinoma (PDAC) (Arumugam, Deng, Boyer, Wang, Logsdon and Ramachandran. Molecular Cancer Therapeutics. 2015 April; 14(4):941-51). Under hypoxic condition, LYPD3 forms a complex with α6β4 integrin and matrix metalloproteinase 14 (MMP14), which promotes cancer cell motility through focalized laminin 332 degradation. (Ngora, Galli, Miyazaki and Zoller. Neoplasia. 2012 February; 14(2): 95-107).

Desmoglein 3 (DSG3) encodes a calcium-binding transmembrane glycoprotein that is a member of cadherin cell adhesion molecule superfamily of proteins. DSG3 is expressed in desmosomes, special structure for cell to cell adhesion, in epithelium and mucosa. DSG3 has five extracellular cadherin domains (ECDs) containing Ca2+-binding sites that are required for DSG3 intercellular interaction (reviewed, e.g., by Thomason, Scothern, McHarg and Garrod, 2010, Biochemical Journal, 429 (3): 419-433). DSG3 intercellular interaction is mediated by trans-homophilic interaction near their N-termini. The loss of DSG3 in animals causes very severe erosion in oral mucosa and hair loss at weaning, indicating how important this gene is for the integrity of epithelial cells in these tissues. Single molecule atomic force microscopy experiment has shown a homophilic trans DSG3-binding via extracellular cadherin domains (Heupel, Zillikens, Drenckhahn and Waschke. Journal of Immunology. Aug. 1, 2008, 181 (3) 1825-1834).

Illustrative, non-limiting examples of tissue-specific Wnt signal enhancing molecules include fusion proteins comprising: 1) a first domain comprising an R-spondin Furin domain 1 or variant thereof and a second domain comprising an antibody or fragment thereof that specifically binds ASGR1 or ASGR2; 2) a first domain comprising an R-spondin Furin domain 1 or variant thereof and a second domain comprising an antibody or fragment thereof that specifically binds SLC10A1; 3) a first domain comprising an R-spondin Furin domain 1 or variant thereof and a second domain comprising an antibody or fragment thereof that specifically binds TFR2; 4) a first domain comprising an R-spondin Furin domain 1 or variant thereof and a second domain comprising a ligand derivative, an antibody or fragment thereof that specifically binds PTH1R; 5) a first domain comprising an R-spondin Furin domain 1 or variant thereof and a second domain comprising a ligand derivative, an antibody or fragment thereof that specifically binds LYPD3; 6) a first domain comprising an R-spondin Furin domain 1 or variant thereof and a second domain comprising a ligand derivative, an antibody or fragment thereof that specifically binds DSG3; and 7) a first domain comprising an R-spondin Furin domain 1 or variant thereof and a second domain comprising a ligand derivative, an antibody or fragment thereof that specifically binds TFR1. In particular embodiments, the two domains are joined via a linker, e.g., a polypeptide linker. In certain embodiments, the linker is albumin, e.g., human serum albumin, where the targeting and action domains are on the N- and C-termini of albumin. In particular embodiments, the tissue-specific Wnt signal enhancing molecules have an appended antibody (e.g., IgG) format comprising an antibody heavy chain and an antibody light chain (or fragments or variants thereof of either or both chains), wherein one or both chains further comprises one or more additional binding domain. In particular embodiments, the tissue-specific Wnt signal enhancing molecules have an appended antibody (e.g., IgG) format, wherein the second domain comprises an antibody heavy chain and an antibody light chain (or fragments or variants thereof of either or both chains), and wherein a first domain comprising an R-spondin Furin domain 1 or variant is appended to one or both of the antibody heavy and/or light chains, e.g., at either or both the N-terminus and/or C-terminus of either or both chains. In particular embodiments, the first domain is appended or fused to the heavy chain, e.g., at either the N-terminus or C-terminus. In particular embodiments, the first domain is appended or fused to the light chain, e.g., at either the N-terminus or C-terminus.

Linkers

In certain embodiments, the targeting domain and the action domain are bound or fused directly to each other, whereas in other embodiments, they are separated by a linker, e.g., a polypeptide linker, or a non-peptidyl linker, etc. In particular embodiments, a linker is an Fc linker, e.g., a region of an antibody Fc domain capable of dimerizing with another Fc linker, e.g., via one or more disulfide bonds. In another particular embodiment, a linker is albumin, e.g., human serum albumin, where the targeting and action domains are on the N- and C-termini of albumin.

In certain embodiments, particularly when joining two polypeptides, the linker is made up of amino acids linked together by peptide bonds. In particular embodiments, the linker comprises, in length, from 1 up to about 40 amino acid residues, from 1 up to about 20 amino acid residues, or from 1 to about 10 amino acid residues. In certain embodiments, the amino acid residues in the linker are from among the twenty canonical amino acids, and in certain embodiments, selected from cysteine, glycine, alanine, proline, asparagine, glutamine, and/or serine. In certain embodiments, a linker comprises one or more non-natural amino acids. In some embodiments, a peptidyl linker is made up of a majority of amino acids that are sterically unhindered, such as glycine, serine, and alanine linked by a peptide bond. Certain linkers include polyglycines, polyserines, and polyalanines, or combinations of any of these. Some exemplary peptidyl linkers are poly(Gly)1-8 (SEQ ID Nos: 159-163, particularly (Gly) 3, (Gly)4 (SEQ ID NO:159), (Gly)5 (SEQ ID NO:160) and (Gly)7 (SEQ ID NO:162), as well as, poly(Gly)4 Ser (SEQ ID NO:164), poly(Gly-Ala)2-4 (SEQ ID Nos: 165-167) and poly(Ala)1-8 (SEQ ID Nos: 168-172). Other specific examples of peptidyl linkers include (Gly)5Lys (SEQ ID NO:173), and (Gly)5LysArg (SEQ ID NO:174). To explain the above nomenclature, for example, (Gly)3Lys(Gly)4 (SEQ ID NO:175) means Gly-Gly-Gly-Lys-Gly-Gly-Gly-Gly (SEQ ID NO:175). Other combinations of Gly and Ala are also useful. Additionally, a peptidyl linker can also comprise a non-peptidyl segment such as a 6 carbon aliphatic molecule of the formula —CH2—CH2—CH2—CH2—CH2—CH2—. The peptidyl linkers can be altered to form derivatives as described herein.

Illustrative non-peptidyl linkers include, for example, alkyl linkers such as —NH—(CH2)s-C(O)—, wherein s=2-20. These alkyl linkers may further be substituted by any non-sterically hindering group such as lower alkyl (e.g., C1-C6) lower acyl, halogen (e.g., Cl, Br), CN, NH2, phenyl, etc. Non-peptide portions of the inventive composition of matter, such as non-peptidyl linkers or non-peptide half-life extending moieties can be synthesized by conventional organic chemistry reactions. Chemical groups that find use in linking binding domains include carbamate; amide (amine plus carboxylic acid); ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), disulfide; hydrazone, lipids, and the like, as known in the art.

The linkage between domains may comprise spacers, e.g. alkyl spacers, which may be linear or branched, usually linear, and may include one or more unsaturated bonds; usually having from one to about 300 carbon atoms; more usually from about one to 25 carbon atoms; and may be from about three to 12 carbon atoms. Spacers of this type may also comprise heteroatoms or functional groups, including amines, ethers, phosphodiesters, and the like. Specific structures of interest include: $(CH_2CH_2O)n$ where n is from 1 to about 12; $(CH_2CH_2NH)n$, where n is from 1 to about 12; $[(CH_2)n(C=O)NH(CH_2)_m]_z$, where n and m are from 1 to about 6, and z is from 1 to about 10; $[(CH_2)nOPO_3(CH_2)_m]_z$ where n and m are from 1 to about 6, and z is from 1 to about 10. Such linkers may include polyethylene glycol, which may be linear or branched.

In certain embodiments, the domains may be joined through a homo- or heterobifunctional linker. Illustrative entities include: azidobenzoyl hydrazide, N-[4-(p-azidosalicylamino)butyl]-3'(2'-pyridyldithiolpropionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, NHS-PEG-MAL; succinimidyl 4-[N-maleimidomethyl] cyclohexane-1-carboxylate; 3-(2-pyridyldithio)propionic acid N-hydroxysuccinimide ester (SPDP); N, N'-(1,3-phenylene) bismaleimide; N, N'-ethylene-bis-(iodoacetamide); or 4-(N-maleimidomethyl)-cyclohexane-1-carboxylic acid N-hydroxysuccinimide ester (SMCC); m-maleimidobenzoyl-N-hydroxysuccinimide ester (MBS), and succinimide 4-(p-maleimidophenyl)butyrate (SMPB), an extended chain analog of MBS. In certain embodiments, the succinimidyl group of these cross-linkers reacts with a primary amine, and the thiol-reactive maleimide forms a covalent bond with the thiol of a cysteine residue.

Other reagents useful include: homobifunctional cross-linking reagents including bismaleimidohexane ("BMH"); p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); disdiazobenzidine (which reacts primarily with tyrosine and histidine); O-benzotriazolyloxy tetramethuluronium hexafluorophosphate (HATU), dicyclohexyl carbodiimde, bromo-tris (pyrrolidino) phosphonium bromide (PyBroP); N,N-dimethylamino pyridine (DMAP); 4-pyrrolidino pyridine; N-hydroxy benzotriazole; and the like.

Wnt Molecules, Norrin Molecules, and Wnt Signal Enhancing Molecules

The present disclosure further relates to Wnt polypeptides, Norrin polypeptides, and Wnt signaling agonist molecules and their use to increase Wnt signaling and treat or prevent Wnt-related diseases or disorders, including those described herein. In certain embodiments, the Wnt polypeptides, Norrin polypeptides and Wnt signaling agonist molecules are provided to a subject alone or in combination with one or more tissue-specific Wnt signal enhancing molecules described herein.

Wnt polypeptides and Wnt-encoding polynucleotide sequences are known in the art and include any and all Wnt polypeptides or polynucleotides, including those of any and all species, including mammalian Wnt polypeptides and polynucleotides, such as human Wnt polypeptides and polynucleotides. Illustrative Wnt polypeptides include Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, and Wnt16, and functional variants and fragments of any of the foregoing. Wnt polypeptide encompasses native Wnt polypeptides, Wnt polypeptide variants, Wnt polypeptide fragments and chimeric Wnt polypeptides. In particular embodiments, a Wnt polypeptide is a native human full length mature Wnt protein.

For example, human native sequence Wnt proteins of interest in the present application include but are not limited to the following: Wnt1 (GenBank Accession No. NM_005430); Wnt-2 (GenBank Accession No. NM_003391); Wnt2B (Wnt-13) (GenBank Accession No. NM_004185 (isoform 1), NM_024494.2 (isoform 2)), Wnt3 (RefSeq.: NM_030753), Wnt3A (GenBank Accession No. NM_033131), Wnt4 (GenBank Accession No. NM_030761), Wnt5A (GenBank Accession No. NM_003392), Wnt5B (GenBank Accession No. NM_032642), Wnt6 (GenBank Accession No. NM_006522), Wnt7A (GenBank Accession No. NM_004625), Wnt7B (GenBank Accession No. NM_058238), Wnt8A (GenBank Accession No. NM_058244), Wnt8B (GenBank Accession No. NM_003393), Wnt9A (Wnt-14) (GenBank Accession No. NM_003395), Wnt9B (Wnt15) (GenBank Accession No.

NM_003396), Wnt10A (GenBank Accession No. NM_025216), Wnt10B (GenBank Accession No. NM_003394), Wnt11 (GenBank Accession No. NM_004626), Wnt16 (GenBank Accession No. NM_016087)). Although each member has varying degrees of sequence identity with the family, all encode small (i.e., 39-46 kD), acylated, palmitoylated, secreted glycoproteins that contain 23-24 conserved cysteine residues whose spacing is highly conserved (McMahon, A P et al., Trends Genet. 1992; 8: 236-242; Miller, J R. Genome Biol. 2002; 3(1): 3001.1-3001.15). Other native sequence Wnt polypeptides of interest include orthologs of the above from any mammal, including domestic and farm animals, and zoo, laboratory or pet animals, such as dogs, cats, cattle, horses, sheep, pigs, goats, rabbits, rats, mice, frogs, zebra fish, fruit fly, worm, etc.

Norrin polypeptides and Norrin-encoding polynucleotide sequences are also known in the art and include any species of Norrin polypeptide or polynucleotide, including mammalian Norrin polypeptides and polynucleotides, such as human Norrin polypeptides and polynucleotides, and functional variants and fragments thereof.

Wnt signaling agonist molecules include any type of molecule that agonizes Wnt signaling. In particular embodiments, the Wnt signaling agonist molecule is described in PCT Patent Application Publication No. WO 2016/040895. A Wnt signaling agonist can be any molecule, e.g. protein or pharmaceutical (e.g., small organic molecule), in certain embodiments water soluble, which directly activates the canonical Wnt signaling through binding to one or more Fzd proteins and to Lrp5/6. In particular embodiments, they are small molecules, which may be less than about 15 Kd. In other embodiments, they are polypeptides. In addition, certain wnt signaling agonists may comprise both a polypeptide region or domain and a non-polypeptide region or domain.

In some embodiments of the invention, the Wnt signaling agonist molecule is a polypeptide, which can comprise separate or contiguous binding domains or elements for Fzd, and for Lrp5/6. A polypeptide Wnt signaling agonist may be a single chain, dimer, or higher order multimer. The Fzd binding domain/element and the Lrp5/6 binding domain/element may be directly joined, or may be separated by a linker, e.g. a polypeptide linker, or a non-peptidic linker, etc.

In polypeptide embodiments, the Fzd binding domain may be selected from any domain that binds Fzd at high affinity, e.g. a KD of at least about 1×10−7 M, at least about 1×10−8 M, at least about 1×10−9 M, or at least about 1×10−10 M. Suitable Fzd binding domains include, without limitation, de novo designed Fzd binding proteins, antibody derived binding proteins, e.g. scFv, Fab, etc. and other portions of antibodies that specifically bind to one or more Fzd proteins; nanobody derived binding domains; knottin-based engineered scaffolds; Norrin and engineered binding fragments derived therefrom, naturally occurring Fzd binding domains, and the like.

In some embodiments the Fzd binding domain binds to one, two, three, four, five or more different frizzled proteins, e.g. one or more of human frizzled proteins Fz1, Fz2, Fz3, Fz4, Fz5, Fz6, Fz7, Fz8, Fz9, Fz10. In some embodiments the antibody based signaling agonist binds to Fz1, Fz2, Fz5, Fz7 and Fz8. In other embodiments the frizzled binding moiety is selective for one or more frizzled protein of interest, e.g. having a specificity for the one or more desired frizzled protein of at least 10-fold, 25-fold, 50-fold, 100-fold, 200-fold or more relative to other frizzled proteins.

In certain embodiments, the frizzled binding domain comprises the six CDR regions of the pan specific frizzled antibody OMP-18R5 (vantictumab). In certain embodiments, the frizzled binding domain is an scFv comprising the six CDR regions of the pan-specific frizzled antibody OMP-18R5 (vantictumab). See, for example, U.S. Pat. No. 8,507, 442, herein specifically incorporated by reference. For example, the CDR sequences of OMP-18R$_5$ include a heavy chain CDR1 comprising GFTFSHYTLS (SEQ ID NO: 176), a heavy chain CDR2 comprising VISGDGSYTYY-ADSVKG (SEQ ID NO:177), and a heavy chain CDR3 comprising NFIKYVFAN (SEQ ID NO:178), and (ii) a light chain CDR1 comprising SGDKLGKKYAS (SEQ ID NO:179) or SGDNIGSFYVH (SEQ ID NO:180), a light chain CDR2 comprising EKDNRPSG (SEQ ID NO:181) or DKSNRPSG (SEQ ID NO:182), and a light chain CDR3 comprising SSFAGNSLE (SEQ ID NO:183) or QSY-ANTLSL (SEQ ID NO:184). In particular embodiments, the frizzled binding domain is an antibody or derivative thereof, including without limitation ScFv, minibodies, nanobodies and various antibody mimetics comprising the CDR sequences of SEQ ID NOs: 176-184. In certain embodiments, these CDR sequences comprise one or more amino acid modifications as compared to SEQ ID NOs: 176-184.

In other embodiments, the Fzd binding domain comprises a variable region sequence, or the CDRs thereof, from any of a number of frizzled specific antibodies, which are known in the art and are commercially available, or can be generated de novo. Any of the frizzled polypeptides can be used as an immunogen or in screening assays to develop an antibody. "Fz", "Fz proteins" and "Fz receptors" is used herein to refer to proteins of the Frizzled receptor family. These proteins are seven-pass transmembrane proteins (Ingham, P. W. (1996) Trends Genet. 12: 382-384; Yang-Snyder, J. et al. (1996) Curr. Biol. 6: 1302-1306; Bhanot, P. et al. (1996) Nature 382: 225-230) that comprise a CRD domain. There are ten known members of the Fz family (Fz1 through Fz10), any of which can serve as receptors of Wnts. The Genbank accession numbers of human frizzled reference sequences are as follows: FZD1 (NM_003505); FZD2 (NM_001466); FZD3 (NM_145866); FZD4 (NM_012193); FZD5 (NM_003468); FZD6 (NM_003506); FZD7 (NM_003507); FZD8 (NM_031866); FZD9 (NM_003508); FZD10 (NM_007197). Non-limiting examples of frizzled binding domains include antibodies available from Biolegend, e.g. Clone CH3A4A7 specific for human frizzled 4 (CD344); Clone W3C4E11 specific for human Fz9 (CD349); antibodies available from Abcam, e.g. ab64636 specific for Fz7; ab83042 specific for human Fz4; ab77379 specific for human Fz7; ab75235 specific for human Fz8; ab102956 specific for human Fz9; and the like. Other examples of suitable antibodies are described in, inter alia, US Patent application 20140105917; US Patent application 20130230521; US Patent application 20080267955; US Patent application 20080038272; US Patent application 20030044409.

The frizzled binding moiety of the surrogate may be an engineered protein that is selected for structural homology to the frizzled binding region of a Wnt protein. Such proteins can be identified by screening a structure database for homologies. The initial protein thus identified, for example the microbial Bh1478 protein. The native protein is then engineered to provide amino acid substitutions that increase affinity, and may further be selected by affinity maturation for increased affinity and selectivity in binding to the desired frizzled protein. Non-limiting examples of frizzled binding moieties include the Fz27 and Fz27-B12 proteins illustrated in FIG. 1 of PCT Patent Application Publication No. Wo 2016/040895.

In certain polypeptide embodiments, the Lrp5/6 binding domain or element may be selected from any domain that binds Lrp5/6 at high affinity, e.g. a KD of at least about $1\times10^{-7}$ M, at least about $1\times10^{-8}$ M, at least about $1\times10^{-9}$ M, at least about $1\times10^{-10}$ M. Suitable Lrp5/6 binding domains include, without limitation, de novo designed Lrp5/6 binding proteins, antibody derived binding proteins, e.g. scFv, Fab, etc. and other portions of antibodies that specifically bind to one or more Fzd proteins; nanobody derived binding domains; knottin-based engineered scaffolds; naturally occurring Lrp5/6 binding proteins or polypeptides, including without limitation, Norrin, DKK1, DKK2, DKK3, DKK4, sclerostin; and the like. In certain embodiments the Lrp5/6 binding domain is a C-terminal portion of DKK1.

An Lrp5/6 binding domain may be selected from any domain that binds Lrp5 or Lrp6 at high affinity, e.g. with a $K_D$ of at least about $1\times10^{-7}$ M, at least about $1\times10^{-8}$ M, at least about $1\times10^{-9}$ M, at least about $1\times10^{-10}$ M1. "LRP", "LRP proteins" and "LRP receptors" is used herein to refer to proteins of the low density lipoprotein receptor-related protein family. These receptors are single-pass transmembrane proteins that bind and internalize ligands in the process of receptor-mediated endocytosis. LRP proteins LRP5 (GenBank Accession No. NM 002335.2) and LRP6 (GenBank Accession No. NM_002336.2) are included in the Wnt receptor complex.

Suitable Lrp5/6 binding domains include, without limitation, de novo designed Lrp5/6 binding proteins, antibody derived binding proteins, e.g., scFv, Fab, etc. and other portions of antibodies that specifically bind to one or more Fzd proteins; nanobody derived binding domains; knottin-based engineered scaffolds; naturally occurring Lrp5/6, including without limitation, DKK1, DKK2, DKK3, DKK4, sclerostin; Wise; fusions proteins comprising any of the above; derivatives of any of the above; variants of any of the above; and biologically active fragments of any of the above, and the like. A Lrp5/6 binding domain may be affinity selected to enhance binding.

Members of the Dickkopf (Dkk) gene family (see Krupnik et al. (1999) Gene 238(2):301-13) include Dkk-1, Dkk-2, Dkk-3, and Dkk-4, and the Dkk-3 related protein Soggy (Sgy). hDkks 1~4 contain two distinct cysteine-rich domains in which the positions of 10 cysteine residues are highly conserved between family members. Exemplary sequences of human Dkk genes and proteins are publicly available, e.g., Genbank accession number NM_014419 (soggy-1); NM_014420 (DKK4); AF177394 (DKK-1); AF177395 (DKK-2); NM_015881 (DKK3); and NM_014421 (DKK2). In some embodiments of the invention, the Lrp6 binding moiety is a DKK1 peptide, including without limitation the C-terminal domain of human DKK1. As shown in FIG. 5, the C-terminal domain may comprise the sequence KMYHTKGQEGSVCLRSSDCASGLCCA-RHFWSKICKPVLKEGQVCTKHRRKGSHGLE IFQRC YCGEGLSCRIQKDHHQASNSSRLHTCQRH (SEQ ID NO:185) (see Genbank accession number NP 036374) or a biologically active fragment thereof.

Binding of DKK proteins to LRP5/6 are discussed, for example in Brott and Sokol Mol. Cell. Biol. 22 (17), 6100-6110 (2002); and Li et al. J. Biol. Chem. 277 (8), 5977-5981 (2002), each herein specifically incorporated by reference. The corresponding region of human DKK2 (Genbank reference NP 055236) may comprise the sequence KMSHIKGHEGDPCLRSSDCIEGFCCARHFWTKICK-PVLHQGEVCTKQRKKGSHGLEI FQRCD CAKGLSCKVWKDATYSSKARLHVCQK (SEQ ID NO:186) or a biologically active fragment thereof.

Antibodies that specifically bind to Lrp5 or Lrp6 are known in the art and are commercially available, or can be generated de novo. Lrp5, Lrp6 or fragments thereof can be used as an immunogen or in screening assays to develop an antibody. Examples of known antibodies include, without limitation, those described in Gong et al. (2010) PLoS One. 5(9): e12682; Ettenberg et al. (2010) Proc Natl Acad Sci USA. 107(35): 15473-8; and those commercially available from, for example Santa Cruz biotechnology antibody clone 1A12, which was raised against synthetic LRP5/6 of human origin and binds to both the full length and proteolytic fragment of LRP 6 and LRP 5 of mouse and human origin; the monoclonal antibody 2B11; Cell Signaling Technology antibody specific for LRP5 (D80F2), catalog number 5731; etc.

Polypeptides and binding domains may also include derivatives, variants, and biologically active fragments of polypeptides described above. A "variant" polypeptide means a biologically active polypeptide as defined below having less than 100% sequence identity with a provided sequence. Such variants include polypeptides comprising one or more amino acid modifications, e.g., insertions, deletions or substitutions, as compared to the provided sequence, e.g., wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. In certain embodiments, a biologically active variant will have an amino acid sequence having at least about 90% amino acid sequence identity with a native sequence polypeptide, at least about 95%, or at least about 99%. A "functional variant" of a sequence is a compound having a qualitative biological property in common with an initial sequence. "Functional variants" include, but are not limited to, fragments of a sequence and variants of a sequence, provided that they have a biological activity in common. The term "variant" encompasses both amino acid sequence variants of polypeptide and covalent modifications thereof.

The Fzd binding domain and the Lrp5/6 binding domain may be contiguous within one globular domain, or separated by a linker, e.g. a polypeptide linker, or a non-peptidic linker, etc., including but not limited to any of those described herein. The length of the linker, and therefore the spacing between the binding domains can be used to modulate the signal strength, and can be selected depending on the desired use of the Wnt signaling agonist. The enforced distance between binding domains can vary, but in certain embodiments may be less than about 100 angstroms, less than about 90 angstroms, less than about 80 angstroms, less than about 70 angstroms, less than about 60 angstroms, or less than about 50 angstroms.

In some embodiments the linker is a rigid linker, in other embodiments the linker is a flexible linker. Where the linker is a peptide linker, in certain embodiments, it may be from about 1, 2, 3, 4, 5, 6, 7, 8, 9, 10, 11, 12, 13, 14, 15, 16, 17, 18, 19, 20 21, 22, 23, 24, 25, 26, 27, 28, 29, 30 or more amino acids in length, and is of sufficient length and amino acid composition to enforce the distance between binding domains. In some embodiments the linker comprises or consists of one or more glycine and/or serine residues.

The present disclosure also includes polynucleotides or nucleic acid sequences that encode one or more Wnt polypeptide, Norrin polypeptide, or Wnt signaling agonist molecule, and vectors comprising these polynucleotides, including expression vectors, and cells comprising these vectors. In certain embodiments, the polynucleotides or nucleic acid sequences are DNA or RNA. In particular embodiments, the RNA is messenger RNA (mRNA). In certain embodiments, the RNA is a modified mRNA comprising one or more modified nucleosides. Modified mRNAs comprising one or more modified nucleoside have been described as having advantages over unmodified mRNAs, including increase stability, higher expression levels and reduced immunogenicity. Non-limiting examples of modified mRNAs that may be used according to the present invention are described, e.g., in PCT Patent Application Publication Nos. WO2011/130624, WO2012/138453, WO2013052523, WO2013151666, WO2013/071047, WO2013/078199, WO2012045075, WO2014081507, WO2014093924 WO2014164253, US Patent Nos: U.S. Pat. No. 8,278,036 (describing modified mRNAs comprising pseudouridine), U.S. Pat. No. 8,691,966 (describing modified mRNAs comprising pseudouridine and/or N1-methylpseudouridine), U.S. Pat. No. 8,835,108 (describing modified mRNAs comprising 5-methylcytidine, U.S. Pat. No. 8,748,089 (describing modified mRNAs comprising pseudouridine or 1-methylpseudouridine). In particular embodiments, the modified mRNA sequence encoding the Wnt polypeptide, Norrin polypeptide, or Wnt signaling agonist molecule comprises at least one modification as compared to an unmodified A, G, U or C ribonucleoside. In particular embodiments, the at least one modified nucleosides include N1-methylpseudouridine and/or 5-methylcytidine. In particular embodiments, the modified mRNA comprises a 5' terminal cap sequence followed by a sequence encoding the Wnt polypeptide, Norrin polypeptide, or Wnt signaling agonist molecule, following by a 3' tailing sequence, such as a polyA or a polyA-G sequence.

In particular embodiments, the polynucleotide is a vector, e.g., an expression vector, and the expression vector comprises a polynucleotide sequence encoding a Wnt polypeptide, Norrin polypeptide, or Wnt signaling agonist molecule described herein operably linked to a promoter sequence, e.g., a promoter sequence that drives expression of the polynucleotide in a cell. In certain embodiments, the vector is a viral vector, e.g., a virus comprising a polynucleotide comprising an expression cassette comprising a promoter operably linked to a DNA or RNA sequence encoding the Wnt polypeptide, Norrin polypeptide, or Wnt signaling agonist molecules. In particular embodiments, the expression cassette comprises 5' and/or 3' cellular or viral UTRs.

The present disclosure also includes functional fragments and variants of the polynucleotides described herein, including variants having at least 50%, at least 60%, at least 70%, at least 80%, at least 85%, at least 90%, at least 95%, at least 98% or at least 99% polynucleotide sequence identity to a polynucleotide described herein. Such variants may comprise one or more nucleotide or nucleoside modifications as compared to any of the sequences disclosed herein, e.g., one or more nucleotide deletion, insertion or substitution. In particular embodiments, the polynucleotides described herein are codon-optimized, e.g., to enhance expression of the encoded polypeptide in a host cell. In particular embodiments, polynucleotide variants comprise one or more modified nucleotide or nucleoside.

The present disclosure also includes cells comprising a polynucleotide or vector that encodes a Wnt polypeptide, Norrin polypeptide, or Wnt signaling agonist molecule described herein. In certain embodiments, the cell is a host cell, such as, e.g., an HEK293 cell that may be used to produce Wnt polypeptides, Norrin polypeptides, or Wnt signaling agonist molecules. In preparing the subject compositions, any host cells may be employed, including but not limited to, for example, mammalian cells (e.g. 293 cells), insect cells (e.g., SF9 cells), microorganisms and yeast. In certain embodiments, the cells are heterologous or autologous to a subject treated with a Wnt polypeptide, Norrin polypeptide, or Wnt signaling agonist molecule described herein. In particular embodiments, the cells were obtained from the subject and transduced with a viral vector described herein. In particular embodiments, the transduced cells are delivered to the subject for treatment. The present disclosure also includes pharmaceutical compositions comprising one or more Wnt polypeptide, Norrin polypeptide, or Wnt signaling agonist molecules, or one or more polynucleotides or vectors comprising sequences encoding a Wnt polypeptide, Norrin polypeptide, ord Wnt signaling agonist molecule.

Pharmaceutical Compositions

Pharmaceutical compositions comprising a tissue-specific Wnt signal enhancing molecule described herein and one or more pharmaceutically acceptable diluent, carrier, or excipient are also disclosed. In particular embodiments, the pharmaceutical composition further comprises one or more Wnt polypeptides, Norrin polypeptides or Wnt signaling agonist molecules described herein.

In further embodiments, pharmaceutical compositions comprising a polynucleotide comprising a nucleic acid sequence encoding a tissue-specific Wnt signal enhancing molecule described herein and one or more pharmaceutically acceptable diluent, carrier, or excipient are also disclosed. In particular embodiments, the pharmaceutical composition further comprises one or more polynucleotides comprising a nucleic acid sequence encoding a Wnt polypeptides, Norrin polypeptides or Wnt signaling agonist molecules as described herein. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences. In certain embodiments, the nucleic acid sequence encoding the tissue-specific Wnt signal enhancing molecule and the nucleic acid sequence encoding the Wnt polypeptide, Norrin polypeptide or Wnt signaling agonist molecule are present in the same polynucleotide.

In further embodiments, pharmaceutical compositions comprising an expression vector, e.g., a viral vector, comprising a polynucleotide comprising a nucleic acid sequence encoding a tissue-specific Wnt signal enhancing molecule described herein and one or more pharmaceutically acceptable diluent, carrier, or excipient are also disclosed. In particular embodiments, the pharmaceutical composition further comprises an expression vector, e.g., a viral vector, comprising a polynucleotide comprising a nucleic acid sequence encoding a Wnt polypeptides, Norrin polypeptides or Wnt signaling agonist molecules as described herein. In certain embodiments, the nucleic acid sequence encoding the tissue-specific Wnt signal enhancing molecule and the nucleic acid sequence encoding the Wnt polypeptide, Norrin polypeptide or Wnt signaling agonist molecule are present in the same polynucleotide, e.g., expression cassette.

The present invention further contemplates a pharmaceutical composition comprising a cell comprising an expression vector comprising a polynucleotide comprising a promoter operatively linked to a nucleic acid encoding a tissue-specific Wnt signal enhancing molecule described herein and one or more pharmaceutically acceptable diluent, carrier, or excipient. In particular embodiments, the pharmaceutical composition further comprises a cell comprising an expression vector comprising a polynucleotide comprising a promoter operatively linked to a nucleic acid sequence encoding a Wnt polypeptide, a Norrin polypeptide or a Wnt signaling agonist molecules as described herein. In certain embodiments, the nucleic acid sequence encoding the tissue-specific Wnt signal enhancing molecule and the nucleic acid sequence encoding the Wnt polypeptide, Norrin polypeptide or Wnt signaling agonist molecule are present in the same polynucleotide, e.g., expression cassette and/or in the same cell. In particular embodiments, the cell is a heterologous cell or an autologous cell obtained from the subject to be treated. In particular embodiments, the cell is a stem cell, e.g., an adipose-derived stem cell or a hematopoietic stem cell.

The present disclosure contemplates pharmaceutical compositions comprising a first molecule for delivery of a tissue-specific Wnt signal enhancing molecule as a first active agent and a second molecule for delivery of a Wnt polypeptide, Norrin polypeptide or Wnt signaling agonist as a second active agent. The first and second molecule may be the same type of molecule or different types of molecules. For example, in certain embodiments, the first and second molecule may each be independently selected from the following types of molecules: polypeptides, small organic molecules, nucleic acids encoding the first or second active agent (optionally DNA or mRNA, optionally modified RNA), vectors comprising a nucleic acid sequence encoding the first or second active agent (optionally expression vectors or viral vectors), and cells comprising a nucleic acid sequence encoding the first or second active agent (optionally an expression cassette).

The subject molecules, alone or in combination, can be combined with pharmaceutically-acceptable carriers, diluents and reagents useful in preparing a formulation that is generally safe, non-toxic, and desirable, and includes excipients that are acceptable for mammalian, e.g., human or primate, use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfate; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide. In particular embodiments, the pharmaceutical compositions are sterile.

Pharmaceutical compositions may further include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In some cases, the composition is sterile and should be fluid to the extent that easy syringability exists. In certain embodiments, it is stable under the conditions of manufacture and storage and is preserved against the contaminating action of microorganisms such as bacteria and fungi. The carrier can be, e.g., a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the tissue-specific Wnt signal enhancing molecule in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the pharmaceutical compositions are prepared with carriers that will protect the fusion protein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions can also be used as pharmaceutically acceptable carriers. These can be prepared according to methods known to those skilled in the art.

It may be advantageous to formulate the pharmaceutical compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser, e.g. syringe, e.g. a prefilled syringe, together with instructions for administration.

The pharmaceutical compositions of the invention encompass any pharmaceutically acceptable salts, esters, or salts of such esters, or any other compound which, upon administration to an animal comprising a human, is capable of providing (directly or indirectly) the biologically active tissue-specific Wnt signal enhancing molecule.

The present invention includes pharmaceutically acceptable salts of the tissue-specific Wnt signal enhancing molecules described herein. The term "pharmaceutically acceptable salt" refers to physiologically and pharmaceutically acceptable salts of the compounds of the invention: i.e., salts that retain the desired biological activity of the parent compound and do not impart undesired toxicological effects thereto. A variety of pharmaceutically acceptable salts are known in the art and described, e.g., in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see "Handbook of Pharmaceutical Salts: Properties, Selection, and Use" by Stahl and Wermuth (Wiley-VCH, 2002).

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. Pharma Sci., 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

In some embodiments, the pharmaceutical composition provided herein comprise a therapeutically effective amount of a tissue-specific Wnt signal enhancing molecule described herein in admixture with a pharmaceutically acceptable carrier, diluent and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer may be in the range of 6.5 to 7.75, preferably 7 to 7.5, and most preferably 7.2 to 7.4.

Methods For Increasing Wnt Activity in a Cell

Tissue-specific Wnt signal enhancing molecules, exemplified herein with respect to fusion proteins, may be used to increase Wnt signaling in a targeted tissue or cell type. In particular embodiments, the Wnt signaling is canonical Wnt signaling. Thus, in some aspects, the present invention provides a method for increasing Wnt increasing or enhancing Wnt signaling in a target tissue or cell, comprising contacting the target tissue or cell with an effective amount of a tissue-specific Wnt signal enhancing molecule of the present invention, wherein the molecule comprises a targeting domain that binds to a cell surface receptor on the target tissue or cell in a tissue- or cell-specific manner. In some embodiments, contacting occurs in vitro, ex vivo, or in vivo, e.g., the subject tissue-specific Wnt signal enhancing molecule is administered or provided to a subject. In particular embodiments, the cell is a cultured cell, and the contacting occurs in vitro.

In certain embodiments, the method comprises further contacting the target tissue or cell with one or more Wnt polypeptides, Norrin polypeptides or Wnt signaling agonist molecules described herein. The present disclosure contemplates contacting a target tissue or cell with a first molecule for delivery of a tissue-specific Wnt signal enhancing molecule as a first active agent and a second molecule for delivery of a Wnt polypeptide, Norrin polypeptide or Wnt signaling agonist as a second active agent. The first and second molecule may be the same type of molecule or different types of molecules. For example, in certain embodiments, the first and second molecule may each be independently selected from the following types of molecules: polypeptides, small organic molecules, nucleic acids encoding the first or second active agent (optionally DNA or mRNA, optionally modified RNA), vectors comprising a nucleic acid sequence encoding the first or second active agent (optionally expression vectors or viral vectors), and cells comprising a nucleic acid sequence encoding the first or second active agent (optionally an expression cassette).

In related aspects, the present invention provides a method for increasing Wnt signaling in a target tissue or cell, comprising contacting the target tissue or cell with an effective amount of a polynucleotide comprising a nucleic acid sequence encoding a tissue-specific Wnt signal enhancing molecule of the present invention, wherein the molecule comprises a targeting domain that binds to a cell surface receptor on the target tissue or cell in a tissue- or cell-specific manner. In certain embodiments, the target tissue or cell is also contacted with a polynucleotide comprising a nucleic acid sequence that encodes a Wnt polypeptide, Norrin polypeptides or Wnt signaling agonist. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences. In certain embodiments, the nucleic acid sequence encoding the tissue-specific Wnt signal enhancing molecule and the nucleic acid sequence encoding the Wnt polypeptide, Norrin polypeptide or Wnt signaling agonist molecule are present in the same polynucleotide.

In related aspects, the present invention provides a method for increasing Wnt signaling in a target tissue or cell, comprising contacting the target tissue or cell with an effective amount of a vector comprising a nucleic acid sequence encoding a tissue-specific Wnt signal enhancing molecule of the present invention, wherein the molecule comprises a targeting domain that binds to a cell surface receptor on the target tissue or cell in a tissue- or cell-specific manner. In certain embodiments, the target tissue or cell is also contacted with a vector comprising a nucleic acid sequence that encodes a Wnt polypeptide, Norrin polypeptides or Wnt signaling agonist. In certain embodiments, the vector is an expression vector, and may comprise a promoter operatively linked to the nucleic acid sequence. In particular embodiments, the vector is a viral vector. In certain embodiments, the nucleic acid sequence encoding the tissue-specific Wnt signal enhancing molecule and the nucleic acid sequence encoding the Wnt polypeptide, Norrin polypeptide or Wnt signaling agonist molecule are present in the same vector, e.g., in the same expression cassette.

In related aspects, the present invention provides a method for increasing Wnt signaling in a target tissue, comprising contacting the target tissue with an effective amount of a cell comprising a nucleic acid sequence encoding a tissue-specific Wnt signal enhancing molecule of the present invention, wherein the molecule comprises a targeting domain that binds to a cell surface receptor on the target tissue or cell in a tissue- or cell-specific manner. In certain embodiments, the target tissue is also contacted with a cell comprising a nucleic acid sequence that encodes a Wnt polypeptide, Norrin polypeptides or Wnt signaling agonist. In certain embodiments, the nucleic acid sequence encoding the tissue-specific Wnt signal enhancing molecule and the nucleic acid sequence encoding the Wnt polypeptide, Norrin polypeptide or Wnt signaling agonist molecule are present in the same cell. In particular embodiments, the cell is a heterologous cell or an autologous cell obtained from the subject to be treated. In certain embodiments, the cell was transduced with a vector comprising an expression cassette encoding the tissue-specific Wnt signal enhancing molecule or the Wnt polypeptide, Norrin polypeptide or Wnt signaling agonist molecule. In particular embodiments, the cell is a stem cell, e.g., an adipose-derived stem cell or a hematopoietic stem cell.

Methods For Treating Diseases and Disorders

Tissue-specific Wnt signal enhancing molecules, exemplified herein with respect to fusion proteins, may be used in to treat a disease, disorder or condition, for example, by increasing Wnt signaling in a targeted cell, tissue or organ. Thus, in some aspects, the present invention provides a method for treating a disease or condition in a subject in need thereof, e.g., a disease or disorder associated with reduced Wnt signaling, or for which increased Wnt signaling would provide a therapeutic benefit, comprising contacting the subject with an effective amount of a composition of the present disclosure. In particular embodiments, the composition is a pharmaceutical composition comprising any of: a tissue-specific Wnt signal enhancing molecule, e.g., a small molecule or a polypeptide; a polynucleotide comprising a nucleic acid sequence encoding a tissue-specific Wnt signal enhancing molecule, e.g., a DNA or mRNA, optionally a modified mRNA; a vector comprising a nucleic acid sequence encoding a tissue-specific Wnt signal enhancing molecule, e.g., an expression vector or viral vector; or a cell comprising a nucleic acid sequence encoding a tissue-specific Wnt signal enhancing molecule, e.g., a cell transduced with an expression vector or viral vector encoding a tissue-specific Wnt signal enhancing molecule. In particular embodiments, the disease or condition is a pathological disease or disorder, or an injury, e.g., an injury resulting from a wound. In certain embodiments, the wound may be the result of another therapeutic treatment. In certain embodiments, the disease or condition comprises impaired tissue repair, healing or regeneration, or would benefit from increased tissue repair, healing or regeneration. In some embodiments, contacting occurs in vivo, i.e., the subject composition is administered to a subject.

In certain embodiments, the method comprises further contacting the subject with a pharmaceutical composition comprising one or more Wnt polypeptides, Norrin polypeptides or Wnt signaling agonist molecules described herein. The present disclosure contemplates contacting a subject with a first molecule for delivery of a tissue-specific Wnt signal enhancing molecule as a first active agent and a second molecule for delivery of a Wnt polypeptide, Norrin polypeptide or Wnt signaling agonist as a second active agent. The first and second molecule may be the same type of molecule or different types of molecules. For example, in certain embodiments, the first and second molecule may each be independently selected from the following types of molecules: polypeptides, small organic molecules, nucleic acids encoding the first or second active agent (optionally DNA or mRNA, optionally modified RNA), vectors comprising a nucleic acid sequence encoding the first or second active agent (optionally expression vectors or viral vectors), and cells comprising a nucleic acid sequence encoding the first or second active agent (optionally an expression cassette).

In related aspects, the present invention provides a method for treating a disease or condition, e.g., a disease or disorder associated with reduced Wnt signaling, or for which in need thereof with a pharmaceutical composition comprising an effective amount of a polynucleotide comprising a nucleic acid sequence encoding a tissue-specific Wnt signal enhancing molecule of the present invention, wherein the molecule comprises a targeting domain that binds to a cell surface receptor on the target tissue or cell in a tissue- or cell-specific manner. In certain embodiments, the subject is also contacted with a pharmaceutical composition comprising an effective amount of a polynucleotide comprising a nucleic acid sequence that encodes a Wnt polypeptide, Norrin polypeptides or Wnt signaling agonist. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences. In certain embodiments, the nucleic acid sequence encoding the tissue-specific Wnt signal enhancing molecule and the nucleic acid sequence encoding the Wnt polypeptide, Norrin polypeptide or Wnt signaling agonist molecule are present in the same polynucleotide.

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a vector comprising a nucleic acid sequence encoding a tissue-specific Wnt signal enhancing molecule of the present invention, wherein the molecule comprises a targeting domain that binds to a cell surface receptor on the target tissue or cell in a tissue- or cell-specific manner. In certain embodiments, the subject is also contacted with a pharmaceutical composition comprising an effective amount of a vector comprising a nucleic acid sequence that encodes a Wnt polypeptide, Norrin polypeptides or Wnt signaling agonist. In certain embodiments, the vector is an expression vector, and may comprise a promoter operatively linked to the nucleic acid sequence. In particular embodiments, the vector is a viral vector. In certain embodiments, the nucleic acid sequence encoding the tissue-specific Wnt signal enhancing molecule and the nucleic acid sequence encoding the Wnt polypeptide, Norrin polypeptide or Wnt signaling agonist molecule are present in the same vector, e.g., in the same expression cassette.

In related aspects, the present invention provides a method for treating a disease or condition, e.g., a disease or disorder associated with reduced Wnt signaling, or for which in need thereof with a pharmaceutical composition comprising an effective amount of a cell comprising a nucleic acid sequence encoding a tissue-specific Wnt signal enhancing molecule of the present invention, wherein the molecule comprises a targeting domain that binds to a cell surface receptor on the target tissue or cell in a tissue- or cell-specific manner. In certain embodiments, the subject is also contacted with a cell comprising a nucleic acid sequence that encodes a Wnt polypeptide, Norrin polypeptides or Wnt signaling agonist. In certain embodiments, the nucleic acid sequence encoding the tissue-specific Wnt signal enhancing molecule and the nucleic acid sequence encoding the Wnt polypeptide, Norrin polypeptide or Wnt signaling agonist molecule are present in the same cell. In particular embodiments, the cell is a heterologous cell or an autologous cell obtained from the subject to be treated. In certain embodiments, the cell was transduced with a vector comprising an expression cassette encoding the tissue-specific Wnt signal enhancing molecule or the Wnt polypeptide, Norrin polypeptide or Wnt signaling agonist molecule. In particular embodiments, the cell is a stem cell, e.g., an adipose-derived stem cell or a hematopoietic stem cell.

In other aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a polynucleotide comprising a nucleic acid sequence encoding a Wnt polypeptide, Norrin polypeptide or Wnt signaling agonist. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences.

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a vector comprising a nucleic acid sequence encoding a Wnt polypeptide, Norrin polypeptide or Wnt signaling agonist. In certain embodiments, the vector is an expression vector, and may comprise a promoter operatively linked to the nucleic acid sequence. In particular embodiments, the vector is a viral vector.

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a cell comprising a nucleic acid sequence encoding a Wnt polypeptide, Norrin polypeptide or Wnt signaling agonist. In particular embodiments, the cell is a heterologous cell or an autologous cell obtained from the subject to be treated. In certain embodiments, the cell was transduced with a vector comprising an expression cassette encoding the Wnt polypeptide, Norrin polypeptide or Wnt signaling agonist molecule. In particular embodiments, the cell is a stem cell, e.g., an adipose-derived stem cell or a hematopoietic stem cell.

Wnt signaling plays key roles in the developmental process and maintenance of stem cells. Reactivation of Wnt signals is associated with regeneration and repair of most tissues after injuries and diseases. Tissue-specific Wnt signal enhancing molecules may provide benefit of healing and tissue repair in response to injuries and diseases. Causes of tissue damage and loss include but are not limited to aging, degeneration, hereditary conditions, infection and inflammation, traumatic injuries, toxins/metabolic-induced toxicities, or other pathological conditions. Wnt signals and enhancers of Wnt signals have been shown to activate adult, tissue-resident stem cells. In some embodiments, the compounds of the invention are administered for use in treating diseased or damaged tissue, for use in tissue regeneration and for use in cell growth and proliferation, and/or for use in tissue engineering.

Human diseases associated with mutations of the Wnt pathway provide strong evidence for enhancement of Wnt signals in the treatment and prevention of diseases. Preclinical in vivo and in vitro studies provide additional evidence of involvement of Wnt signals in many disease conditions and further support utilization of tissue-specific Wnt signal enhancing molecules in various human diseases. For example, compositions of the present invention may be used to promote or increase bone growth or regeneration, bone grafting, healing of bone fractures, treatment of osteoporosis and osteoporotic fractures, spinal fusion, osseointegration of orthopedic devices, tendon-bone integration, tooth growth and regeneration, dental implantation, periodontal diseases, maxillofacial reconstruction, and osteonecrosis of the jaw. They may also be used in the treatment of alopecia; enhancing regeneration of sensory organs, e.g. treatment of hearing loss, treatment of vestibular hypofunction, treatment of macular degeneration, treatment of vitreoretinopathy, diabetic retinopathy, or other diseases of retinal degeneration, Fuchs' dystrophy, other cornea disease, etc.; treatment of stroke, traumatic brain injury, Alzheimer's disease, multiple sclerosis and other conditions affecting the blood brain barrier; treatment of spinal cord injuries, other spinal cord diseases. The compositions of this invention may also be used in treatment of oral mucositis, intestinal mucositis, treatment of short bowel syndrome, inflammatory bowel diseases (IBD), other gastrointestinal disorders; treatment of metabolic syndrome; treatment of diabetes, treatment of pancreatitis, conditions where exocrine or endocrine pancreas tissues are damaged; conditions where enhanced epidermal regeneration is desired, e.g., epidermal wound healing, treatment of diabetic foot ulcers, syndromes involving tooth, nail, or dermal hypoplasia, etc., conditions where angiogenesis is beneficial; treatment of myocardial infarction, coronary artery disease, heart failure; enhanced growth of hematopoietic cells, e.g. enhancement of hematopoietic stem cell transplants from bone marrow, mobilized peripheral blood, treatment of immunodeficiencies, graft versus host diseases, etc.; treatment of acute kidney injuries, chronic kidney diseases; treatment of lung diseases, chronic obstructive pulmonary diseases (COPD), idiopathic pulmonary fibrosis, enhanced regeneration of lung tissues. The compositions of the present invention may also be used in enhanced regeneration of liver cells, e.g. liver regeneration, treatment of cirrhosis, enhancement of liver transplantations, treatment of acute liver failure, treatment of chronic liver diseases with hepatitis C or B virus infection or post-antiviral drug therapies, alcoholic liver diseases, non-alcoholic liver diseases with steatosis or steatohepatitis, and the like. The compositions of this invention may treat diseases and disorders including, without limitation, conditions in which regenerative cell growth is desired.

Human genetics involving loss-of-function or gain-of-function mutations in Wnt signaling components show strong evidence supporting enhancing Wnt signals for bone growth. Conditions in which enhanced bone growth is desired may include, without limitation, fractures, grafts, ingrowth around prosthetic devices, osteoporosis, osteoporotic fractures, spinal fusion, osteonecrosis of the jaw, dental implantation, periodontal diseases, maxillofacial reconstruction, and the like. Tissue-specific Wnt signal enhancing molecules enhance and promote Wnt signals which are critical in promoting bone regeneration. Methods for regeneration of bone tissues benefit from administration of the compounds of the invention, which can be systemic or localized. In some embodiments, bone marrow cells are exposed to molecules of the invention, such that stem cells within that marrow become activated.

In some embodiments, bone regeneration is enhanced by contacting a responsive cell population, e.g. bone marrow, bone progenitor cells, bone stem cells, etc. with an effective dose of a molecule of the invention. Methods for regeneration of bone tissues benefit from administration of the compounds of the invention, which can be systemic or localized. In some such embodiments, the contacting is performed in vivo. In other such embodiments, the contacting is performed ex vivo. The molecule may be localized to the site of action, e.g. by loading onto a matrix, which is optionally biodegradable, and optionally provides for a sustained release of the active agent. Matrix carriers include, without limitation, absorbable collagen sponges, ceramics, hydrogels, polymeric microspheres, nanoparticles, bone cements, and the like.

Compositions comprising one or more of the molecules of the invention can be used for the in vivo treatment of skeletal tissue deficiencies. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions. The compositions of the present invention can be used as part of a regimen for restoring cartilage function to a connective tissue, for the repair of defects or lesions in cartilage tissue such as degenerative wear and arthritis, trauma to the tissue, displacement of torn meniscus, meniscectomy, a luxation of a joint by a torn ligament, malalignment of joints, bone fracture, or by hereditary disease.

The compositions of the invention may also be used for treatment of periodontal diseases. Periodontal diseases are a leading cause of tooth loss and are linked to multiple systemic conditions. In some embodiments, tooth or underlying bone regeneration is enhanced by contacting a responsive cell population. In some such embodiments, the contacting is performed in vivo. In other such embodiments, the contacting is performed ex vivo, with subsequent implantation of the activated stem or progenitor cells. The molecule may be localized to the site of action, e.g. by loading onto a matrix, which is optionally biodegradable, and optionally provides for a sustained release of the active agent. Matrix carriers include, without limitation, absorbable collagen sponges, ceramics, hydrogels, bone cements, polymeric microspheres, nanoparticles, and the like.

Studies have shown that biology of Wnt signaling and R-spondins are capable of promoting sensory hair cell regeneration in the inner ear following injuries, aging, or degeneration. Loss of sensory hair cells in the inner ear involved in hearing loss or vestibular hypofunction may also benefit from the compositions of the invention. In the inner ear, the auditory organ houses mechanosensitive hair cells required for translating sound vibration to electric impulses. The vestibular organs, comprised of the semicircular canals (SSCs), the utricle, and the saccule, also contain sensory hair cells in order to detect head position and motion. Compositions of the present invention can be used, for example, in an infusion; in a matrix or other depot system; or other topical application to the ear for enhancement of auditory regeneration.

The compositions of this invention may also be used in regeneration of retinal tissue. In the adult mammalian retina, Muller glia cells are capable of regenerating retinal cells, including photoreceptors, for example after neurotoxic injury in vivo. Wnt signaling and enhancers of Wnt signals can promote proliferation of Muller glia-derived retinal progenitors after damage or during degeneration. The compositions of the invention may also be used in the regeneration of tissues and other cell types in the eye. For examples age-related macular degeneration (AMD), other retina degenerative diseases, cornea diseases, Fuchs' dystrophy, vitreoretinopathy, hereditary diseases, etc. can benefit from the compositions of the present inventions. AMD is characterized by progressively decreased central vision and visual acuity. Fuchs' dystrophy is characterized by progressive loss of cornea endothelial cells. Wnt signal and enhancing of Wnt signal can promote regeneration of cornea endothelium, retina epithelium, etc. in the eye tissue. In other embodiments, compositions of the present invention can be used, for example, in an infusion; in a matrix or other depot system; or other topical application to the eye for retinal regeneration and treatment of macular degeneration.

Specific populations of proliferating cells for homeostatic renewal of hepatocytes have been identified through lineage tracing studies, for example Axin2-positive cells in pericentral region. Lineage tracing studies also identified additional potential liver progenitor cells, including but not limited to Lgr-positive cells. The self-renewing liver cells and other populations of potential progenitor cells, including Lgr5-positive and Axin2-positive cells, are identified to be capable of regeneration responding to Wnt signals and/or R-spondins following injuries. Numerous preclinical models of acute liver injury and failure and chronic liver diseases showed recovery and regeneration of hepatocytes benefit from enhancing Wnt signals. The compositions of this invention may be used in treatment of acute liver failure, acute alcoholic liver injuries, treatment of chronic liver diseases with hepatitis C or B virus infection or post-antiviral drug therapies, chronic alcoholic liver diseases, non-alcoholic fatty liver diseases and non-alcoholic steatohepatitis (NASH), treatment of cirrhosis and severe chronic liver diseases of all causes, and enhanced regeneration of liver cells. Methods for regeneration of liver tissue benefit from administration of the compounds of the invention, which can be systemic or localized. These include, but are not limited to, methods of systemic administration and methods of localized administration e.g. by injection into the liver tissue, by injection into veins or blood vessels leading into the liver, by implantation of a sustained release formulation, and the like.

Wnt signals play an important role in regeneration of various epithelial tissues. Various epidermal conditions benefit from treatment with the compounds of the present invention. Mucositis occurs when there is a breakdown of the rapidly divided epithelial cells lining the gastro-intestinal tract, leaving the mucosal tissue open to ulceration and infection. The part of the epithelial lining that covers the mouth, called the oral mucosa, is one of the most sensitive parts of the body and is particularly vulnerable to chemotherapy and radiation. Oral mucositis is probably the most common, debilitating complication of cancer treatments, particularly chemotherapy and radiation. In addition, the compositions of the invention may also benefit treatment of intestinal mucositis, short bowel syndrome, inflammatory bowel diseases (IBD), or other gastrointestinal disorders. Other epidermal conditions include epidermal wound healing, diabetic foot ulcers, syndromes involving tooth, nail, or dermal hypoplasia, and the like. Molecules of the present invention may be used in all these conditions, where regenerative cells are contacted with compounds of the invention. Methods for regeneration of epithelial tissues benefit from administration of the compounds of the invention, which can be systemic or localized. Contacting can be, for example, topical, including intradermal, subdermal, in a gel, lotion, cream etc. applied at targeted site, etc.

In addition to skin and gastrointestinal tract, Wnt signals and enhancement and promotion of Wnt signals also play an important role in repair and regeneration of tissues including pancreas, kidney, and lung in preclinical models. Tissue-specific Wnt signal enhancing molecules may benefit various disease conditions involving exocrine and endocrine pancreas, kidney, or lung. The compositions of the invention may be used in treatment of metabolic syndrome; treatment of diabetes, treatment of acute or chronic pancreatitis, exocrine pancreatic insufficiency, treatment of acute kidney injuries, chronic kidney diseases, treatment of lung diseases, including but not limited to chronic obstructive pulmonary diseases (COPD), idiopathic pulmonary fibrosis, other conditions that cause loss of lung epithelial tissues. Methods for regeneration of these tissues benefit from administration of the compounds of the invention, which can be systemic or localized.

Epidermal Wnt signaling, in coordination with signaling via other development factors, is critical for adult hair follicle regeneration. Hair loss is a common problem, and androgenetic alopecia, often called male pattern baldness, is the most common form of hair loss in men. In some embodiments, hair follicle regeneration is enhanced by contacting a responsive cell population with a molecule of the present invention. In some such embodiments, the contacting is performed in vivo. In other such embodiments, the contacting is performed ex vivo. The molecule may be localized to the site of action, e.g. topical lotions, gels, creams and the like.

Stroke, traumatic brain injury, Alzheimer's disease, multiple sclerosis and other conditions affecting the blood brain barrier (BBB) may be treated with tissue-specific Wnt signal enhancing molecules of the invention. Angiogenesis is critical to ensure the supply of oxygen and nutrients to many tissues throughout the body, and is especially important for the CNS as the neural tissue is extremely sensitive to hypoxia and ischemia. CNS endothelial cells which form the BBB differ from endothelial cells in non-neural tissue, in that they are highly polarized cells held together by tight junctions and express specific transporters. Wnt signaling regulates CNS vessel formation and/or function. Conditions in which the BBB is compromised can benefit from administration of the compounds of the invention, which can be systemic or localized e.g. by direct injection, intrathecal administration, implantation of sustained release formulations, and the like. In addition, Wnt signal is actively involved in neurogenesis and plays a role of neuroprotection following injury. The compositions of the present invention may also be used in treatment of spinal cord injuries, other spinal cord diseases, stroke, traumatic brain injuries, etc.

Wnt signals also play a role in angiogenesis. Tissue-specific Wnt signal enhancing molecules may benefit conditions where angiogenesis is beneficial, treatment of myocardial infarction, coronary artery disease, heart failure, etc., and conditions from hereditary diseases. Methods for regeneration of these tissues benefit from administration of the compounds of the invention, which can be systemic or localized.

In certain embodiments, methods of the present invention promote tissue regeneration, e.g., in a tissue subjected to damage or tissue or cell reduction or loss. The loss or damage can be anything which causes the cell number to diminish, including diseases or injuries. For example, an accident, an autoimmune disorder, a therapeutic side-effect or a disease state could constitute trauma. Tissue regeneration increases the cell number within the tissue and preferably enables connections between cells of the tissue to be re-established, and more preferably the functionality of the tissue to be regained.

In particular embodiments, a composition is administered parenterally, e.g., intravenously, orally, rectally, or by injection. In some embodiments, it is administered locally, e.g., topically or intramuscularly. In some embodiments, a composition is administered to target tissues, e.g., to bone, joints, ear tissue, eye tissue, gastrointestinal tract, skin, a wound site or spinal cord. Methods of the invention may be practiced in vivo or ex vivo. In some embodiments, the contacting of a target cell or tissue with a tissue-specific Wnt signal enhancing molecule is performed ex vivo, with subsequent implantation of the cells or tissues, e.g., activated stem or progenitor cells, into the subject. The skilled artisan can determine an appropriate site of and route of administration based on the disease or disorder being treated.

The dose and dosage regimen may depend upon a variety of factors readily determined by a physician, such as the nature of the disease or disorder, the characteristics of the subject, and the subject's history. In particular embodiments, the amount of tissue-specific Wnt signal enhancing molecule, e.g., fusion protein, administered or provided to the subject is in the range of about 0.01 mg/kg to about 50 mg/kg, 0.1 mg/kg to about 500 mg/kg, or about 0.1 mg/kg to about 50 mg/kg of the subject's body weight.

In certain embodiments, the subject may be any mammal, e.g. human, rodent (e.g. mice, rats, gerbils), rabbit, feline, canine, goat, ovine, pig, equine, bovine, or primate.

In some embodiments, the subject method results in a therapeutic benefit, e.g., preventing the development of a disorder, halting the progression of a disorder, reversing the progression of a disorder, etc. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy.

In certain embodiments, the disclosure provides a method for treating or preventing a disease or disorder associated with reduced Wnt signaling or that would benefit from increased Wnt signaling activity in bone tissue, such as, for example, any of the conditions dsclosed herein wherein bone growth is desirable, comprising providing to a subject in need thereof a pharmaceutical composition comprising a Wnt signal enhancing molecule comprising a targeting domain that binds bone tissue, e.g., a targeting domain that specifically binds to PTH1R, wherein the Wnt signal enhancing molecule increases or enhances Wnt signaling in the subject's bone tissue. In certain embodiments, the pharmaceutical composition is administered orally or systemically, e.g., parenterally. In particular embodiments, the Wnt signal enhancing molecule comprises an action domain comprising an R-spondin Furin domain 1 or a fragment or variant thereof and, optionally, a mutated Furin domain 2 or a fragment or variant thereof.

In certain embodiments, the disclosure provides a method for treating or preventing a disease or disorder associated with reduced Wnt signaling or that would benefit from increased Wnt signaling activity in liver tissue, such as, for example, any of the diseases or disorders disclosed herein that would benefit from liver regeneration, comprising providing to a subject in need thereof a pharmaceutical composition comprising a Wnt signal enhancing molecule comprising a targeting domain that binds liver tissue, e.g., a targeting domain that specifically binds to ASGR1, ASGR2, TFR2 or SLC10A1, wherein the Wnt signal enhancing molecule increases or enhances Wnt signaling in the subject's liver tissue. In certain embodiments, the pharmaceutical composition is administered orally or systemically, e.g., parenterally. In particular embodiments, the Wnt signal enhancing molecule comprises an action domain comprising an R-spondin Furin domain 1 or a fragment or variant thereof and, optionally, a mutated Furin domain 2 or a fragment or variant thereof.

In certain embodiments, the disclosure provides a method for treating or preventing a disease or disorder associated with reduced Wnt signaling or that would benefit from increased Wnt signaling activity in oral mucosa tissue, such as, for example, oral mucositis, comprising providing to a subject in need thereof a pharmaceutical composition comprising a Wnt signal enhancing molecule comprising a targeting domain that binds oral mucosa tissue, e.g., a targeting domain that specifically binds to LYPD3 or DSG3, wherein the Wnt signal enhancing molecule increases or enhances Wnt signaling in the subject's oral mucosa tissue. In certain embodiments, the pharmaceutical composition is administered orally or systemically, e.g., parenterally. In particular embodiments, the Wnt signal enhancing molecule comprises an action domain comprising an R-spondin Furin domain 1 or a fragment or variant thereof and, optionally, a mutated Furin domain 2 or a fragment or variant thereof.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular biology, cell biology and biochemistry can be found in such standard textbooks as "Molecular Cloning: A Laboratory Manual, 3rd Ed." (Sambrook et al., Harbor Laboratory Press 2001); "Short Protocols in Molecular Biology, 4th Ed." (Ausubel et al. eds., John Wiley & Sons 1999); "Protein Methods" (Bollag et al., John Wiley & Sons 1996); "Nonviral Vectors for Gene Therapy" (Wagner et al. eds., Academic Press 1999); "Viral Vectors" (Kaplift & Loewy eds., Academic Press 1995); "Immunology Methods Manual" (I. Lefkovits ed., Academic Press 1997); and "Cell and Tissue Culture: Laboratory Procedures in Biotechnology" (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech In the following examples, recombinant human Rspo2 preparations composed of a fragment (S36-E143) containing the Fu1 and Fu2 domains, were used as the positive controls. For the Wnt signal enhancers in the format of scFv (FIGS. 8, 11, 12, 15, and 16), a monomeric form of Rspo2 was used (specified by SEQ ID NO 33 and 34, with short tags to assistant protein purification). For the Wnt signal enhancers in the format of appended IgG (FIGS. 13, 14, 17, 18, and 19), fusions of the same Rspo2 Fu1 and Fu2 domains in frame with human IgG Fc fragments were used. When tested in parallel under the same experimental conditions, no significant difference was observed in vitro between these two forms, thus both are generally referred to as Rspo2 positive control without further specification.

A brief summary of the various constructs and sequences described in the Examples and accompanying Figures is provided below in Table 1.

TABLE 1

| | | Description of Sequence Identifiers |
|---|---|---|
| FIG. | SEQ ID NO: | Brief Description |
| 4 | 1 | Full length human Rspo1 (polypeptide (PP)) |
| 4 | 2 | Full length human Rspo2 (PP) |
| 4 | 3 | Full length human Rspo3 (PP) |
| 4 | 4 | Full length human Rspo4 (PP) |
| 5 | 5 & 6 | anti-GFP, Rspo2 wild type (polynucleotide (PN) and PP) |
| 5 | 7 & 8 | anti-GFP, Rspo2 (F105A/F109A) (PN & PP) |

TABLE 1-continued

Description of Sequence Identifiers

| FIG. | SEQ ID NO: | Brief Description |
|---|---|---|
| 5 | 9 & 10 | anti-ASGR1, Rspo2 (F105A/F109A) (PN & PP) |
| 6A | 5, 6, 7, 8, 9, 10 | see above |
| 6A | 11 & 12 | anti-GFP, Rspo2 (S47A/N50A/F105A/F109A) (PN & PP) |
| 6A | 13 & 14 | anti-ASGR1, Rspo2 (S47A/N50A/F105A/F109A) (PN & PP) |
| 6A | 15 & 16 | anti-GFP, Rspo2 (R65A/R69A/Q70A/F105A/F109A) (PN & PP) |
| 6A | 17 & 18 | anti-ASGR1, Rspo2 (R65A/R69A/Q70A/F105A/F109A) (PN & PP) |
| 6B | 5, 6, 7, 8, 9, 10 | see above |
| 6B | 19 & 20 | anti-GFP, Rspo2 (F105A) (PN & PP) |
| 6B | 21 & 22 | anti-ASGR1, Rspo2 (F105A) (PN & PP) |
| 6B | 23 & 24 | anti-GFP, Rspo2 (F109A) (PN & PP) |
| 6B | 25 & 26 | anti-ASGR1, Rspo2 (F109A) (PN & PP) |
| 6C | 5, 6, 7, 8 | |
| 6C | 27 & 28 | anti-TFR, Rspo2 (F105A/F109A) (PN & PP) |
| 6C | 29 & 30 | anti-GFP, Rspo2 (F105R/F109A) (PN & PP) |
| 6C | 31 & 32 | anti-TFR1, Rspo2 (F105R/F109A) (PN & PP) |
| 7 | 5, 6, 7, 8, 27, 28 | see above |
| 8A | 7, 8, 9, 10, 25, 26, 27, 28 | see above |
| 8B-C | 33 & 34 | Rspo2 Furin domains (S36-E143) (PN & PP) |
| 9 | 35 & 36 | anti-GFP IgG2 N-HC<br>anti-GFP light chain (PN & PP) |
| 9 | 37 & 38 | Rspo2 (F105R/F109A), anti-GFP Heavy chain IgG2 (PN & PP) |
| 9 | 39 & 40 | anti-TFR1 IgG2 N-HC<br>anti-TFR1 light chain (PN & PP) |
| 9 | 41 & 42 | Rspo2 (F105R/F109A), anti-TFR1 Heavy chain, IgG2 (PN & PP) |
| 9 | 43 & 44 | anti-GFP IgG2 N-LC<br>Rspo2 (F105R/F109A), anti-GFP light chain (PN & PP) |
| 9 | 45 & 46 | anti-GFP Heavy chain IgG2 (PN & PP) |
| 9 | 47 & 48 | anti-TFR1 IgG2 N-LC<br>Rspo2 (F105R/F109A), anti-TFR1 light chain (PN & PP) |
| 9 | 49 & 50 | anti-TFR1 Heavy chain, IgG2 (PN & PP) |
| 10 | 5, 6, 7, 8, 9, 10, 27, 28, 29, 30 | see above |
| 10 | 51 & 52 | anti-ASGR1, Rspo2 (F105R/F109A) (PN & PP) |
| 10 | 31 & 32 | see above |
| 10 | 53 & 54 | anti-GFP, Rspo2 (R86E/F105R/F109A) (PN & PP) |
| 10 | 55 & 56 | anti-ASGR1, Rspo2 (R86E/F105R/F109A) (PN & PP) |
| 10 | 57 & 58 | anti-TFR1, Rspo2 (R86E/F105R/F109A) (PN & PP) |
| 10 | 59 & 60 | anti-GFP, Rspo2 (R86E/F105R/F109A/R121E) (PN & PP) |
| 10 | 61 & 62 | anti-ASGR1, Rspo2 (R86E/F105R/F109A/R121E) (PN & PP) |
| 10 | 63 & 64 | anti-TFR1, Rspo2 (R86E/F105R/F109A/R121E) (PN & PP) |
| 10 | 65 & 66 | anti-GFP, Rspo2 (K58E/R86E/F105R/F109A/R121E) (PN & PP) |
| 10 | 67 & 68 | anti-ASGR1, Rspo2 (K58E/R86E/F105R/F109A/R121E) (PN & PP) |
| 10 | 69 & 70 | anti-TFR1, Rspo2 (K58E/R86E/F105R/F109A/R121E) (PN & PP) |
| 11 | 29-32 | see above |
| 12 | 9 & 10 | see above |
| 13 | 35-42 | see above |
| 14 A-C | 35 & 36 | anti-GFP IgG2 N-HC<br>see above |
| 14 A-C | 37 & 38 | see above |
| 14 A-C | 71 & 72 | anti-ASGR1 IgG2 N-HC<br>anti-ASGR1 light chain (PN & PP) |
| 14 A-C | 73 & 74 | Rspo2 (F105R/F109A), anti-ASGR1 Heavy chain IgG2 (PN & PP) |
| 14 A-C | 39 & 40 | anti-TFR1 IgG2 N-HC<br>see above |
| 14 A-C | 41 & 42 | see above |
| 14 A-C | 43 & 44 | anti-GFP IgG2 N-LC<br>see above |
| 14 A-C | 45 & 46 | see above |
| 14 A-C | 47 & 48 | anti-TFR1 IgG2 N-LC<br>see above |
| 14 A-C | 49 & 50 | see above |
| 14 A-C | 75 & 76 | anti-GFP IgG2 C-LC<br>anti-GFP light chain, Rspo2 (F105R/F109A) (PN & PP) |
| 14 A-C | 45 & 46 | see above |
| 14 A-C | 77 & 78 | anti-ASGR1 IgG2 C-LC<br>anti-ASGR1 light chain, Rspo2 (F105R/F109A) (PN & PP) |
| 14 A-C | 79 & 80 | anti-ASGR1 Heavy chain IgG2 (PN & PP)<br>anti-TFR1 IgG2 C-LC |

TABLE 1-continued

Description of Sequence Identifiers

| FIG. | SEQ ID NO: | Brief Description |
|---|---|---|
| 14 A-C | 81 & 82 | anti-TFR1 light chain, Rspo2 (F105R/F109A) (PN & PP) |
| 14 A-C | 49 & 50 | see above |
| | | anti-GFP IaG1 N297GN-HC |
| 14 D-E | 35 & 36 | see above |
| 14 D-E | 83 & 84 | Rspo2 (F105R/F109A), anti-GFP Heavy chain N297G (PN &PP) |
| | | anti-ASGR1 IaG1 N297GN-HC |
| 14 D-E | 71 & 72 | see above |
| 14 D-E | 85 & 86 | Rspo2 (F105R/F109A), anti-ASGR1 Heavy chain N297G (PN & PP) |
| | | anti-TFR1 IaG1 N297G N-HC |
| 14 D-E | 39 & 40 | see above |
| 14 D-E | 87 & 88 | Rspo2 (F105R/F109A), anti-TFR1 Heavy chain N297G (PN &PP) |
| | | anti-GFP IeG1 N297GN-LC |
| 14 D-E | 43 & 44 | see above |
| 14 D-E | 89 & 90 | anti-GFP Heavy chain N297G (PN & PP) |
| | | anti-TFR1 IeG1 N297GN-LC |
| 14 D-E | 47 & 48 | see above |
| 14 D-E | 91 & 92 | anti-TFR1 Heavy chain N297G (PN & PP) |
| | | anti-GFP IeG1 N297G C-LC |
| 14 D-E | 75 & 76 | see above |
| 14 D-E | 89 & 90 | see above |
| | | anti-ASGR1 IeG1 N297G C-LC |
| 14 D-E | 77 & 78 | see above |
| 14 D-E | 93 & 94 | anti-ASGR1 Heavy chain N297G (PN & PP) |
| | | anti-TFR1 IeG1 N297G C-LC |
| 14 D-E | 81 & 82 | see above |
| 14 D-E | 91 & 92 | see above |
| 15A | 95 & 96 | anti-GFP, Rspo1 wild type (PN & PP) |
| 15A | 5 & 6 | see above |
| 15A | 97 & 98 | anti-GFP, Rspo3 wild type (PN & PP) |
| 15A | 99 & 100 | anti-GFP, Rspo4 wild type (PN & PP) |
| 15B | 7 & 8 | see above |
| 15B | 29 & 30 | see above |
| 15B | 9 & 10 | see above |
| 15B | 51 & 52 | see above |
| 15B | 27 & 28 | see above |
| 15B | 31 & 32 | see above |
| 15C | 101 & 102 | anti-GFP, Rspo3 (F106A/F110A) (PN & PP) |
| 15C | 103 & 104 | anti-GFP, Rspo3 (F106R/F110A) (PN & PP) |
| 15C | 105 & 106 | anti-ASGR1, Rspo3 (F106A/F110A) (PN & PP) |
| 15C | 107 & 108 | anti-ASGR1, Rspo3 (F106R/F110A) (PN & PP) |
| 15C | 109 & 110 | anti-TFR1, Rspo3 (F106A/F110A) (PN & PP) |
| 15C | 111 & 112 | anti-TFR1, Rspo3 (F106R/F110A) (PN & PP) |
| 16B | 97 & 98 | see above |
| 16B | 103 & 104 | see above |
| 16B | 113 & 114 | anti-GFP Rspo3 RR (PN & PP) |
| 16B | 115 & 116 | anti-GFP Rspo3 EE (PN & PP) |
| 16B | 117 & 118 | anti-GFP Rspo3 RE (PN & PP) |
| 16B | 119 & 120 | anti-GFP Rspo3 EA (PN & PP) |
| 16B | 121 & 122 | anti-GFP Rspo3 EEARA (PN & PP) |
| 16C | 97 & 98 | see above |
| 16C | 107 & 108 | see above |
| 16C | 123 & 124 | anti-ASGR1 Rspo3 RR (PN & PP) |
| 16C | 125 & 126 | anti-ASGR1 Rspo3 EE (PN & PP) |
| 16C | 127 & 128 | anti-ASGR1 Rspo3 RE (PN & PP) |
| 16C | 129 & 130 | anti-ASGR1 Rspo3 EA (PN & PP) |
| 16C | 131 & 132 | anti-ASGR1 Rspo3 EEARA (PN & PP) |
| | | anti-ZNRF3-anti-GFP |
| 17 | 133 & 134 | anti-GFP light chain (S176K) (PN & PP) |
| 17 | 135 & 136 | anti-ZNRF3 light chain (S176E) (PN & PP) |
| 17 | 137 & 138 | anti-ZNRF3, anti-GFP Heavy chain (PN & PP) |
| | | anti-ZNRF3-anti-ASGR1 |
| 17 | 139 & 140 | anti-ASGR1 light chain (S176K) (PN & PP) |
| 17 | 135 & 136 | see above |
| 17 | 141 & 142 | anti-ZNRF3, anti-ASGR1 Heavy chain (PN & PP) |
| | | anti-ZNRF3-anti-TFR1 |
| 17 | 143 & 144 | anti-TFR1 light chain (S176K) (PN & PP) |
| 17 | 135 & 136 | see above |
| 17 | 145 & 146 | anti-ZNRF3, anti-TFR1 Heavy chain (PN & PP) |
| | | anti-GFP Rspo2 (F105R/F109A). N-HC |
| 18 | 35 & 36 | see above |
| 18 | 37 & 38 | see above |
| | | anti-LYPD3 Rspo2 (F105R/F109A). N-HC |
| 18 | 147 & 148 | anti-LYPD3 light chain (PN & PP) |

TABLE 1-continued

Description of Sequence Identifiers

| FIG. | SEQ ID NO: | Brief Description |
|---|---|---|
| 18 | 149 & 150 | Rspo2 (F105R/F109A), anti-LYPD3 Heavy chain LALA-PG (PN & PP) |
| | | anti-DSG3 Rsno2 (F105R/F109A), N-HC |
| 18 | 151 & 152 | anti-DSG3 light chain (PN & PP) |
| 18 | 153 & 154 | Rspo2 (F105R/F109A), anti-DSG3 Heavy chain LALA-PG (PN & PP) |
| | | anti-GFP IaG1 LALA-PG |
| 19 | 35 & 36 | see above |
| 19 | 155 & 156 | anti-GFP heavy chain, IgG1 LALA-PG (PN & PP) |
| | | anti-GFP Rsno2 (F105R/F109A), N-HC |
| 19 | 35 & 36 | see above |
| 19 | 37 & 38 | see above |
| | | anti-ASGR1 IgG2 N-HC |
| 19 | 71 & 72 | see above |
| 19 | 73 & 74 | see above |
| 19 | 157 & 158 | 18R5-Dkk1c (PN & PP) |

Example 1

ASGR1—Specific Enhancement of Wnt Signaling in Scfv Format

Tissue-specific enhancement of Wnt signaling was first demonstrated using a tissue-specific Wnt signal enhancing molecule containing a scFv antibody against human ASGR1 (designed based on patent WO 2014/023709 A1, clone 4F3) fused to a mutant human Rspo2 (amino acid residues 37-143, with two point mutations F105A and F109A) (α-ASGR-mtRspo2). These mutations in human Rspo2 reduce/abolish binding to LGR4-6 without compromising interaction with ZNRF3/RNF43, as diagrammed in FIG. 1, and makes Rspo2 function as an action domain, as diagrammed in FIG. 2. As a negative control for the targeting domain (see FIG. 2), a scFv antibody against green fluorescent protein (GFP) was fused to the same mutant human Rspo2 (α-GFP-mtRspo2). As a positive control for Wnt signal enhancing activity, the GFP antibody was fused to a wild-type human Rspo2 (amino residues 37-143) (α-GFP-Rspo2). These constructs are diagrammed in FIG. 5A, and their amino acid sequences and encoding polynucleotide sequences are set forth as follows: α-GFP-Rspo2 (SEQ ID NOs:6 and 5, respectively); α-GFP-mtRspo2 (SEQ ID NOs:8 and 7, respectively); and α-ASGR-mt-Rspo2 (SEQ ID NOs:10 and 9, respectively). These tissue specific Wnt signal enhancing molecules also contained a signaling peptide at the N-terminus for secretion and a FLAG tag at the C-terminus for detection, followed by a (His)$_8$ tag for affinity purification. Expression constructs encoding tissue-specific Wnt signal enhancing fusion proteins and controls were generated by standard molecular cloning techniques.

Wnt signaling activity was measured using two cell lines containing a luciferase gene controlled by a Wnt-responsive promoter (Super Top Flash reporter assay, STF), the human liver carcinoma Huh-7 and human epidermoid carcinoma A431 cells. As demonstrated by quantitative-PCR analysis shown in FIG. 5B, both cell lines expressed the E3 ligases targeted by R-spondins, while the liver-specific gene ASGR1/2 expression was only detected in the Huh-7.

Transient transfection was performed with Lipofectamine 2000 (Invitrogen) following vender recommended procedures to test the activity of ASGR-targeting constructs in Huh-7 reporter cells. Wnt3a-conditioned media (prepared with ATCC L-Wnt-3A cell line using vendor recommended procedure) was added to comprise 10% of the total media volume three hours after transfection. Forty hours post-transfection, the cells were assayed for luciferase activity using standard luciferase assay-readout protocols (e.g., Stop and Glo Dual Luciferase Assay Kit (Promega)), which included cell lysis followed by addition of the luciferase substrate, luciferin. Luciferase-mediated conversion of the luciferin substrate to oxyluciferin resulted in the emission of light, which was read by a plate reader to quantify luminescence. The results are shown in FIG. 5C. As compared to the mock transfection control ("No DNA"), the construct expressing the anti-ASGR1 antibody fused to the mutant Rspo2 showed about a twenty-fold increase in luciferase activity, which was much higher than the anti-GFP fused to the same mutant. This suggested that the ASGR1 antibody part (the targeting domain) of the construct is responsible for the increase in the activity.

Western blot analysis was performed to confirm the expression and stability of the various fusion proteins under experimental conditions. 10 μl of the culture supernatant, 40 hours post-transfection (the same time point as the luciferase activity was measured), was analyzed using the anti-FLAG monoclonal antibody, M2 (Sigma Aldrich). As shown in FIG. 5C, all proteins were detectable at comparable levels. Therefore, the difference in Wnt signal enhancing activity among tested constructs was most likely a reflection on the proteins' activity, not expression level or protein stability.

A431 cells were used to test the ASGR1 dependence of the anti-ASGR1-based construct. The anti-ASGR1-mutant Rspo2 construct, in parallel with the anti-GFP fusions with wild-type or mutant Rspo2, were co-transfected with human TFR2 or human ASGR1 into A431 cells. 10% Wnt3a conditioned media was supplemented after transfection, and the luciferase activity was assayed forty hours after transfection. Supernatants from the same cells were taken for Western blot. As shown in FIG. 5D, with ASGR1 co-transfection, the anti-ASGR1 construct showed an activity of several fold higher than the negative control. This effect was not observed with the TFR2 co-transfection. This suggested that the specific Wnt-enhancing activity observed here was dependent on the presence of the specific receptor being targeted by the design of the fusion molecule. These results demonstrate that ASGR and TFR2-targeting constructs may be used for specific targeting of Wnt signal enhancing molecules to tissues where they are expressed, such as liver.

Example 2

Mechanism of the Action Domain and Modulation of Dynamic Range of the Activity To validate the mechanism of action of the fusion construct design of tissue-specific Wnt signal enhancing molecules, additional mutations were introduced into Rspo2 (which functions as an action domain), and the activity of these constructs was analyzed in Huh-7 cells in the same transient transfection-based reporter assay described in Example 1. The role of ZNRF3/RNF43 interaction was first tested by introducing point mutations to residues within Rspo2 that are known to bind to ZNRF3/RNF43, such as S47, N50, R65, R69, and Q70 (in addition to the F105A and F109A mutations). The amino acid sequence of the α-GFP-mtRspo2 containing the F105A/F109A/S47A/N50A mutations is provided in SEQ ID NO:12, and the encoding polynucleotide sequence is provided in SEQ ID NO:11. The amino acid sequence of the α-ASGR1-mtRspo2 containing the F105A/F109A/S47A/N50A mutations is provided in SEQ ID NO:14, and the encoding polynucleotide sequence is provided in SEQ ID NO:13. The amino acid sequence of the α-GFP-mtRspo2 containing the F105A/F109A/R65A/R69A/Q70A mutations is provided in SEQ ID NO:16, and the encoding polynucleotide sequence is provided in SEQ ID NO:15. The amino acid sequence of the α-ASGR1-mtRspo2 containing the F105A/F109A/R65A/R69A/Q70A mutations is provided in SEQ ID NO:18, and the encoding polynucleotide sequence is provided in SEQ ID NO:17. As shown in FIG. 6A, introducing mutations of S47A/N50A or R65A/R69A/Q70A abolished the Wnt signal enhancing activity of both the anti-GFP and the anti-ASGR1 constructs. These results are consistent with the mechanism that these two E3 ligases are targeted by the action domain.

To test the possibility of increasing the activity of the mutant Rspo2, attempts were made to alleviate the defects in LGR interactions by limiting the mutation to a single amino acid residue, F105A or F109A, instead of the initial F105A/F109A double mutation. The amino acid sequence of the α-GFP-mtRspo2 containing only the F105A mutation is provided in SEQ ID NO:20, and the encoding polynucleotide sequence is provided in SEQ ID NO:19. The amino acid sequence of the α-ASGR1-mtRspo2 containing only the F105A mutation is provided in SEQ ID NO:22, and the encoding polynucleotide sequence is provided in SEQ ID NO:21. The amino acid sequence of the α-GFP-mtRspo2 containing only the F109A mutation is provided in SEQ ID NO:24, and the encoding polynucleotide sequence is provided in SEQ ID NO:23. The amino acid sequence of the α-ASGR1-mtRspo2 containing only the F109A mutation is provided in SEQ ID NO:26, and the encoding polynucleotide sequence is provided in SEQ ID NO:25. These constructs were tested in Huh-7 reporter cells by transient transfection assays. As shown in FIG. 6B, the F109A single mutant had higher activity than the double mutant. Although this is at the cost of higher basal activity in the anti-GFP control, this approach suggested that the dynamic range of the activity of the fusion construct can be fine-tuned by mutations affecting R-spondin-LGR interactions.

Besides alanine ("A"), other amino acid residues can also be used as mutations to replace residues critical for LGR protein interactions. As an example, FIG. 6C demonstrated the use of Rspo2 F106R/F109A mutant as the action domain. Fusion of this Rspo2 mutant to the anti-TFR1 targeting domain led to clear Wnt signal enhancing activity, as compared to the corresponding anti-GFP control, in Huh-7 cells in transient transfection based STF assays (at the presence of 10% Wnt3a condition media). The amino acid sequence of the α-TFR1-mtRspo2 containing the F105A/F109A mutations is provided in SEQ ID NO:28, and the encoding polynucleotide sequence is provided in SEQ ID NO:27. The amino acid sequence of the α-GFP-mtRspo2 containing the F105R/F109A mutations is provided in SEQ ID NO:30, and the encoding polynucleotide sequence is provided in SEQ ID NO:29. The amino acid sequence of the α-TFR1-mtRspo2 containing the F105R/F109A mutations is provided in SEQ ID NO:32, and the encoding polynucleotide sequence is provided in SEQ ID NO:31.

Example 3

Validation of the Targeting Strategy with Another Cell Surface Receptor

To validate that the anti-ASGR1 based design of tissue-specific Wnt signal enhancing molecule is not just a particular case but rather an example representing a general principle, the mutant (F105A/F109A) Rspo2 fragment (amino acid residues 37-143) was fused to a scFv antibody against another cell surface receptor, human transferrin receptor 1 (TFR1) (designed based on patent WO 2016/081640, clone 7A4), which is broadly expressed in almost all types of cells. The amino acid sequence of the construct is provided in SEQ ID NO:28. Using the transient transfection and reporter assays described in Example 1, it was demonstrated that this new construct had activity comparable or even higher than that of the positive control, anti-GFP fused to the wild-type Rspo2 (SEQ ID NO:6; FIGS. 7A and 7B). This not only supported the generalization of the targeting strategy, but also testified to the full potential of this approach to significantly enhance the specific Wnt signal enhancing activity, as long as a targeting domain recognizing the appropriate cell surface receptor is used. The broad distribution of the TFR1 receptor also provided an opportunity to use this fusion construct to screen for tissues/cells that are sensitive to this Wnt signal enhancing strategy.

Example 4

Purified Fusion Proteins (in SCFV Format) as Tissue/Cell-Specific Wnt Enhancers To directly test the activity of the designed fusion proteins, the constructs were sub-cloned into the baculovirus transfer vector pAcGP67-A and expressed and purified from SF9/hi5 cells as previously described (Janda et al, 2017 Nature). The expressed proteins were purified via the His-tag using cOmplete his-tag purification resin (Sigma-Aldrich) following vendor recommender procedures, then further polished by a size exclusion column (S200, GE Healthcare) fractionation. FIG. 8A shows representatives of Coomassie-stained gel images of purified fusion proteins having the indicated targeting domains and action domains (the anti-TFR1 construct was not further purified by size exclusion column), with estimated purify of >90%.

FIG. 8B (left graph) shows a comparison of the anti-ASGR1 constructs (F105A/F109A double mutant with Rspo2 (SEQ ID NO:10) and F109A single mutant with Rspo2 (SEQ ID NO:26)) with the anti-GFP negative control (F105A/F109A double mutant (SEQ ID NO:8)) on the targeted Huh-7 cells. The anti-ASGR1 fused to the Rspo2 double mutant, at 10 μM final concentration, was about three-fold more active than the anti-GFP control at 100 µM concentration, clearly demonstrating specific enhancement of the activity by the specific antibody. The fusion protein containing the Rspo2 single F109A mutant (SEQ ID NO:26) was even more active, consistent with the results from transient transfection assays. FIG. 8B (right graph) shows a comparison of the maximum of efficacy ($E_{max}$) of the ASGR1-targting fusions with a his-tagged Rspo2 construct (containing amino acid residues S36-E143) (SEQ ID NO:34 and encoding polynucleotide sequence provided in SEQ ID NO:33) that was purified by the same procedure. The results suggest that the targeted Rspo2 double mutant can reach an $E_{max}$ comparable to the functional Rspo2 protein, while activity of the targeted Rspo2 single mutant $E_{max}$ can be even higher. Although higher concentrations (10~100 µM) were required to reach $E_{max}$, as opposed to 1-3 µM for the Rspo2 protein, at these concentrations, the negative control (anti-GFP fusion in FIG. 8B, left panel) had little activity.

To verify the specificity of tissue/cell targeting, activities of the purified fusion proteins were compared in three cell lines: the human liver Huh-7 cells, the human colorectal adenocarcinoma HT29 cells, and the mouse liver FL83B cells, all engineered to contain a luciferase reporter for Wnt signaling (shown left to right in FIG. 8C). Epithelial cells in liver and intestinal/rectal tract are known to be sensitive to R-spondin-mediated Wnt signaling upregulation, and Rspo proteins are highly conserved between mouse and human. Not surprisingly, all three cell lines responded to Rspo2 well. Significant activity from the anti-ASGR1 based fusion proteins was observed on Huh-7 cells, but almost no activity on the HT29 cells. Intestine tract epithelial cells were the most sensitive to Rspo proteins. The lack of stimulation on HT29 cells by the ASGR1-tageting fusion proteins is a good indication that they might have a much lower chance of off-target effects if applied in vivo. In contrast, the TFR1-targeting fusion protein was much more active, even at a very low 0.1 µM concentration, further validating the potency and efficacy of this protein. This activity was likely specifically dependent on the presence of the receptor, because this human TFR1-targeting construct showed no activity on mouse FL83B cells, indicating the targeting binder is specific to the human receptor. Some response to the human ASGR1-targeting fusion proteins was observed with the mouse liver cells, suggesting cross-species reactivity of the antibody.

Example 5

Figure 9:
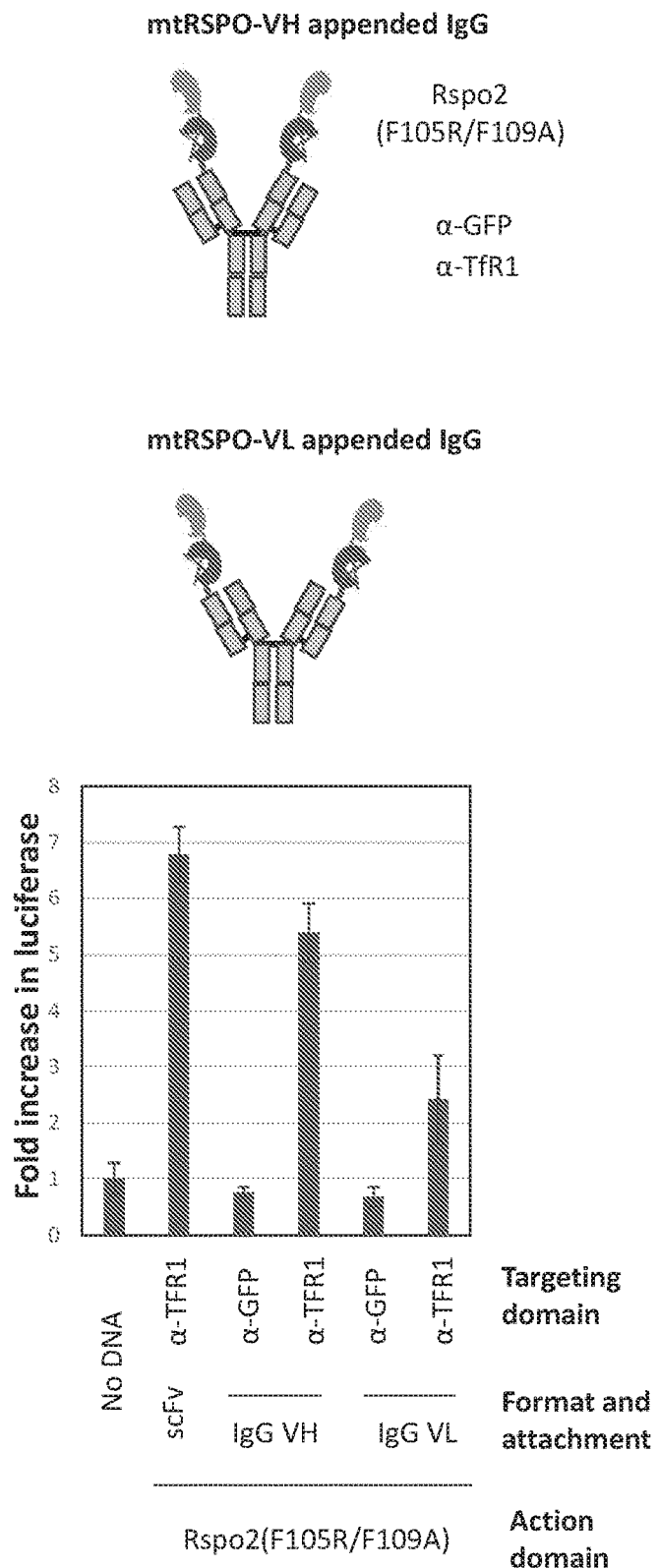
FIG. 9 demonstrates the targeted Wnt signal enhancing activity of a construct with the targeting domain in the form of full IgG. On the top are diagrams of the appended IgG constructs. The upper diagram depicts the Rspo2 F105R/F109A mutant appended on to the N-terminus of human IgG2 heavy chain against either GFP or human TFR1 receptor. The lower diagram depicts the Rspo2 F105R/F109A mutant appended onto N-terminus of human IgG2 light chain against either GFP or human TFR1 receptor. These constructs (with respective light chain and heavy chain) together with the TFR1 single-chain variable fragment (scFv) fused to Rspo2 F105R/F109A mutant were transiently transfected into HEK293T cells (which express the TFR1 receptor) with a luciferase reporter. On the bottom is the graphical summary of the STF assay 40 hours after transfection. 10% Wnt3a conditioned media was added to the culture after transfection. STF assay was performed as described in the description of FIGS. 5A-5D.

Active Wnt Signal Enhancer in Full-Length IGG Format, Demonstrated by Transient Transfection Antibodies in the full IgG format have been associated with superior pharmaco kinetic properties and stability among other advantages. To demonstrate that the tissue-specific Wnt signal enhancing molecules described in the previous Examples were active in the full IgG format, these tissue-specific Wnt signal enhancing fusion proteins were converted into the full IgG format. The TFR1 binder was chosen as a proof-of-concept for the IgG formatted Wnt signal enhancing molecules because of its supreme activities from previous example in this application. As shown in the diagram of FIG. 9A, the mutant (F105R/F109A) Rspo2 was fused to the N-terminus of the light chain or heavy chain of the TFR1 antibody (or GFP antibody as a negative control, both as IgG2), and the activity of these molecules was determined by transient transfection into 293 cells with a reporter responsive to Wnt signaling. For the construct having the Rspo2 (F105R/F109A) domain appended to the N-terminus of the heavy chain of the α-GFP IgG, the amino acid sequence of the α-GFP light chain is provided in SEQ ID NO:36, and its encoding polynucleotide sequence is provided in SEQ ID NO:35, and the amino acid sequence of the Rspo2 (F105R/F109A), α-GFP heavy chain IgG2 is provided in SEQ ID NO:38, and its encoding polynucleotide sequence is provided in SEQ ID NO:37. For the construct having the Rspo2 (F105R/F109A) domain appended to the N-terminus of the heavy chain of the α-TFR1 IgG, the amino acid sequence of the α-TFR1 light chain is provided in SEQ ID NO:40, and its encoding polynucleotide sequence is provided in SEQ ID NO:39, and the amino acid sequence of the Rspo2 (F105R/F109A), α-TFR1 heavy chain IgG2 is provided in SEQ ID NO:42, and its encoding polynucleotide sequence is provided in SEQ ID NO:41. For the construct having the Rspo2 (F105R/F109A) domain appended to the N-terminus of the light chain of the α-GFP IgG, the amino acid sequence of the α-GFP heavy chain IgG2 is provided in SEQ ID NO:46, and its encoding polynucleotide sequence is provided in SEQ ID NO:45, and the amino acid sequence of the Rspo2 (F105R/F109A), α-GFP light chain is provided in SEQ ID NO:44, and its encoding polynucleotide sequence is provided in SEQ ID NO:43. For the construct having the Rspo2 (F105R/F109A) domain appended to the N-terminus of the light chain of the α-TFR1 IgG, the amino acid sequence of the α-TFR1 heavy chain IgG2 is provided in SEQ ID NO:50, and its encoding polynucleotide sequence is provided in SEQ ID NO:49, and the amino acid sequence of the Rspo2 (F105R/F109A), α-TFR1 light chain is provided in SEQ ID NO:48, and its encoding polynucleotide sequence is provided in SEQ ID NO:47.

As indicated in FIG. 9B, the full IgG format retained the potent Wnt signal enhancing activity observed with the scFv format, particularly when the Rspo2 mutant was fused to the heavy chain. These results demonstrated one feasible example of how to apply the design of the receptor-targeting Wnt-enhancer towards to other scaffolds.

Example 6

Additional Rspo Mutants to Support the Targeted Wnt Signal Enhancing Activity

Besides the two hydrophobic residues (F105 and F109 in case of human Rspo2) known to be most critical for the interaction between Rspo and LGR proteins, additional residues can also contribute to the interaction. These residues include, for example, K58, H76, S77, R86, N91, and R121 of Rspo2. Mutations in these residues could be used in combination to the F105/F109 mutations to abolish/compromise the interaction of Rspo with LGR proteins. The amino acid sequences and encoding polynucleotide sequences of various constructs are provided as follows: anti-ASGR1, Rspo2 (F105R/F109A), SEQ ID NOs: 52 and 51; anti-GFP, Rspo2 (R86E/F105R/F109A), SEQ ID NOs: 54 and 53; anti-ASGR1, Rspo2 (R86E/F105R/F109A), SEQ ID NOs: 56 and 55; anti-TFR1, Rspo2 (R86E/F105R/F109A), SEQ ID NOs: 58 and 57; anti-GFP, Rspo2 (R86E/F105R/F109A/R121E), SEQ ID NOs: 60 and 59; anti-ASGR1, Rspo2 (R86E/F105R/F109A/R121E), SEQ ID NOs: 62 and 61; anti-TFR1, Rspo2 (R86E/F105R/F109A/R121E), SEQ ID NOs: 64 and 63; anti-GFP, Rspo2 (K58E/R86E/F105R/F109A/R121E), SEQ ID NOs: 66 and 65; anti-ASGR1, Rspo2 (K58E/R86E/F105R/F109A/R121E), SEQ ID NOs: 68 and 67; and anti-TFR1, Rspo2 (K58E/R86E/F105R/F109A/R121E), SEQ ID NOs: 70 and 69.

Figure 10:
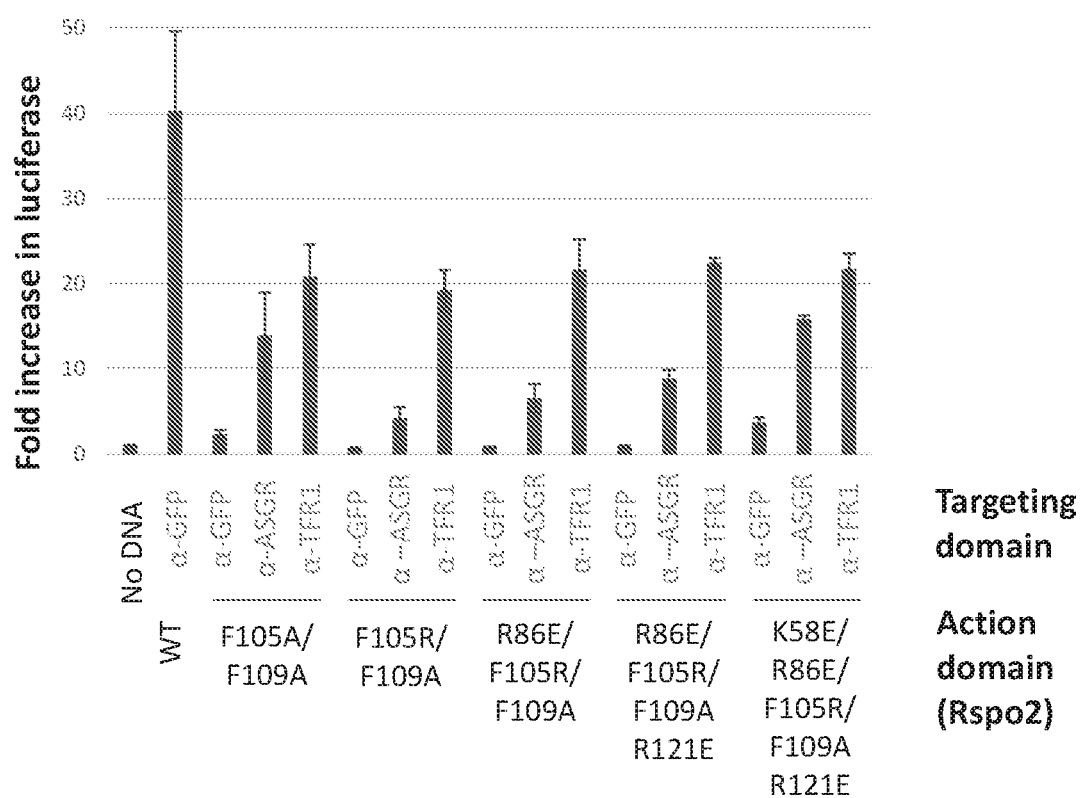
FIG. 10 provides a graph showing results obtained with additional combinations of Rspo2 mutations, as ways to reduce the interaction with LGR proteins and support targeted Wnt enhancing activities when fused to a targeting domain. The specified constructs were introduced into Huh-7 cells by transient transfection. More procedure details can be found in the description of FIGS. 5A-5D.
Figure 11:
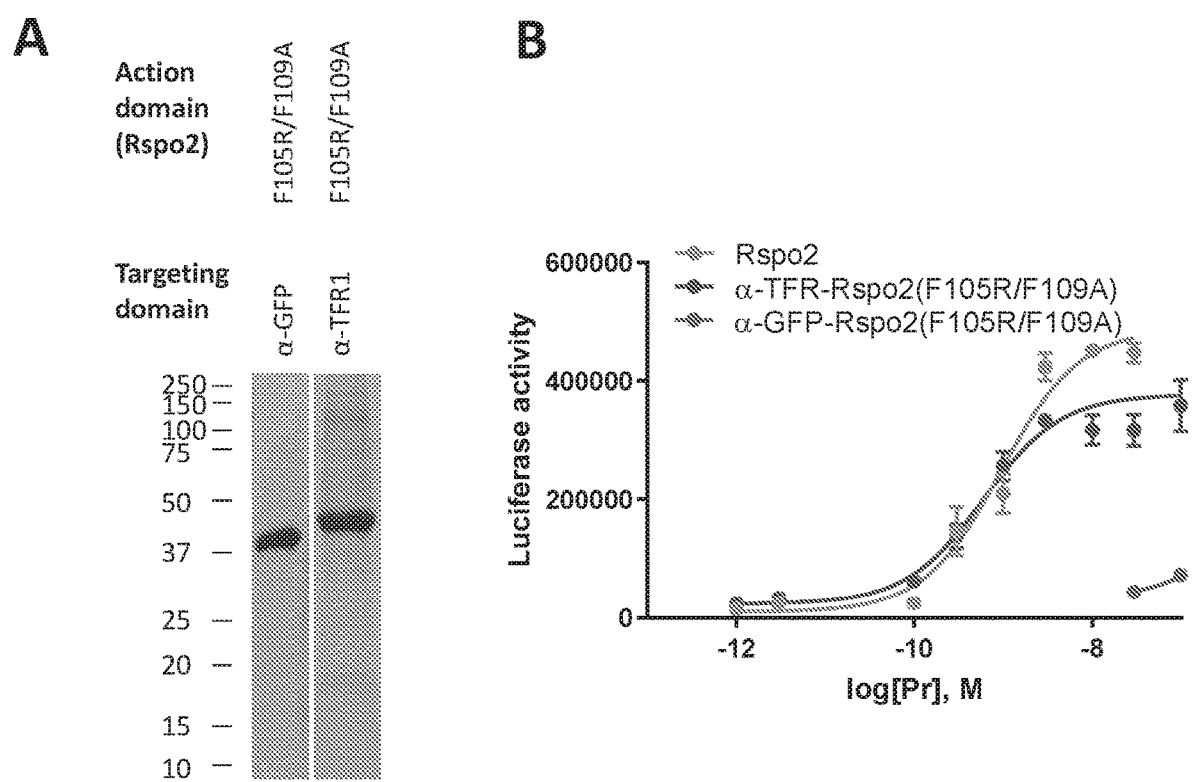
FIGS. 11A and 11B compare the STF activity, in Huh-7 cells, of the TFR1-targeting Rspo2 (F105R/F109A) mutant fusion proteins with a negative control (the anti-GFP construct) and a positive control (Rspo2). The luciferase activity is in arbitrary units. More procedure details can be found in the description of FIGS. 8A-8C.

As demonstrated in FIG. 10, in transient transfection based STF assay in Huh-7 cells at the presence of 10% Wnt3a conditioned media, mutations in these LGR-interacting residues can be used in various combination to create action domains supporting Wnt signal enhancing activity.

Example 7

Wnt Signal Enhancing Activity of Additional Recombinant Proteins in SCFV Format

The Wnt signal enhancing activity of the scFv anti-TFR1-based construct observed by transient transfection experiments (FIG. 6C) was further validated with purified proteins. Plasmid vectors encoding fusion proteins of anti-hTFR1-Rspo2(F105R/F109A) and an anti-GFP control (SEQ ID NOs: 30 and 32, respectively) were transfected into Expi293F cells (Thermo Fisher Scientific), and purified using cOmplete his-tag purification resin (Sigma-Aldrich) following vendor recommender procedures. FIG. 11A shows Coomassie-stained gel images of the purified proteins. As shown in FIG. 11B, the TFR1 targeted recombinant protein demonstrated a much more potent activity than the anti-GFP fusion control. Additionally, the $E_{max}$ of this targeted molecule is comparable to that of the Rspo2 positive control.

Example 8

Cell Surface Receptor Dependence Demonstrated with Purified Proteins

Figure 12:
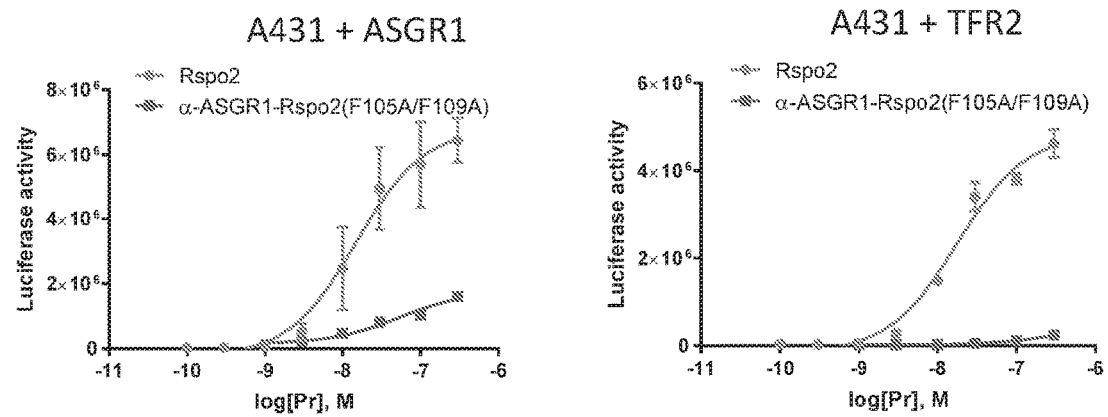
FIG. 12 provides a comparison of the non-ASGR1 expressing cell line A431 in response to the anti-ASGR1-Rspo2(F105A/F109A) fusion protein upon transfection with plasmids over expressing either ASGR1 (left) or TFR2 (right, used as the control). All cell lines have the luciferase reporter gene integrated, and were first transfected by the specified receptor plasmids. After 24 hours, the cells were treated by the proteins at specified concentration for ~18 hours at the presence of 10% Wnt3a conditioned media, then assayed for luciferase activity.

To further demonstrate the dependence on the presence of a specific cell surface receptor of the designed Wnt signal enhancing molecules, the human ASGR1 targeting molecule (anti-ASGR1-Rspo2(F105A/F109A); SEQ ID NO:10) was tested in the STF assay on A431 cells, which do not naturally express the ASGR1 receptor. The cells were first transiently transfected with vector expressing either human ASGR1 or human TFR2 using Lipofectamine 2000 (Invitrogen) following vendor recommended procedures in 96 well plates. After 24 hours, the transfected cells were treated with the hASGR1 targeted fusion protein, with Rspo2 as the positive control. Transient transfection with a ASGR1-expressing vector was found to make the A431 cells responsive, while the control transfection with a TFR2-expressing vector failed to respond to the Wnt signal enhancing molecules (FIG. 12).

Example 9

Wnt Signal Enhancing Activity of Purified Proteins in Appended IGG Format

Figure 13:
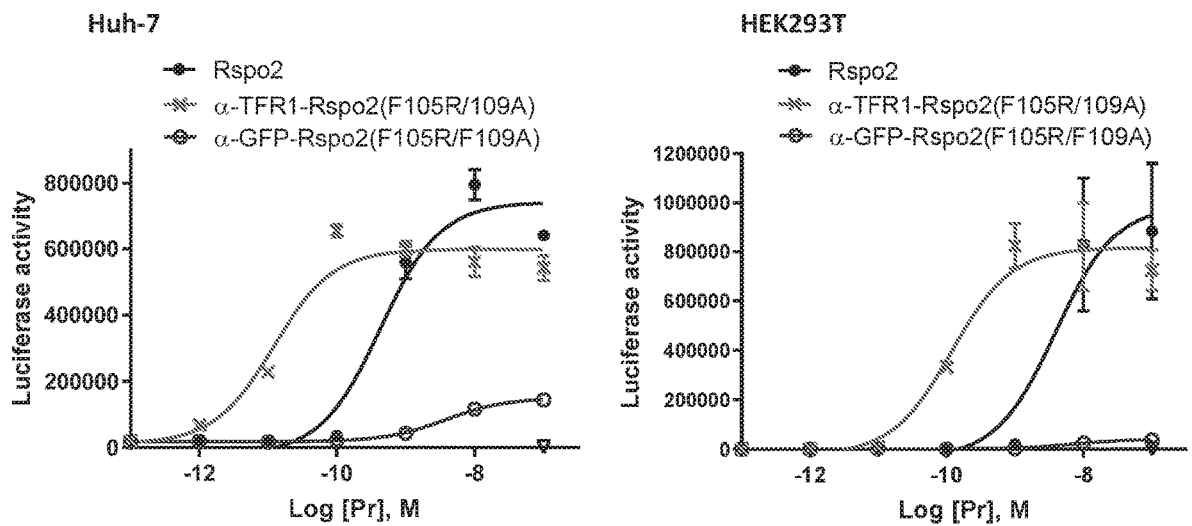
FIG. 13 demonstrates Wnt signal-stimulating activity of a purified appended IgG protein targeting human TFR1 receptor. The F105R/F109A Rspo2 mutant fused to the N-terminus of heavy chain of IgG2 against TFR1 was compared to the fusion with anti-GFP, with a Rspo2 positive control. The STF assay was carried out in two cells lines, Huh-7 on the left and HEK293T on the right, containing the STF reporter. Both cell lines express the targeted receptor TFR1. The luciferase activity is in arbitrary units.
Figure 18:
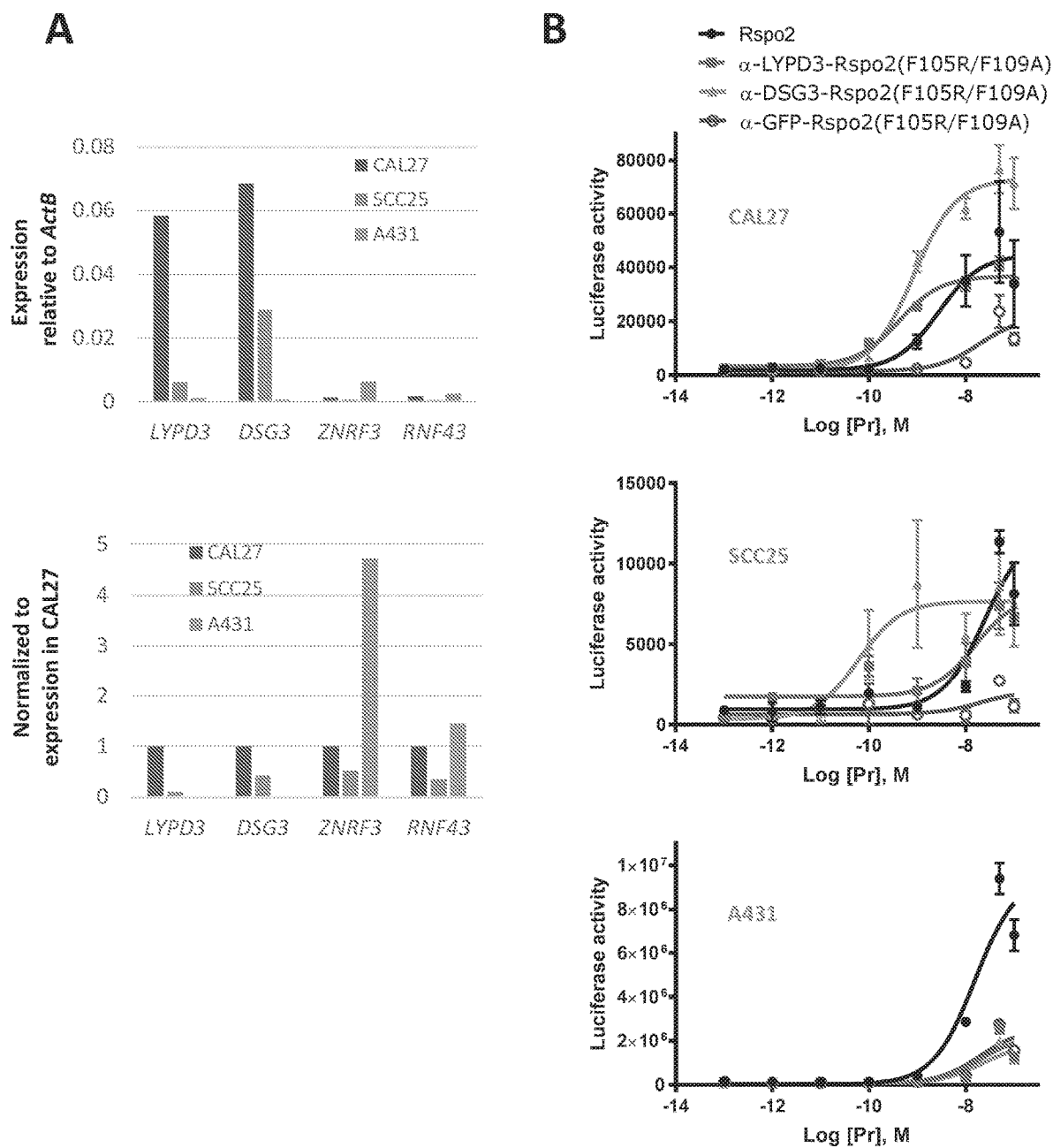
FIGS. 18A-18B demonstrate examples of applying the tissue-specific Wnt signal enhancer design to another targeted tissue, oral mucous through specific cell surface receptors.
Figure 19:
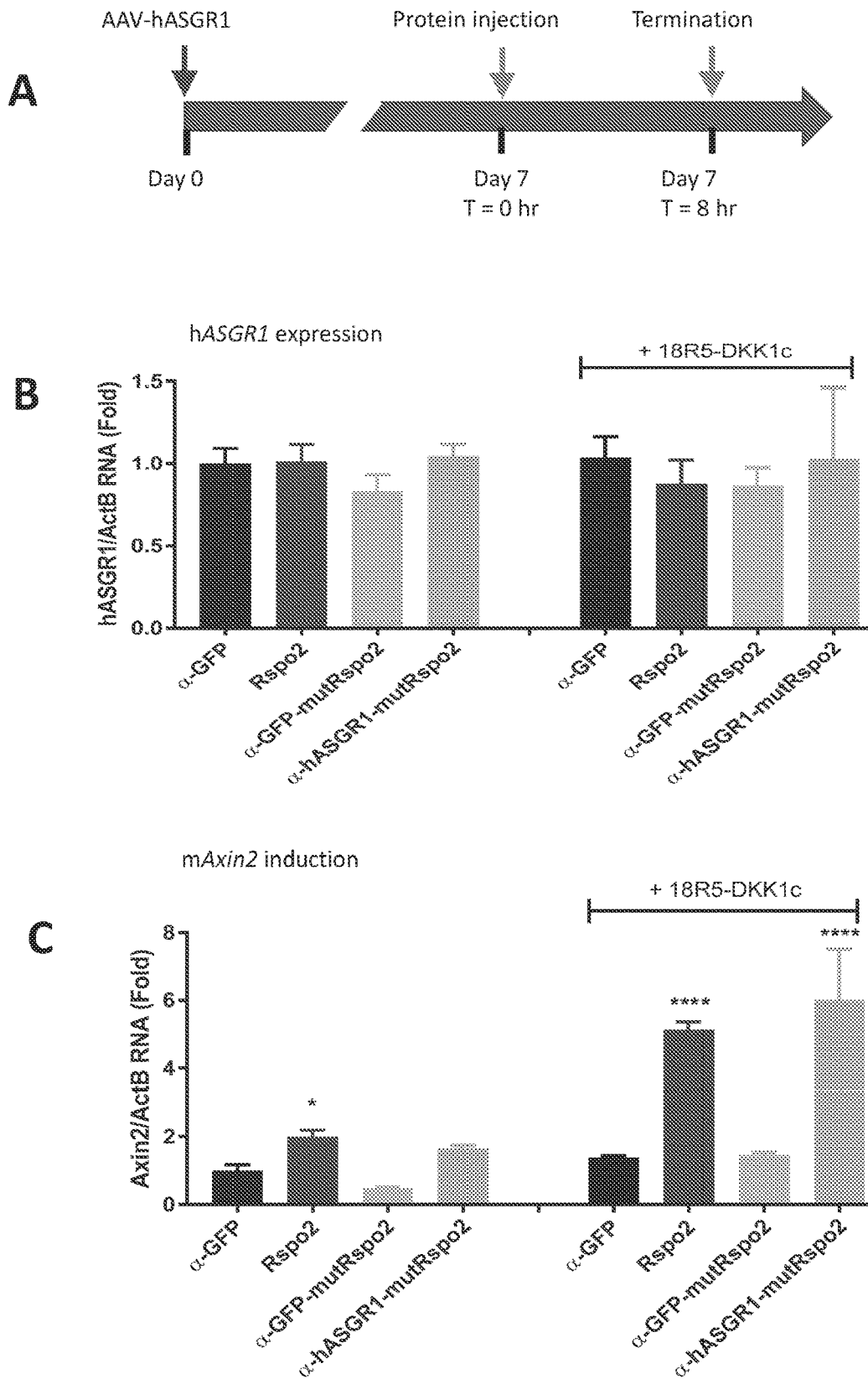
FIGS. 19A-19C demonstrate in vivo function of an illustrative liver-specific Wnt signal enhancing molecule.

To further validate the Wnt signal enhancing activity of the TFR1 targeting appended IgG molecules demonstrated by transient transfection experiments (FIG. 9), these molecules were expressed as recombinant proteins using Expi293F cells (Thermo Fisher Scientific). The recombinant protein was first purified by a Protein A affinity resin (standard practice), then polished by a size exclusion column (S200, GE Healthcare) fractionation. The purified proteins were tested directly on Huh-7 and 293T cells with STF assay, both of which express human TFR1 receptor. As shown in FIG. 13, the TFR1-targeted molecule demonstrated a potency of 3-4 orders of magnitude better than the anti-GFP fusion control and a higher $E_{max}$.

Example 10

Structure-Activity-Relationship Analysis of Appended IGG Scaffold

With the targeting domain in the format of full-length IgG, multiple ways of attaching the action domain were compared. A summary of the activity of various IgG2 scaffolds tested is shown in FIGS. 14A-14B, where the mutant Rspo2 (F105R/F109A) is attached to the N-terminus of the heavy chain, the N-terminus of the light chain, or the C-terminus of the light chain of either anti-ASGR1 or anti-TFR1 as the targeting domain, or to anti-GFP as the control antibody. Some constructs used are described in Example 5, and additional constructs tested included: the Rspo2 (F105R/F109A) domain appended to the N-terminus of the heavy chain of the α-ASGR1 IgG, wherein the amino acid sequence of the α-ASGR1 light chain is provided in SEQ ID NO:72, and its encoding polynucleotide sequence is provided in SEQ ID NO:71, and the amino acid sequence of the Rspo2 (F105R/F109A), α-ASGR1 heavy chain IgG is provided in SEQ ID NO:74, and its encoding polynucleotide sequence is provided in SEQ ID NO:73; the Rspo2 (F105R/F109A) domain appended to the C-terminus of the light chain of the α-GFP IgG2, wherein the amino acid sequence of the α-GFP heavy chain IgG2 is provided in SEQ ID NO:46, and its encoding polynucleotide sequence is provided in SEQ ID NO:45, and the amino acid sequence of the Rspo2 (F105R/F109A), α-GFP light chain is provided in SEQ ID NO:76, and its encoding polynucleotide sequence is provided in SEQ ID NO:75; the Rspo2 (F105R/F109A) domain appended to the C-terminus of the light chain of the α-ASGR1 IgG, wherein the amino acid sequence of the α-ASGR1 heavy chain IgG2 is provided in SEQ ID NO:80, and its encoding polynucleotide sequence is provided in SEQ ID NO:79, and the amino acid sequence of the Rspo2 (F105R/F109A), α-ASGR1 light chain is provided in SEQ ID NO:78, and its encoding polynucleotide sequence is provided in SEQ ID NO:77; the Rspo2 (F105R/F109A) domain appended to the C-terminus of the light chain of the α-TFR1 IgG, wherein the amino acid sequence of the α-TFR1 heavy chain IgG2 is provided in SEQ ID NO:50, and its encoding polynucleotide sequence is provided in SEQ ID NO:49; and the amino acid sequence of the Rspo2 (F105R/F109A), α-TFR1 light chain is provided in SEQ ID NO: 82, and its encoding polynucleotide sequence is provided in SEQ ID NO:81.

These proteins were over-expressed in Expi193T cells by transient transfection and purified by a Protein A affinity resin followed by a size exclusion chromatography. In Huh-7 cells (FIG. 14A), all the targeted molecules demonstrated an activity clearly better than the corresponding anti-GFP fusion controls. The anti-TFR1 fusion constructs are generally more active than the anti-ASGR1 fusion proteins, which is consistent with the observations where these targeting domains were in scFv format (FIG. 8C). The dynamic range (the difference in potency and $E_{max}$ between the targeted and control molecules in the same format) is overall bigger with the N-terminus heavy chain and N-terminus light chain-attached molecules than the C-terminus light chain-attached molecules, suggesting that some format might be more preferred while multiple formats are suitable for further development. The STF activity of these molecules was also compared in human 293T cells, which only express TFR1 but not ASGR1 receptor (FIG. 14B). As expected, only the anti-TFR1 fusion proteins, but not the anti-hASGR1 fusions, remained significantly more potent than the anti-GFP fusion controls, suggesting the specific Wnt signal enhancing activity of the designed molecules, in the IgG format, remained dependent on the presence of the specific cell surface receptor. This notion was further validated with the mouse FL83B cells, which express neither human ASGR1 nor human TFR1 (FIG. 14C). On FL83B cells, no difference between the targeted molecules and the anti-GFP control fusion protein was observed. The attachment location of the Rspo mutant could also be on the C-terminus of the IgG heavy chain (data not shown).

IgG1 is another immunoglobin isotype frequently used for therapeutic antibody development. Multiple ways of attaching the mutant Rspo2 action domain to different ends of an N297G effector-less mutant form of IgG1 (Jacobsen F W et al., The Journal of Biological Chemistry 2017, 292:1865) were compared. Some constructs used are described in Example 5, and additional constructs tested included: the Rspo2 (F105R/F109A) domain appended to the N-terminus of the heavy chain of the anti-GFP IgG1 (N297G), wherein the amino acid sequence of the anti-GFP light chain is provided in SEQ ID NO:36, and its encoding polynucleotide sequence is provided in SEQ ID NO:35, and the amino acid sequence of the Rspo2 (F105R/F109A), anti-GFP heavy chain is provided in SEQ ID NO:84, and its encoding polynucleotide sequence is provided in SEQ ID NO:83; the Rspo2 (F105R/F109A) domain appended to the N-terminus of the heavy chain of the anti-ASGR1 IgG1 (N297G), wherein the amino acid sequence of the anti-ASGR1 light chain is provided in SEQ ID NO:72, and its encoding polynucleotide sequence is provided in SEQ ID NO:71, and the amino acid sequence of the Rspo2 (F105R/F109A), anti-ASGR1 heavy chain is provided in SEQ ID NO:86, and its encoding polynucleotide sequence is provided in SEQ ID NO:85; the Rspo2 (F105R/F109A) domain appended to the N-terminus of the heavy chain of the anti-TFR1 IgG1 (N297G), wherein the amino acid sequence of the anti-TFR1 light chain is provided in SEQ ID NO:40, and its encoding polynucleotide sequence is provided in SEQ ID NO:39, and the amino acid sequence of the Rspo2 (F105R/F109A), anti-TFR1 heavy chain is provided in SEQ ID NO:88, and its encoding polynucleotide sequence is provided in SEQ ID NO:87; the Rspo2 (F105R/F109A) domain appended to the N-terminus of the light chain of the anti-GFP IgG1 (N297G), wherein the amino acid sequence of the anti-GFP heavy chain is provided in SEQ ID NO:90, and its encoding polynucleotide sequence is provided in SEQ ID NO:89, and the amino acid sequence of the Rspo2 (F105R/F109A), anti-GFP light chain is provided in SEQ ID NO:44, and its encoding polynucleotide sequence is provided in SEQ ID NO:43; the Rspo2 (F105R/F109A) domain appended to the N-terminus of the light chain of the anti-TFR1 IgG1 (N297G), wherein the amino acid sequence of the anti-TFR1 heavy chain is provided in SEQ ID NO:92, and its encoding polynucleotide sequence is provided in SEQ ID NO:91, and the amino acid sequence of the Rspo2 (F105R/F109A), anti-TFR1 light chain is provided in SEQ ID NO:48, and its encoding polynucleotide sequence is provided in SEQ ID NO:47; and the Rspo2 (F105R/F109A) domain appended to the C-terminus of the light chain of the anti-ASGR1 IgG1 (N297G), wherein the amino acid sequence of the anti-ASGR1 heavy chain is provided in SEQ ID NO:94, and its encoding polynucleotide sequence is provided in SEQ ID NO:93, and the amino acid sequence of the Rspo2 (F105R/F109A), anti-ASGR1 light chain is provided in SEQ ID NO:78, and its encoding polynucleotide sequence is provided in SEQ ID NO:77.

Following the same procedure of protein purification and activity testing as described for the appended IgG2 proteins, it was found that having the action domain (mutant Rspo2) attached to the N-terminus of the heavy chain or the light chain of anti-ASGR1 or anti-TFR1 in the IgG1 (N297G) isotype also supported specific Wnt signal enhancing activity in Huh-7 cells in contrast to the corresponding anti-GFP controls (FIG. 14D). Such specific activity was lost in 293T cells with the anti-ASGR1 fusions, but preserved with the anti-TFR1 fusions, consistent with the expected dependence on the presence of targeted receptor(s) (FIG. 14E). Thus, multiple immunoglobulin isotypes, with multiple sites for the attachment of the action domain, were demonstrated to be suitable formats for the tissue-specific Wnt signal enhancing molecules.

Example 11

Structure-Activity-Relationship Analysis of Four R-Spondin as Action Domains

Humans have four R-spondin proteins with high sequence homology, particularly within the Furin domains (FIG. 4). To directly compare their capabilities in enhancing Wnt signaling in vitro, Fu1-Fu2 domains of each of the four human R-spondins were expressed as fusions to the C-terminus of scFv binders to ASGR1, TFR1 and GFP in Expi293F cells by transient transfection following standard His-tag and size exclusion chromatography purification procedures. The amino acid sequence and encoding polynucleotide sequence of the anti-GFP, Rspo1 wild-type fusion protein are provided in SEQ ID NOs:96 and 95, respectively. The amino acid sequence and encoding polynucleotide sequence of the anti-GFP, Rspo2 wild-type fusion protein are provided in SEQ ID NOs: 6 and 5, respectively. The amino acid sequence and encoding polynucleotide sequence of the anti-GFP, Rspo3 wild-type fusion protein are provided in SEQ ID NOs:98 and 97, respectively. The amino acid sequence and encoding polynucleotide sequence of the anti-GFP, Rspo4 wild-type fusion protein are provided in SEQ ID NOs:100 and 99, respectively. The purified proteins were then tested by STF assay in Huh-7 and 293T cells in the presence of Wnt3a conditioned media. As shown in FIG. 15A, Rspo2 and 3 were more potent than Rspo4 and 1, consistent with previous reports.

Given the structural and functional conservation among the R-spondin molecules, it's likely that not only Rspo2 but other Rspo molecules can also be suitable to support the construction of action domains for the tissue-specific Wnt signal enhancing proteins. Shown in FIG. 15B-15C is a side-by-side comparison of a series of human Rspo2- and Rspo3-based constructs tested in STF assay in Huh-7 and HEK293T cells. These constructs include the polypeptides disclosed in SEQ ID NOs: 8, 10, 28, 30, 32, and 52. In addition, constructs tested also included the following (shown with SEQ ID NOs corresponding to their amino acid sequence and encoding polynucleotide sequence): anti-GFP, Rspo3 (F106A/F110A), SEQ ID NOs:102 and 101; anti-GFP, Rspo3 (F106R/F110A), SEQ ID NOs:104 and 103; anti-ASGR1, Rspo3 (F106A/F110A), SEQ ID NOs:106 and 105; anti-ASGR1, Rspo3 (F106R/F110A), SEQ ID NOs:108 and 107; anti-TFR1, Rspo3 (F106A/F110A), SEQ ID NOs: 110 and 109; and anti-TFR1, Rspo3 (F106R/F110A), SEQ ID NOs: 112 and 111.

In the context of the specific fusion to the particular tissue targeting binder used here, Rspo3 mutants demonstrated the highest efficacy, while other Rspo mutants also demonstrated significant tissue targeting, demonstrating that multiple Rspo variant could be considered for the Wnt signal enhancing protein generation.

Example 12

Diverse RSPO Mutants Supporting Specific Wnt Signal Enhancing Activity in the Appended IGG Format To further demonstrate the diversity of mutations and their combinations that can support the construction of Wnt signal enhancing molecules, a series of additional Rspo3 mutant-based molecules fusded to anti-GFP or anti-ASGR1 were made, and their activities were tested in Huh-7 cells using the STF assay. These mutations included F106R/F110A (RA), F106R/F110R (RR), F106E/F110E (EE), F106R/F110E (RE), F106E/F110A (EA), R60E/R88E/N93A/F106R/F110A (EEARA; R60, R88, and N93 are residues participating in LGR interactions based on homologies with other Rspo proteins) (FIG. 16A). The amino acid and encoding polynucleotide sequences for these constructs are provided as follows: anti-GFP Rspo3 wild-type, SEQ ID NOs:98 and 97; anti-GFP Rspo3 RA, SEQ ID NOs: 104 and 103; anti-GFP Rspo3 RR, SEQ ID NOs: 114 and 113; anti-GFP Rspo3 EE, SEQ ID NOs: 116 and 115; anti-GFP Rspo3 RE, SEQ ID NOs: 118 and 117; anti-GFP Rspo3 EA, SEQ ID NOs: 120 and 119; anti-GFP Rspo3 EEARA, SEQ ID NOs: 122 and 121; anti-ASGR1 Rspo3 RA, SEQ ID NOs: 108 and 107; anti-ASGR1 Rspo3 RR, SEQ ID NOs: 124 and 123; anti-ASGR1 Rspo3 EE, SEQ ID NOs: 126 and 125; anti-ASGR1 Rspo3 RE, SEQ ID NOs: 128 and 127; anti-ASGR1 Rspo3 EA, SEQ ID NOs: 130 and 129; and anti-ASGR1 Rspo3 EEARA, SEQ ID NOs: 132 and 131.

As demonstrated in FIG. 16B, all of these combinations significantly reduced the protein's activity as compared to the wild-type Rspo3 fused to the anti-GFP control, consistent with their disruption of Rspo-LGR interactions. When fused to the anti-ASGR1 targeting domain, all mutants showed enhanced activity, even though the dynamic range (the difference between the targeted activity and that of the anti-GFP control fusion protein) varied depending on the particular mutation(s) selected, suggesting that they all support the construction on tissue-specific Wnt signal enhancing molecule design (FIG. 16C).

Example 13

Non-RSPO-Based Action Domains

To demonstrate the feasibility of using non-Rspo based structures as the action domain, "Fab-IgG" fusion proteins were designed, in which the Fab fragment of an anti-human ZNRF3 mAb (Ab2 from patent WO2013054307A2) was fused to the IgG of anti-ASGR1, anti-TFR1, or anti-GFP (FIG. 17A). The anti-ZNRF3-anti-GFP construct included the following polypeptides having the indicated polypeptide sequences and encoding polynucleotide sequences: anti-GFP light chain (S176K) (SEQ ID NOs: 134 and 133), anti-ZNRF3 light chain (S176E) (SEQ ID NOs: 136 and 135), and anti-ZNRF3-anti-GFP fused heavy chain (SEQ ID NOs: 138 and 137). The anti-ZNRF3-anti-ASGR1 construct included the following polypeptides having the indicated polypeptide sequences and encoding polynucleotide sequences: anti-ASGR1 light chain (S176K) (SEQ ID NOs: 140 and 139), anti-ZNRF3 light chain (S176E) (SEQ ID NOs: 136 and 135), and anti-ZNRF3-anti-ASGR1 fused heavy chain (SEQ ID NOs: 142 and 141). The anti-ZNRF3-anti-TFR1 construct included the following polypeptides having the indicated polypeptide sequences and encoding polynucleotide sequences: anti-TFR1 light chain (S176K) (SEQ ID NOs: 144 and 143), anti-ZNRF3 light chain (S176E) (SEQ ID NOs: 136 and 135), and anti-ZNRF3-anti-TFR1 fused heavy chain (SEQ ID NOs: 146 and 145).

These proteins were transiently transfected to Expi293F cells and purified by Protein A affinity resin followed by size exclusion chromatography, then tested in Huh-7 cells by STF assay at the presence of 30% Wnt3a conditioned media. As shown in FIG. 17B, the anti-ASGR1 and anti-TFR1 "targeted" anti-ZNRF3 modules both demonstrated activities over that of the anti-GFP fusion protein, validating the feasibility of constructing tissue-specific Wnt signal enhancing molecules using purely binders to the ZNRF3/RNF43 E3 ligases, independently of the Rspo structures.

Example 14

Tissue-Targeted Wnt Enhancers in Addition to Liver-Targeted Wnt Enhancers

The examples provided above utilized ASGR1 binders to generate Wnt signaling enhancing molecules with the ability to target liver for various uses. The TFR1 binders may also target liver, as well as a broader range of tissues where it is expressed. To provide tissue targeting beyond liver, additional tissue specific cell surface molecules were identified by searching the public gene expression database (https://www.proteinatlas.org/). LYPD3, Ly6/PLAUR domain-containing protein 3, and DSG3, Desmoglein 3, were selected as target molecules, because they were expressed very abundantly and specifically in mucosal epithelial cells from oral mucosa, skin and tonsil. In addition, their specific antibody sequences were published previously (US20170158775A1, mAb clone M31-B01 was selected as the LYPD3 binder; US20100092457A1, mAb clone DF364c was selected as the DSG3 binder).

To obtain mucosal epithelial cell-specific WNT enhancers, the Rspo2 (F105R/F109A) mutant was fused to the N-terminus of the heavy chain of either anti-LYPD3 or anti-DSG3 in the form of an "effector-less" IgG1 (Lo M et al., 2017 The Journal of Biological Chemistry, 292). The anti-GFP Rspo2 (F105R/F109A) construct included the following polypeptides having the indicated polypeptide sequences and encoding polynucleotide sequences: anti-GFP light chain (SEQ ID NOs: 36 and 35), and Rspo2 (F105R/F109A), anti-GFP heavy chain IgG2 (SEQ ID NOs: 38 and 37). The anti-LYPD3 Rspo2 (F105R/F109A) construct included the following polypeptides having the indicated polypeptide sequences and encoding polynucleotide sequences: anti-LYPD3 light chain (SEQ ID NOs: 148 and 147), and Rspo2 (F105R/F109A), anti-LYPD3 heavy chain LALA-PG (SEQ ID NOs: 150 and 149). The anti-DSG3 Rspo2 (F105R/F109A) construct included the following polypeptides having the indicated polypeptide sequences and encoding polynucleotide sequences: anti-DSG3 light chain (SEQ ID NOs: 152 and 151), and Rspo2 (F105R/F109A), anti-DSG3 heavy chain LALA-PG (SEQ ID NOs: 154 and 153).

The fusion proteins were expressed from Expi293Fcells (Thermo Fisher Scientific) and purified using protein-A resin followed by a size exclusion column (S200, GE Healthcare) fractionation, with typical estimated purify of >90%. The Wnt signal enhancing activity of these proteins were tested in two oral mucosal cell lines CAL27 and SCC25, and the control A431 cell line.

As shown in FIG. 18A, LYPD3 and DSG3 genes were highly expressed in CAL27 and SCC25 cells but very low expression was observed in A431 cells. Both the LYPD3 and DSG3 targeted Rspo2 mutant fusion proteins demonstrated a much more potent activity than the anti-GFP control in CAL27 cells. In SCC25 cells, the DSG3 targeted molecule was much more active than the anti-GFP control, while that of the LYPD3 targeting protein was less striking, which might be a reflection of lower LYPD3 receptor level on SCC25 cells. These results confirm that the tissue specific antibodies, when used as targeting domains, can enhance Rspo mutant activity on the targeted cells. In contrast, the activities of the LYPD3 and DSG3 targeting molecules were indistinguishable from anti-GFP control fusion protein in A431 cells, which lack expression of LYPD3 and DSG3, clearly demonstrating that the specific binding to the cell surface receptor is required to enhanced activity. In addition to the enhancement of the tissue specific activity, the anti-LYPD3 and anti DSG3 fusion proteins were more potent than Rspo2 positive control in targeted CAL17 cells, showing better $EC_{50}$ and better or comparable $E_{max}$ to Rspo2 positive control.

Example 15

In Vivo Induction of a WNT Responsive Gene by a Tissue-Specific WNT Signal Enhancer To examine the in vivo activity of the designed Wnt signal enhancers, the induction of Axing, which is a Wnt responsive gene, was examined. As laid out in FIG. 19A, AAV-hASGR1 was first injected into 8-week old male mice intravenously at a titer of 1E11 per animal. This led to human ASGR1 gene expression in mice liver. Seven days later, purified proteins were injected intravenously in groups of eight at specified doses: anti-GFP at 1 mg/kg; Rspo2 positive control at 0.46 mg/kg, anti-GFP-Rspo2 (F105R/F109A) at 1 mg/kg, and anti-ASGR1-Rspo2 (F105R/F109A) at 1 mg/kg, either alone, or in combination with an Wnt signal agonist 18R5-Dkk1c (Janda et al., 2017 Nature) at 3 mg/kg. Eight hours later, the mice were euthanized and liver samples were taken for Quantitative-PCR analysis of gene expression. The anti-GFP construct included the following polypeptides having the indicated polypeptide and encoding polynucleotide sequences: anti-GFP light chain (SEQ ID NOs: 36 and 35) and anti-GFP heavy chain, IgG1 (LALA-PG) (SEQ ID NOs: 156 and 155). The anti-GFP Rspo2 (F105R/F109A), N-HC construct included the polypeptides provided in SEQ ID NOs: 35-38; and the antiA-SGR1 IgG2 N-HC construct included the polypeptides provided in SEQ ID NOs: 71-74. The 18R5-Dkk1c construct had the polypeptide sequence disclosed in SEQ ID NO: 158 and was encoded by the polynucleotide sequence disclosed in SEQ ID NO: 157.

FIG. 19B shows the expression levels of ectopic hASGR1 in mice livers, which were comparable across all experimental groups. Treating mice with Rspo2 positive control protein alone induced a moderate but statistically significant induction of Axin2 gene expression (FIG. 19C, left), consistent with the in vivo function of Rspo proteins. Interestingly, treatment with anti-ASGR1-Rspo2 (F105/F109) alone also induced a trended increase in Axin2 levels that was not observed with the control anti-GFP fusion protein. 18R5-Dkk1c is a Wnt surrogate. At 3 mg/kg, it didn't cause a significant change in Axin2 gene expression by itself. However, a clear synergy was observed between Rspo2 and 18R5-Dkk1c (FIG. 19C, right), which is consistent with the Wnt signal enhancing activity of Rspo proteins. Such a synergy was also observed with the anti-ASGR1 fusion protein, but not the anti-GFP control, suggesting that the induction of Axin2, representing Wnt signal enhancement in mouse liver, is specifically dependent on the anti-ASGR1 targeting domain.

REFERENCES

Clevers H, Loh K M and Nusse R. 2014, An integral program for tissue renewal and regeneration: Wnt signaling and stem cell control. Science 346(6205): 1248012.

Knight M N and Hankenson K D. R-spondins: novel matricellular regulators of the skeleton. Matrix Biology 37: 157-161.

Yan J J, Liao J Z, Lin J S and He X X. 2015, Active radar guides missile to its target: receptor-based targeted treatment of hepatocellular carcinoma by nanoparticulate systems. Tumor Biology 36: 55-67.

Stockert R J, Morell A G and Ashwell G. 1991, Structural characteristics and regulation of the asialoglycoprotein receptor. Targeted Diagnostic and Therapy 4: 41-64.

D'Souza A A and Devarajan P V. 2015, Asialoglycoprotein receptor mediated hepatocyte targeting—strategies and applications. Journal of Controlled Release, 203: 126-139.

Yan H, Zhong G, Xu G, He W, Jing Z, Gao Z, Huang Y, Qi Y, Peng B, Wang H, Fu L, Song M, Chen P, Gao W, Ren B, Sun Y, Cai T, Feng X, Sui J, Li W. 2012, Sodium taurocholate cotransporting polypeptide is a functional receptor for human hepatitis B and D virus. eLife, 1: e00049.

Worthen C A and Enns C A. 2014, The role of hepatic transferrin receptor 2 in the regulation of iron homeostasis in the body. Frontiers in Pharmacology 5: 34

Mannstadt M, Juppner H, and Gardella T J. 1999, Receptors for PTH and PTHrP: their biological importance and functional properties. American Journal of Physiology 277: F665-F675.

Janda C Y, Dang L T, You C, Chang J, de Lau W, Zhong Z A, Yan K S, Marecic O, Siepe D, Li X, Moody J D, Williams B O, Clevers H, Piehler J, Baker D, Kuo C J, and Garcia K C. 2017, Surrogate Wnt agonists that phenocopy canonical Wnt and β-catenin signaling. Nature 545: 234-237.

Lo M, Kim H S, Tong R K, Bainbridge T W, Vernes J M, Zhang Y, Lin Y L, Chung S, Dennis M S, Zuchero Y J, Watts R J, Couch J A, Meng Y G, Atwal J K, Brerski R J, Spiess C, Ernst J A. 2017, Effector-attenuating Substitutions That Maintain Antibody Stability and Reduce Toxicity in Mice. J Biol Chem. 292:3900-3908.

Jacobsen F W, Stevenson R, Li C, Salimi-Moosavi H, Liu L, Wen J, Luo Q, Daris K, Buck L, Miller S, Ho S Y, Wang W, Chen Q, Walker K, Wypych J, Narhi L, Gunasekaran K. 2017 Engineering an IgG Scaffold Lacking Effector Function with Optimized Developability. J Biol Chem. 292:1865-1875.

Paret C, Bourouba M, Beer A, Miyazaki K, Schnölzer M, Fiedler S, Zoller M. International Journal of Cancer. 2005 Jul. 10; 115(5):724-33. Ly6 family member C4.4A binds laminins 1 and 5, associates with galectin-3 and supports cell migration.

Arumugam T, Deng D, Bover L, Wang H, Logsdon C D, Ramachandran V. Molecular Cancer Therapeutics. 2015 April; 14(4):941-51. New Blocking Antibodies against Novel AGR2-C4.4A Pathway Reduce Growth and Metastasis of Pancreatic Tumors and Increase Survival in Mice.

Ngora H1, Galli U M, Miyazaki K, Zoller M. Neoplasia. 2012 February; 14(2):95-107. Membrane-bound and exosomal metastasis-associated C4.4A promotes migration by associating with the α(6)β(4) integrin and MT1-MMP.

Wolfgang-Moritz Heupel, Detlef Zillikens, Detlev Drenckhahn and Jens Waschke Pemphigus. Vulgaris IgG Directly Inhibit Desmoglein 3-Mediated Transinteraction. Journal of Immunology. Aug. 1, 2008, 181 (3) 1825-1834.

The invention claimed is:

1. A tissue-specific Wnt ("Wingless-related integration site" or "Wingless and Int-I" or "Wingless-Int") signal enhancing molecule, or a pharmaceutically acceptable salt thereof, comprising:
   (a) a first domain comprising two R-spondin 2 polypeptides, or fragments thereof comprising the furin I domain of the R-spondin 2 polypeptide, wherein the R-spondin 2 polypeptides comprise amino acid substitutions at amino acids corresponding to F105 and F109 of human R-spondin 2 of SEQ ID NO:2, and wherein the first domain specifically binds one or more-transmembrane E3 ubiquitin ligases, wherein the one or more transmembrane E3 ubiquitin ligases are Zinc and Ring Finger 3 (ZNRF3) and Ring Finger Protein 43 (RNF43); and
   (b) a second domain comprising an Immunoglobulin G (IgG) antibody; wherein the second domain specifically binds a tissue-specific cell surface molecule, wherein the tissue-specific cell surface molecule is an asialoglycoprotein receptor I (ASGRI), and wherein the IgG antibody comprises two heavy chain polypeptides and two light chain polypeptides, wherein each light chain polypeptide comprises SEQ ID NO: 72, and each heavy chain polypeptide comprises SEQ ID NO: 86,
wherein the R-spondin 2 polypeptides are fused to the heavy chain polypeptides of the IgG antibody.

2. The molecule or pharmaceutically acceptable salt thereof of claim 1, wherein the tissue is liver tissue.

3. The molecule or pharmaceutically acceptable salt thereof of claim 1, wherein the amino acid substitutions are F105R and F109A.

4. The molecule or pharmaceutically acceptable salt thereof of claim 1, wherein each of the modified R-spondin 2 polypeptides is fused to one of the heavy chain polypeptides by a linker moiety.

5. The molecule or pharmaceutically acceptable salt thereof of claim 4, wherein the linker moieties are peptidyl linker sequences.

6. The molecule or pharmaceutically acceptable salt thereof of claim 5, wherein the linker sequences comprises one or more amino acids selected from the group consisting of: Glycine, Asparagine, Serine, Threonine and Alanine.

7. A pharmaceutical composition comprising:
(i) the molecule or pharmaceutically acceptable salt thereof of claim 1; and
(ii) a pharmaceutically acceptable diluent, adjuvant or carrier.

8. The pharmaceutical composition of claim 7, further comprising a mammalian Wnt polypeptide or a functional variant or fragment thereof.

9. A tissue-specific Wnt ("Wingless-related integration site" or "Wingless and Int-I" or "Wingless-Int") signal enhancing molecule, or pharmaceutically acceptable salt thereof, wherein the molecule comprises:
a) two polypeptides of SEQ ID NO:72 and two polypeptides of SEQ ID NO:74; or
b) two polypeptides of SEQ ID NO:72 and two polypeptides of SEQ ID NO:86.

10. The molecule or pharmaceutically acceptable salt thereof of claim 9, wherein the molecule comprises two polypeptides of SEQ ID NO: 72, and
two polypeptides of SEQ ID NO: 74.

11. A pharmaceutical composition comprising the molecule or pharmaceutically acceptable salt thereof of claim 10 and a pharmaceutically acceptable diluent, adjuvant or carrier.

12. A pharmaceutical composition comprising the molecule or pharmaceutically acceptable salt thereof of claim 9.

13. The molecule or pharmaceutically acceptable salt thereof of claim 9, wherein the molecule comprises two polypeptides of SEQ ID NO:72 and two polypeptides of SEQ ID NO:86.

14. A pharmaceutical composition comprising the molecule or pharmaceutically acceptable salt thereof of claim 13.

* * * * *